(12) United States Patent
Pantaleo et al.

(10) Patent No.: US 10,294,299 B2
(45) Date of Patent: May 21, 2019

(54) IMMUNOLOGICAL REAGENTS

(71) Applicant: MabQuest SA, Pully (CH)

(72) Inventors: Giuseppe Pantaleo, Pully (CH); Craig Fenwick, Lausanne (CH)

(73) Assignee: MabQuest SA, Pully (CH)

( * ) Notice: Subject to any disclaimer, the term of this patent is extended or adjusted under 35 U.S.C. 154(b) by 0 days.

(21) Appl. No.: 15/513,395

(22) PCT Filed: Jan. 20, 2017

(86) PCT No.: PCT/IB2017/000031
§ 371 (c)(1),
(2) Date: Mar. 22, 2017

(87) PCT Pub. No.: WO2017/125815
PCT Pub. Date: Jul. 27, 2017

(65) Prior Publication Data

US 2018/0265582 A1 Sep. 20, 2018

Related U.S. Application Data

(60) Provisional application No. 62/286,269, filed on Jan. 22, 2016, provisional application No. 62/290,745, filed on Feb. 3, 2016.

(51) Int. Cl.
| | | |
|---|---|---|
| *C07K 16/28* | (2006.01) | |
| *A61K 39/395* | (2006.01) | |
| *A61P 31/18* | (2006.01) | |
| *A61P 35/00* | (2006.01) | |
| *A61K 39/00* | (2006.01) | |

(52) U.S. Cl.
CPC .... *C07K 16/2803* (2013.01); *A61K 39/39541* (2013.01); *A61P 31/18* (2018.01); *A61P 35/00* (2018.01); *C07K 16/2818* (2013.01); *A61K 39/39558* (2013.01); *A61K 2039/507* (2013.01); *C07K 2317/24* (2013.01); *C07K 2317/33* (2013.01); *C07K 2317/34* (2013.01); *C07K 2317/75* (2013.01); *C07K 2317/76* (2013.01)

(58) Field of Classification Search
CPC ... C07K 16/00–16/468; C07K 16/2818; A61K 39/395–39/39558; A61K 2039/507
See application file for complete search history.

(56) References Cited

U.S. PATENT DOCUMENTS

| | | | |
|---|---|---|---|
| 4,816,567 A | 3/1989 | Cabilly et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,629,204 A | 5/1997 | Honjo et al. | |
| 5,633,425 A | 5/1997 | Lonberg et al. | |
| 5,661,016 A | 8/1997 | Lonberg et al. | |
| 5,693,761 A | 12/1997 | Queen et al. | |
| 5,698,520 A | 12/1997 | Honjo et al. | |
| 6,407,213 B1 | 6/2002 | Carter et al. | |
| 6,808,710 B1 | 10/2004 | Wood et al. | |
| 7,101,550 B2 | 9/2006 | Wood et al. | |
| 7,488,802 B2 | 2/2009 | Collins et al. | |
| 7,521,051 B2 | 4/2009 | Collins et al. | |
| 7,563,869 B2 | 7/2009 | Honjo et al. | |
| 7,595,048 B2 | 9/2009 | Honjo et al. | |
| 7,638,492 B2 | 12/2009 | Wood et al. | |
| 7,858,746 B2 | 12/2010 | Honjo et al. | |
| 8,008,449 B2 | 8/2011 | Korman et al. | |
| 8,168,179 B2 | 5/2012 | Honjo et al. | |
| 8,168,757 B2 | 5/2012 | Finnefrock et al. | |
| 8,287,856 B2 | 10/2012 | Li et al. | |
| 8,354,509 B2 | 1/2013 | Carven et al. | |
| 8,552,154 B2 | 10/2013 | Freeman et al. | |
| 8,652,465 B2 | 2/2014 | Freeman et al. | |
| 8,728,474 B2 | 5/2014 | Honjo et al. | |
| 8,735,553 B1 | 5/2014 | Li et al. | |
| 8,741,295 B2 | 6/2014 | Olive | |
| 8,829,165 B2 | 9/2014 | Jackson et al. | |

(Continued)

FOREIGN PATENT DOCUMENTS

| | | |
|---|---|---|
| JP | 05-336973 | 6/1992 |
| WO | 9428933 A1 | 12/1994 |

(Continued)

OTHER PUBLICATIONS

Rutigliano, J.A., et al., "Highly pathological influenza A virus infection is associated with augmented expression of PD-1 by functionally compromised virus-specific CD8+ T cells," J Virol, 2014. 88(3): p. 1636-1651.

Sakthivel, P., M. Gereke, and D. Bruder, "Therapeutic intervention in cancer and chronic viral infections: antibody mediated manipulation of PD-1/PD-L1 interaction," Rev Recent Clin Trials, 2012. 7(1): p. 10-23.

Sharma, P. and J.P. Allison, "The future of immune checkpoint therapy," Science, 2015. 348(6230): p. 56-61.

Sheppard, K.A., et al., "PD-1 inhibits T-cell receptor induced phosphorylation of the ZAP70/CD3zeta signalosome and downstream signaling to PKCtheta," FEBS Lett, 2004. 574(1-3): p. 37-41.

(Continued)

*Primary Examiner* — Jessica H Roark
(74) *Attorney, Agent, or Firm* — Patrick J Halloran

(57) ABSTRACT

This disclosure relates to binding agents with specificity for programmed cell death 1 (PD-1) and to methods for using the same to treat, prevent and/or ameliorate an infectious disease (e.g., human immunodeficiency virus (HIV)), cancer and/or autoimmunity. In addition, this disclosure identifies a novel binding patch ("P2") on PD-1 that is linked with a previously unidentified functional activity of PD-1 that is distinct from the interaction site involved with either the PD-L1 or PD-L2 ligands. Furthermore, we demonstrate that antibodies that interact with this region of PD-1 are able to act as antagonists of PD-1 and that this antagonism is further enhanced with the addition of antibodies that act through the blockade of the PD-1/PD-L1/L2 interaction.

29 Claims, 33 Drawing Sheets
Specification includes a Sequence Listing.

(56) References Cited

U.S. PATENT DOCUMENTS

| | | | |
|---|---|---|---|
| 8,900,587 | B2 | 12/2014 | Carven et al. |
| 8,927,697 | B2 | 1/2015 | Davis et al. |
| 8,952,136 | B2 | 2/2015 | Carven et al. |
| 8,993,731 | B2 | 3/2015 | Tyson |
| 9,029,315 | B2 | 5/2015 | Chen et al. |
| 9,067,999 | B1 | 6/2015 | Honjo et al. |
| 9,090,994 | B2 | 6/2015 | Zhang et al. |
| 9,073,994 | B2 | 7/2015 | Honjo et al. |
| 9,102,728 | B2 | 8/2015 | Tyson |
| 9,163,087 | B2 | 10/2015 | Kuchroo et al. |
| 9,205,148 | B2 | 12/2015 | Langermann et al. |
| 9,220,776 | B2 | 12/2015 | Sharma et al. |
| 9,402,899 | B2 | 8/2016 | Honjo et al. |
| 9,982,052 | B2 | 5/2018 | Pantaleo et al. |
| 9,982,053 | B2 | 5/2018 | Pantaleo et al. |
| 2002/0160000 | A1 | 10/2002 | Nood et al. |
| 2004/0209243 | A1 | 10/2004 | Nixon et al. |
| 2004/0213795 | A1 | 10/2004 | Collins et al. |
| 2009/0217401 | A1 | 8/2009 | Kormann et al. |
| 2010/0028330 | A1 | 2/2010 | Collins et al. |
| 2010/0040614 | A1 | 2/2010 | Ahmed et al. |
| 2011/0081341 | A1 | 4/2011 | Honjo et al. |
| 2011/0171215 | A1 | 7/2011 | Davis et al. |
| 2011/0229461 | A1 | 9/2011 | Tyson |
| 2012/0039906 | A1 | 2/2012 | Olive |
| 2013/0071403 | A1 | 3/2013 | Rolland et al. |
| 2013/0202623 | A1 | 8/2013 | Chomont et al. |
| 2014/0044738 | A1 | 2/2014 | Langermann et al. |
| 2014/0341902 | A1 | 11/2014 | Maecker et al. |
| 2015/0203579 | A1 | 6/2015 | Papadopoulus et al. |
| 2015/0290316 | A1 | 10/2015 | Graziano et al. |
| 2016/0075783 | A1 | 3/2016 | King et al. |
| 2016/0251436 | A1 | 9/2016 | Amirina et al. |
| 2016/0272708 | A1 | 9/2016 | Chen |
| 2016/0319019 | A1 | 11/2016 | Amirina et al. |
| 2017/0166642 | A1 | 6/2017 | Pantaleo et al. |

FOREIGN PATENT DOCUMENTS

| | | |
|---|---|---|
| WO | 2009114335 A2 | 9/2009 |
| WO | 2010029434 A1 | 3/2010 |
| WO | 2010029435 A1 | 3/2010 |
| WO | 2011110604 A1 | 9/2011 |
| WO | 2013169693 A1 | 11/2013 |
| WO | 2016020856 A2 | 2/2016 |
| WO | 2017125815 A2 | 7/2017 |

OTHER PUBLICATIONS

Soria, J.C., et al., "Immune checkpoint modulation for non-small cell lung cancer," Clin Cancer Res, 2015.21(10): p. 2256-62.

Swaika, A., W.A. Hammond, and R.W. Joseph, "Current state of anti-PD-L1 and anti-PD-1 agents in cancer therapy," Mol Immunol, 2015. 67(2 Pt A): p. 4-17.

Tan, M. and L. Quintal, "Pembrolizumab: a novel antiprogrammed death 1 (PD-1) monoclonal antibody for treatment of metastatic melanoma," J Clin Pharm Ther, 2015.

Tan, S., C.W.H. Zhang, and G.F. Gao, "Seeing is believing: anti-PD-1/PD-L1 monoclonal antibodies in action for checkpoint blockade tumor immunotherapy," Signal Transduction and Targeted Therapy, 2016. 1: p. 16029.

Topalian, S.L., C.G. Drake, and D.M. Pardoll, "Immune checkpoint blockade: a common denominator approach to cancer therapy," Cancer Cell, 2015. 27(4): p. 450-61.

Topalian, S.L., et al., "Safety, activity, and immune correlates of anti-PD-1 antibody in cancer," N Engl J Med, 2012. 366(26): p. 2443-54.

Trautmann, L., et al., "Upregulation of PD-1 expression on HIV-specific CD8+ T cells leads to reversible immune dysfunction," Nat Med, 2006. 12(10): p. 1198-202.

Tumeh, P.C., et al., "PD-1 blockade induces responses by inhibiting adaptive immune resistance," Nature, 2014. 515(7528): p. 568-71.

Wei, F., et al., "Strength of PD-1 signaling differentially affects T-cell effector functions," Proc Natl Aced Sci U S A, 2013. 110(27): p. E2480-9.

Wherry, E.J. and M. Kurachi, "Molecular and cellular insights into T cell exhaustion," Nat Rev Immunol, 2015. 15(8): p. 486-99.

Winograd, R., et al., "Induction of T-cell Immunity Overcomes Complete Resistance to PD-1 and CTLA-4 Blockade and Improves Survival in Pancreatic Carcinoma," Cancer Immunol Res, 2015. 3(4): p. 399-411.

Xia, Y., L. Jeffrey Medeiros, and K.H. Young, "Signaling pathway and dysregulation of PD1 and its ligands in lymphoid malignancies," Biochim Biophys Acta, 2016. 1865(1): p. 58-71.

Zak, K.M., et al., "Structure of the Complex of Human Programmed Death 1, PD-1, and Its Ligand PD-L1," Structure, 2015. 23(12): p. 2341-8.

Zaretsky, J.M., et al., "Mutations Associated with Acquired Resistance to PD-1 Blockade in Melanoma," N Engl J Med, 2016. 375(9): p. 819-29.

Zhang, J.Y., et al., "PD-1 up-regulation is correlated with HIV-specific memory CD8+ T-cell exhaustion in typical progressors but not in long-term nonprogressors," Blood, 2007. 109(11): p. 4671-8.

Zhang, X., et al., "Structural and functional analysis of the costimulatory receptor programmed death-1," Immunity, 2004. 20(3): p. 337-47.

"Enumeral Announces Identification of Anti-PD-1 Antibodies with Potential for Differentiated Mechanism of Action". Enumeral.com. Sep. 24, 2015.

"Enumeral Reports That Its Novel Class of Anti-PD-1 Antibodies Elicits Higher T Cell Activation in Ex Vivo Human Assays than Currently Marketed Anti-PD-1 Antibodies". Enumeral.com. Nov. 3, 2015.

"Enumeral Reports That Its Novel Class of Potentially Allosteric Anti-PD-1 Antibodies Can Elicit an Additive Effect on T Cell Activation in Ex Vivo Human Assays When Used in Combination With a Currently Marketed Anti-PD-1 Antibody". Enumeral.com. Nov. 18, 2015.

CD279 (PD-1) Monoclonal Antibody (J116), Functional Grade, eBioscienceTM. ://www.thermofisher.com/antibody/product/CD279-PD-1-Antibody-clone-J116-Monoclonal/16-9989-82, last visited: Nov. 2017.

Alvarez, I.B., et al., "Role played by the programmed death-1-programmed death ligand pathway during innate immunity against *Mycobacterium tuberculosis*," J Infect Dis, 2010. 202(4): p. 524-32.

Ansell, S.M., et al., "PD-1 blockade with nivolumab in relapsed or refractory Hodgkin's lymphoma," N Engl J Med, 2015. 372(4): p. 311-9.

Ascierto, M.L., et al., "Transcriptional mechanisms of resistance to anti-PD-1 therapy," Clin Cancer Res, 2017.

Baitsch, L., et al., "Exhaustion of tumor-specific CD8(+) T cells in metastases from melanoma patients," J Clin Invest, 2011. 121(6): p. 2350-60.

Barber, D.L., et al., "Restoring function in exhausted CD8 T cells during chronic viral infection," Nature, 2006. 439(7077): p. 682-7.

Blackburn, S.D., et al., "Tissue-specific differences in PD-1 and PD-L1 expression during chronic viral infection: implications for CD8 T-cell exhaustion," J Virol, 2010. 84(4): p. 2078-89.

Blackburn, S.D., et al., "Coregulation of CD8+ T cell exhaustion by multiple inhibitory receptors during chronic viral infection," Nat Immunol, 2009. 10(1): p. 29-37.

Boussiotis, V.A., "Molecular and Biochemical Aspects of the PD-1 Checkpoint Pathway," N Engl J Med, 2016. 375(18): p. 1767-1778.

Brown, K.E., et al., "Role of PD-1 in regulating acute infections," Curr Opin Immunol, 2010. 22(3): p. 397-401.

Callahan, M.K., M.A. Postow, and J.D. Wolchok, "Targeting T Cell Co-receptors for Cancer Therapy," Immunity, 2016. 44(5): p. 1069-78.

Carbognin, L., et al., "Differential Activity of Nivolumab, Pembrolizumab and MPDL3280A according to the Tumor Expression of Programmed Death-Ligand-1 (PD-L1): Sensitivity Analysis of Trials in Melanoma, Lung and Genitourinary Cancers," PLoS One, 2015. 10(6): p. e0130142.

(56) References Cited

OTHER PUBLICATIONS

Cheng, X., et al., "Structure and interactions of the human programmed cell death 1 receptor," J Biol Chem, 2013. 288(17): p. 11771-85.
Chinai, J.M., et al., "New immunotherapies targeting the PD-1 pathway," Trends Pharmacol Sci, 2015. 36(9): p. 587-95.
Daud, A.I., et al., "Tumor immune profiling predicts response to anti-PD-1 therapy in human melanoma," J Clin Invest, 2016. 126(9): p. 3447-52.
Day, C.L., et al., "PD-1 expression on HIV-specific T cells is associated with T-cell exhaustion and disease progression," Nature, 2006. 443(7109): p. 350-4.
Drake, C.G., E.J. Lipson, and J.R. Brahmer, "Breathing new life into immunotherapy: review of melanoma, lung and kidney cancer," Nat Rev Clin Oncol, 2014. 11(1): p. 24-37.
Driessens, G., J. Kline, and T.F. Gajewski, "Costimulatory and coinhibitory receptors in anti-tumor immunity," Immunol Rev, 2009. 229(1): p. 126-44.
Freeman, G.J., et al., "Reinvigorating exhausted HIV-specific T cells via PD-1-PD-1 ligand blockade," J Exp Med, 2006. 203(10): p. 2223-7.
Gandini, S., D. Massi, and M. Mandala, "PD-L1 expression in cancer patients receiving anti PD-1/PD-L1 antibodies: A systematic review and meta-analysis," Crit Rev Oncol Hematol, 2016. 100: p. 88-98.
Garon, E.B., et al., "Pembrolizumab for the treatment of non-small-cell lung cancer," N Engl J Med, 2015. 372(21): p. 2018-28.
Goldberg, M.V., et al., "Role of PD-1 and its ligand, B7-H1, in early fate decisions of CD8 T cells," Blood, 2007. 110(1): p. 186-92.
Ha, S.J., et al., "Enhancing therapeutic vaccination by blocking PD-1-mediated inhibitory signals during chronic nfection," J Exp Med, 2008. 205(3): p. 543-55.
Hamid, O., et al., "Safety and tumor responses with lambrolizumab (anti-PD-1) in melanoma," N Engl J Med, 2013. 369(2): p. 134-44.
Herati, R.S., et al., "Circulating CXCR5+PD-1+ response predicts influenza vaccine antibody responses in young adults but not elderly adults," J Immunol, 2014. 193(7): p. 3528-37.
Horita, S., et al., "High-resolution crystal structure of the therapeutic antibody pembrolizumab bound to the human PD-1," Sci Rep, 2016. 6: p. 35297.
Huang, R.Y., et al., "LAG3 and PD1 co-inhibitory molecules collaborate to limit CD8+ T cell signaling and dampen antitumor immunity in a murine ovarian cancer model," Oncotarget, 2015. 6(29): p. 27359-77.
Hui, E., et al., "T cell costimulatory receptor CD28 is a primary target for PD-1-mediated inhibition," Science, 2017. 355(6332): p. 1428-1433.
Kamphorst, A.O., et al., "Rescue of exhausted CD8 T cells by PD-1-targeted therapies is CD28-dependent," Science, 2017. 355(6332): p. 1423-1427.
Kao, C., et al., "Transcription factor T-bet represses expression of the inhibitory receptor PD-1 and sustains virus-specific CD8+ T cell responses during chronic infection," Nat Immunol, 2011. 12(7): p. 663-71.
Larkin, J., et al., "Combined Nivolumab and Ipilimumab or Monotherapy in Untreated Melanoma," N Engl J Med, 2015. 373(1): p. 23-34.
Lazar-Molnar, E., et al., "Crystal structure of the complex between programmed death-1 (PD-1) and its ligand PD-L2," Proc Natl Acad Sci U S A, 2008. 105(30): p. 10483-8.
Lee, J.Y., et al., "Structural basis of checkpoint blockade by monoclonal antibodies in cancer immunotherapy," Nat Commun, 2016. 7: p. 13354.
Li, Q.X., et al., "Experimental animal modeling for immuno-oncology," Pharmacol Ther, 2017.
Lin, D.Y., et al., "The PD-1/PD-L1 complex resembles the antigen-binding Fv domains of antibodies and T cell receptors," Proc Natl Acad Sci U S A, 2008. 105(8): p. 3011-6.

Maier, H., et al., "PD-1:PD-L1 interactions contribute to the functional suppression of virus-specific CD8+ T lymphocytes in the liver," J Immunol, 2007. 178(5): p. 2714-20.
Mellman, I., G. Coukos, and G. Dranoff, "Cancer immunotherapy comes of age," Nature, 2011. 480(7378): p. 480-9.
Na, Z., et al., "Structural basis for blocking PD-1-mediated immune suppression by therapeutic antibody pembrolizumab," Cell Res, 2017. 27(1): p. 147-150.
Nakamoto, N., et al., "Functional restoration of HCV-specific CD8 T cells by PD-1 blockade is defined by PD-1 expression and compartmentalization," Gastroenterology, 2008. 134(7): p. 1927-37, 1937 e1-2.
Nghiem, P.T., et al., "PD-1 Blockade with Pembrolizumab in Advanced Merkel-Cell Carcinoma," N Engl J Med, 2016. 374(26): p. 2542-52.
Palucka, A.K. and L.M. Coussens, "The Basis of Oncoimmunology," Cell, 2016. 164(6): p. 1233-47.
Pardoll, D.M., "The blockade of immune checkpoints in cancer immunotherapy," Nat Rev Cancer, 2012. 12(4): p. 252-64.
Parry, R.V., et al., "CTLA-4 and PD-1 receptors inhibit T-cell activation by distinct mechanisms," Mol Cell Biol, 2005. 25(21): p. 9543-53.
Patnaik, A., et al., "Phase I Study of Pembrolizumab (MK-3475; Anti-PD-1 Monoclonal Antibody) in Patients with Advanced Solid Tumors," Clin Cancer Res, 2015. 21(19): p. 4286-93.
Patsoukis, N., et al., "Selective effects of PD-1 on Akt and Ras pathways regulate molecular components of the cell cycle and inhibit T cell proliferation," Sci Signal, 2012. 5(230): p. ra46.
Pauken, K.E. and E.J. Wherry, "Overcoming T cell exhaustion in infection and cancer," Trends Immunol, 2015. 36(4): p. 265-76.
Petrovas, C., et al., "PD-1 is a regulator of virus-specific CD8+ T cell survival in HIV infection," J Exp Med, 2006. 203(10): p. 2281-92.
Quigley, M., et al., "Transcriptional analysis of HIV-specific CD8+ T cells shows that PD-1 inhibits T cell function by upregulating BATF," Nat Med, 2010. 16(10): p. 1147-51.
Riley, J.L., "PD-1 signaling in primary T cells," Immunol Rev, 2009. 229(1): p. 114-25.
Rizvi, N.A., et al., "Activity and safety of nivolumab, an anti-PD-1 immune checkpoint inhibitor, for patients with advanced, refractory squamous non-small-cell lung cancer (CheckMate 063): a phase 2, single-arm trial," Lancet Oncol, 2015. 16(3): p. 257-65.
Robert, C., et al., "Pembrolizumab versus Ipilimumab in Advanced Melanoma," N Engl J Med, 2015. 372(26): p. 2521-32.
Agata, Y., et al., "Expression of the PD-1 antigen on the surface of stimulated mouse T and B lymphocytes", International Immunology, vol. 8, No. 5, Nov. 5, 1995, pp. 765-772.
Azvolinsky, A., "Another Anti-PD1 Immunotherapy Shows Promise for Melanoma Patients", CancerCommons, Nov. 25, 2013, 3 pages.
Barber, D.L., et al., "Restoring function in exhausted CD8 T cells during chronic viral infection." (Abstract), Nature, 439(7077), Dec. 28, 2005, pp. 682-687 (Abstract).
Batra, S.K., et al., "Isolation and Characterization of a Complementary DNA (PD-1) Differentially Expressed by Human Pancreatic Ductal Cell Tumors", Cell Growth & Differentiation, vol. 2, Aug. 1, 1991, pp. 385-390.
Biolegend, Inc., "Purified anti-human CD279 (PD-1) Antibody", www.biolegend.com, Dec. 30, 2013, 3 pages.
Blank C., et al., "Contribution of the PD-L1/PD-1 pathway to T-cell exhaustion: an update on implications for chronic infections and tumor evasion.", Cancer Immunol Immunother, 56(5), Dec. 29, 2006, pp. 739-745.
Bristol-Myers Squibb Company, "Additional Survival Data on Nivolumab, an Investigational PD-1 Immune checkpoint Inhibitor, from Lung Cancer Cohort of a Phase 1 Study Presented at 15th World Conference on Lung Cancer", Business Wire NewsHQ, Oct. 25, 2013, 4 pages.
Da Silva, et al. Nivolumab: Anti-PD-1 monoclonal antibody cancer immunotherapy. Drugs of the Future. 39(1): 15-24 (2014).
Das, R., et al., "Combination Therapy with Anti-CTLA-4 and Anti-PD-1 Leads to Distinct Immunologic Changes In Vivo", The Journal of Immunology, 194, Dec. 24, 2014, pp. 1-10.

(56) References Cited

OTHER PUBLICATIONS

Day, C., et al., "PD-1 expression on HIV-specific T cells is associated with T-cell exhaustion and disease progression", Nature, vol. 443, Sep. 21, 2006, pp. 350-354.
Ebersbach, et al. Affilin—Novel Binding Molecules Based on Human γ-B-Crystallin, an All β-Sheet Protein. J. Mol. Biol. 372 (1): 172-85 (Abstract) (2007).
Eichbaum, Q., "PD-1 signaling in HIV and chronic viral infection—potential for therapeutic intervention?" (Abstract), Curr Med Chem, 18(26), 2011, , pp. 3971-3980 (Abstract).
Faghfuri, et al. Nivolumab and Pembrolizumab as Immune-Modulating Monoclonal Antibodies Targeting the PD-1 Receptor to Treat Melanoma. Expert Rev. Anticancer Ther., 15(9): 981-993 (2015).
Finnefrock, A.G., et al., "PD-1 Blockade in Rhesus Macaques: Impact on Chronic Infection and Prophylactic Vaccination", The Journal of Immunology, 182, 2009, , pp. 980-987.
Freeman et al. Engagement of the PD-1 Immunoinhibitory Receptor by a Novel B7 Family Member Leads to Negative Regulation of Lymphocyte Activation. J. Exp. Med. 192(7): 1027-34 (2000).
Grabulovski, D., et al., "A Novel, Non-immunogenic Fyn SH3-derived Binding Protein with Tumor Vascular Targeting Properties", The Journal of Biological Chemistry, vol. 282, No. 5, Feb. 2, 2007, pp. 3196-3204.
Ha, S-J., et al., "Enhancing therapeutic vaccination by blocking PD-1-mediated inhibitory signals during chronic infection", The Journal of Experimental Medicine, vol. 205, No. 3, Mar. 17, 2008, pp. 543-555.
Haile, et al. Soluble CD80 Restores T Cell Activation and Overcomes Tumor Cell Programmed Cell Death Ligand 1-Mediated Immune Suppression. J. Immunol. 191(5): 2829-2836 (2013).
Hamid, et al. Safety and Tumor Responses with Lambrolizumab (Anti-PD-1) in Melanoma. N. Eng. J. Med. 369: 134-144 (2013).
Ingram, I., "FDA Approves Anti-PD-1 Drug for Advanced Melanoma", Cancer Network, Sep. 4, 2014, 1 page.
Ishida, Y., et al., "Induced expression of PD-1, a novel member of the immunoglobulin gene superfamily, upon programmed cell death", The EMBO Journal, vol. 11 No. 11, 1992, pp. 3887-3895.
Iwai, Y., et al., "Involvement of PD-L1 on tumor cells in the escape from host immune system and tumor immunotherapy by PD-L1 blockade", PNAS, vol. 99 No. 19, Sep. 17, 2002, pp. 12293-12297.
Iwai, Y., et al., "PD-1 Inhibits Antiviral Immunity at the Effector Phase in the Liver", The Journal of Experimental Medicine, vol. 198, No. 1, Jul. 7, 2003, pp. 39-50.
Katlama, C., et al., "Barriers to a cure for HIV: new ways to target and eradicate HIV-1 reservoirs", The Lancet, vol. 381 , Issue 9883, Mar. 29, 2013, pp. 2109-2117.
Kaufmann, D.E., "The PD-1 Inhibitory Pathway in HIV Infection and the Potential for Therapeutic Intervention", DART 2010, Dec. 8, 2010, 19 pages.
Koide et al. Monobodies: antibody mimics based on the scaffold of the fibronectin type III domain. Methods Mol. Biol. 352, 95-109 (Abstract) (2007).
Kolata, G., "Breaking Through Cancer's Shield", The New York Times, Oct. 14, 2013 Oct. 14, 2013, 4 pages.
Kolmar, H., et al., "Alternative binding proteins get mature: Rivalling antibodies", FEBS Journal, vol. 275, 2008, p. 2667.
Krehenbrink, et al. Artificial Binding Proteins (Affitins) as Probes for Conformational Changes in Secretin PulD. J. Mol. Biol. 383 (5): 1058-68 (Abstract) (2008).
McDermott, et al. PD-1 as a potential target in cancer therapy. Cancer Med. 2(5): 662-673 (2013).
Mkrtichyan, et al. Anti-PD1 Antibody Significantly Increases Therapeutic Efficacy of Listeria monocytogenes (Lm)-LLO Immunotherapy. J. Immunotherapy of Cancer, 1:15 (2013).
Merck & Co., Inc., "KEYTRUDA Product Information", U.S. License No. 0002, Revised Oct. 2016, pp. 1-26.
Merck & Co., Inc., Estimated Overall Survival Rate of 81 Percent at One Year in Patients with Advanced Melanoma, Business Wire NewsHQ, Nov. 18, 2013, 3 pages.
Mkrtichyan, M., et al., "Anti-PD-1 antibody significantly increases therapeutic efficacy of Listeria monocytogenes (Lm)-LLO immunotherapy", Journal for ImmunoTherapy of Cancer, vol. 1 No. 15, Aug. 29, 2013, 7 pages.
National Cancer Institute, "Nivolumab", NCI Drug Dictionary, Dec. 30, 2013, 1 page.
Nishimura, H., et al., "Development of Lupus-like Autoimmune Diseases by Disruption of the PD-1 Gene Encoding an ITIM Motif-Carrying Immunoreceptor", Immunity, vol. 11, Aug. 1999, pp. 141-151.
Nishimura, H., et al., "Developmentally regulated expression of the PD-1 protein on the surface of double negative (CD4~CD8~) thymocytes", International Immunology, vol. 8, No. 5, Feb. 6, 1996, pp. 773-780.
Nishimura, H., et al., "Immunological studies on PD-1-deficient mice: implication of PD-1 as a negative regulator for B cell responses", International Immunology, vol. 10, No. 10, Jul. 7, 1998, pp. 1563-1572.
Nygren et al. Alternative binding proteins: affibody binding proteins developed from a small three-helix bundle scaffold. FEBS J. 275 (11): 2668-76 (2008).
Palmer, B.E., et al., "In vivo blockade of the PD-1 receptor suppresses HIV-1 viral loads and improves CD4+ T cell levels in humanized mice." J Immunol., 190(1), Jan. 1, 2013, pp. 211-219.
PCT/IB2015/055943, "International Preliminary Report on Patentability dated Feb. 7, 2017", 13 pages.
PCT/IB2015/055943, "International Search Report and Written Opinion dated Jan. 27, 2016", 26 pages.
Perreau, M., et al., "Follicular helper T cells serve as the major CD4 T cell compartment for HIV-1 infection, replication, and production", The Journal of Experimental Medicine, vol. 210 No. 1, Dec. 17, 2012, pp. 143-156.
Porichis, F., et al., "Role of PD-1 in HIV Pathogenesis and as Target for Therapy", Curr HIV/AIDS Rep. Author Manuscript, Aug. 3, 2012, pp. 1-14.
Seung, E., et al., "PD-1 Blockade in Chronically HIV-1-Infected Humanized Mice Suppresses Viral Loads", PLoS ONE, 8(10): e77780, Oct. 2013, pp. 1-10.
Sievers, et al. Antibody-Drug Conjugates in Cancer Therapy. Ann. Rev. Med. 64: 15-29 (Abstract) (2013).
Siewe, B., et al., "Regulatory B Cells Inhibit Cytotoxic T Lymphocyte (CTL) Activity and Elimination of Infected CD4 T Cells after In Vitro Reactivation of HIV Latent Reservoirs", PLoS ONE, 9(4): e92934, Apr. 16, 2014, pp. 1-9.
Silverman, et al. Corrigendum: Multivalent avimer proteins evolved by exon shuffling of a family of human receptor domains. Nat. Biotechnol. 23 (12): 1556-61 (Abstract) (2005).
Stumpp, et al. DARPins: A new generation of protein therapeutics. Drug Discov. Today 13 (15-16): 695-701 (2008).
Tesaro. Immuno-Oncology Collaboration and License Agreement for TIM-3, LAG-3 and PD-1 Antibody Program. Mar. 13, 2014.
Topalian et al. Safety, Activity, and Immune Correlates of Anti-PD-1 Antibody in Cancer. N. Eng. J. Med. 2012; 366(26): 2443-2454.
Trautman, et al. Corrigendum: Upregulation of PD-1 expression on HIV-specific CD8+ T cells leads to reversible immune dysfunction. Nat. Med. 12: 1198-1202 (Abstract) (2006).
USAN Council, "Statement on a NonProprietary Name Adopted by the USAN Council USAN (ZZ-165) Lambrolizumab", Jan. 30, 2013, 1 page.
Velu, V., et al., "Enhancing SIV-Specific Immunity In Vivo by PD-1 Blockade", Nature Author Manuscript, Sep. 28, 2009, pp. 1-14.
Weber, J., "Immune checkpoint proteins: a new therapeutic paradigm for cancer—preclinical background: CTLA-4 and PD-1 blockade." (Abstract), Semin Oncol., 37(5), Oct. 2010, 2 pages.
Wikipedia Foundation, Inc., "Programmed cell death 1", Wikipedia, Oct. 8, 2013, 7 pages.
Zhou, et al. PD1-based DNA vaccine amplifies HIV-1 GAG-specific CD8+ T cells in mice. J. Clin. Invest. 123(6): 2629-2642 (2013).
Zolot, et al. Antibody-drug Conjugates. Nature Rev. Drug. Disc. 12: 259-260 (Abstract) (2013).

(56) References Cited

OTHER PUBLICATIONS

Zuberek, K., et al., "The role of in vivo PD-1/PD-LI interactions in syngeneic and allogeneic antitumor responses in murine tumor models.", Blood, vol. 98, No. 11 Part 2, Nov. 16, 2001, 2 pages.

Rao, et al. Anti-PD-1/PD-L1 therapy for infectious diseases: learning from the cancer paradigm. Intl. J. Infect. Dis. 56: 221-228 (2017).

Shin & Ribas. The evolution of checkpoint blockage as a cancer therapy: what's here, what's next? Curr. Op. Immunol. 33: 23-25 (2015).

Fuller, et al. Immunotherapy of chronic hepatitis C virus infection with antibodies against programmed cell death-1 (PD-1). Proc. Natl. Acad. Sci. USA 110(37): 15001-006 (2013).

PCT/IB2017/00031, "Notification of Transmittal of the International Search Report and the Written Opinion of the International Searching Authority dated Jul. 14, 2017", 25 pages.

Figures 3A-B

A. Modifications to PD-1 (SEQ ID NO. 275)

```
21      M1   M2   33   M3   M4   M31   M5   M6    M7    M8       M9   M10   70
PGWFL DSPDR  PWNP PTFSPA  LLVVTEGD NA TFTCSFSNTS  ESFVLNWYRM
----- A--AA  -A-- -K-AA-  A--L----AA AAA-A-AA--  AA-A-A-A--

71  M11 M12       M13    M14 M15   M16     M17 M18 M19   M20 M21 M22  120
SFSNQTDKLA AFPEDRSQPG QDCRFRVTQL PNGRDFHMSV VRARRNDSGT
--A-AA-A-- ----AA--AA GA---A-A-- -A-AA-A-A- AA-AA-A-A-

121    M23    M24   M25   M26   M27 M28^149      M29      M30      170
YLCGAISLAP KAQIKESLRA ELRVTERRAE VPTAHPSPSP RPAGQFQTLV
---AGA-A-- T--TA-A-A --AAA-C ----AAA--- TA--------
```

B. Human PD-1 Mutants (modifications highlighted in bold)

1. M1

```
1   MQIPQAPWPV VWAVLQLGWR PGWFLASPAR PWNPPTFSPA LLVVTEGDNA TFTCSFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 244)
```

2. M2

```
1   MQIPQAPWPV VWAVLQLGWR PGWFLDSPDA PANPPTFSPA LLVVTEGDNA TFTCSFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 245)
```

3. M3

```
1   MQIPQAPWPV VWAVLQLGWR PGWFLDSPDR PWNPPKFSPA LLVVTEGDNA TFTCSFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 246)
```

4. M4

```
1   MQIPQAPWPV VWAVLQLGWR PGWFLDSPDR PWNPPTFAAA ALVVTEGDNA TFTCSFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 247)
```

```
1   MQIPQAPWPV VWAVLQLGWR PGWFLDSPDR PWNPPTFSPA LLVVTEGANA TFTCSFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 248)
```

6. M6

```
1   MQIPQAPWPV VWAVLQLGWR PGWFLDSPDR PWNPPTFSPA LLVVTEGDAA AFTCSFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 249)
```

7. M7

```
1   MQIPQAPWPV VWAVLQLGWR PGWFLDSPDR PWNPPTFSPA LLVVTEGDNA TAACAFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 250)
```

8. M8

```
1   MQIPQAPWPV VWAVLQLGWR PGWFLDSPDR PWNPPTFSPA LLVVTEGDNA TFTCSFAATS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 251)
```

9. M9

```
1   MQIPQAPWPV VWAVLQLGWR PGWFLDSPDR PWNPPTFSPA LLVVTEGDNA TFTCSFSNTS
61  AAFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 252)
```

10. M10

```
1   MQIPQAPWPV VWAVLQLGWR PGWFLDSPDR PWNPPTFSPA LLVVTEGDNA TFTCSFSNTS
61  ESFALAWARM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 253)
```

```
  1  MQIPQAPWPV VWAVLQLGWR PGWFLDSPDR PWNPPTFSPA LLVVTEGDNA TFTCSFSNTS
 61  ESFVLNWYRM SPANAADKLA AFPEDRSQPG QDCRFRVTQL PNGRDFHMSV VRARRNDSGT
121  YLCGAISLAP KAQIKESLRA ELRVTERRAE VPTAHPSPSP RPAGQFQTLV VGVVGGLLGS
181  LVLLVWVLAV ICSRAARGTI GARRTGQPLK EDPSAVPVFS VDYGELDFQW REKTPEPPVP
241  CVPEQTEYAT IVFPSGMGTS SPARRGSADG PRSAQPLRPE DGHCSWPL (SEQ ID NO. 254)
```

12. M12

```
  1  MQIPQAPWPV VWAVLQLGWR PGWFLDSPDR PWNPPTFSPA LLVVTEGDNA TFTCSFSNTS
 61  ESFVLNWYRM SPSNQADALA AFPEDRSQPG QDCRFRVTQL PNGRDFHMSV VRARRNDSGT
121  YLCGAISLAP KAQIKESLRA ELRVTERRAE VPTAHPSPSP RPAGQFQTLV VGVVGGLLGS
181  LVLLVWVLAV ICSRAARGTI GARRTGQPLK EDPSAVPVFS VDYGELDFQW REKTPEPPVP
241  CVPEQTEYAT IVFPSGMGTS SPARRGSADG PRSAQPLRPE DGHCSWPL (SEQ ID NO. 255)
```

13. M13

```
  1  MQIPQAPWPV VWAVLQLGWR PGWFLDSPDR PWNPPTFSPA LLVVTEGDNA TFTCSFSNTS
 61  ESFVLNWYRM SPSNQTDKLA AFPEAASQPG QDCRFRVTQL PNGRDFHMSV VRARRNDSGT
121  YLCGAISLAP KAQIKESLRA ELRVTERRAE VPTAHPSPSP RPAGQFQTLV VGVVGGLLGS
181  LVLLVWVLAV ICSRAARGTI GARRTGQPLK EDPSAVPVFS VDYGELDFQW REKTPEPPVP
241  CVPEQTEYAT IVFPSGMGTS SPARRGSADG PRSAQPLRPE DGHCSWPL (SEQ ID NO. 256)
```

14. M14

```
  1  MQIPQAPWPV VWAVLQLGWR PGWFLDSPDR PWNPPTFSPA LLVVTEGDNA TFTCSFSNTS
 61  ESFVLNWYRM SPSNQTDKLA AFPEDRSQAA GDCRFRVTQL PNGRDFHMSV VRARRNDSGT
121  YLCGAISLAP KAQIKESLRA ELRVTERRAE VPTAHPSPSP RPAGQFQTLV VGVVGGLLGS
181  LVLLVWVLAV ICSRAARGTI GARRTGQPLK EDPSAVPVFS VDYGELDFQW REKTPEPPVP
241  CVPEQTEYAT IVFPSGMGTS SPARRGSADG PRSAQPLRPE DGHCSWPL (SEQ ID NO. 257)
```

15. M15

```
  1  MQIPQAPWPV VWAVLQLGWR PGWFLDSPDR PWNPPTFSPA LLVVTEGDNA TFTCSFSNTS
 61  ESFVLNWYRM SPSNQTDKLA AFPEDRSQPG AACRFRVTQL PNGRDFHMSV VRARRNDSGT
121  YLCGAISLAP KAQIKESLRA ELRVTERRAE VPTAHPSPSP RPAGQFQTLV VGVVGGLLGS
181  LVLLVWVLAV ICSRAARGTI GARRTGQPLK EDPSAVPVFS VDYGELDFQW REKTPEPPVP
241  CVPEQTEYAT IVFPSGMGTS SPARRGSADG PRSAQPLRPE DGHCSWPL (SEQ ID NO. 258)
```

16. M16

```
  1  MQIPQAPWPV VWAVLQLGWR PGWFLDSPDR PWNPPTFSPA LLVVTEGDNA TFTCSFSNTS
 61  ESFVLNWYRM SPSNQTDKLA AFPEDRSQPG QDCRFAVAQL PNGRDFHMSV VRARRNDSGT
121  YLCGAISLAP KAQIKESLRA ELRVTERRAE VPTAHPSPSP RPAGQFQTLV VGVVGGLLGS
181  LVLLVWVLAV ICSRAARGTI GARRTGQPLK EDPSAVPVFS VDYGELDFQW REKTPEPPVP
241  CVPEQTEYAT IVFPSGMGTS SPARRGSADG PRSAQPLRPE DGHCSWPL (SEQ ID NO. 259)
```

```
1   MQIPQAPWPV VWAVLQLGWR PGWFLDSPDR PWNPPTFSPA LLVVTEGDNA TFTCSFSNTS
61  ESFVLNWYRM SPSNQTDKLA AFPEDRSQPG QDCRFRVTQL PAGADFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 260)
```

18. M18

```
1   MQIPQAPWPV VWAVLQLGWR PGWFLDSPDR PWNPPTFSPA LLVVTEGDNA TFTCSFSNTS
61  ESFVLNWYRM SPSNQTDKLA AFPEDRSQPG QDCRFRVTQL PNGRAFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 261)
```

19. M19

```
1   MQIPQAPWPV VWAVLQLGWR PGWFLDSPDR PWNPPTFSPA LLVVTEGDNA TFTCSFSNTS
61  ESFVLNWYRM SPSNQTDKLA AFPEDRSQPG QDCRFRVTQL PNGRDFAMAV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 262)
```

20. M20

```
1   MQIPQAPWPV VWAVLQLGWR PGWFLDSPDR PWNPPTFSPA LLVVTEGDNA TFTCSFSNTS
61  ESFVLNWYRM SPSNQTDKLA AFPEDRSQPG QDCRFRVTQL PNGRDFHMSV AAARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 263)
```

21. M21

```
1   MQIPQAPWPV VWAVLQLGWR PGWFLDSPDR PWNPPTFSPA LLVVTEGDNA TFTCSFSNTS
61  ESFVLNWYRM SPSNQTDKLA AFPEDRSQPG QDCRFRVTQL PNGRDFHMSV VRAAANDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 264)
```

22. M22

```
1   MQIPQAPWPV VWAVLQLGWR PGWFLDSPDR PWNPPTFSPA LLVVTEGDNA TFTCSFSNTS
61  ESFVLNWYRM SPSNQTDKLA AFPEDRSQPG QDCRFRVTQL PNGRDFHMSV VRARRNASGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 265)
```

```
  1 MQIPQAPWPV VWAVLQLGWR PGWFLDSPDR PWNPPTFSPA LLVVTEGDNA TFTCSFSNTS
 61 ESFVLNWYRM SPSNQTDKLA AFPEDRSQPG QDCRFRVTQL PNGRDFHMSV VRARRNDSGT
121 YLCAGASAAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 266)
```

24. M24

```
  1 MQIPQAPWPV VWAVLQLGWR PGWFLDSPDR PWNPPTFSPA LLVVTEGDNA TFTCSFSNTS
 61 ESFVLNWYRM SPSNQTDKLA AFPEDRSQPG QDCRFRVTQL PNGRDFHMSV VRARRNDSGT
121 YLCGAISLAP TAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 267)
```

25. M25

```
  1 MQIPQAPWPV VWAVLQLGWR PGWFLDSPDR PWNPPTFSPA LLVVTEGDNA TFTCSFSNTS
 61 ESFVLNWYRM SPSNQTDKLA AFPEDRSQPG QDCRFRVTQL PNGRDFHMSV VRARRNDSGT
121 YLCGAISLAP KAQITASLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 268)
```

26. M26

```
  1 MQIPQAPWPV VWAVLQLGWR PGWFLDSPDR PWNPPTFSPA LLVVTEGDNA TFTCSFSNTS
 61 ESFVLNWYRM SPSNQTDKLA AFPEDRSQPG QDCRFRVTQL PNGRDFHMSV VRARRNDSGT
121 YLCGAISLAP KAQIKESLAA ALRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 269)
```

27. M27

```
  1 MQIPQAPWPV VWAVLQLGWR PGWFLDSPDR PWNPPTFSPA LLVVTEGDNA TFTCSFSNTS
 61 ESFVLNWYRM SPSNQTDKLA AFPEDRSQPG QDCRFRVTQL PNGRDFHMSV VRARRNDSGT
121 YLCGAISLAP KAQIKESLRA ELRVTARRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 270)
```

28. M28

```
  1 MQIPQAPWPV VWAVLQLGWR PGWFLDSPDR PWNPPTFSPA LLVVTEGDNA TFTCSFSNTS
 61 ESFVLNWYRM SPSNQTDKLA AFPEDRSQPG QDCRFRVTQL PNGRDFHMSV VRARRNDSGT
121 YLCGAISLAP KAQIKESLRA ELRVTEAAAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 271)
```

```
1   MQIPQAPWPV VWAVLQLGWR PGWFLDSPDR PWNPPTFSPA LLVVTEGDNA TFTCSFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAAAAPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 272)
```

30. M30

```
1   MQIPQAPWPV VWAVLQLGWR PGWFLDSPDR PWNPPTFSPA LLVVTEGDNA TFTCSFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP AAAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 273)
```

31. M31

```
1   MQIPQAPWPV VWAVLQLGWR PGWFLDSPDR PWNPPTFSPA ALLVTEGDNA TFTCSFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 274)
```

Figure 3H

*Human PD-1 Amino Acid Sequence (accession NM_005018.2)*

```
1   MQIPQAPWPV VWAVLQLGWR PGWFLDSPDR PWNPPTFSPA LLVVTEGDNA TFTCSFSNTS
61  ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO. 275)
```

Figure 3I

*Rhesus Monkey PD-1 Amino Acid Sequence (accession NM_001114358.1)*
*(Differences from human PD-1 highlighted in bold)*

```
1   MQIPQAPWPV VWAVLQLGWR PGWFLESPDR PWNPPTFSPA LLLVTEGDNA TFTCSFSNAS
61  ESFVLNWYRM SPSNQTDKLA AFPEDRSQPG RDCRFRVTQL PNGRDFHMSV VRARRNDSGT
121 YLCGAISLAP KAQIKESLRA ELRVTERRAE VPTAHPSPSP RPAGQFQALV VGVVGGLLGS
181 LVLLVWVLAV ICSRAAQGTI EARRTGQPLK EDPSAVPVFS VDYGELDFQW REKTPEPPAP
241 CVPEQTEYAT IVFPSGLGTS SPARRGSADG PRSPRPLRPE DGHCSWPL (SEQ ID NO. 276)
```

Figure 9
A
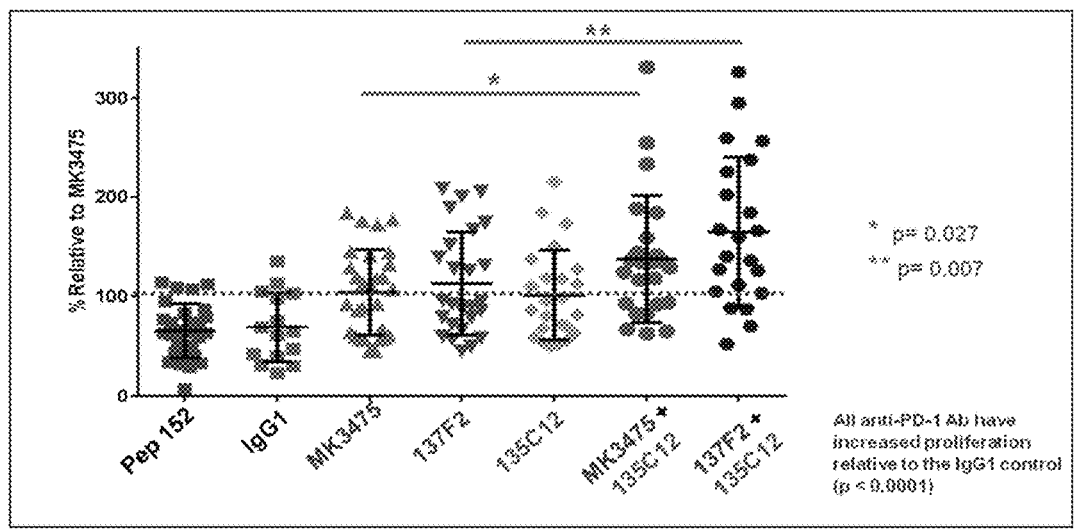
B
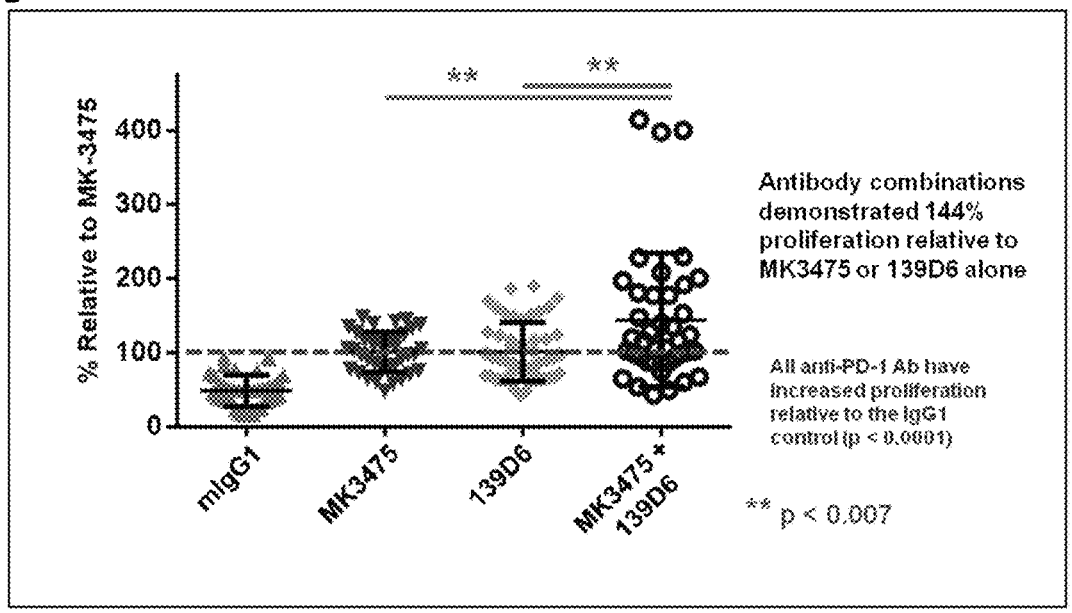

Figure 11c: Alignment of ectodomain amino acid sequences from different species

```
            21              →      41              61              81
Human    PGWFLDSPDR PW NPPTFSPA LLVVTEGDNA TFTCSFSNTS ESFVLNWYRM SPSNQTDKLA AFPEDRSQPG QDCRFRVTQL
Monkey   PGWFLSSPDR PW NPPTFSPA LLVVTEGDNA TFTCSFSNAS ESFVLNWYRM SPSNQTDKLA AFPEDRSQPG RDCRFRVTQL
Horse    SVSLLDSPDR PW RPLTFSPA SLSVSEGANA TFTCSFSNTS ESFVLNWYRM SPSNQTDKLA AFPEDSSQPG SSSRFRVTSL
Dog      PGWLLDSPDR PW SPLTFSPA QLSVQEGSNA TFTCSLSLSP DSFVLNWYRS SPSNQTDKLA AFQEDRSSPG SDRFRVTSL
Mouse    SGWLLEVPNG PW RSLTFYPA WLTVSEGANA TFTCSLSNWS EDLMLNWNRL SPSNQTEKQA AFCNGLSQPV QDARFQIIQL
Rat      SGWLLSVLSK PW RPLTFSPT WLSVSEGANA TFTCSFSNWS ESLSLNWYRL SPSNQTSKQA AFCNSYSQPV SDARFQIVQL 101             121             141    ←       161
Human    PNGRDFHMSV VRARRNDSGT YLCGAISLAP KAQIKESLRA ELRVTERRA E VPTAHPSPSP RPAGQFQTL    (SEQ ID NO. 281)
Monkey   PNGRDFHMSV VRARRNDSGT YLCGAISLAP KAQIKESLRA ELRVTERRA E VPTAHPSPSP RPAGQFQAL    (SEQ ID NO. 282)
Horse    PNGRDFHMSV LSARRNDSGI YLCGAISLSP KSQISESSRA ELSVTERIS E SPTSHPSPPP SPAGQSQSL    (SEQ ID NO. 283)
Dog      PNGRDFHMSI VAARLNDSGI YLCGAIYLSP NSQISESSRA ELSVTERTL E PPTQSPSPPP RLSGQLQSL    (SEQ ID NO. 284)
Mouse    PNRHDFHMNI LDTRRNDSGI YLCGAISLHP KAKIEESPGA ELVVTERIL E TSTRYPSPSP KPEGRFQGM    (SEQ ID NO. 285)
Rat      PNGSDFHMSI LSARRNDSGL YLCGAISLSP KAQIKESSSA ELVVTERIL E SPTSYPSPSP KPSGQFQSL    (SEQ ID NO. 286)
```

Figure 12

| Competitor Antibody Clone | Affinity nM | Binding Class (Luminex Studies) | Functional effect % CD3low CD8 T cells | Inhibition of PD-1/PD-L1 interaction | Binding of labeled mAb in the presence of competitor mAb ||||
|---|---|---|---|---|---|---|---|---|
| | | | | | MK3475 | 137F2 | 135C12 | 134D2 |
| 137F2 | 1.5 | 1 | 250% | Blocking | | | | |
| 139F11 | 3.1 | 1 | 252% | Blocking | | | | |
| 140G5 | 1.6 | 1 | 195% | Blocking | | | | |
| 131D11 | 2.7 | 1 | 190% | Blocking | | | | |
| 135C12 | 1.7 | 2 | 195% | Non-blocking | | | | |
| 139D6 | 2.4 | 2 | 195% | Non-blocking | | | | |
| 136B4 | 1.4 | 2 | 202% | Non-blocking | | | | |
| 135D1 | 6.5 | 2 | 187% | Non-blocking | | | | |
| 140A1 | 1.4 | 3 | 160% | Blocking | | | | |
| 135E10 | 1.5 | 3 | 165% | Blocking | | | | |
| 134D2 | 4.8 | 4 | 202% | Blocking | | | | |
| 136E10 | 7.1 | 4 | 133% | Non-blocking | | | | |
| 136F4 | 8.3 | 4 | 108% | Non-blocking | | | | |
| 121G1 | 11.9 | 4 | 120% | Non-blocking | | | | |
| 136B5 | 7.7 | 4 | 200% | Blocking | | | | |
| 122F10 | 2.2 | 4 | 140% | Non-blocking | | | | |
| BMS-5C4 | 0.6 | 1 | 175% | na | | | | |
| MK3475 | 0.5 | 1 | 198% | Blocking | | | | |
| IgG1 | na | na | 100% | Non-blocking | | | | |

Legend: 0-29%, 30-59%, 60-79%, 80-100%

● Residues at the PD-1/PD-L1 or PD-1/PD-L2 interaction site
Blocking  Anti-PD-1 antibodies that are blocking of the PD-1/PD-L1 interaction
NB  Anti-PD-1 antibodies that are non-blocking of the PD-1/PD-L1 interaction Figure 20
A.
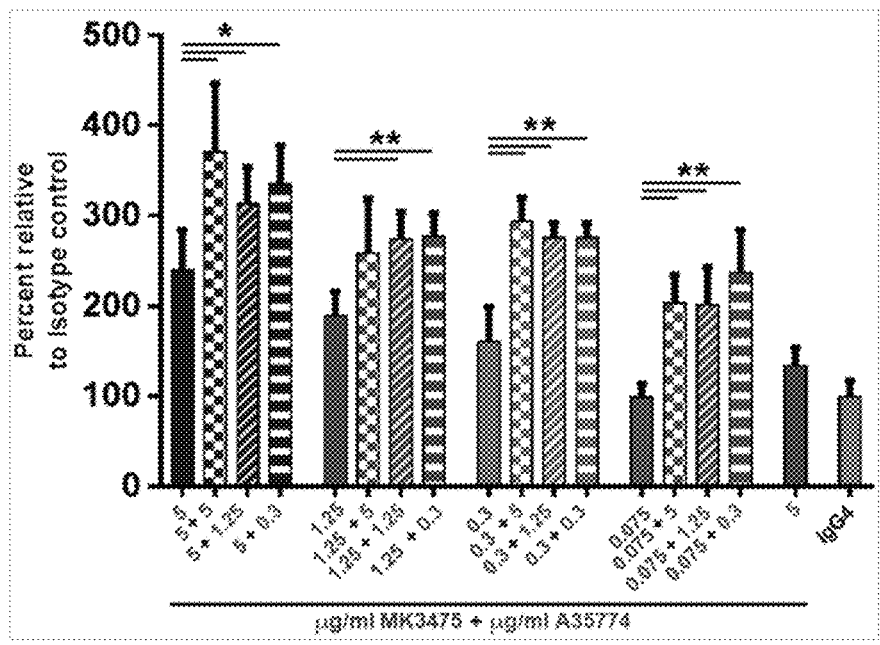
B.
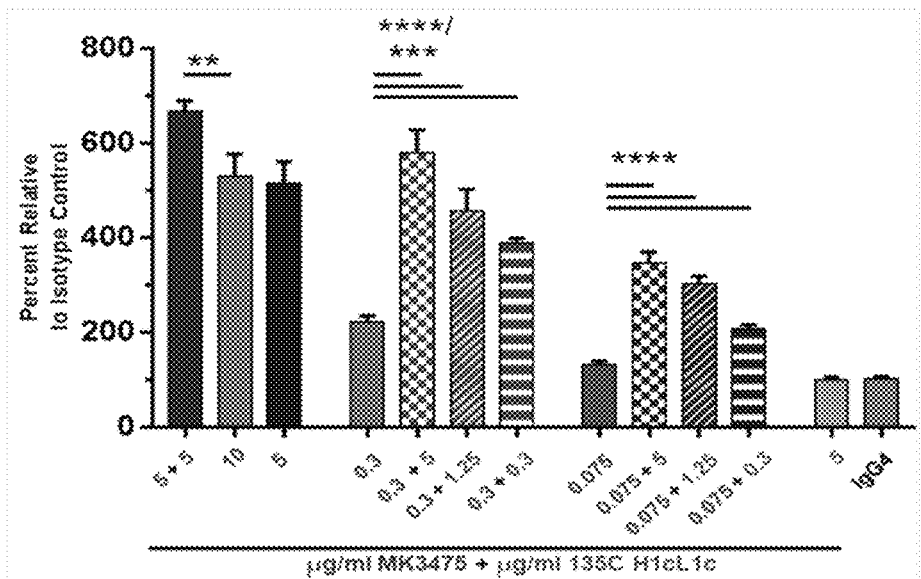
* p-value= 0.05 to 0.01,  p-value < 0.01, * p-value < 0.001, **** p-value< 0.0001

Figure 22
A.
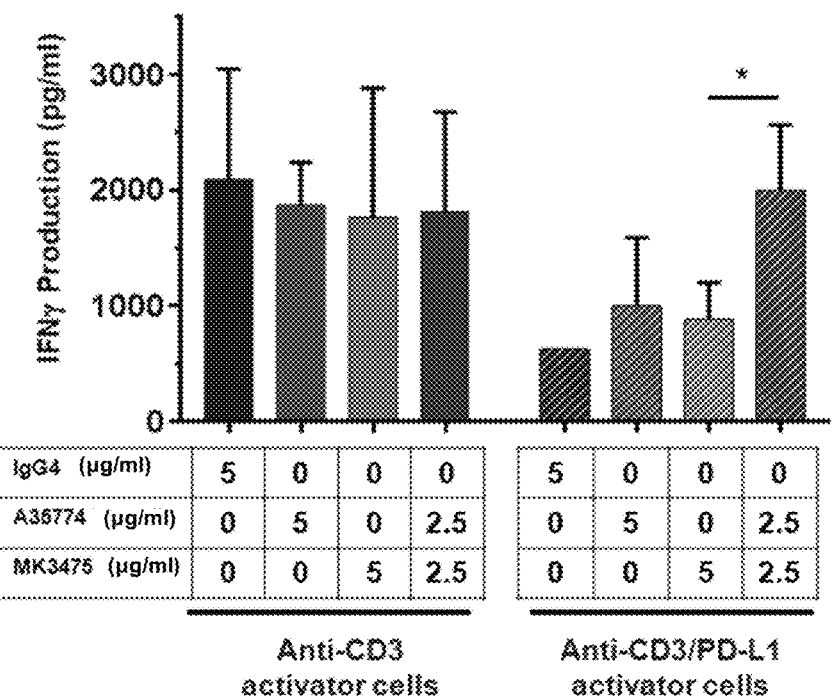
B.
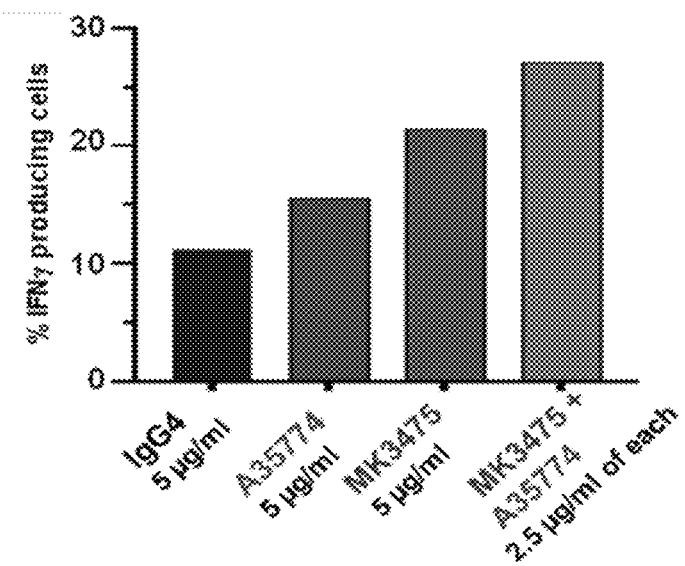

Figure 25A
*137F2 Variable Heavy (V<sub>H</sub>) Chains*

```
Mouse   QVQLQQPGAELVRPGTSVKMSCKAAGYTFTNYWIGWIKQRPGHGLEWIGDIYPGGGYTNY
A35790  QMQLVQSGPEVKKPGTSVKVSCKASGFTFTNYWIGWVRQAPGQALEWMGDIYPGGGYTNY
A35796  QMQLVQSGPEVKKPGTSVKVSCKASGFTFTNYWIGWVRQAPGQALEWMGDIYPGGGYTNY
A35793  QMQLVQSGPEVKKPGTSVKVSCKASGFTFTNYWIGWVRQAPGQALEWMGDIYPGGGYTNY
A35818  QMQLVQSGPEVKKPGTSVKVSCKASGFTFTNYWIGWVRQAPGQALEWMGDIYPGGGYTNY
A35795  QVQLVQSGAEVKKPGASVKVSCKASGYTFTNYWIGWVRQAPGQGLEWMGDIYPGGGYTNY
A35797  EVQLVQSGAEVKKHGESLKISCKGSGYSFTNYWIGWVRQATGQGLEWMGDIYPGGGYTNY
A35799  QMQLVQSGAEVKKTGSSVKVSCKASGYTFTNYWIGWVRQMPGKGLEWMGDIYPGGGYTNY
A35805  QVQLVQSGSELKKPGASVKVSCKASGYTFTNYWIGWVRQAPGKGLEWMGDIYPGGGYTNY
VH1     QVQLVQSGAEVKKPGASVKVSCKASGYTFTNYWIGWVRQAPGQGLEWMGDIYPGGGYTNY
VH2     QVQLVQSGAEVKKPGASVKVSCKAAGYTFTNYWIGWVRQAPGQGLEWMGDIYPGGGYTNY
VH1b    QVQLVQSGAEVKKPGASVKVSCKASGYTFTNYWIGWVRQAPGQGLEWIGDIYPGGGYTNY
VH1c    QVQLVQSGAEVKKPGASVKVSCKASGYTFTNYWIGWIRQAPGQGLEWIGDIYPGGGYTNY Mouse   NEKFKGKATLTADTSSSTAYMQVSSLTSEDTGIYYCARGYDFVLDRWGQGTSVTVSS (SEQ ID NO. 277)
A35790  NEKFKGRVTITADKSTSTAYMELSSLRSEDTAVYYCARGYDFVLDRWGQGTTVTVSS (SEQ ID NO. 139)
A35796  NEKFKGRVTITADKSTSTAYMELSSLRSEDTAVYYCARGYDFVLDRWGQGTTVTVSS (SEQ ID NO. 140)
A35793  NEKFKGRVTITADKSTSTAYMELSSLRSEDTAVYYCARGYDFVLDRWGQGTTVTVSS (SEQ ID NO. 141)
A35818  NEKFKGRVTITADKSTSTAYMELSSLRSEDTAVYYCARGYDFVLDRWGQGTTVTVSS (SEQ ID NO. 142)
A35795  NEKFKGRVTITADKSTSTAYMELSSLRSEDTAVYYCARGYDFVLDRWGQGTTVTVSS (SEQ ID NO. 143)
A35797  NEKFKGRVTITADKSTSTAYMELSSLRSEDTAVYYCARGYDFVLDRWGQGTTVTVSS (SEQ ID NO. 144)
A35799  NEKFKGRVTITADKSTSTAYMELSSLRSEDTAVYYCARGYDFVLDRWGQGTTVTVSS (SEQ ID NO. 145)
A35805  NEKFKGRVTITADKSTSTAYMELSSLRSEDTAVYYCARGYDFVLDRWGQGTTVTVSS (SEQ ID NO. 146)
VH1     NEKFKGRVTMTRDTSTSTVYMELSSLRSEDTAVYYCARGYDFVLDRWGQGTLVTVSS (SEQ ID NO. 147)
VH2     NEKFKGRVTMTADTSTSTVYMELSSLRSEDTAVYYCARGYDFVLDRWGQGTLVTVSS (SEQ ID NO. 148)
VH1b    NEKFKGRVTMTADTSTSTVYMELSSLRSEDTAVYYCARGYDFVLDRWGQGTLVTVSS (SEQ ID NO. 149)
VH1c    NEKFKGRATLTADTSTSTVYMEVSSLRSEDTAVYYCARGYDFVLDRWGQGTLVTVSS (SEQ ID NO. 150)
```

Figure 25B
*137F2 Variable Light (V$_L$) Chains*

```
Mouse   DIVMSQSPSSLAVSTGEKVTMTCKSSQSLFNSETQKNYLAWYQQKPGQPPKLLIFWASTRES
A35790  DVVMTQSPAFLSVTPGEKVTITCKSSQSLFNSETQKNYLAWYQQKPGQPPKLLIYWASTRES
A35796  DVVMTQSPAFLSVTPGEKVTITCKSSQSLFNSETQKNYLAWYQQKPGQPPKLLIYWASTRES
A35793  DVVMTQSPAFLSVTPGEKVTITCKSSQSLFNSETQKNYLAWYQQKPGQPPKLLIYWASTRES
A35818  DVVMTQSPAFLSVTPGEKVTITCKSSQSLFNSETQKNYLAWYQQKPGQAPRLLIYWASTRES
A35795  DVVMTQSPAFLSVTPGEKVTITCKSSQSLFNSETQKNYLAWYQQKPGQAPRLLIYWASTRES
A35797  DIQMTQSPSSLSASVGDRVTITCKSSQSLFNSETQKNYLAWYQQKPGQPPKLLIYWASTRES
A35799  DVVMTQSPAFLSVTPGEKVTITCKSSQSLFNSETQKNYLAWYQQKPGQPPKLLIYWASTRES
A35805  DVVMTQSPAFLSVTPGEKVTITCKSSQSLFNSETQKNYLAWYQQKPGQPPKLLIYWASTRES
VL1     DIVMTQSPDSLAVSLGERATINCKSSQSLFNSETQKNYLAWYQQKPGQPPKLLIYWASTRES
VL2     DIVMTQSPDSLAVSLGERATITCKSSQSLFNSETQKNYLAWYQQKPGQPPKLLIFWASTRES
VL1b    DIVMTQSPDSLAVSLGERATINCKSSQSLFNSETQKNYLAWYQQKPGQPPKLLIYWASTRES
VL1c    DIVMTQSPDSLAVSLGERATITCKSSQSLFNSETQKNYLAWYQQKPGQPPKLLIFWASTRES
VL1d    DIVMTQSPDSLAVSLGERATMTCKSSQSLFNSETQKNYLAWYQQKPGQPPKLLIFWASTRES Mouse   GVPDRFLGSGSGTDFTLTISSVQAEDLAVYYCKQSYTLRTFGGGTKLEIK(SEQ ID NO. 278)
A35790  GVPSRFSGSGSGTDFTLTISSLQPEDFATYYCKQSYTLRTFGGGTKLEIK(SEQ ID NO. 151)
A35796  GVPSRFSGSGSGTDFTLTISSLQPEDFATYYCKQSYTLRTFGGGTKLEIK(SEQ ID NO. 152)
A35793  GVPSRFSGSGSGTDFTFTISSLEAEDAATYYCKQSYTLRTFGGGTKLEIK(SEQ ID NO. 153)
A35818  GVPSRFSGSGSGTDFTFTISSLEAEDAATYYCKQSYTLRTFGGGTKLEIK(SEQ ID NO. 154)
A35795  GVPSRFSGSGSGTDFTLTISSLQPEDFATYYCKQSYTLRTFGGGTKLEIK(SEQ ID NO. 155)
A35797  GVPSRFSGSGSGTDFTLTISSLQPEDFATYYCKQSYTLRTFGGGTKLEIK(SEQ ID NO. 156)
A35799  GVPSRFSGSGSGTDFTLTISSLQPEDFATYYCKQSYTLRTFGGGTKLEIK(SEQ ID NO. 157)
A35805  GVPSRFSGSGSGTDFTFTISSLEAEDAATYYCKQSYTLRTFGGGTKLEIK(SEQ ID NO. 158)
VL1     GVPDRFSGSGSGTDFTLTISSLQAEDVAVYYCKQSYTLRTFGQGTKLEIK(SEQ ID NO. 159)
VL2     GVPDRFLGSGSGTDFTLTISSLQAEDVAVYYCKQSYTLRTFGQGTKLEIK(SEQ ID NO. 160)
VL1b    GVPDRFSGSGSGTDFTLTISSLQAEDVAVYYCKQSYTLRTFGQGTKLEIK(SEQ ID NO. 161)
VL1c    GVPDRFSGSGSGTDFTLTISSLQAEDVAVYYCKQSYTLRTFGQGTKLEIK(SEQ ID NO. 162)
VL1d    GVPDRFSGSGSGTDFTLTISSVQAEDVAVYYCKQSYTLRTFGQGTKLEIK(SEQ ID NO. 163)
```

Figure 25C
135C12 Variable Heavy (V_H) Chains

```
Mouse  EVQLHQSGPELLKPGASVRMSCKASGYTFTNFYIHWVKQSHGKSIEWIGSIYPNYGDTAY
A35775 EVQLVQSGAEVKKPGESLKISCKGSGYSFTNFYIHWVRQAPGQRLEWMGSIYPNYGDTAY
A35783 EVQLVQSGAEVKKPGESLKISCKGSGYSFTNFYIHWVRQARGQRLEWIGSIYPNYGDTAY
A35774 EVQLVQSGAEVKKPGESLKISCKGSGYSFTNFYIHWVRQAPGQRLEWMGSIYPNYGDTAY
A36443 EVQLVQSGAEVKKPGATVKISCKVSGYTFTNFYIHWVRQARGQRLEWIGSIYPNYGDTAY
A35777 EVQLVQSGAEVKKPGATVKISCKVSGYTFTNFYIHWVRQAPGKGLEWMGSIYPNYGDTAY
A35789 EVQLVQSGAEVKKPGESLKISCKGSGYSFTNFYIHWVRQMPGKGLEWMGSIYPNYGDTAY
A36448 EVQLVQSGAEVKKPGESLKISCKGSGYSFTNFYIHWVRQMPGKGLEWMGSIYPNYGDTAY
A36437 EVQLVQSGAEVKKPGESLKISCKGSGYSFTNFYIHWVRQMPGKGLEWMGSIYPNYGDTAY
VH1    QVQLVQSGAEVKKPGASVKVSCKASGYTFTNFYIHWVRQAPGQGLEWMGSIYPNYGDTAY
VH2    QVQLVQSGAEVKKPGASVKVSCKASGYTFTNFYIHWVRQAPGQGLEWMGSIYPNYGDTAY
VH3    QVQLVQSGAEVKKPGASVKVSCKASGYTFTNFYIHWVRQAHGQGLEWMGSIYPNYGDTAY
VH1b   QVQLVQSGAEVKKPGASVKVSCKASGYTFTNFYIHWVRQAPGQGLEWIGSIYPNYGDTAY
VH1c   QVQLVQSGAEVKKPGASVKMSCKASGYTFTNFYIHWVRQAPGQGLEWIGSIYPNYGDTAY
VH1d   QVQLVQSGAEVKKPGASVKMSCKASGYTFTNFYIHWVRQAPGQGLEWIGSIYPNYGDTAY Mouse  NQKFKDKATLTVDKSSSTAYMALRSLTSEDSAVYYCARGYSYAMDYWGQGTSVTVSS(SEQ ID NO. 279)
A35775 NQKFKDRFVFSLDTSVSTAYLQISSLKAEDTAVYYCARGYSYAMDYWGQGTTVTVSS(SEQ ID NO. 164)
A35783 NQKFKDRFVFSLDTSVSTAYLQISSLKAEDTAVYYCARGYSYAMDYWGQGTTVTVSS(SEQ ID NO. 165)
A35774 NQKFKDRFVFSLDTSVSTAYLQISSLKAEDTAVYYCARGYSYAMDYWGQGTTVTVSS(SEQ ID NO. 166)
A36443 NQKFKDRVTITADKSTSTAYMELSSLRSEDTAVYYCARGYSYAMDYWGQGTTVTVSS(SEQ ID NO. 167)
A35777 NQKFKDRVTITADKSTSTAYMELSSLRSEDTAVYYCARGYSYAMDYWGQGTTVTVSS(SEQ ID NO. 168)
A35789 NQKFKDRVTITADKSTSTAYMELSSLRSEDTAVYYCARGYSYAMDYWGQGTTVTVSS(SEQ ID NO. 169)
A36448 NQKFKDRFVFSLDTSVSTAYLQISSLKAEDTAVYYCARGYSYAMDYWGQGTTVTVSS(SEQ ID NO. 170)
A36437 NQKFKDRFVFSLDTSVSTAYLQISSLKAEDTAVYYCARGYSYAMDYWGQGTTVTVSS(SEQ ID NO. 171)
VH1    NQKFKDRVTMTRDTSTSTVYMELSSLRSEDTAVYYCARGYSYAMDYWGQGTLVTVSS(SEQ ID NO. 172)
VH2    NQKFKDRVTMTVDKSTSTVYMELRSLRSEDTAVYYCARGYSYAMDYWGQGTLVTVSS(SEQ ID NO. 173)
VH3    NQKFKDRVTMTVDKSTSTVYMELRSLRSEDTAVYYCARGYSYAMDYWGQGTLVTVSS(SEQ ID NO. 174)
VH1b   NQKFKDRVTMTVDTSTSTVYMELSSLRSEDTAVYYCARGYSYAMDYWGQGTLVTVSS(SEQ ID NO. 175)
VH1c   NQKFKDRATLTVDTSTSTAYMELSSLRSEDTAVYYCARGYSYAMDYWGQGTLVTVSS(SEQ ID NO. 176)
VH1d   NQKFKDRATLTVDKSTSTAYMELSSLRSEDTAVYYCARGYSYAMDYWGQGTLVTVSS(SEQ ID NO. 177)
```

Figure 25D

*135C12 Variable Light (V$_L$) chains*

```
Mouse   DIQMTQTTSSLSASLGDRVTISCSASQGISGDLNWYQQKSDGTVKLLIYHTSSLHSGVPLR
A35775  DIQMTQSPSSVSASVGDRVTITCSASQGISGDLNWYQQKPGQAPRLLIYHTSSLHSGVPSR
A35783  DIQMTQSPSSLSASVGDRVTITCSASQGISGDLNWYQQKPGKTPKLLIYHTSSLHSGVPSR
A35774  DIQMTQSPSSVSASVGDRVTITCSASQGISGDLNWYQQKPGKAPKLLIYHTSSLHSGVPSR
A36443  DIQMTQSPSSVSASVGDRVTITCSASQGISGDLNWYQQKPGQAPRLLIYHTSSLHSGVPSR
A35777  DIQMTQSPSTLSASVGDRVTITCSASQGISGDLNWYQQKPGQAPRLLIYHTSSLHSGVPSR
A35789  DIQMTQSPSSVSASVGDRVTITCSASQGISGDLNWYQQKPGQAPRLLIYHTSSLHSGIPAR
A36448  DIQMTQSPSTLSASVGDRVTITCSASQGISGDLNWYQQKPGKTPKLLIYHTSSLHSGVPSR
A36437  DIQMTQSPSTLSASVGDRVTITCSASQGISGDLNWYQQKPGQAPRLLIYHTSSLHSGIPAR
VL1     DIQMTQSPSSLSASVGDRVTITCSASQGISGDLNWYQQKPGKAPKLLIYHTSSLHSGVPSR
VL2     DIQMTQSPSSLSASVGDRVTITCSASQGISGDLNWYQQKPGKAVKLLIYHTSSLHSGVPLR
VL3     DIQMTQSPSSLSASVGDRVTITCSASQGISGDLNWYQQKSDGAVKLLIYHTSSLHSGVPLR
VL1b    DIQMTQSPSSLSASVGDRVTITCSASQGISGDLNWYQQKPGKAPKLLIYHTSSLHSGVPSR
VL1c    DIQMTQSPSSLSASVGDRVTITCSASQGISGDLNWYQQKPGKAVKLLIYHTSSLHSGVPSR Mouse   FSGSGSGTDYSLTISDLDPEDIATYYCQYYSKDLLTFGAGTKLELK(SEQ ID NO. 280)
A35775  FSGSGSGTDFTLTISSLQPEDFATYYCQYYSKDLLTFGGGTKLEIK(SEQ ID NO. 178)
A35783  FSGSGSGTDFTLTISSLQPEDFATYYCQYYSKDLLTFGGGTKLEIK(SEQ ID NO. 179)
A35774  FSGSGSGTDFTLTISSLQPEDFATYYCQYYSKDLLTFGGGTKLEIK(SEQ ID NO. 180)
A36443  FSGSGSGTEFTLTISRLEPEDFAVYYCQYYSKDLLTFGGGTKLEIK(SEQ ID NO. 181)
A35777  FSGSGSGTDFTLTISSLQPEDFATYYCQYYSKDLLTFGGGTKLEIK(SEQ ID NO. 182)
A35789  FSGSGSGTDFTLTISRLEPEDFAVYYCQYYSKDLLTFGGGTKLEIK(SEQ ID NO. 183)
A36448  FSGSGSGTDFTLTISSLQPEDFATYYCQYYSKDLLTFGGGTKLEIK(SEQ ID NO. 184)
A36437  FSGSGSGTDFTLTISSLQPEDFAVYYCQYYSKDLLTFGGGTKLEIK(SEQ ID NO. 185)
VL1     FSGSGSGTDFTLTISSLQPEDFATYYCQYYSKDLLTFGGGTKLEIK(SEQ ID NO. 186)
VL2     FSGSGSGTDYTLTISSLQPEDFATYYCQYYSKDLLTFGGGTKLEIK(SEQ ID NO. 187)
VL3     FSGSGSGTDYTLTISSLQPEDFATYYCQYYSKDLLTFGGGTKLEIK(SEQ ID NO. 188)
VL1b    FSGSGSGTDYTLTISSLQPEDFATYYCQYYSKDLLTFGGGTKLEIK(SEQ ID NO. 189)
VL1c    FSGSGSGTDYTLTISSLQPEDFATYYCQYYSKDLLTFGGGTKLELK(SEQ ID NO. 190)
```

IMMUNOLOGICAL REAGENTS

RELATED APPLICATIONS

This application was filed under 35 U.S.C. § 371 and claims priority to International Application No. PCT/IB2017/000031 filed Jan. 20, 2017, and claims priority to U.S. Ser. No. 62/286,269 filed Jan. 22, 2016 and U.S. Ser. No. 62/290,745 filed Feb. 3, 2016, each of which being hereby incorporated into this disclosure in their entirety.

FIELD OF THE DISCLOSURE

This disclosure relates to binding agents with specificity for programmed cell death 1 (PD-1) (e.g., human PD-1) and to methods for using the same to treat and/or prevent infection (e.g., by human immunodeficiency virus (HIV)), cancer and/or autoimmunity.

BACKGROUND OF THE DISCLOSURE

As we enter the fourth decade of the HIV epidemic, significant advances have been made in the understanding of HIV pathogenesis and in the development of potent and safe antiviral drugs. More than 30 antiviral drugs have been registered and the impact of combination antiretroviral therapy (ART) on both morbidity and mortality has been remarkable. However, despite the long-term suppression of HIV replication achieved in patients with optimal adherence to ART, HIV invariably rebounds after interruption of therapy. Furthermore, successful therapy does not induce or allow restoration/development of virus-specific immune responses capable of controlling HIV replication in the absence of ART. Thus, life-long ART is needed to control HIV replication and associated disease in the large majority of HIV infected subjects.

A population of long-lived central memory CD4 T-cells latently infected with HIV has been identified in the blood as an important component of the HIV cell reservoir and as the primary cause of HIV persistence. The life-span of this latent cell reservoir is estimated to be approximately 70 years in the presence of full HIV suppression with ART. However, recent studies have demonstrated that two populations of CD4 T-cells resident in lymph nodes serve as the primary CD4 T-cell compartment for HIV infection, replication and production. These two CD4 T-cell populations are defined by the expression of PD-1 and CXCR5 and include the PD-1+CXCR5+, i.e. T follicular helper cells (Tfh) and PD-1+CXCR5−CD4 T-cell populations.

A number of mechanisms responsible for the establishment and maintenance of the HIV latent cell reservoir(s) have been proposed. One of the mechanisms is the persistent of minimal virus replication under ART which may replenish the HIV cell reservoir. Therefore, ART is unable to induce full suppression of HIV replication and the "natural" HIV-1 specific immune response under ART is also unable to totally suppress and eliminate ongoing residual virus replication. The failures of ART and of the HIV-specific immune response provide the rationale for investigating alternative interventions to target also the persistent HIV cell reservoir.

A number of immunological interventions have been investigated in the past and currently being further developed with the goal to achieve HIV functional cure, wherein viral replication is suppressed without sustained antiviral therapy (9). Therapeutic vaccine strategies have been the primary intervention strategy investigated but the results have shown modest efficacy in experimental animal models and patients with the exception of a CMV-based vector HIV vaccine (50% efficacy in the NHP model; 10). Recent studies have generated interesting results on the possibility of using anti-envelope broad neutralizing antibodies (bNabs) as therapeutic agents in HIV infection (11,12). Furthermore, antagonist PD-1 Abs have been shown to restore T-cell functions in HIV infected patients and the possibility to use these Abs as a therapeutic strategy to augment the potency of HIV-specific T-cell responses has been proposed (13,14).

It is well established that infiltrating tumor-specific CD8 T-cells are dysfunctional with regard their ability to proliferate and to mediate cytotoxic activity. The large majority of infiltrating tumor-specific CD8 T-cells are in a so-called exhaustion functional state. The primary mechanism responsible for the exhaustion of infiltrating tumor-specific CD8 T-cells is the increased expression of a number of regulatory receptors and particularly PD-1 regulatory receptor. The observation that the blockade of the PD-1/PDL-1/2 (PD-1 ligands) is associated with the recovery of CD8 T-cells from exhaustion has provided the rationale for developing intervention strategies targeting the PD-1 molecule expressed by exhausted CD8 T-cells. Recent studies have shown very promising results with the use of PD-1 antibodies with antagonist activity in patients with advanced cancer-associated disease. Studies have show substantial rates of response, ranging from 18 to 40%, in patients with advanced melanoma, non-small cell lung carcinoma and renal carcinoma. Anti-PD-1 antibodies in these studies have been used either alone or in combination with an anti-CTL-A4 antibody. After these initial studies, the current studies are being performed in patients with a variety of tumors including also hematological tumors.

There is a need in the art for additional reagents for targeting PD-1 and methods for using the same. This disclosure addresses those needs by providing reagents and methods that may be used to target PD-1 and cells and/or tissues expressing the same.

BRIEF DESCRIPTION OF THE DRAWINGS

FIG. 3. A. Amino acid sequence of human PD-1 ectodomain. Residues that were targeted for amino acid substitutions are indicated for each of the 31 mutations (M1 to M31). Residues in purple text correspond to amino acids that are implicated in the PD-1/PD-L1 interaction and asparagine residues in green are potential sites for N-linked glycosylation. B-G. Modified PD-1 polypeptides. H. Human PD-1 amino acid sequence (SEQ ID NO. 275). I. Monkey PD-1 amino acid sequence.

FIG. 9. Combination of two antagonistic anti-PD-1 antibodies binding to different epitopes on PD-1, one blocking and one non-blocking (A: 135C12; B: 139D6) with the PD-1/PD-L1 interaction, results in an enhanced relief of functional exhaustion and increased proliferation of HIV specific CD8 T cells beyond what either antibody alone can achieve.

FIG. 12. Antibody competitive binding studies for cell surface PD-1 on activated CD4$^+$ T cells.

FIG. 20. Jurkat PD-1 NFAT reporter cell line stimulation with a transiently transfected 293T cell line expressing a TCR activator and the PD-L1 protein. A. MK3475 and A35774. B. MK3475 and 135C H1cL1c.

FIG. 22. PBMCs from a chronically infected HIV donor possessing memory T cells with high basal levels of PD-1 were incubated with either blocking (MK3475), non-blocking (A35774), or a combination of blocking and non-blocking anti-PD-1 antibodies (A35774 and MK3475), followed by a 24 hr stimulation with TCR activator cells in the presence or absence of PD-L1. In stimulations with TCR activator cells expressing PD-L1, treatments that combined blocking and non-blocking anti-PD-1 antibodies lead to enhanced level of IFN-γ in the cell medium (A) and in intracellular IFN-γ associated with PD-1+CD8 T cell (B).

FIG. 25. A. 137F2 Variable Heavy ($V_H$) Chains. B. 137F2 Variable Light ($V_L$) Chains. C. 135C Variable Heavy ($V_H$) Chains. D. 135C Variable Light ($V_L$) Chains.

SUMMARY OF THE DISCLOSURE

Figure 1:
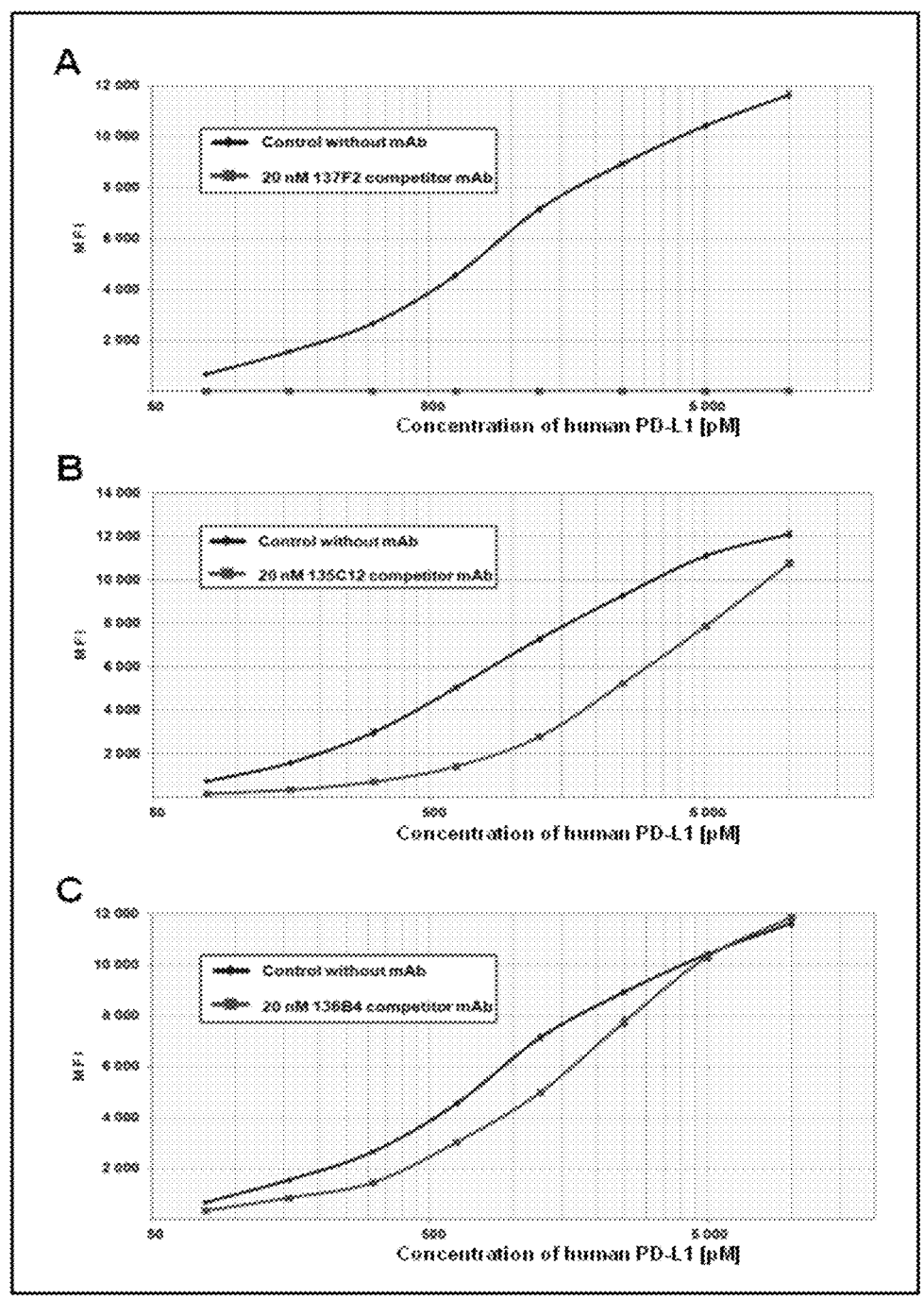
FIG. 1. Antibody concentration response curves for the inhibition of the PD-1/PD-L1 interaction (panels A-C).

This disclosure relates to binding agents with specificity for programmed cell death 1 (PD-1) (e.g., human PD-1) and to methods for using the same such as to treat, prevent and/or ameliorate infection (e.g., by human immunodeficiency virus (HIV)), cancer and/or an autoimmune condition and/or a neurodegenerative condition). Functional assays for identifying binding agents that interact with PD-1 are also provided. Combinations of binding agents, such as a first binding agent that blocks the interaction of PD-1 and PD-L1 with a second binding agent that does not block the interaction of PD-1 and PD-L1, are also provided that act synergistically to rescue T cells from exhaustion.

DETAILED DESCRIPTION

This disclosure relates to binding agents that bind programmed cell death (PD-1) protein (e.g., SEQ ID NO:1, FIG. 1A, FIG. 1B of U.S. Pat. No. 5,698,520 (Honjo, et al.) which is hereby incorporated by reference in its entirety) (e.g., human PD-1) on the surface of cells in vitro and/or in vivo. The binding agents may also bind isolated PD-1 polypeptide (e.g., human PD-1) and/or fragments and/or derivatives thereof, typically in vitro. Also provided are methods for using such binding agents to diagnose, treat, prevent and/or ameliorate one or more diseases associated with the existence of cells expressing PD-1. For instance, the binding agents may be antibodies (e.g., monoclonal antibodies) that may react with and/or bind to the epitopes of PD-1. The "binding agents" described herein may include, for example, an agonist or an antagonist of PD-1. An agonist binding agent is one that is not typically capable of restoring T-cell function and/or expression of PD-1. An agonist PD-1 binding agent may be useful for treating autoimmune diseases and others in which PD-1 expressing cells are involved in disease progression. In contrast, an antagonist binding agent is one capable for restoring T-cell function and/or reducing cell surface expression of PD-1. For instance, a PD-1 antagonist binding agent may be capable of restoring the function of PD-1 expressing T-cells from functional exhaustion as is known to occur in HIV infection and in a variety of tumors. Restoration of T cell function may be determined by, for instance, measuring proliferation, cytokine production, cytotoxic activity or other characteristics of such cells. Another use for the binding agents described herein is the selective targeting and elimination of HIV-infected $CD4^+$ T-cell populations containing replication competent HIV (e.g., in a latent and/or replication state). Such PD-1 expressing cells expressing PD-1 are known to serve as a major cell reservoir for replication competent HIV. A potential mechanism for the elimination of these $CD4^+$ T-cell populations is antibody-dependent cellular cytotoxicity (ADCC) using the binding agents described herein (e.g., mono- and/or bi-specific PD-1 antibodies). In some embodiments, one or more PD-1 antagonistic binding agents having, for instance, different specificities (e.g., recognizing different epitopes) may be combined to induce rescue of antigen-specific $CD8^+$ T-cells from functional exhaustion caused by PD-1 expression in those cells (e.g., restoring or improving proliferation, cytokine production and/or cytotoxic activity). In some embodiments, the binding agents described herein may also provide for the selective elimination and/or suppression of PD-1 expressing cells. In some embodiments, the PD-1 agonist or antagonist binding agents described herein may be used to supress and/or eliminate PD-1 expressing cells to treat, for instance, infectious diseases (e.g., HIV), cancer, and/or, especially, autoimmune conditions. Other embodiments, uses and the like are described below.

The binding agents may be antibodies such as monoclonal antibodies that may comprise, for instance, any one or more of the amino acid sequences shown in Table 1 (and/or one or more fragments and/or derivatives thereof). This disclosure also provides for the use of such monoclonal antibodies to isolate, identify, and/or target cells expressing PD-1. In certain embodiments, these monoclonal antibodies may be reactive against PD-1 expressed on the surface of cells. The term "antibody" or "antibodies" may refer to whole or fragmented antibodies in unpurified or partially purified form (e.g., hybridoma supernatant, ascites, polyclonal antisera) or in purified form. The antibodies may be of any suitable origin or form including, for example, murine (e.g., produced by murine hybridoma cells), or expressed as humanized antibodies, chimeric antibodies, human antibodies, and the like. For instance, antibodies may be wholly or partially derived from human (e.g., IgG (IgG1, IgG2, IgG2a, Ig2b, IgG3, IgG4), IgM, IgA (IgA1 and IgA2), IgD, and IgE), canine (e.g., IgGA, IgGB, IgGC, IgGD), chicken (e.g., IgA, IgD, IgE, IgG, IgM, IgY), goat (e.g., IgG), mouse (e.g., IgG, IgD, IgE, IgG, IgM), and/or pig (e.g., IgG, IgD, IgE, IgG, IgM), rat (e.g., IgG, IgD, IgE, IgG, IgM) antibodies, for instance. Methods of preparing, utilizing and storing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al. *Using Antibodies: A Laboratory Manual, Portable Protocol No. 1*, 1998; Kohler and Milstein, Nature, 256:495 (1975)); Jones et al. Nature, 321:522-525 (1986); Riechmann et al. Nature, 332:323-329 (1988); Presta (Curr. Op. Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; 5,661,016, and 9,090,994 B2, among others). In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L, and/or other, ligands covalently coupled to a solid support such as agarose beads, or combinations of these techniques. The antibodies may be stored in any suitable format, including as a frozen preparation (e.g., $-20°$ C. or $-70°$ C.), in lyophilized form, or under normal refrigeration conditions (e.g., $4°$ C.). When stored in liquid form, for instance, it is preferred that a suitable buffer such as Tris-buffered saline (TBS) or phosphate buffered saline (PBS) is utilized. In some embodiments, the binding agent may be prepared as an injectable preparation, such as in suspension in a non-toxic parenterally acceptable diluent or solvent. Suitable vehicles and solvents that may be utilized include water, Ringer's solution, and isotonic sodium chloride solution, TBS and/or PBS, among others. Such preparations may be suitable for use in vitro or in vivo may be prepared as is known in the art and the exact preparation may depend on the particular application.

However, the binding agents described are not in any way limited to antibodies. For example, the binding agent may be any compound exhibiting similar binding properties as another (e.g., a mimetic). For example, an exemplary binding agent may be one that binds PD-1 and/or can compete with binding agent having specificity therefor (e.g., a monoclonal antibody). In some embodiments, the mimetic may exhibit substantially the same affinity in binding assays as the binding agent (e.g., monoclonal antibody) to which it is being compared. The affinity a particular binding agent may be measured by any suitable assay including but not limited to FACS staining of endogenous cell surface PD-1 on activated CD4$^+$ T cells as described in the Examples. One binding agent may be said to have "substantially the same affinity" as another where the measurements (e.g., apparent binding constant with nano molar affinity) are within about any of 1-20, 1-5, 5-10, 10-15, 15-20, 30, 40, 50, 60, 70, 80, 90, 100, 110, 120, 130, 140, 150, 160, 170, 180, 190, 200, 210, 220, 230, 240, or 250 percent of one another. Exemplary mimetics may include, for example, organic compounds that specifically bind PD-1, or an affibody (Nygren, et al. FEBS J. 275 (11): 2668-76 (2008)), affilin (Ebersbach, et al. J. Mol. Biol. 372 (1): 172-85 (2007)), affitin (Krehenbrink, et al. J. Mol. Biol. 383 (5): 1058-68 (2008)), anticalin (Skerra, A. FEBS J. 275 (11): 2677-83 (2008)), avimer (Silverman, et al. Nat. Biotechnol. 23 (12): 1556-61 (2005)), DARPin (Stumpp, et al. Drug Discov. Today 13 (15-16): 695-701 (2008)), Fynomer (Grabulovski, et al. J. Biol. Chem. 282 (5): 3196-3204 (2007)), Kunitz domain peptide (Nixon, et al. Curr. Opin. Drug Discov. Devel. 9 (2): 261-8 (2006)), and/or a monobody (Koide, et al. Methods Mol. Biol. 352: 95-109 (2007)). Other mimetics may include, for example, a derivative of an antibody such as, for example, an $F_{ab}$, $F_{ab2}$, Fab' single chain antibody, $F_v$, single domain antibody, mono-specific antibody, bi-specific antibody, tri-specific antibody, multi-valent antibody, chimeric antibody, canine-human chimeric antibody, canine-mouse chimeric antibody, antibody comprising a canine Fc, humanized antibody, human antibody, caninized, CDR-grafted antibody, shark antibody, nanobody, canelid antibody, microbody, and/or intrabody, or derivative thereof. Other binding agents are also provided herein as would be understood by one of ordinary skill in the art.

Any method known to those of ordinary skill in the art may be used to generate binding agents having specificity for (e.g., binding to) PD-1. For instance, to generate and isolate monoclonal antibodies an animal such as a mouse may be administered (e.g., immunized) with one or more PD-1 proteins (e.g., PD-1 Fc fusion protein and/or PD-1 His tag protein). Animals exhibiting serum reactivity to PD-1 expressed on activated human T lymphocytes (as determined by, for instance, flow cytometry and/or microscopy) may then be selected for generation of anti-PD-1 hybridoma cell lines. This may be repeated for multiple rounds. For instance, the primary criteria for the first round of binding agent selection may be include but are not limited to: i) level of staining of PD-1 on activated human T lymphocytes by flow cytometry; (ii) diversity of CDR VH and VL sequences as compared to those of the existing anti-PD-1 antibodies; and, (iii) epitope mapping performed by competitive binding studies with PD-1 conjugated Luminex beads pre-coupled with PD-L1 or one of several commercially available anti-PD-1 antibodies binding to different epitopes on PD-1. An exemplary first or second round of selection may also include, for instance, affinity binding (not a primary criteria since it may not correlate with the stimulatory potential of anti-PD-1 antibodies); and/or, functional characterization to identify the binding agent as an agonist or an antagonist.

As described in Example 1 herein, for instance, the Exhaustion Functional Recovery Assay (EFRA) may be used. In this assay, test binding agents may be assayed for the ability to rescue immune cells such as T cells from exhaustion. This may be determined by measuring the ability of a binding agent to restore proliferation to such cells in the presence of an antigen, such as a test peptide derived from a virus such as human immunodeficiency virus (HIV). Proliferation is measured in a CFSE assay in comparison to a control, such as the test peptide alone or a positive control anti-PD-1 antibody such as MK-3475 (pembrolizumab). In some embodiments, a binding agent is determined to restore proliferation where the comparison shows a signficant difference (such as a P value of <0.001) compared to either a peptide alone control or peptide with an isotype control mouse IgG1 antibody. This assay may be used to identify binding agents (such as antibodies) that compete with other binding agents for binding to PD-1 (such as PD-L1 or PD-L2) and/or lead to the functional restoration of immune cells. Example 1 also describes two methods of epitope mapping the antibodies described herein (e.g., listed in Table 3) using Luminex-based assays. In one biochemical assay, a PD-1 Fc fusion protein is bound to beads and competitive binding studies are performed between the anti-PD-1 antibodies described in Table 3 and one of two different commercially available anti-PD-1 antibodies. Example 1 describes four classes of monoclonal antibodies binding to distinct epitopes on PD-1 that were: class 1 (competitive with a first monoclonal antibody that blocks the interaction of PD-1 with PD-L1), class 2 (competitive with a second monoclonal antibody that binds PD-1 but does not block the interaction of PD-1 with PD-L1), class 3 (competitive with both the first and second monoclonal antibodies), and class 4 (non-competitive with either the first or second antibodies). In a separate assay, competition for binding to a recombinant PD-1 protein was evaluated for the anti-PD-1 antibodies listed in Table 3 and a biotinylated PD-L1 recombinant protein. Antibodies that induced proliferation in the EFRA were identified from all four binding classes that are proposed of binding to different epitopes on PD-1. Likewise, the EFRA allowed for the identification of anti-PD-1 antibodies that were either blocking or non-blocking of the PD-1/PD-L1 interaction and specifically restored proliferative function to HIV specific CD8$^+$ T-cell.

Combinations of binding agents may also be identified. In some embodiments, the combinations may be identified to provide statistically significant differences from results obtained using only one or more of the binding agents and not others. In some embodiments, combinations exhibiting synergistic or cooperative ability to restore immune cell function may be identified. In some embodiments, the combination may comprise a first binding agent that blocks the interaction of PD-1 and PD-L1 with a second binding agent that does not block the interaction of PD-1 and PD-L1. The first and second binding agents may be different entities such as two or more different monoclonal antibodies or derivatives thereof, or may be found on the same entity such as a bi-functional antibody (a single antibody or derivative thereof comprising multiple binding specificities). For instance, an exemplary bi-functional antibody may comprise a first binding region that blocks the interaction of PD-1 and PD-L1 and a second binding region that does not block the interaction of PD-1 and PD-L1. Also contemplated are combinations that provide multiple types of each binding agent. For instance, the combination may comprise multiple types of binding agents that block the interaction of PD-1 and PD-L1 with one or more that does not block the interaction of PD-1 and PD-L1. In some embodiments, the combination may comprise one or more of binding agents that block the interaction of PD-1 and PD-L1 with multiple binding agents that do not block the interaction of PD-1 and PD-L1. In some embodiments, the combination may comprise multiple binding agents that block the interaction of PD-1 and PD-L1 with multiple binding agents that do not block the interaction of PD-1 and PD-L1. Such combinations as described herein may also be combined with one or more other agents that may effect immune cell function such as antibodies against CTLA-4 and the like. One of ordinary skill in the art would recognize that many such combinations may be suitable for use as described herein.

Where the binding agent is an antibody, it may be identified with reference to the nucleotide and/or amino acid sequence corresponding to the variability and/or complementarity determining regions ("CDRs") thereof. The variable region/CDR sequences may be used in combination with one or more other variable region/CDR amino acid sequences. The variable region/CDR amino acid sequences may alternatively and/or also be adjoined to one or more types of constant region polypeptides of an antibody molecule. For instance, the CDR amino acid sequences shown in Tables 1A and 1B may be adjoined to or associated with the constant regions of any antibody molecule of the same or a different species (e.g., human, goat, rat, sheep, chicken) and/or antibody subtype of that from which the CDR amino acid sequence was derived. For instance, an exemplary binding agent may be, or may be derived from, or may be related to the monoclonal antibody produced by the hybridomas listed in, and/or may have about the same affinity and/or proliferation effect, and/or exhibit the same binding class shown in Table 3 and 11-13 and/or may have any one or more of the amino acid sequences of SEQ ID NOS. 1-190 and/or as shown in Tables 1A and 1B. The binding agent may comprise an antibody heavy and/or a light chain that each comprises one or more constant and/or variable regions. The variable regions typically comprise one or more CDRs that may determine the binding specificity of the antibody. The monoclonal antibodies may also be identified by analysis of the amino acid sequences of (e.g., which may be encoded by such nucleotide sequences) such variable regions. For instance, exemplary amino acid sequences of the heavy chain CDRs of binding agents that bind PD-1 may include any one or more of comprising at least one amino acid sequence selected from the group consisting of SEQ ID NOS. 1-190, and/or any other shown in Tables 1A and/or 1B. Any of the amino acid sequences described herein, and/or any fragments and/or derivatives thereof may also be combined with any other variable region and/or CDR in any order and/or combination to form hybrid and/or fusion binding agents and/or inserted into other heavy and/or light chain variable regions using standard techniques. Exemplary combinations of CDRs (e.g., combination of heavy and/or light chain CDR1, CDR2 and CDR3 amino acid sequences) that may be found in a PD-1 (e.g., human PD-1) binding agent of this disclosure may include, for instance, the embodiments shown in Tables 1A and/or 1B.

TABLE 1A

Heavy chain: Amino acids sequence

| Clone | CDR1 | CDR2 | CDR3 |
|---|---|---|---|
| 122F10 | DDFLH (SEQ ID NO: 1) | RIDPANGESRYAPKFQD (SEQ ID NO: 24) | TDYRGYYYAMDY (SEQ ID NO: 47) |
| 139D6 | NYYIH (SEQ ID NO: 2) | SIYPNYGDTNYNQKVKD (SEQ ID NO: 25) | GYSYAMDY (SEQ ID NO: 48) |
| 135D1 | NYYIH (SEQ ID NO: 3) | SIYPNYGETNYNQEFKG (SEQ ID NO: 26) | GYSYAMDY (SEQ ID NO: 49) |
| 134D2 | SNWMH (SEQ ID NO: 4) | AVNPGNSDTTYNQKFKG (SEQ ID NO: 27) | GRSYDGSFDY (SEQ ID NO: 50) |
| 121G1 | RYWMH (SEQ ID NO: 5) | NIDPSDSTTHYNPKFRD (SEQ ID NO: 28) | DLDDFYVGSHEDFDY (SEQ ID NO: 51) |
| 136B5 | SNWMH (SEQ ID NO: 6) | AVYPGNSDTTYNQNFKG (SEQ ID NO: 29) | GRSYDGSFDY (SEQ ID NO: 52) |
| 127C2 | NSYIH (SEQ ID NO: 7) | WISPGDGSTNYNEKFKG (SEQ ID NO: 30) | EEYDYDNY (SEQ ID NO: 53) |
| 137F2 | NYWIG (SEQ ID NO: 8) | DIYPGGGYTNYNEKFKG (SEQ ID NO: 31) | GYDFVLDR (SEQ ID NO: 54) |
| 138H5 | SYAMS (SEQ ID NO: 9) | TISGGGADTYYLDNVKG (SEQ ID NO: 32) | QRGENLFAH (SEQ ID NO: 55) |
| 140A1 | SDYAWN (SEQ ID NO: 10) | YINYSGYTNYNPFLKS (SEQ ID NO: 33) | YGGSYPWNFDV (SEQ ID NO: 56) |
| 135H12 | SYWIN (SEQ ID NO: 11) | NIYPGSSSTDYNEKFKS (SEQ ID NO: 34) | GLYWYFDV (SEQ ID NO: 57) |
| 131D11 | SSYIH (SEQ ID NO: 12) | WIFPGDGKTNYNEKFRD (SEQ ID NO: 35) | NDFDRGVY (SEQ ID NO: 58) |
| 132F7 | NHGMS (SEQ ID NO: 13) | SINTGGYSTYYPDNVKG (SEQ ID NO: 36) | DDYNWFAY (SEQ ID NO: 59) |
| 126E4 | NYWIG (SEQ ID NO: 14) | DIYPGSEYENYNEKFKG (SEQ ID NO: 37) | GYDFVLDH (SEQ ID NO: 60) |

TABLE 1A-continued

Heavy chain: Amino acids sequence

| Clone | CDR1 | CDR2 | CDR3 |
|---|---|---|---|
| 135G1 | DSYIH (SEQ ID NO: 15) | RIDPAHGNVIYASKFRD (SEQ ID NO: 38) | IYYDYGEGDF (SEQ ID NO: 61) |
| 136E10 | DTYIH (SEQ ID NO: 16) | RIDLANDDILYASKFQG (SEQ ID NO: 39) | IYYDYGEGDY (SEQ ID NO: 62) |
| 135C12 | NFYIH (SEQ ID NO: 17) | SIYPNYGDTAYNQKFKD (SEQ ID NO: 40) | GYSYAMDY (SEQ ID NO: 63) |
| 136F4 | DSYIH (SEQ ID NO: 18) | RIDPARDNIIYASKFRD (SEQ ID NO: 41) | IYYDYGEGDY (SEQ ID NO: 64) |
| 136B4 | DDFLH (SEQ ID NO: 19) | RIDPANGESRYAPQFQD (SEQ ID NO: 42) | TDYRGYYYAMDY (SEQ ID NO: 65) |
| 135E10 | SYFMS (SEQ ID NO: 20) | GISTGGADTYYADSMKG (SEQ ID NO: 43) | LSHYYDGIPLDC (SEQ ID NO: 66) |
| 140G5 | NHGMS (SEQ ID NO: 21) | SISGGGDNTYYPDNLKG (SEQ ID NO: 44) | VRQLGLHRAAMDY (SEQ ID NO: 67) |
| 122H2 | NYWIG (SEQ ID NO: 22) | DIYPGGDHKNYNEKFKD (SEQ ID NO: 45) | GFDFVLDY (SEQ ID NO: 68) |
| 139F11 | SFAMS (SEQ ID NO: 23) | TITGGGVNTYYPDTVKG (SEQ ID NO: 46) | QAIYDGHYVLDY (SEQ ID NO: 69) |

TABLE 1B

Light chain: Amino acids sequence

| Clone | CDR1 | CDR2 | CDR3 |
|---|---|---|---|
| 122F10 | KSSQSVLYSSNQKNYLA (SEQ ID NO: 70) | WASTRES (SEQ ID NO: 93) | HQYLSSYT (SEQ ID NO: 116) |
| 139D6 | SASQGISDGLN (SEQ ID NO: 71) | HTSTLHS (SEQ ID NO: 94) | QQYSKFPLT (SEQ ID NO: 117) |
| 135D1 | SASQGISNGLN (SEQ ID NO: 72) | HTSTLHS (SEQ ID NO: 95) | QQYSKFPLT (SEQ ID NO: 118) |
| 134D2 | KASQDINKYIA (SEQ ID NO: 73) | YTSTLRP (SEQ ID NO: 96) | LQYDNLWT (SEQ ID NO: 119) |
| 121G1 | RSSQSIVYSNGNTYLE (SEQ ID NO: 74) | KVSHRFS (SEQ ID NO: 97) | FQGSHVPYT (SEQ ID NO: 120) |
| 136B5 | KASQDINKYMA (SEQ ID NO: 75) | YTSTLRP (SEQ ID NO: 98) | LQYDNLWT (SEQ ID NO: 121) |
| 127C2 | KASQNVGTNVG (SEQ ID NO: 76) | SASYRYN (SEQ ID NO: 99) | QQYNTYPWT (SEQ ID NO: 122) |
| 137F2 | KSSQSLFNSETQKNYLA (SEQ ID NO: 77) | WASTRES (SEQ ID NO: 100) | KQSYTLRT (SEQ ID NO: 123) |
| 138H5 | LASQTIGTWLA (SEQ ID NO: 78) | AATSLAD (SEQ ID NO: 101) | QQLYSTPWT (SEQ ID NO: 124) |
| 140A1 | RSSQTIVHNNGDTYLE (SEQ ID NO: 79) | KISNRFF (SEQ ID NO: 102) | FQGSHVPYT (SEQ ID NO: 125) |
| 135H12 | KSSQSLFNSGTRKNYLA (SEQ ID NO: 80) | WASTRDS (SEQ ID NO: 103) | KQSYNLYT (SEQ ID NO: 126) |
| 131D11 | KASQNVDTNVA (SEQ ID NO: 81) | SASYRYN (SEQ ID NO: 104) | QQYNNYPYT (SEQ ID NO: 127) |

TABLE 1B-continued

Light chain: Amino acids sequence

| Clone | CDR1 | CDR2 | CDR3 |
|---|---|---|---|
| 132F7 | KSSQSLLNSGNQKNYLT (SEQ ID NO: 82) | WASTRES (SEQ ID NO: 105) | QSDYSYPLT (SEQ ID NO: 128) |
| 126E4 | KSSQSLFNSGTRKSYLA (SEQ ID NO: 83) | WASTRET (SEQ ID NO: 106) | MQSYNLRT (SEQ ID NO: 129) |
| 135G1 | HASQNINVWLS (SEQ ID NO: 84) | KASNLHT (SEQ ID NO: 107) | QQGQSWPLT (SEQ ID NO: 130) |
| 136E10 | HASQNINVWLS (SEQ ID NO: 85) | KASNLHT (SEQ ID NO: 108) | QQGQSYPLT (SEQ ID NO: 131) |
| 135C12 | SASQGISGDLN (SEQ ID NO: 86) | HTSSLHS (SEQ ID NO: 109) | QYYSKDLLT (SEQ ID NO: 132) |
| 136F4 | HASQNINVWLS (SEQ ID NO: 87) | KASNLHT (SEQ ID NO: 110) | QQGQSWPLT (SEQ ID NO: 133) |
| 136B4 | KSSQSVLYSSNQKNYLA (SEQ ID NO: 88) | WASTRES (SEQ ID NO: 111) | HQYLSSYT (SEQ ID NO: 134) |
| 135E10 | RASESVDNSGVSFLT (SEQ ID NO: 89) | AASNQGS (SEQ ID NO: 112) | QQTKEVPWT (SEQ ID NO: 135) |
| 140G5 | KASQSVSDDVS (SEQ ID NO: 90) | SAFFRYP (SEQ ID NO: 113) | QQDYSSPLT (SEQ ID NO: 136) |
| 122H2 | KSSQSLFNSGTRKNYLA (SEQ ID NO: 91) | WASTRES (SEQ ID NO: 114) | MQSFNLRT (SEQ ID NO: 137) |
| 139F11 | RTSGNIHNYLA (SEQ ID NO: 92) | NVKTLTD (SEQ ID NO: 115) | QQFWSIPWT (SEQ ID NO: 138) |

In preferred embodiments, the heavy chain CDRs of each clone are combined with their respective light chain CDRs into a binding agent. In some embodiments, the binding agent may comprise the heavy chain CDRs and light chain CDRs shown below:

122F10 (SEQ ID NOS. 1, 24, 47, 70, 93, and 116);
139D6 (SEQ ID NOS. 2, 25, 48, 71, 94, and 117);
135D1 (SEQ ID NOS. 3, 26, 49, 72, 95, and 118);
134D2 (SEQ ID NOS. 4, 27, 50, 73, 96, and 119);
121G1 (SEQ ID NOS. 5, 28, 51, 74, 97, and 120);
136B5 (SEQ ID NOS. 6, 29, 52, 75, 98, and 121);
127C2 (SEQ ID NOS. 7, 30, 53, 76, 99, and 122);
137F2 (SEQ ID NOS. 8, 31, 54, 77, 100, and 123);
138H5 (SEQ ID NOS. 9, 32, 55, 78, 101, and 124);
140A1 (SEQ ID NOS. 10, 33, 56, 79, 102, and 125);
135H12 (SEQ ID NOS. 11, 34, 57, 80, 103, and 126);
131D11 (SEQ ID NOS. 12, 35, 58, 81, 104, and 127);
132F7 (SEQ ID NOS. 13, 36, 59, 82, 105, and 128);
126E4 (SEQ ID NOS. 14, 37, 60, 83, 106, and 129);
135G1 (SEQ ID NOS. 15, 38, 61, 84, 107, and 130);
136E10 (SEQ ID NOS. 16, 39, 62, 85, 108, and 131);
135C12 (SEQ ID NOS. 17, 40, 63, 86, 109, and 132);
136F4 (SEQ ID NOS. 18, 41, 64, 87, 110, and 133);
136B4 (SEQ ID NOS. 19, 42, 65, 88, 111, and 134);
135E10 (SEQ ID NOS. 20, 43, 66, 89, 112, and 135);
140G5 (SEQ ID NOS. 21, 44, 67, 90, 113, and 136);
122H2 (SEQ ID NOS. 22, 45, 68, 91, 114, and 137); or
139F11 (SEQ ID NOS. 23, 46, 69, 92, 115, and 138).

Exemplary heavy and light chain variable regions comprising one or more of the CDRs described herein may include but are not limited to humanized heavy and/or light chain variable regions. For instance, exemplary humanized "137F2" variable heavy chain sequences comprising the 137F2 heavy chain CDRs SEQ ID NOS. 8, 31 and 54 may include:

(A35790-VH (SEQ ID NO. 139))
QMQLVQSGPEVKKPGTSVKVSCKASGFTFTNYWIGWVRQAPGQALEWMG

DIYPGGGYTNYNEKFKGRVTITADKSTSTAYMELSSLRSEDTAVYYCAR

GYDFVLDRWGQGTTVTVSS;

(A35796-VH (SEQ ID NO. 140))
QMQLVQSGPEVKKPGTSVKVSCKASGFTFTNYWIGWVRQAPGQALEWMG

DIYPGGGYTNYNEKFKGRVTITADKSTSTAYMELSSLRSEDTAVYYCAR

GYDFVLDRWGQGTTVTVSS;

(A35793-VH (SEQ ID NO. 141))
QMQLVQSGPEVKKPGTSVKVSCKASGFTFTNYWIGWVRQAPGQALEWMG

DIYPGGGYTNYNEKFKGRVTITADKSTSTAYMELSSLRSEDTAVYYCAR

GYDFVLDRWGQGTTVTVSS;

(A35818-VH (SEQ ID NO. 142))
QMQLVQSGPEVKKPGTSVKVSCKASGFTFTNYWIGWVRQAPGQALEWM

GDIYPGGGYTNYNEKFKGRVTITADKSTSTAYMELSSLRSEDTAVYYC

ARGYDFVLDRWGQGTTVTVSS;

(A35795-VH (SEQ ID NO. 143))
QVQLVQSGAEVKKPGASVKVSCKASGYTFTNYWIGWVRQAPGQGLEWM

GDIYPGGGYTNYNEKFKGRVTITADKSTSTAYMELSSLRSEDTAVYYC

ARGYDFVLDRWGQGTTVTVSS;

(A35797-VH (SEQ ID NO. 144))
EVQLVQSGAEVKKHGESLKISCKGSGYSFTNYWIGWVRQATGQGLEWM
GDIYPGGGYTNYNEKFKGRVTITADKSTSTAYMELSSLRSEDTAVYYC
ARGYDFVLDRWGQGTTVTVSS;

(A35799-VH (SEQ ID NO. 145))
QMQLVQSGAEVKKTGSSVKVSCKASGYTFTNYWIGWVRQMPGKGLEWM
GDIYPGGGYTNYNEKFKGRVTITADKSTSTAYMELSSLRSEDTAVYYC
ARGYDFVLDRWGQGTTVTVSS;

(A35805-VH (SEQ ID NO. 146))
QVQLVQSGSELKKPGASVKVSCKASGYTFTNYWIGWVRQAPGKGLEWM
GDIYPGGGYTNYNEKFKGRVTITADKSTSTAYMELSSLRSEDTAVYYC
ARGYDFVLDRWGQGTTVTVSS;

(137F VH1 (SEQ ID NO. 147))
QVQLVQSGAEVKKPGASVKVSCKASGYTFTNYWIGWVRQAPGQGLEWM
GDIYPGGGYTNYNEKFKGRVTMTRDTSTSTVYMELSSLRSEDTAVYYC
ARGYDFVLDRWGQGTLVTVSS;

(137F VH2 (SEQ ID NO. 148))
QVQLVQSGAEVKKPGASVKVSCKAAGYTFTNYWIGWVRQAPGQGLEWM
GDIYPGGGYTNYNEKFKGRVTMTADTSTSTVYMELSSLRSEDTAVYYC
ARGYDFVLDRWGQGTLVTVSS;

(137F VH1b (SEQ ID NO. 149))
QVQLVQSGAEVKKPGASVKVSCKASGYTFTNYWIGWVRQAPGQGLEWI
GDIYPGGGYTNYNEKFKGRVTMTADTSTSTVYMELSSLRSEDTAVYYC
ARGYDFVLDRWGQGTLVTVSS;
and/or, (137F VH1c (SEQ ID NO. 150))
QVQLVQSGAEVKKPGASVKVSCKASGYTFTNYWIGWIRQAPGQGLEWI
GDIYPGGGYTNYNEKFKGRATLTADTSTSTVYMEVSSLRSEDTAVYYC
ARGYDFVLDRWGQGTLVTVSS.

Exemplary humanized "137F2" variable light chain sequences comprising the 137F2 light chain CDRs SEQ ID NOS. 77, 100 and 123 may include:

(A35790-VL (SEQ ID NO. 151))
DVVMTQSPAFLSVTPGEKVTITCKSSQSLFNSETQKNYLAWYQQKPGQP
PKLLIYWASTRESGVPSRFSGSGSGTDFTLTISSLQPEDFATYYCKQSY
TLRTFGGGTKLEIK;

(A35796-VL (SEQ ID NO. 152))
DVVMTQSPAFLSVTPGEKVTITCKSSQSLFNSETQKNYLAWYQQKPGQP
PKLLIYWASTRESGVPSRFSGSGSGTDFTLTISSLQPEDFATYYCKQSY
TLRTFGGGTKLEIK;

(A35793-VL (SEQ ID NO. 153))
DVVMTQSPAFLSVTPGEKVTITCKSSQSLFNSETQKNYLAWYQQKPGQP
PKLLIYWASTRESGVPSRFSGSGSGTDFTFTISSLEAEDAATYYCKQSY
TLRTFGGGTKLEIK;

(A35818-VL (SEQ ID NO. 154))
DVVMTQSPAFLSVTPGEKVTITCKSSQSLFNSETQKNYLAWYQQKPGQA
PRLLIYWASTRESGVPSRFSGSGSGTDFTFTISSLEAEDAATYYCKQSY
TLRTFGGGTKLEIK;

(A35795-VL (SEQ ID NO. 155))
DVVMTQSPAFLSVTPGEKVTITCKSSQSLFNSETQKNYLAWYQQKPGQA
PRLLIYWASTRESGVPSRFSGSGSGTDFTLTISSLQPEDFATYYCKQSY
TLRTFGGGTKLEIK;

(A35797-VL (SEQ ID NO. 156))
DIQMTQSPSSLSASVGDRVTITCKSSQSLFNSETQKNYLAWYQQKPGQP
PKLLIYWASTRESGVPSRFSGSGSGTDFTLTISSLQPEDFATYYCKQSY
TLRTFGGGTKLEIK;

(A35799-VL (SEQ ID NO. 157))
DVVMTQSPAFLSVTPGEKVTITCKSSQSLFNSETQKNYLAWYQQKPGQP
PKLLIYWASTRESGVPSRFSGSGSGTDFTLTISSLQPEDFATYYCKQSY
TLRTFGGGTKLEIK;

(A35805-VL (SEQ ID NO. 158))
DVVMTQSPAFLSVTPGEKVTITCKSSQSLFNSETQKNYLAWYQQKPGQP
PKLLIYWASTRESGVPSRFSGSGSGTDFTFTISSLEAEDAATYYCKQSY
TLRTFGGGTKLEIK;

(137F VL1 (SEQ ID NO. 159))
DIVMTQSPDSLAVSLGERATINCKSSQSLFNSETQKNYLAWYQQKPGQP
PKLLIYWASTRESGVPDRFSGSGSGTDFTLTISSLQAEDVAVYYCKQSY
TLRTFGQGTKLEIK;

(137F VL2 (SEQ ID NO. 160))
DIVMTQSPDSLAVSLGERATITCKSSQSLFNSETQKNYLAWYQQKPGQP
PKLLIFWASTRESGVPDRFLGSGSGTDFTLTISSLQAEDVAVYYCKQSY
TLRTFGQGTKLEIK;

(137F VL1b (SEQ ID NO. 161))
DIVMTQSPDSLAVSLGERATINCKSSQSLFNSETQKNYLAWYQQKPGQP
PKLLIYWASTRESGVPDRFSGSGSGTDFTLTISSLQAEDVAVYYCKQSY
TLRTFGQGTKLEIK;

(137F VL1c (SEQ ID NO. 162))
DIVMTQSPDSLAVSLGERATITCKSSQSLFNSETQKNYLAWYQQKPGQP
PKLLIFWASTRESGVPDRFSGSGSGTDFTLTISSLQAEDVAVYYCKQSY
TLRTFGQGTKLEIK;
and/or, (137F VL1d (SEQ ID NO. 163))
DIVMTQSPDSLAVSLGERATMTCKSSQSLFNSETQKNYLAWYQQKPGQP
PKLLIFWASTRESGVPDRFSGSGSGTDFTLTISSVQAEDVAVYYCKQSY
TLRTFGQGTKLEIK.

Exemplary humanized "135C12" variable heavy chain sequences comprising the 135C12 heavy chain CDRs SEQ ID NOS. 17, 40 and 63 may include:

(A35775-VH (SEQ ID NO. 164))
EVQLVQSGAEVKKPGESLKISCKGSGYSFTNFYIHWVRQAPGQRLEWMGS
IYPNYGDTAYNQKFKDRFVFSLDTSVSTAYLQISSLKAEDTAVYYCARGY
SYAMDYWGQGTTVTVSS;

(A35783-VH (SEQ ID NO. 165))
EVQLVQSGAEVKKPGESLKISCKGSGYSFTNFYIHWVRQARGQRLEWIGS
IYPNYGDTAYNQKFKDRFVFSLDTSVSTAYLQISSLKAEDTAVYYCARGY
SYAMDYWGQGTTVTVSS;

(A35774-VH (SEQ ID NO. 166))
EVQLVQSGAEVKKPGESLKISCKGSGYSFTNFYIHWVRQAPGQRLEWMGS
IYPNYGDTAYNQKFKDRFVFSLDTSVSTAYLQISSLKAEDTAVYYCARGY
SYAMDYWGQGTTVTVSS;

(A36443-VH (SEQ ID NO. 167))
EVQLVQSGAEVKKPGATVKISCKVSGYTFTNFYIHWVRQARGQRLEWIGS
IYPNYGDTAYNQKFKDRVTITADKSTSTAYMELSSLRSEDTAVYYCARGY
SYAMDYWGQGTTVTVSS;

(A35777-VH (SEQ ID NO. 168))
EVQLVQSGAEVKKPGATVKISCKVSGYTFTNFYIHWVRQAPGKGLEWMGS
IYPNYGDTAYNQKFKDRVTITADKSTSTAYMELSSLRSEDTAVYYCARGY
SYAMDYWGQGTTVTVSS;

(A35789-VH (SEQ ID NO. 169))
EVQLVQSGAEVKKPGESLKISCKGSGYSFTNFYIHWVRQMPGKGLEWMGS
IYPNYGDTAYNQKFKDRVTITADKSTSTAYMELSSLRSEDTAVYYCARGY
SYAMDYWGQGTTVTVSS;

(A36448-VH (SEQ ID NO. 170))
EVQLVQSGAEVKKPGESLKISCKGSGYSFTNFYIHWVRQMPGKGLEWMGS
IYPNYGDTAYNQKFKDRFVFSLDTSVSTAYLQISSLKAEDTAVYYCARGY
SYAMDYWGQGTTVTVSS;

(A36437-VH (SEQ ID NO. 171))
EVQLVQSGAEVKKPGESLKISCKGSGYSFTNFYIHWVRQMPGKGLEWMGS
IYPNYGDTAYNQKFKDRFVFSLDTSVSTAYLQISSLKAEDTAVYYCARGY
SYAMDYWGQGTTVTVSS;

(135C VH1 (SEQ ID NO. 172))
QVQLVQSGAEVKKPGASVKVSCKASGYTFTNFYIHWVRQAPGQGLEWMGS
IYPNYGDTAYNQKFKDRVTMTRDTSTSTVYMELSSLRSEDTAVYYCARGY
SYAMDYWGQGTLVTVSS;

(135C VH2 (SEQ ID NO. 173))
QVQLVQSGAEVKKPGASVKVSCKASGYTFTNFYIHWVRQAPGQGLEWMGS
IYPNYGDTAYNQKFKDRVTMTVDKSTSTVYMELRSLRSEDTAVYYCARGY
SYAMDYWGQGTLVTVSS;

(135C VH3 (SEQ ID NO. 174))
QVQLVQSGAEVKKPGASVKVSCKASGYTFTNFYIHWVKQAHGQGLEWMGS
IYPNYGDTAYNQKFKDRVTMTVDKSTSTVYMELRSLRSEDTAVYYCARGY
SYAMDYWGQGTLVTVSS;

(135C VH1b (SEQ ID NO. 175))
QVQLVQSGAEVKKPGASVKVSCKASGYTFTNFYIHWVRQAPGQGLEWIGS
IYPNYGDTAYNQKFKDRVTMTVDTSTSTVYMELSSLRSEDTAVYYCARGY
SYAMDYWGQGTLVTVSS;

(135C VH1c (SEQ ID NO. 176))
QVQLVQSGAEVKKPGASVKMSCKASGYTFTNFYIHWVRQAPGQGLEWIGS
IYPNYGDTAYNQKFKDRATLTVDTSTSTAYMELSSLRSEDTAVYYCARGY
SYAMDYWGQGTLVTVSS;
and/or, (135C VH1d (SEQ ID NO. 177))
QVQLVQSGAEVKKPGASVKMSCKASGYTFTNFYIHWVRQAPGQGLEWIGS
IYPNYGDTAYNQKFKDRATLTVDKSTSTAYMELSSLRSEDTAVYYCARGY
SYAMDYWGQGTLVTVSS.

Exemplary humanized "135C12" variable light chain sequences comprising the 135C12 light chain CDRs SEQ ID NOS. 86, 109 and 132 may include:

(A35775-VL (SEQ ID NO. 178))
DIQMTQSPSSVSASVGDRVTITCSASQGISGDLNWYQQKPGQAPRLLIYH
TSSLHSGVPSRFSGSGSGTDFTLTISSLQPEDFATYYCQYYSKDLLTFGG
GTKLEIK;

(A35783-VL (SEQ ID NO. 179))
DIQMTQSPSSLSASVGDRVTITCSASQGISGDLNWYQQKPGKTPKLLIYH
TSSLHSGVPSRFSGSGSGTDFTLTISSLQPEDFATYYCQYYSKDLLTFGG
GTKLEIK;

(A35774-VL (SEQ ID NO. 180))
DIQMTQSPSSVSASVGDRVTITCSASQGISGDLNWYQQKPGKAPKLLIYH
TSSLHSGVPSRFSGSGSGTDFTLTISSLQPEDFATYYCQYYSKDLLTFGG
GTKLEIK;

(A36443-VL (SEQ ID NO. 181))
DIQMTQSPSSVSASVGDRVTITCSASQGISGDLNWYQQKPGQAPRLLIYH
TSSLHSGVPSRFSGSGSGTEFTLTISRLEPEDFAVYYCQYYSKDLLTFGG
GTKLEIK;

(A35777-VL (SEQ ID NO. 182))
DIQMTQSPSTLSASVGDRVTITCSASQGISGDLNWYQQKPGQAPRLLIYH
TSSLHSGVPSRFSGSGSGTDFTLTISSLQPEDFATYYCQYYSKDLLTFGG
GTKLEIK;

(A35789-VL (SEQ ID NO. 183))
DIQMTQSPSSVSASVGDRVTITCSASQGISGDLNWYQQKPGQAPRLLIYH
TSSLHSGIPARFSGSGSGTDFTLTISRLEPEDFAVYYCQYYSKDLLTFGG
GTKLEIK;

(A36448-VL (SEQ ID NO. 184))
DIQMTQSPSTLSASVGDRVTITCSASQGISGDLNWYQQKPGKTPKLLIYH
TSSLHSGVPSRFSGSGSGTDFTLTISSLQPEDFATYYCQYYSKDLLTFGG
GTKLEIK;

-continued (A36437-VL (SEQ ID NO. 185))
DIQMTQSPSTLSASVGDRVTITCSASQGISGDLNWYQQKPGQAPRLLIYH

TSSLHSGIPARFSGSGSGTDFTLTISSLQPEDFAVYYCQYYSKDLLTFGG

GTKLEIK;

(135C VL1 (SEQ ID NO. 186))
DIQMTQSPSSLSASVGDRVTITCSASQGISGDLNWYQQKPGKAPKLLIYH

TSSLHSGVPSRFSGSGSGTDFTLTISSLQPEDFATYYCQYYSKDLLTFGG

GTKLEIK;

(135C VL2 (SEQ ID NO. 187))
DIQMTQSPSSLSASVGDRVTITCSASQGISGDLNWYQQKPGKAVKLLIYH

TSSLHSGVPLRFSGSGSGTDYTLTISSLQPEDFATYYCQYYSKDLLTFGG

GTKLEIK;

(135C VL3 (SEQ ID NO. 188))
DIQMTQSPSSLSASVGDRVTITCSASQGISGDLNWYQQKSDGAVKLLIYH

TSSLHSGVPLRFSGSGSGTDYTLTISSLQPEDFATYYCQYYSKDLLTFGG

GTKLEIK;

(135C VL1b (SEQ ID NO. 189))
DIQMTQSPSSLSASVGDRVTITCSASQGISGDLNWYQQKPGKAPKLLIYH

TSSLHSGVPSRFSGSGSGTDYTLTISSLQPEDFATYYCQYYSKDLLTFGG

GTKLEIK;
and/or, (135C VL1c (SEQ ID NO. 190))
DIQMTQSPSSLSASVGDRVTITCSASQGISGDLNWYQQKPGKAVKLLIYH

TSSLHSGVPSRFSGSGSGTDYTLTISSLQPEDFATYYCQYYSKDLLTFGG

GTKLELK.

Exemplary nucleic acid sequences encoding these amino acid sequences, and/or methods for determining the same, are also described herein (e.g., SEQ ID NOS. 191-243). Any of the compatible humanized variable sequences shown above or otherwise disclosed herein may be combined with one another to provide a binding agent(s) such as an antibody that binds PD-1. For example, in some embodiments, SEQ ID NOS. 143 and 155 may be combined into a binding agent (e.g., as in mAb A35795); SEQ ID NOS. 166 and 180 may be combined into a binding agent (e.g., as in mAb A35774); SEQ ID NOS. 196 and 189 may be combined into a binding agent (e.g., as in mAb 135cH1cL1b); SEQ ID NOS. 196 and 190 may be combined into a binding agent (e.g., as in mAb 135cH1cL1c). Furthermore, the variable heavy and light chains may be present within a binding agent (e.g., combined) as shown in Table 2:

TABLE 2

| Variable Chains of Exemplary "Blocking" Humanized Antibodies | | Variable Chains of Exemplary "Non-Blocking" Humanized Antibodies | | |
|---|---|---|---|---|
| Antibody | SEQ ID NO: | SEQ ID NO: | Antibody | SEQ ID NO: | SEQ ID NO: |
| A35790 | 139 | 151 | A35575 | 164 | 178 |
| A35796 | 140 | 152 | A35783 | 165 | 179 |
| A35793 | 141 | 153 | A35774 | 166 | 180 |
| A35818 | 142 | 154 | A36443 | 167 | 181 |
| A35795 | 143 | 155 | A35777 | 168 | 182 |
| A35797 | 144 | 156 | A35789 | 169 | 183 |
| A35799 | 145 | 157 | A36448 | 170 | 184 |

TABLE 2-continued

| Variable Chains of Exemplary "Blocking" Humanized Antibodies | | | Variable Chains of Exemplary "Non-Blocking" Humanized Antibodies | | |
|---|---|---|---|---|---|
| Antibody | SEQ ID NO: | SEQ ID NO: | Antibody | SEQ ID NO: | SEQ ID NO: |
| A35805 | 146 | 158 | A36437 | 171 | 185 |
| 137F $V_H1/V_L1$ | 147 | 159 | 135C $V_H1/V_L1$ | 172 | 186 |
| 137F $V_H2/V_L2$ | 148 | 160 | 135C $V_H2/V_L2$ | 173 | 187 |
| 137F $V_H1b/V_L1b$ | 149 | 161 | 135C $V_H3/V_L3$ | 174 | 188 |
| 137F $V_H1c/V_L1c$ | 150 | 162 | 135C $V_H1b/V_L1b$ | 175 | 189 |
| 137F $V_H1b/V_L1d$ | 149 | 163 | 135C $V_H1c/V_L1c$ | 176 | 190 |
|  |  |  | 135C $V_H1d/V_L1c$ | 177 | 190 |

A "blocking" antibody is one that competes with PD-L1 for binding to PD-1 on the cell surface as determined by any suitable assay including but not limited to the Luminex biochemical PD-1/PD-L1 interation assay (FIG. 1). Epitope mapping studies performed with blocking anti-PD-1 antibodies also map to regions of PD-1 that overlap with the PD-1/PD-L1 interaction. A "non-blocking" antibody is one that only partially competes or does not compete with PD-L1 for binding to PD-1 in a suitable assay including but not limited to the Luminex biochemical PD-1/PD-L1 interation assay (FIG. 1). Epitope mapping studies and/or human PD-1/$F_{ab}$ co-crystallization studies confirm that the non-blocking antibodies do not bind PD-1 at a site that overlaps with the PD-1/PD-L1 interaction. In some embodiments, a binding agent may comprise two or more pairs of such sequences in, for example, a bi-specific antibody (e.g., SEQ ID NOS. 143 and 155 as well as SEQ ID NOS. 166 and 180 may be combined into a binding agent, or a combination of binding agents). Other combinations may also be useful as may ascertained by one of ordinary skill in the art.

Binding agents comprising the CDRs of Tables 1A and/or 1B, or otherwise described herein (e.g., comprising any of SEQ ID NOS. 139-190 and/or shown in Table 2), may also exhibit the following characteristics:

TABLE 3

| Clone | Affinity* (nM) | Binding Class** | Antibody competition with the PD-1/PD-L1 interaction*** | EFRA % relative to peptide stimulation alone‡ |
|---|---|---|---|---|
| 122F10 | 2.2 | 4 | Non-blocker | 146% |
| 139D6 | 2.4 | 2 | Non-blocker | 195% |
| 135D1 | 6.5 | 2 | Non-blocker | 187% |
| 134D2 | 4.8 | 4 | Blocker | 205% |
| 121G1 | 11.9 | 4 | Non-blocker | 120% |
| 136B5 | 7.7 | 4 | Blocker | 200% |
| 127C2 | 1.0 | 2 | Non-blocker | 100% |
| 137F2 | 1.5 | 1 | Blocker | 250% |
| 138H5 | 1.6 | 3 | Blocker | 210% |
| 140A1 | 1.4 | 3 | Blocker | 160% |
| 135H12 | 1.9 | 1 | Blocker | 190% |
| 131D11 | 2.7 | 1 | Blocker | 180% |
| 132F7 | 100 | 2 | Non-blocker | 210% |
| 126E4 | 0.5 | 4 | Blocker | 130% |
| 135G1 | 32 | 4 | NA | 138% |
| 136E10 | 7.1 | 4 | Non-blocker | 148% |
| 135C12 | 1.7 | 2 | Non-blocker | 195% |
| 136F4 | 8.3 | 4 | Non-blocker | 108% |
| 136B4 | 1.4 | 2 | Non-blocker | 185% |

TABLE 3-continued

| Clone | Affinity* (nM) | Binding Class** | Antibody competition with the PD-1/PD-L1 interaction*** | EFRA % relative to peptide stimulation alone‡ |
|---|---|---|---|---|
| 135E10 | 1.5 | 3 | Blocker | 165% |
| 140G5 | 1.6 | 1 | Blocker | 205% |
| 122H2 | 4.3 | 1 | Blocker | 200% |
| 139F11 | 3.1 | 1 | Blocker | 250% |

Figure 2:
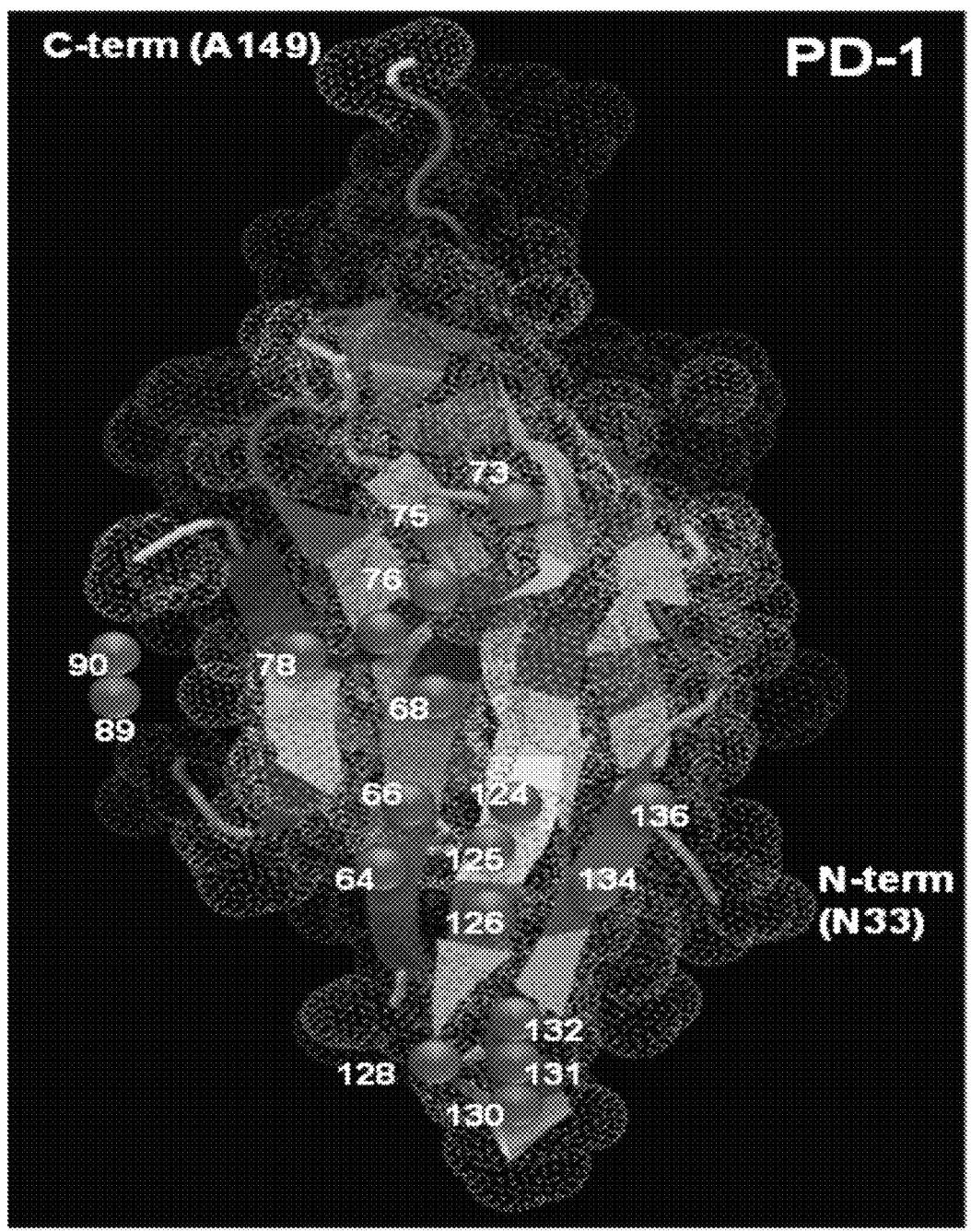
FIG. 2. Structural representation of the PD-1 protein ectodomain from residues 33 to 149. Amino acids implicated in the interaction with either PD-L1 or PD-L2 are situated on the structure by the purple circles with the residue number indicated (residue number being relative to SEQ ID NO. 275 (FIG. 3H)).
Figure 4:
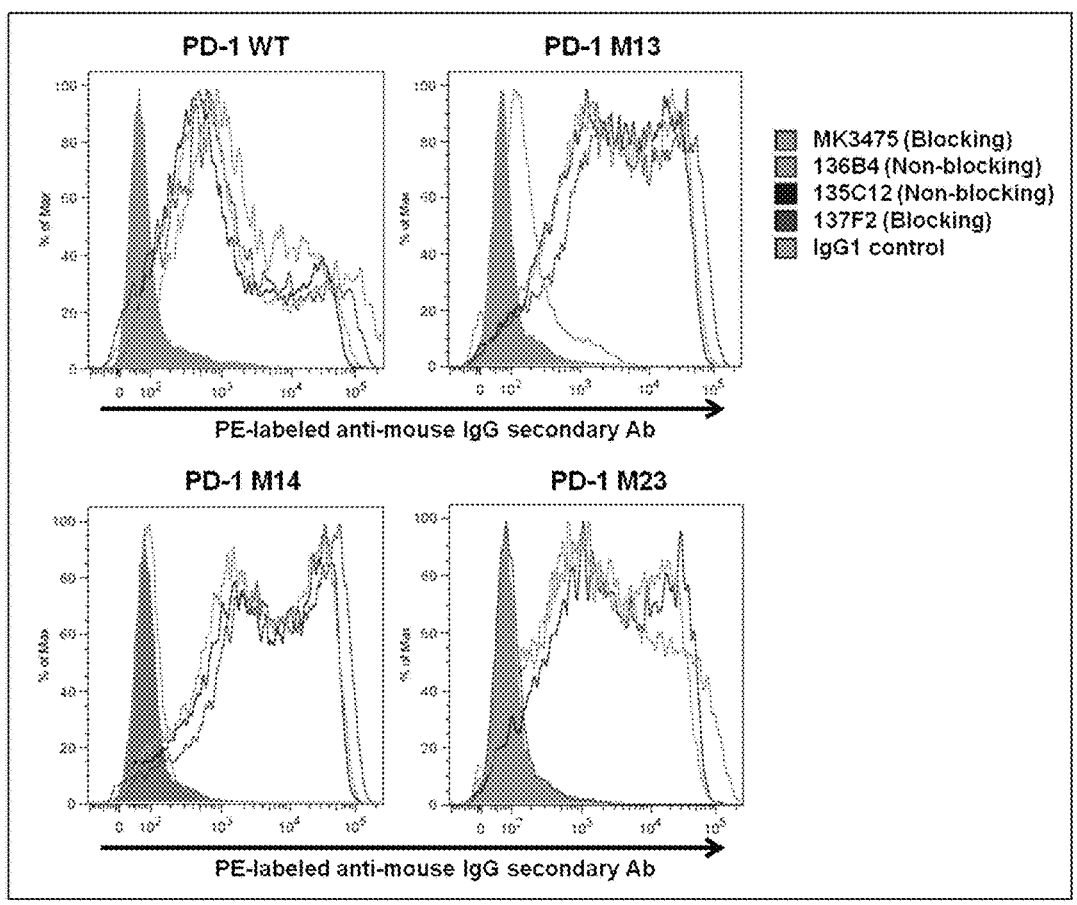
FIG. 4. Binding of blocking and non-blocking anti-PD-1 antibodies to modified PD-1 proteins M13, M14 and M23 (wild-type (WT) control (SEQ ID NO. 275)) expressed at the surface of transiently transfected HeLa cells.
Figure 5:
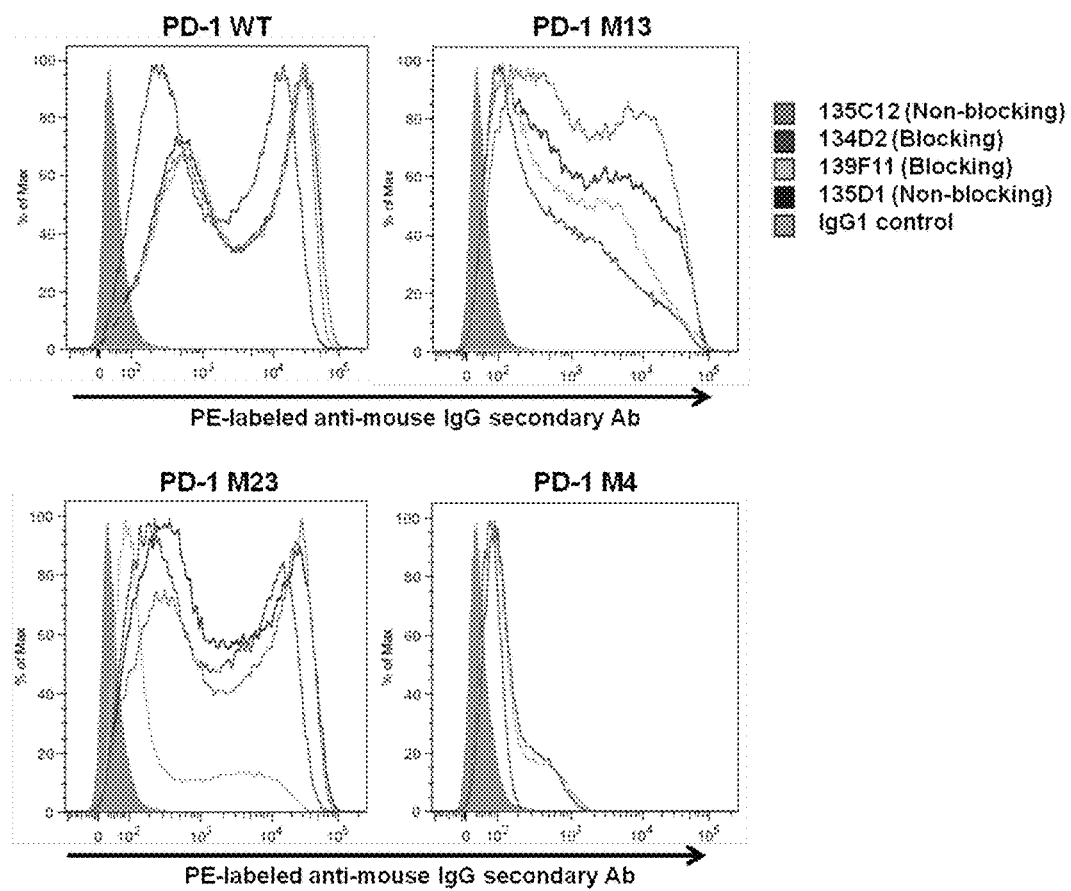
FIG. 5. Binding of blocking and non-blocking anti-PD-1 antibodies to modified PD-1 proteins M13, M23 and M4 (wild-type (WT) control (SEQ ID NO. 275)) expressed at the surface of transiently transfected HeLa cells.
Figure 6:
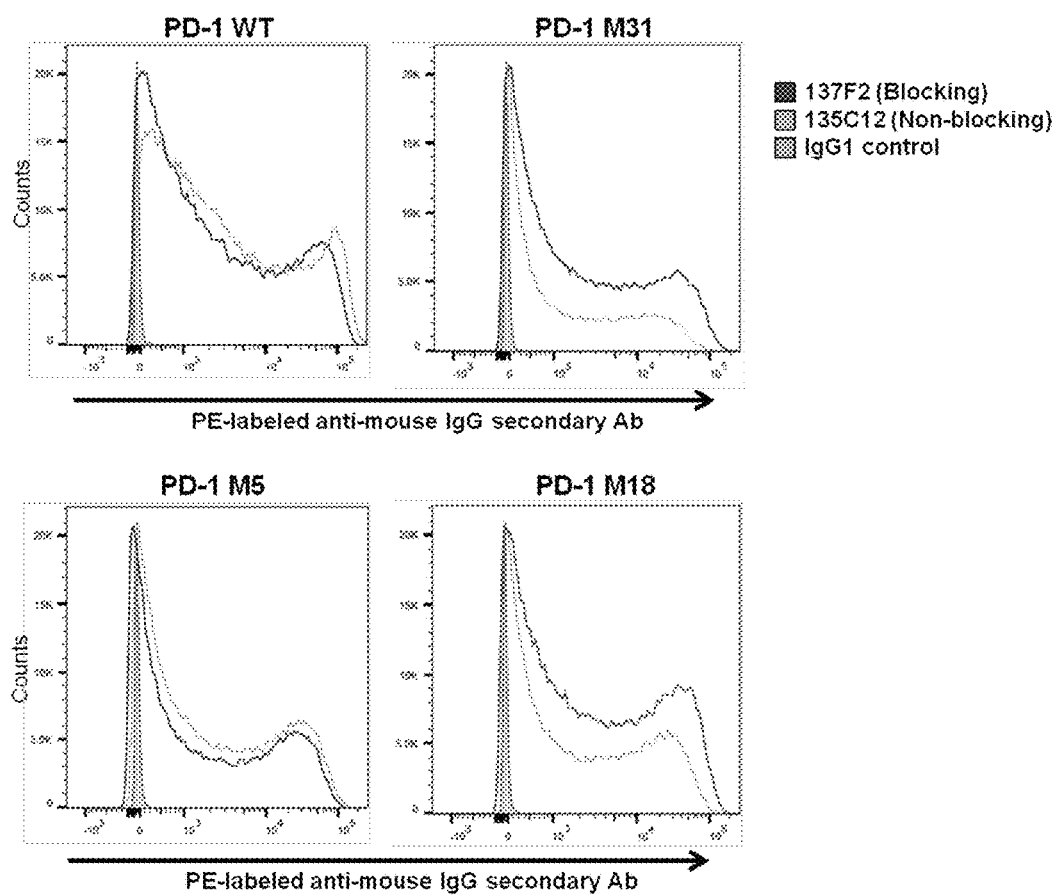
FIG. 6. Binding of blocking and non-blocking anti-PD-1 antibodies to modified PD-1 proteins M31, M5 and M18 (wild-type (WT) control (SEQ ID NO. 275)) expressed at the surface of transiently transfected HeLa cells.
Figure 7:
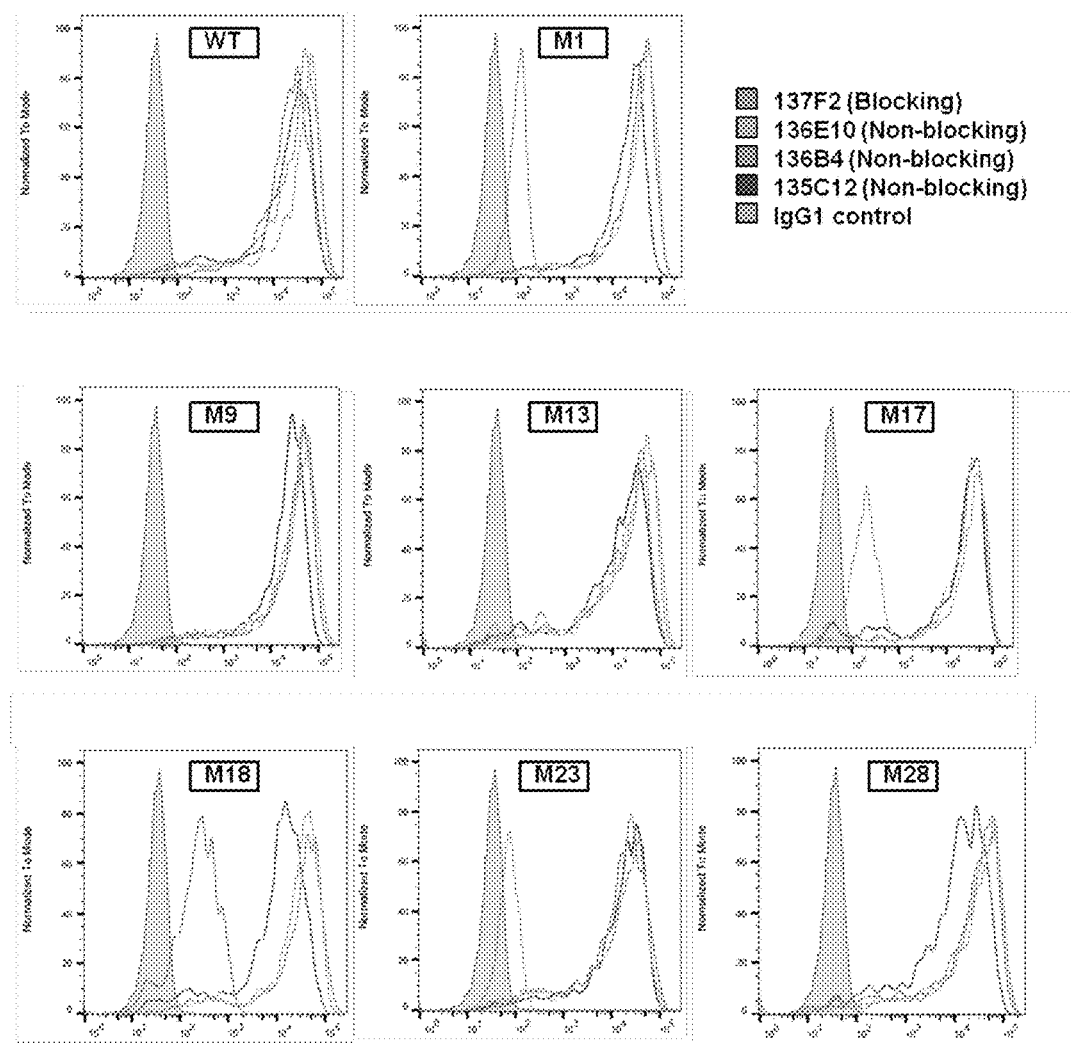
FIG. 7. Binding of blocking and non-blocking anti-PD-1 antibodies to modified PD-1 proteins M1, M9, M13, M17, M18, M23, and M28 (wild-type (WT) control (SEQ ID NO. 275)) expressed at the surface of transiently transfected HeLa cells.
Figure 11:
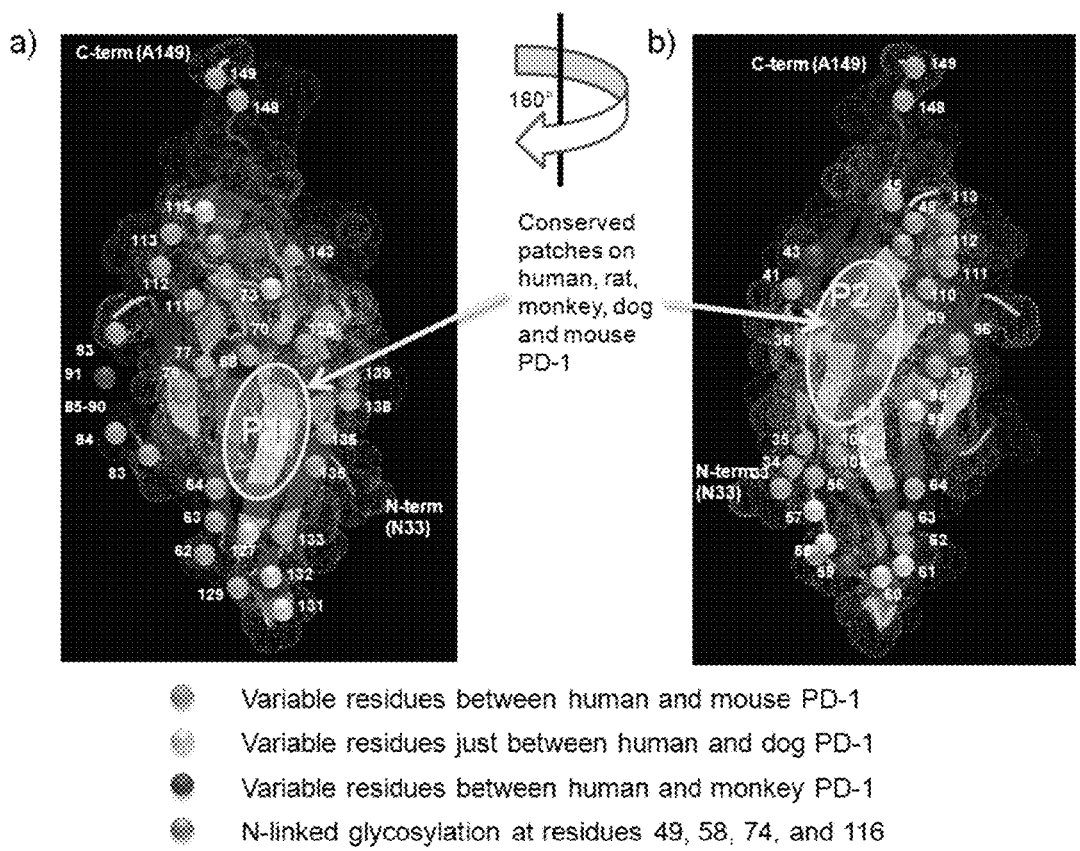
FIG. 11. Structural representation of the P1 (a) and P2 (b) evolutionarily conserved patches of PD-1 along with the alignments of PD-1 ectodomain amino acid sequences from different species (c).

*Binding affinity for the antibodies listed in Table 1 was evaluated by FACS staining of endogenous cell surface PD-1 on activated CD4 T cells.
**Binding class was determined by Luminex assay competitive binding studies. Binding class 1 mAb clones are competitive with the EH12.2H7 clone commercial antibody, class 2 mAb clones are competitive with the J116 clone commercial antibody, class 3 mAb clones are competitive with both EH12.2H7 and J116 antibodies and class 4 mAb clones bind in the presence of both EH12.2H7 and J116 antibodies.
***Antibody competition with the PD-1/PD-L1 interaction was determined in a second Luminex binding assay. In this assays, PD-1 Fc fusion protein coated beads were incubated in the absence or presence of an anti-PD-1 antibody from Table 3 at a concentration of 20 nM. A fixed concentration of 1.25 nM biotinylated PD-L1, approximately equivalent to the IC$_{50}$ of the PD-1/PD-L1 interaction, was then incubated with the PD-1/antibody complex and PD-L1 binding was detected by fluorescence with phycoerythrin labeled streptavidin. Based on PD-L1 binding to the PD-1/antibody complex, antibodies were defined as being blocking, or non-blocking of the PD-1/PD-L1 interaction.
‡Proliferative effect is evaluated using a CFSE assay (an embodiment of the Exhaustion Functional Recovery Assay, "EFRA"). PBMCs isolated from a chronically infected HIV subject were stimulated with an HIV specific peptide in the presence and absence of an anti-PD-1 antibody. Following a 6 day incubation, proliferation of HIV specific CD8 T cells was evaluated in the anti-PD-1 treated samples relative to the peptide alone control.
NA = not available As explained in the Examples section, epitope mapping studies revealed at least two conserved patches (comprising linear and/or conformational epitopes) on PD-1 to which the binding agents described herein may bind, designated "P1" and "P2" (see, e.g., FIGS. 11a and 11b). The P1 patch is evolutionarily conserved and corresponds to the central region of PD-1 involved in the interaction between PD-1 and the PD-L1/PD-L2 ligands, and corresponds with purple circles in FIG. 2 and FIG. 11a. The second "patch" P2 is also evolutionarily conserved and occupies a similar surface area but different amino acid sequences (FIG. 11b) as the P1 patch. P2 has no previously identified structural or functional role on PD-1. PD-1 binding agents described herein, such as anti-PD-1 antibodies comprising the amino acid sequences of 135C12 (SEQ ID NOS. 17, 40, 63, 86, 109, and 132), 139D6 (SEQ ID NOS. 2, 25, 48, 71, 94, and 117), 135D1 (SEQ ID NOS. 3, 26, 49, 72, 95, and 118), and 136B4 (SEQ ID NOS. 19, 42, 65, 88, 111, and 134), bind epitopes overlapping the P2 patch, thereby providing direct evidence for the functional importance of this newly identified functional region of PD-1. The Examples section describes epitope mapping studies that were carried out using modified PD-1 polypeptides shown in FIG. 3 and SEQ ID NOS. 244-274. These studies revealed that the non-blocking antibodies with the greatest "functional potency" or "antagonistic activity" bind to a "patch" of PD-1 that overlaps with the region of the M4 amino acid substitutions (serine 38 to alanine, proline 39 to alanine and leucine 41 to alanine (FIG. 3; SEQ ID NO. 247)), and/or the region of the M17 amino acid substitutions (asparagine 102 to alanine and arginine 104 to alanine (FIG. 3; SEQ ID NO. 260), and/or the region of the M18 amino acid substitutions (aspartic acid 105 to alanine (FIG. 11; SEQ ID NO. 261), and/or the region of the M26 amino acid substitutions (arginine 138 to alanine and glutamic acid 141 to alanine (FIG. 3; SEQ ID NO. 269)) and/or the region of the M31 amino acid substitutions (leucine 41 to alanine and valine 43 to leucine (FIG. 3; SEQ ID NO. 274). This "patch" is referred to herein as "P2". These studies demonstrate that P2 comprises at least one epitope (linear, conformational, or a combination of the same) to which such non-blocking antibodies bind. Given that this region has no previous implication in the functional activity of PD-1, it is proposed herein that binding to P2 represents a novel mechanism of action at a novel site on PD-1 at which antagonistic activity towards PD-1 may be exerted. It is further proposed herein that other antibodies, antibody fragments, or other protein binding agents that can interact with the P2 region of PD-1 may also act as PD-1 antagonists in a manner distinct from and complementary to anti-PD-1 antibodies that act through blockade of the PD-1/PD-L1 interaction. The binding agents described herein may, for instance, interact with an as yet unidentified ligand; interfere with, induce and/or enhance PD-1 multimerization; and/or, by interacting with (e.g., binding) P2, altering intracellular signaling associated with PD-1. Accordingly, the binding agents described herein that interact with (e.g., bind) P2 may provide the PD-1 antagonistic function through any of these, or any other yet to be identified, mechanisms.

Accordingly, this disclosure provides methods for affecting the function of PD-1 by interacting with this P2 patch of PD-1 in or on a cell. Amino acid residues in the P2 patch of PD-1 may comprise threonine 36, phenylalanine 37, serine 38, proline 39, leucine 41, valine 43, alanine 50, threonine 51, phenylalanine 52, threonine 53, cysteine 54, serine 55, asparagine 102, arginine 104, aspartic acid (aspartate) 105, phenylalanine 106, histidine 107, methionine 108, arginine 138 and glutamic acid (glutamate) 141, the amino acid numbering corresponding to SEQ ID NO. 275. In some embodiments, the amino acid residues of the P2 patch may comprise threonine 36, phenylalanine 37, alanine 50, threonine 51, phenylalanine 52, threonine 53, cysteine 54, serine 55, aspartic acid (aspartate) 105, phenylalanine 106, histidine 107 and methionine 108, the amino acid numbering corresponding to SEQ ID NO. 275. In some embodiments, the amino acid residues of the P2 patch may comprise amino acid residues serine 38, proline 39, leucine 41, valine 43, asparagine 102, arginine 104, and/or aspartic acid (aspartate) 105. Thus, in some embodiments, the method may comprise interacting with amino acids threonine 36, phenylalanine 37, serine 38, proline 39, leucine 41, valine 43, alanine 50, threonine 51, phenylalanine 52, threonine 53, cysteine 54, serine 55, asparagine 102, arginine 104, aspartic acid (aspartate) 105, phenylalanine 106, histidine 107, and/or methionine 108, the amino acid numbering corresponding to SEQ ID NO. 275. In some embodiments, the method may comprise interacting with amino acids threonine 36, phenylalanine 37, alanine 50, threonine 51, phenylalanine 52, threonine 53, cysteine 54, serine 55, aspartic acid (aspartate) 105, phenylalanine 106, histidine 107 and/or methionine 108. In some embodiments, the method may comprise interacting with amino acid serine 38, proline 39, leucine 41, valine 43, asparagine 102, arginine 104, and/or aspartic acid (aspartate) 105. In some embodiments, the method comprises interacting with any amino acids within and/or overlapping the P2 patch (e.g., portions of PD-1 comprising the above-described amino acid residues). In some embodiments of such methods, the method comprises interacting with one or more amino acid residues corresponding to serine 38, proline 39, and/or leucine 41 of SEQ ID NO. 275 (M4; FIG. 3; SEQ ID NO. 247); and/or one or more amino acid residues corresponding to asparagine 102 and/or arginine 104 relative to SEQ ID NO. 275 (M17; FIG. 3; SEQ ID NO. 260); and/or one or more amino acid residues corresponding to aspartic acid (aspartate) 105 relative to SEQ ID NO. 204 (M18; FIG. 3; SEQ ID NO. 261); and/or one or more amino acid residues corresponding to arginine 138 and/or glutamic acid (glutamate) 141 (M26; FIG. 3; SEQ ID NO. 269) and/or one or more amino acid residues corresponding to leucine 41 and/or valine 43 (M31; FIG. 3; SEQ ID NO. 274). In some such embodiments, the interaction may be decreased and/or eliminated by modifying (e.g., substituting, eliminating) any one or more of such amino acid residues. In some embodiments, the methods comprise antagonistically affecting the function of PD-1. In some embodiments, the methods comprise interacting with PD-1 using a PD-1 binding agent. In some embodiments, the PD-1 binding agent has specificity for a region (e.g., an epitope) comprising one or more of such amino acid residues corresponding such as, for instance, leucine 41 and/or valine 43 (M4) of SEQ ID NO. 275; and/or one or more amino acid residues corresponding to asparagine102 and/or arginine104 (M17) relative to SEQ ID NO. 275. In some embodiments, the interaction may be involve a binding agent having the ability to bind PD-1 (SEQ ID NO. 275) but not PD-1 M4 (SEQ ID NO. 247), and/or involve a binding agent having the ability to bind PD-1 (SEQ ID NO. 275) but not PD-1 M17 (SEQ ID NO. 260). In some embodiments, the methods may comprise interacting with PD-1 at a site involved in the interaction of PD-1 with PD-L1 and/or PD-L2 (e.g., the P1 patch) and P2. The phrase "one or more amino acid residues corresponding to" an amino acid "of SEQ ID NO. 275" refers to an amino acid in another version of PD-1 similarly positioned as found in SEQ ID NO. 275 (FIG. 3H). Those of ordinary skill in the art will understand, however, that an amino acid in a PD-1 polypeptide other than SEQ ID NO. 275 (FIG. 3H) may be determined to "correspond to" a particular amino acid in SEQ ID NO. 275 (FIG. 3H) by its context within the polypeptide. For instance, monkey PD-1 (SEQ ID NO. 276 (FIG. 3I)) comprises leucine at position 41, as does SEQ ID NO. 275. But the numbering of another PD-1 may differ due to, for instance, one or more additions, deletions, and/or substitution such that the "corresponding" leucine in that particular PD-1 may be found at, for instance, position 40 or 43. However, that leucine would be understood by those of ordinary skill in the art to "correspond to" leucine 41 relative to its context within SEQ ID NO. 275 (FIG. 3H) (e.g., it may be surrounded by the amino acids PA and LV as in SEQ ID NO. 275 (FIG. 3H)). In some embodiments, the binding agent has the ability to bind amino acids F37, P39, A40, L41, V43, L138, R139, and R143 of PD-1 (SEQ ID NO. 275); and/or P34, S137 and R139 of PD-1 (SEQ ID NO. 275) (e.g., A35774 include F37, P39, A40, L41, V43, L138, R139 and R143 for the $V_H$ CDR loops and P34, E136, S137 and R139 for the $V_L$ CDR loops). Other embodiments of such methods and amino acids (e.g., one "corresponding to" another) are also contemplated herein, as would be understood by those of ordinary skill in the art.

Binding affinity may be determined by any technique available to those of ordinary skill in the art. The binding affinity data presented in Table 3 was evaluated by flow cytometry staining of endogenous cell surface PD-1 on CD4 T cells that were stimulated for a period of 3 to 6 days with phytohaemagglutinin (PHA). Binding class may also be determined by any technique available to those of ordinary skill in the art. The binding class data presented in Table 3 was determined by Luminex assay competitive binding studies. In Table 3, binding class 1 mAb antibodies are those determined to be competitive with the EH12.2H7 clone commercial antibody (available from BioLegend, San Diego, Calif. (e.g., Cat. No. 329905)); class 2 antibodies are those determined to be competitive with the J116 clone commercial antibody (available from Affymetrix eBioscience, San Diego, Calif. (e.g., Cat. No. 16-9989-80)); and class 3 antibodies are those determined to be competitive with both EH12.2H7 and J116 antibodies; and class 4 mAb clone antibodies are those determined to bind PD-1 in the presence of both EH12.2H7 and J116 antibodies.

Proliferative effect may be determined by any technique available to those of ordinary skill in the art. For instance, the EFRA system described above and used in Example 1 may be used. Such an assay was used to determine the proliferative effect data presented in Table 3. Briefly, a carboxyfluorescein succinimidyl ester (CFSE) assay in which peripheral blood mononuclear cells (PBMCs) were isolated from a chronically infected HIV subject and stimulated with an HIV-specific peptide in the presence and absence of an anti-PD-1 antibody. A control anti-PD1 antibody (the Merck antibody MK-3475, also referred to as pembrolizumab or Keytruda® (described in U.S. Pat. Nos. 8,354,509 and 8,900,587 and available from Merck & Co.); and/or comprising RASKGVSTSGYSYLH (SEQ ID NO. 287), LASYLES (SEQ ID NO. 288), QHSRDLPLT (SEQ ID NO. 289), NYYMY (SEQ ID NO. 290), GINPSNGGT-NFNEKFKN (SEQ ID NO. 291), and/or RDYRFDMGFDY (SEQ ID NO. 292)) was also tested as a positive control. Following a six-day incubation, proliferation of HIV-specific CD8 T cells was evaluated in the anti-PD-1 treated samples relative to the peptide alone control and the result expressed as a percentage above control ("Proliferation effect").

In some embodiments, the techniques used to identify and characterize PD-1 binding agents such as antibodies may be combined to provide a system for identifying and characterizing such binding agents. For instance, one or more candidate binding agents such one or more monoclonal antibodies may be assayed by EFRA or a similar assay to determine the ability of the candidate binding agent to restore function to immune cells as measured by, for instance, proliferation in the presence of an immunogenic peptide. In some embodiments, this type of assay may be used as an initial screen to ensure the candidate binding agents to be further studied are capable of restoring immune cell function. In some embodiments, these types of assays may be followed by one for determining the binding affinity to immune cells such as activated peripheral blood mononuclear cells (PBMCs). In some embodiments, this assay may use a technique such as fluorescence activated cell sorting (FACS). In some embodiments, the assay may include the presence or absence of non-specific binding and/or competitive binding studies using known binding reagents such as anti-PD1 antibody (e.g., the Merck antibody MK-3475). These assays may then be followed by sequencing of the CDRs of the candidate binding agents such as provided in Tables 1A and/or 1B above. Together, then, the EFRA, affinity determination, epitope mapping studies and CDR identification methods described herein provide a system with which a candidate binding agent may be identified.

Any of the amino acid sequences of Tables 1A and/or 1B, and/or any of SEQ ID NOS. 139-190 (and/or any one or more fragments and/or derivatives thereof) may be also substituted by any other amino acid as desired by one of ordinary skill in the art. For example, one of skill in the art may make conservative substitutions by replacing particular amino acids with others as shown in Table 4 below. The specific amino acid substitution selected may depend on the location of the site selected. Such conservative amino acid substitutions may involve a substitution of a native amino acid residue with a non-native residue such that there is little or no effect on the size, polarity, charge, hydrophobicity, or hydrophilicity of the amino acid residue at that position and, in particular, does not result in decreased PD-1 binding.

TABLE 4

| Original Amino Acid Residues in SEQ ID NOS. 1-190 | Exemplary Conservative Substitutions of the Original Amino Acid Residues of SEQ ID NOS. 1-190 | Preferred Conservative Substitution of the Original Amino Acid Residues of SEQ ID NOS. 1-190 |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

Amino acid substitutions, conservative or non-conservative, in the amino acid sequences of the binding agents described herein are thus contemplated herein. For example, amino acid substitutions may be made that correspond to the amino acid sequences of the humanized variable heavy ($V_H$) and light ($V_L$) chains described herein (e.g., SEQ ID NOS. 139-190). Exemplary non-conservative and conservative substitutions, as the same may be characterized using Table 4, are shown below in Tables 5-8 (see also FIG. 25A-D):

TABLE 5

Exemplary Substitutions Corresponding to A35790 $V_H$ (137F2, SEQ ID NO. 139)

| A35790 $V_H$ | | | | | | | | | | |
|---|---|---|---|---|---|---|---|---|---|---|
| | Q1 | M2 | P9 | P14 | T16 | V18 | V20 | S25 | F27 | V37 | Q43 |
| Exemplary Substitutions | E* | V* | A** | H* | A* | L** | I** | A** | Y** | I** | K* |
| | | | S* | T* | E* | | | | | T* | |
| | | | | | S** | | | | | | |

| A35790 $V_H$ | | | | | | | | | |
|---|---|---|---|---|---|---|---|---|---|
| | A44 | M48 | V68 | I70 | A72 | K74 | A79 | L83 | T112 |
| Exemplary Substitutions | G* | I** | A** | M** | R* | T* | V** | V** | L* |

*Exemplary non-conservative substitutions
**Exemplary conservative substitutions

TABLE 6

Exemplary Substitutions Corresponding to A35790 $V_L$ (137F2, SEQ ID NO. 151)

| A35790 $V_L$ | | | | | | | | | | | |
|---|---|---|---|---|---|---|---|---|---|---|---|
| | V2 | V3 | A9 | F10 | S12 | V13 | T14 | P15 | E17 | K18 | V19 | I21 | T22 |
| Exemplary Substitutions | I** | Q* | S* | S* | A** | A** | S** | V* | D** | R** | A** | M** | N* |
| | | | D* | | | | | L* | | | | | |

| A35790 $V_L$ | | | | | | | | | |
|---|---|---|---|---|---|---|---|---|---|
| | K51 | Y55 | S66 | S69 | L79 | Q85 | P86 | F89 | T91 | G105 |
| Exemplary Substitutions | R** | F** | D* | L* | F** | E* | A** | A** | V* | Q* |
| | | | | | | | | V** | | |

*Exemplary non-conservative substitutions
**Exemplary conservative substitutions

TABLE 7

Exemplary Substitutions Corresponding to A35775 V$_H$ (135C12, SEQ ID NO. 164)

| | \multicolumn{13}{c|}{A35775 V$_H$} |
|---|---|---|---|---|---|---|---|---|---|---|---|---|---|
| | E1 | E16 | S17 | L18 | I20 | G24 | S28 | P41 | Q43 | R44 | M48 | F68 | V69 |
| Exemplary Substitutions | Q* | A* | T** | V** | V** M** | V* A** | T** | R* H* | K* | G* | I** | V** A** | T* |

| | \multicolumn{13}{c|}{A35575 V$_H$} |
|---|---|---|---|---|---|---|---|---|---|---|---|---|---|
| | F70 | S71 | L72 | T74 | V76 | A79 | L81 | Q82 | I83 | S84 | K87 | A88 | T112 |
| Exemplary Substitutions | I** M* L** | T** | A** R* V** | K* | T* | V** | M** | E* | L** | R* | R** | S* | L* |

*Exemplary non-conservative substitutions
**Exemplary conservative substitutions

TABLE 8

Exemplary Substitutions Corresponding to A35775 V$_L$ (135C12, SEQ ID NO. 178)

| | \multicolumn{13}{c|}{A35775 V$_L$} |
|---|---|---|---|---|---|---|---|---|---|---|---|---|---|
| | V11 | P40 | G41 | Q42 | A43 | R45 | S60 | D70 | F71 | S77 | Q79 | T85 | I106 |
| Exemplary Substitutions | L** | S* | D* | K* G* | T* | K** | A** L* | E** | Y** | R* | E* | V* | L** |

*Exemplary non-conservative substitutions
**Exemplary conservative substitutions In some embodiments, this disclosure provides binding agents with multiple specificities such that PD-1 and at least one other secondary antigen (e.g., a cell surface protein) may be bound by a single binding agent. In some embodiments, the secondary antigen may be one expressed by cells infected by an infectious agent. For instance, an exemplary secondary antigen may be HIV Env antigen. Such binding agents may bind the secondary antigen and/or may serve to neutralize the infectious agent. In certain embodiments, such as for a bi-specific binding agent having dual specificity for PD-1 and an HIV antigen such as Env and/or another antigen, for instance. The HIV immunogen may be derived from any of the subtypes described herein, or any other. In some embodiments, such binding agents may include: PD-1 agonist/Env binding; PD-1 agonist PD-1/Env binding and neutralization; PD-1 antagonist/Env binding; and/or PD-1 antagonist/PD-1/Env binding and neutralization. Given the prevalence of the various subtypes, it may be preferable to select antigens from HIV-1 subtypes B and/or C. It may also be desirable to include binding agents having specificity for antigens from multiple HIV subtypes (e.g., HIV-1 subtypes B and C, HIV-2 subtypes A and B, or a combination of HIV-1 and HIV-2 subtypes) in a single composition. For treating a disease such as cancer, it may be beneficial to obtain binding agents with multiple PD-1 specificities (e.g., bi-specific PD-1a/PD1b antagonist PD-1 antibodies specific to two different epitopes) and/or specificity to both PD-1 and one or more tumor antigens (e.g., cancer-testis (CT) antigen (i.e., MAGE, NY-ESO-1); melanocyte differentiation antigen (i.e., Melan A/MART-1, tyrosinase, gp100); mutational antigen (i.e., MUM-1, p53, CDK-4); overexpressed 'self' antigen (i.e., HER-2/neu, p53); and/or viral antigens (i.e., HPV, EBV)). The binding agents (e.g., monoclonal antibodies) may be generated as generally described above. The specificities of such binding agents may be recombined into a single binding agent using techniques that are widely available to those of ordinary skill in the art. In some embodiments, multiple single specifity binding agents may also be combined and used (e.g., administered) to provide an effective multiple specificity reagent.

In some embodiments, the binding agents described herein may be conjugated to active agents to target and inhibit the function of and/or eliminate cell populations expressing PD-1 (and/or another antigen in the case of binding agents with multiple specificities). For instance, CD4$^+$ T-cell populations containing replication competent HIV may be targeted and eliminated using binding agent/drug conjugates (e.g., antibody-drug conjugates (ADC)). Mono- and/or bi-specific candidate binding agents may be conjugated with one or more types of drugs (e.g., drugs damaging DNA, targeting microtubules). The binding agents described herein and/or derivatives thereof may also be adjoined to and/or conjugated to functional agents for in vitro and/or in vivo use. For instance, the binding agent may be adjoined to and/or conjugated to functional moieties such as cytotoxic drugs or toxins, and/or active fragments thereof such as diphtheria A chain, exotoxin A chain, ricin A chain, abrin A chain, curcin, crotin, phenomycin, enomycin, among others. Suitable functional moieties may also include radio-chemicals. Binding agents, such as antibodies, may be adjoined to and/or conjugated to the one or more functional agents using standard techniques in the art.

In some embodiments, the binding agents may be administered in conjunction with other agents such as anti-infective agents (e.g., antibiotics, anti-viral medications). For instance, the binding agents described herein may be combined with monoclonal antibodies and/or other reagents such as Nivolumab (also known as MDX-1106, BMS-936558 (Topalian, et al. N. Eng. J. Med. 2012; 366(26): 2443-2454), MDX-1106, ONO-4538, a fully human IgG4 mAb available from Bristol-Myers Squibb), Pembrolizumab (also known as MK-3475 and SCH 900475, a humanized IgG4 monoclonal antibody available from Merck), Pidilizumab (a humanized IgG1 monoclonal antibody available from CureTech), AMP-224 (a B7-DC/IgG1 fusion protein available from GlaxoSmithKline/Amplimmune), and/or an antibody or other reagent or method described in any of U.S. Pat. No. 8,354,509B2 (Carven, et al), U.S. Pat. No. 8,008,449B2 (Korman, et al), WO 2012/135408A1 (Manoj, et al.), US 2010/026617 (Carven, et al.), WO 2011/110621A1 (Tyson, et al), U.S. Pat. No. 7,488,802B2 (Collins, et al.), WO 2010/029435A1 (Simon, et al.), WO 2010/089411A2 (Olive, D.), WO 2012/145493A1 (Langermann, et al.), WO 2013/0435569A1 (Rolland, et al.), WO 2011/159877A2 (Kuchroo, et al.), U.S. Pat. No. 7,563,869B2 (Ono Pharm.), U.S. Pat. No. 7,858,746B2 (Honjo, et al.), U.S. Pat. No. 8,728,474B2 (Ono Pharm.), and/or U.S. Pat. No. 9,067,999 (Ono Pharm.), each of which is hereby incorporated in its entirety into this disclosure. According to a preferred embodiment, any of the PD-1 binding agents may be fused to other binding agents to form bi-specific binding molecules, in particular bi-specific antibodies. Such bi-specific molecules advantageously couple the PD1 binding agent with another PD1 binding agent, or with another binding agent that targets checkpoint inhibitors or modulators, in particular CTLA-4, LAG3, TIM3, CD137, 4-1BB, OX40, CD27, GITR (Glucocorticoid-induced Tumor Necrosis Factor), CD40, KIR, IDO IL-2, IL-21 and CSF-1R (Colony Stimulatory Factor 1 Receptor). Other combinations and/or bi-specific binding molecules are also contemplated herein, as would be understood by those of ordinary skill in the art.

As mentioned above, the PD-1 binding agents described herein (e.g., a PD-1 antagonist) may be used to treat and/or prevent and/or ameliorate the symptoms of infection by HIV. As is well-known in the art, HIV isolates are now classified into discrete genetic subtypes. HIV-1 is known to comprise at least ten subtypes (A1, A2, A3, A4, B, C, D, E, F1, F2, G, H, J and K) (Taylor et al, NEJM, 359(18):1965-1966 (2008)). HIV-2 is known to include at least five subtypes (A, B, C, D, and E). Subtype B has been associated with the HIV epidemic in homosexual men and intravenous drug users worldwide. Most HIV-1 immunogens, laboratory adapted isolates, reagents and mapped epitopes belong to subtype B. In sub-Saharan Africa, India and China, areas where the incidence of new HIV infections is high, HIV-1 subtype B accounts for only a small minority of infections, and subtype HIV-1 C appears to be the most common infecting subtype. Any of these types of isolates may be addressed using the binding agents described herein. One or more binding agents may also be administered with or in conjunction with one or more agents used to prevent, treat and/or ameliorate HIV such as for example, a protease inhibitor, an HIV entry inhibitor, a reverse transcriptase inhibitor, and/or an anti-retroviral nucleoside analog. Suitable compounds include, for example, Agenerase (amprenavir), Combivir (Retrovir/Epivir), Crixivan (indinavir), Emtriva (emtricitabine), Epivir (3tc/lamivudine), Epzicom, Fortovase/Invirase (saquinavir), Fuzeon (enfuvirtide), Hivid (ddc/zalcitabine), Kaletra (lopinavir), Lexiva (Fosamprenavir), Norvir (ritonavir), Rescriptor (delavirdine), Retrovir/AZT (zidovudine), Reyatax (atazanavir, BMS-232632), Sustiva (efavirenz), Trizivir (abacavir/zidovudine/lamivudine), Truvada (Emtricitabine/Tenofovir DF), Videx (ddI/didanosine), Videx EC (ddI, didanosine), Viracept (nevirapine), Viread (tenofovir disoproxil fumarate), Zerit (d4T/stavudine), and Ziagen (abacavir) may be utilized. Other suitable agents are known to those of skill in the art and may be suitable for use as described herein. Such agents may either be used prior to, during, or after administration of the binding agents and/or use of the methods described herein.

As mentioned above, the PD-1 binding agents described herein (e.g., a PD-1 antagonist) may be used to treat and/or prevent and/or ameliorate the symptoms of cancer. Exemplary cancers may include, for instance, any of the breast, blood, colon, stomach, rectum, skeletal tissue, skin (e.g., melanoma) brain, lung, bladder, kidney, ovary, and/or liver, among others. In addition, the PD-1 binding agents described herein, preferably the antibodies that are non-blocking with respect to the PD-1/PD-L1 interaction, in particular those referred to herein as binding Class II, such as but not limited to 135C12, 139D6, 136B4 and 135D1, are particularly useful, alone or in combination with one another and/or other PD-1 antibodies, for treating various types of malignancies, in particular melanoma (e.g., metastatic malignant melanoma), renal cancer (e.g., clear cell carcinoma), bladder cancer, prostate cancer (e.g., castration resistant prostate cancer), pancreatic cancer, breast cancer, colon cancer, lung cancer (e.g., non-small cell lung cancer), esophageal cancer, squamous cell carcinoma of the head and neck, Merkel cell carcinoma, liver cancer, ovarian cancer, cervical cancer, thyroid cancer, glioblastoma, glioma, leukemia, lymphoma, sarcomas and other neoplastic malignancies. The above preferred PD-1 binding agents are more particularly dedicated to the treatment of hematological malignancies such as Hodgkin's disease, Non-Hodgkin's Lymphoma such as Follicular lymphoma, Diffuse large B cell lymphoma, Multiple myeloma (MM), Acute myeloid leukemia (AML), Acute Lymphoblastic leukemia (ALL), and myelodysplastic syndromes. The binding agents described herein may be used to treat other types of cancers as well, as would be understood by those of ordinary skill in the art.

In some embodiments, one or more of the PD-1 binding agents may also be combined with and/or administered with or in conjunction with one or more agents used to prevent, treat and/or ameliorate cancer such as for example, an alkylating agent (e.g., any nitrogen mustard, nitrosourea, tetrazine, aziridine, cisplatin and/or derivative thereof), anti-metabolite (e.g., any of the methotrexates, pemetrexeds, fluoropyrimidines and/or derivative thereof), anti-microtubule agent (e.g., vinca alkyloids, taxanes, podophyllotoxin and/or derivative thereof), topoisomerase I and/or II inhibitors (e.g., a camptothecin, irinotecan, topotecan, etoposide, doxorubicin, mitoxantrone, teniposide, novobiocin, merbarone, aclarubicin and/or derivative thereof) and/or cytotoxic antibiotic (e.g., any anthracyclines, actinomycin, bleomycin, plicamycin, and mitomycin and/or derivative thereof). The one or more binding agents may also, or alternatively, be combined with one or more other binding agents available to those of ordinary skill in the art for treating, preventing and/or ameliorating cancer such as, for example, Nivolumab, Pembrolizumab, Pidilizumab and/or other similar agents and/or derivatives thereof. The one or more PD-1 binding agents may also be used alone or in combination with other binding agents targeting PD-1, PDL-1 and/or other immune checkpoints effectors. These may also be used in combination with other anti-neoplastic agents or immunogenic agents (for example, attenuated cancerous cells, tumor antigens (including recombinant proteins, peptides, and carbohydrate molecules), antigen presenting cells such as dendritic cells pulsed with tumor derived antigen or nucleic acids, immune stimulating cytokines (for example, IL-2, IFNa2, GM-CSF), and/or cells transfected with genes encoding immune-stimulating cytokines such as but not limited to GM-CSF; standard cancer treatments (for example, chemotherapy, radiotherapy or surgery); or other agents directed to VEGF, EGFR, Her2/neu, VEGF receptors, other growth factor receptors. According to a preferred embodiment, the one or more PD-1 binding agents is combined with vaccine agents and/or immune checkpoint modulators acting more particularly on CTLA-4, LAG3, TIM3, CD137, 4-1BB, OX40, CD27, GITR (Glucocorticoid-induced Tumor Necrosis Factor), CD40, KIR, IDO IL-2, IL-21 and/or CSF-1R (Colony Stimulatory Factor 1 Receptor) to form a therapeutic composition and/or a kit for sequential therapeutic administration. Other suitable agents are known to those of skill in the art and may be suitable for use as described herein. Such agents may either be used prior to, during, or after administration of the binding agents and/or use of the methods described herein.

As mentioned above, the PD-1 binding agents described herein (e.g., a PD-1 agonist) may be used to treat and/or prevent and/or ameliorate the symptoms of autoimmunity. Exemplary autoimmune conditions may include, for instance, any in which PD-1 is involved in maintaining self-tolerance and/or one involving inflammatory T cells (e.g., autoreactive or self antigen-specific T cells) such as, for instance, systemic lupus erythematosus (SLE), type I diabetes, rheumatoid arthritis, glomerulonephritis, and multiple sclerosis. Such PD-1 binding agents may also be combined with other agents such as anti-CTLA-4 agents (e.g., ipilimumab). One or more of the binding agents may also be combined with and/or administered with or in conjunction with one or more agents used to prevent, treat and/or ameliorate autoimmunity such as, for example, glucocorticoids, cytostatics (e.g., alkylating agent, anti-metabolite, methotrexate, azathioprine, mercaptopurine, cytotoxic antibiotics (e.g., dactinomycin, anthracyclines, mitomycin C, bleomycin, mithramycin), antibodies (e.g., Atgam, Thymoglobuline, Simulect, Zenapax), drugs acting on immunophilins (e.g., ciclosporin, tacrolimus, sirolimus), interferons, opioids, TNF-binding agents (e.g., Remicade, Enbrel, Humira), mycophenolate, fingolimod, myriocin, and/or derivatives thereof. Other suitable agents are known to those of skill in the art and may be suitable for use as described herein. Such agents may either be used prior to, during, or after administration of the binding agents and/or use of the methods described herein.

In some embodiments, the binding agents may be adjoined to and/or conjugated to one or more detectable labels. For instance, suitable detectable labels may include, for instance, fluorosceins (e.g., DyLight, Cy3, Cy5, FITC, HiLyte Fluor 555, HiLyte Fluor 647; 5-carboxy-2,7-dichlorofluorescein; 5-Carboxyfluorescein (5-FAM); 5-HAT (Hydroxy Tryptamine); 5-Hydroxy Tryptamine (HAT); 6-JOE; 6-carboxyfluorescein (6-FAM); FITC; 6-carboxy-1,4-dichloro-2',7'-dichlorofluorescein (TET); 6-carboxy-1,4-dichloro-2',4',5',7'-tetra-chlorofluorescein (HEX); 6-carboxy-4',5'-dichloro-2',7'-dimethoxyfluorescein (JOE); Alexa fluors (e.g., 350, 405, 430, 488, 500, 514, 532, 546, 555, 568, 594, 610, 633, 635, 647, 660, 680, 700, 750); BODIPY fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE)), rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, ROX (6-carboxy-X-rhodamine), 5-ROX (carboxy-X-rhodamine), Sulphorhodamine B can C, Sulphorhodamine G Extra, TAMRA (6-carboxytetramethylrhodamine), Tetramethylrhodamine (TRITC), WT), Texas Red, and/or Texas Red-X. Other detectable labels known in the art may also be suitable for use. Binding agents, such as antibodies, may be adjoined to and/or conjugated to the one or more detectable labels using standard techniques in the art.

In certain embodiments, a nucleic acid molecule encoding one or more binding agents described herein may be inserted into one or more expression vectors, as discussed below in greater detail. In such embodiments, the binding agent may be encoded by nucleotides corresponding to the amino acid sequence. The particular combinations of nucleotides (codons) that encode the various amino acids (AA) are well known in the art, as described in various references used by those skilled in the art (e.g., Lewin, B. *Genes V*, Oxford University Press, 1994). The nucleotide sequences encoding the amino acids of said binding agents may be ascertained with reference to Table 9, for example. Nucleic acid variants may use any combination of nucleotides that encode the binding agent.

TABLE 9

Codons Encoding Amino Acids (AA) of SEQ ID NOS. 1-138 of Variants Thereof

| AA | Codon | AA | Codons | AA | Codons | AA | Codons |
|---|---|---|---|---|---|---|---|
| Phe (F) | TTT | Ser (S) | TCT | Tyr (Y) | TAT | Cys (C) | TGT |
|  | TTC |  | TCC |  | TAC |  | TGC |
| Leu (L) | TTA |  | TCA | TERM | TAA | TERM | TGA |
|  | TTG |  | TCG |  | TAG | Trp (W) | TGG |
|  | CTT | Pro (P) | CCT | His (H) | CAT | Arg (R) | CGT |
|  | CTC |  | CCC |  | CAC |  | CGC |
|  | CTA |  | CCA | Gln (Q) | CAA |  | CGA |
|  | CTG |  | CCG |  | CAG |  | CGG |
| Ile (I) | ATT | Thr (T) | ACT | Asn (N) | AAT | Ser (S) | AGT |
|  | ATC |  | ACC |  | AAC |  | AGC |
|  | ATA |  | ACA | Lys (K) | AAA | Arg (R) | AGA |
| Met (M) | ATG |  | ACG |  | AAG |  | AGG |
| Val (V) | GTT | Ala (A) | GCT | Asp (D) | GAT | Gly (G) | GGT |
|  | GTC |  | GCC |  | GAC |  | GGC |
|  | GTA |  | GCA | Glu (E) | GAA |  | GGA |
|  | GTG |  | GCG |  | GAG |  | GGG |

Those of ordinary skill in the art understand that a nucleotide sequence encoding a particular amino acid sequence may be easily derived from the amino acid sequence and the information presented in Table 9 (and, in some embodiments, e.g., Tables 5-8). For instance, it may be deduced from the amino acid sequence DDFLH (SEQ ID NO.: 1) and the information presented in Table 9 that the amino acid sequence may be encoded by the nucleotide sequence GAT GAT TTT TTA CAT (SEQ ID NO.:191). Those of ordinary skill in the art would understand that nucleotide sequences encoding any of SEQ ID NOS. 2-190 may be deduced in the same way, and such nucleotide sequences are contemplated herein. Where the binding agents are antibodies, nucleotide sequences encoding the variable regions thereof may also be isolated from the phage and/or hybridoma cells expressing the same cloned into expression vectors to produce certain preparations (e.g., humanized antibodies). Exemplary nucleic acid sequences encoding the variable region sequences of SEQ ID NOS. 139-190 are shown in Table 10.

TABLE 10

| $V_H/V_L$ SEQ ID NO. and identifier | Exemplary nucleic acid (coding) sequence |
|---|---|
| 139 A35790-VH | cagatgcagctggtgcagagcggcccggaagtgaaaaaaccgggcaccagcgtgaaagtg agctgcaaagcgagcggctttacctttaccaactattggattggctgggtgcgccaggcg ccgggccaggcgctggaatggatgggcgatatttatccgggcggcggctataccaactat aacgaaaaatttaaaggccgcgtgaccattaccgcggataaaagcaccagcaccgcgtat atggaactgagcagcctgcgcagcgaagataccgcggtgtattattgcgcgcgcggctat gattttgtgctggatcgctggggccagggcaccaccgtgaccgtgagcagc (SEQ ID NO.: 192) |
| 140 A35796-VH | cagatgcagctggtgcagagcggcccggaagtgaaaaaaccgggcaccagcgtgaaagtg agctgcaaagcgagcggctttacctttaccaactattggattggctgggtgcgccaggcg ccgggccaggcgctggaatggatgggcgatatttatccgggcggcggctataccaactat aacgaaaaatttaaaggccgcgtgaccattaccgcggataaaagcaccagcaccgcgtat atggaactgagcagcctgcgcagcgaagataccgcggtgtattattgcgcgcgcggctat gattttgtgctggatcgctggggccagggcaccaccgtgaccgtgagcagc (SEQ ID NO.: 193) |
| 141 A35793-VH | cagatgcagctggtgcagagcggcccggaagtgaaaaaaccgggcaccagcgtgaaagtg agctgcaaagcgagcggctttacctttaccaactattggattggctgggtgcgccaggcg ccgggccaggcgctggaatggatgggcgatatttatccgggcggcggctataccaactat aacgaaaaatttaaaggccgcgtgaccattaccgcggataaaagcaccagcaccgcgtat atggaactgagcagcctgcgcagcgaagataccgcggtgtattattgcgcgcgcggctat gattttgtgctggatcgctggggccagggcaccaccgtgaccgtgagcagc (SEQ ID NO.: 194) |
| 142 A35818-VH | cagatgcagctggtgcagagcggcccggaagtgaaaaaaccgggcaccagcgtgaaagtg agctgcaaagcgagcggctttacctttaccaactattggattggctgggtgcgccaggcg ccgggccaggcgctggaatggatgggcgatatttatccgggcggcggctataccaactat aacgaaaaatttaaaggccgcgtgaccattaccgcggataaaagcaccagcaccgcgtat atggaactgagcagcctgcgcagcgaagataccgcggtgtattattgcgcgcgcggctat gattttgtgctggatcgctggggccagggcaccaccgtgaccgtgagcagc (SEQ ID NO.: 195) |
| 143 A35795-VH | caggtgcagctggtgcagagcggcgcggaagtgaaaaaaccgggcgcgagcgtgaaagtg agctgcaaagcgagcggctataccttaccaactattggattggctgggtgcgccaggcg ccgggccagggcctggaatggatgggcgatatttatccgggcggcggctataccaactat aacgaaaaatttaaaggccgcgtgaccattaccgcggataaaagcaccagcaccgcgtat atggaactgagcagcctgcgcagcgaagataccgcggtgtattattgcgcgcgcggctat gattttgtgctggatcgctggggccagggcaccaccgtgaccgtgagcagc (SEQ ID NO.: 196) |
| 144 A35797-VH | gaagtgcagctggtgcagagcggcgcggaagtgaaaaaacatggcgaaagcctgaaaatt agctgcaaaggcagcggctatagctttaccaactattggattggctgggtgcgccaggcg accggccagggcctggaatggatgggcgatatttatccgggcggcggctataccaactat aacgaaaaatttaaaggccgcgtgaccattaccgcggataaaagcaccagcaccgcgtat atggaactgagcagcctgcgcagcgaagataccgcggtgtattattgcgcgcgcggctat gattttgtgctggatcgctggggccagggcaccaccgtgaccgtgagcagc (SEQ ID NO.: 197) |
| 145 A35799-VH | cagatgcagctggtgcagagcggcgcggaagtgaaaaaaaccggcagcagcgtgaaagtg agctgcaaagcgagcggctataccttaccaactattggattggctgggtgcgccagatg ccgggcaaaggcctggaatggatgggcgatatttatccgggcggcggctataccaactat aacgaaaaatttaaaggccgcgtgaccattaccgcggataaaagcaccagcaccgcgtat atggaactgagcagcctgcgcagcgaagataccgcggtgtattattgcgcgcgcggctat gattttgtgctggatcgctggggccagggcaccaccgtgaccgtgagcagc (SEQ ID NO.: 198) |
| 146 A35805-VH | caggtgcagctggtgcagagcggcagcgaactgaaaaaaccgggcgcgagcgtgaaagtg agctgcaaagcgagcggctataccttaccaactattggattggctgggtgcgccaggcg ccgggcaaaggcctggaatggatgggcgatatttatccgggcggcggctataccaactat aacgaaaaatttaaaggccgcgtgaccattaccgcggataaaagcaccagcaccgcgtat atggaactgagcagcctgcgcagcgaagataccgcggtgtattattgcgcgcgcggctat gattttgtgctggatcgctggggccagggcaccaccgtgaccgtgagcagc (SEQ ID NO.: 199) |

TABLE 10-continued

| V_H/V_L SEQ ID NO. and identifier | Exemplary nucleic acid (coding) sequence |
|---|---|
| 147 137F VH1 | caggtgcagctggtgcagagcggcgcggaagtgaaaaaaccgggcgcgagcgtgaaagtg agctgcaaagcgagcggctataccttaccaactattggattggctgggtgcgccaggcg ccgggccagggcctggaatggatgggcgatatttatccgggcggcggctataccaactat aacgaaaaatttaaaggccgcgtgaccatgacccgcgataccagcaccagcaccgtgtat atggaactgagcagcctgcgcagcgaagataccgcggtgtattattgcgcgcgcggctat gattttgtgctggatcgctggggccagggcaccctggtgaccgtgagcagc (SEQ ID NO.: 200) |
| 148 137F VH2 | caggtgcagctggtgcagagcggcgcggaagtgaaaaaaccgggcgcgagcgtgaaagtg agctgcaaagcggcgggctataccttaccaactattggattggctgggtgcgccaggcg ccgggccagggcctggaatggatgggcgatatttatccgggcggcggctataccaactat aacgaaaaatttaaaggccgcgtgaccatgaccgcgcgataccagcaccagcaccgtgtat atggaactgagcagcctgcgcagcgaagataccgcggtgtattattgcgcgcgcggctat gattttgtgctggatcgctggggccagggcaccctggtgaccgtgagcagc (SEQ ID NO.: 201) |
| 149 137F VH1b | caggtgcagctggtgcagagcggcgcggaagtgaaaaaaccgggcgcgagcgtgaaagtg agctgcaaagcgagcggctataccttaccaactattggattggctgggtgcgccaggcg ccgggccagggcctggaatggattggcgatatttatccgggcggcggctataccaactat aacgaaaaatttaaaggccgcgtgaccatgacccgcgataccagcaccagcaccgtgtat atggaactgagcagcctgcgcagcgaagataccgcggtgtattattgcgcgcgcggctat gattttgtgctggatcgctggggccagggcaccctggtgaccgtgagcagc (SEQ ID NO.: 202) |
| 150 137F VH1c | caggtgcagctggtgcagagcggcgcggaagtgaaaaaaccgggcgcgagcgtgaaagtg agctgcaaagcgagcggctataccttaccaactattggattggctggattcgccaggcg ccgggccagggcctggaatggattggcgatatttatccgggcggcggctataccaactat aacgaaaaatttaaaggccgcgcgaccctgaccgcgcgataccagcaccagcaccgtgtat atggaagtgagcagcctgcgcagcgaagataccgcggtgtattattgcgcgcgcggctat gattttgtgctggatcgctggggccagggcaccctggtgaccgtgagcagc (SEQ ID NO.: 203) |
| 151 A35790-VL | gatgtggtgatgacccagagcccggcgtttctgagcgtgaccccgggcgaaaaagtgacc attacctgcaaaagcagccagagcctgtttaacagcgaaaaccagaaaaaactatctggcg tggtatcagcagaaaccgggccagccgccgaaactgctgatttattgggcgagcacccgc gaaagcggcgtgccgagccgctttagcggcagcggcagcggcaccgattttaccctgacc attagcagcctgcagccggaagattttgcgacctattattgcaaacagagctataccctg cgcacctttggcggcggcaccaaactggaaattaaa (SEQ ID NO.: 204) |
| 152 A35796-VL | gatgtggtgatgacccagagcccggcgtttctgagcgtgaccccgggcgaaaaagtgacc attacctgcaaaagcagccagagcctgtttaacagcgaaacccagaaaaaactatctggcg tggtatcagcagaaaccgggccagccgccgaaactgctgatttattgggcgagcacccgc gaaagcggcgtgccgagccgctttagcggcagcggcagcggcaccgattttaccctgacc attagcagcctgcagccggaagattttgcgacctattattgcaaacagagctataccctg cgcacctttggcggcggcaccaaactggaaattaaa (SEQ ID NO.: 205) |
| 153 A35793-VL | gatgtggtgatgacccagagcccggcgtttctgagcgtgaccccgggcgaaaaagtgacc attacctgcaaaagcagccagagcctgtttaacagcgaaaaccagaaaaaactatctggcg tggtatcagcagaaaccgggccagccgccgaaactgctgatttattgggcgagcacccgc gaaagcggcgtgccgagccgctttagcggcagcggcagcggcaccgattttaccttacc attagcagcctggaagcggaagatgcggcgacctattattgcaaacagagctataccctg cgcacctttggcggcggcaccaaactggaaattaaa (SEQ ID NO.: 206) |
| 154 A35818-VL | gatgtggtgatgacccagagcccggcgtttctgagcgtgaccccgggcgaaaaagtgacc attacctgcaaaagcagccagagcctgtttaacagcgaaacccagaaaaaactatctggcg tggtatcagcagaaaccgggccaggcgccgcgcctgctgatttattgggcgagcacccgc gaaagcggcgtgccgagccgctttagcggcagcggcagcggcaccgattttaccttacc attagcagcctggaagcggaagatgcggcgacctattattgcaaacagagctataccctg cgcacctttggcggcggcaccaaactggaaattaaa (SEQ ID NO.: 207) |
| 155 A35795-VL | gatgtggtgatgacccagagcccggcgtttctgagcgtgaccccgggcgaaaaagtgacc attacctgcaaaagcagccagagcctgtttaacagcgaaacccagaaaaaactatctggcg tggtatcagcagaaaccgggccaggcgccgcgcctgctgatttattgggcgagcacccgc gaaagcggcgtgccgagccgctttagcggcagcggcagcggcaccgatttacccctgacc attagcagcctgcagccggaagattttgcgacctattattgcaaacagagctataccctg cgcacctttggcggcggcaccaaactggaaattaaa (SEQ ID NO.: 208) |
| 156 A35797-VL | gatattcagatgacccagagcccgagcagcctgagcgcgagcgtgggcgatcgcgtgacc attacctgcaaaagcagccagagcctgtttaacagcgaaaaccagaaaaaactatctggcg tggtatcagcagaaaccgggccagccgccgaaactgctgatttattgggcgagcacccgc gaaagcggcgtgccgagccgctttagcggcagcggcagcggcaccgattttaccctgacc attagcagcctgcagccggaagattttgcgacctattattgcaaacagagctataccctg cgcacctttggcggcggcaccaaactggaaattaaa (SEQ ID NO.: 209) |

TABLE 10-continued

| V_H/V_L SEQ ID NO. and identifier | Exemplary nucleic acid (coding) sequence |
|---|---|
| 157 A35799-VL | gatgtggtgatgacccagagcccggcgtttctgagcgtgaccccgggcgaaaaagtgacc attacctgcaaaagcagccagagcctgtttaacagcgaaacccagaaaaactatctggcg tggtatcagcagaaaccgggccagccgccgaaactgctgatttattgggcgagcacccgc gaaagcggcgtgccgagccgctttagcggcagcggcagcggcaccgattttacccctgacc attagcagcctgcagccggaagattttgcgacctattattgcaaacagagctataccctg cgcacctttggcggcggcaccaaactggaaattaaa (SEQ ID NO.: 210) |
| 158 A35805-VL | gatgtggtgatgacccagagcccggcgtttctgagcgtgaccccgggcgaaaaagtgacc attacctgcaaaagcagccagagcctgtttaacagcgaaacccagaaaaactatctggcg tggtatcagcagaaaccgggccagccgccgaaactgctgatttattgggcgagcacccgc gaaagcggcgtgccgagccgctttagcggcagcggcagcggcaccgattttaccttttacc attagcagcctggaagcggaagatgcggcgacctattattgcaaacagagctataccctg cgcacctttggcggcggcaccaaactggaaattaaa (SEQ ID NO.: 211) |
| 159 137F VL1 | gatattgtgatgacccagagcccggatagcctggcggtgagcctgggcgaacgcgcgacc attaactgcaaaagcagccagagcctgtttaacagcgaaacccagaaaaactatctggcg tggtatcagcagaaaccgggccagccgccgaaactgctgatttattgggcgagcacccgc gaaagcggcgtgccggatcgctttagcggcagcggcagcggcaccgattttaccctgacc attagcagcctgcaggcggaagatgtggcggtgtattattgcaaacagagctataccctg cgcacctttggccagggcaccaaactggaaattaaa (SEQ ID NO.: 212) |
| 160 137F VL2 | gatattgtgatgacccagagcccggatagcctggcggtgagcctgggcgaacgcgcgacc attacctgcaaaagcagccagagcctgtttaacagcgaaacccagaaaaactatctggcg tggtatcagcagaaaccgggccagccgccgaaactgctgatttttgggcgagcacccgc gaaagcggcgtgccggatcgctttctgggcagcggcagcggcaccgattttaccctgacc attagcagcctgcaggcggaagatgtggcggtgtattattgcaaacagagctataccctg cgcacctttggccagggcaccaaactggaaattaaa (SEQ ID NO.: 213) |
| 161 137F VL1b | gatattgtgatgacccagagcccggatagcctggcggtgagcctgggcgaacgcgcgacc attaactgcaaaagcagccagagcctgtttaacagcgaaacccagaaaaactatctggcg tggtatcagcagaaaccgggccagccgccgaaactgctgatttattgggcgagcacccgc gaaagcggcgtgccggatcgctttagcggcagcggcagcggcaccgattttaccctgacc attagcagcctgcaggcggaagatgtggcggtgtattattgcaaacagagctataccctg cgcacctttggccagggcaccaaactggaaattaaa (SEQ ID NO.: 214) |
| 162 137F VL1c | gatattgtgatgacccagagcccggatagcctggcggtgagcctgggcgaacgcgcgacc attacctgcaaaagcagccagagcctgtttaacagcgaaacccagaaaaactatctggcg tggtatcagcagaaaccgggccagccgccgaaactgctgatttttgggcgagcacccgc gaaagcggcgtgccggatcgctttagcggcagcggcagcggcaccgattttaccctgacc attagcagcctgcaggcggaagatgtggcggtgtattattgcaaacagagctataccctg cgcacctttggccagggcaccaaactggaaattaaa (SEQ ID NO.: 215) |
| 163 137F VL1d | gatattgtgatgacccagagcccggatagcctggcggtgagcctgggcgaacgcgcgacc atgacctgcaaaagcagccagagcctgtttaacagcgaaacccagaaaaactatctggcg tggtatcagcagaaaccgggccagccgccgaaactgctgatttttgggcgagcacccgc gaaagcggcgtgccggatcgctttagcggcagcggcagcggcaccgattttaccctgacc attagcagcgtgcaggcggaagatgtggcggtgtattattgcaaacagagctataccctg cgcacctttggccagggcaccaaactggaaattaaa (SEQ ID NO.: 216) |
| 164 A35775-VH | gtgcatgaagtgcagctggtgcagagcggcgcggaagtgaaaaaaccgggcgaaagcctg aaaattagctgcaaaggcagcggctatagctttaccaactttatattcattgggtgcgc caggcgccgggccagcgcctggaatggatgggcagcatttatccgaactatggcgataac gcgtataaccagaaatttaaagatcgctttgtgtttagcctggataccagcgtgagcacc gcgtatctgcagattagcagcctgaaagcggaagataccgcggtgtattattgcgcgcgc ggctatagctatgcgatggattattgggccagggcaccaccgtgaccgtgagcagc (SEQ ID NO.: 217) |
| 165 A35783-VH | gaagtgcagctggtgcagagcggcgcggaagtgaaaaaaccgggcgaaagcctgaaaatt agctgcaaaggcagcggctatagctttaccaactttatattcattgggtgcgccaggcg cgcggccagcgcctggaatggattggcagcatttatccgaactatggcgataccgcgtat aaccagaaatttaaagatcgctttgtgtttagcctggataccagcgtgagcaccgcgtat ctgcagattagcagcctgaaagcggaagataccgcggtgtattattgcgcgcgcggctat agctatgcgatggattattgggccagggcaccaccgtgaccgtgagcagc (SEQ ID NO.: 218) |
| 166 A35774-VH | gaagtgcagctggtgcagagcggcgcggaagtgaaaaaaccgggcgaaagcctgaaaatt agctgcaaaggcagcggctatagctttaccaactttatattcattgggtgcgccaggcg ccgggccagcgcctggaatggatgggcagcatttatccgaactatggcgataccgcgtat aaccagaaatttaaagatcgctttgtgtttagcctggataccagcgtgagcaccgcgtat ctgcagattagcagcctgaaagcggaagataccgcggtgtattattgcgcgcgcggctat agctatgcgatggattattgggccagggcaccaccgtgaccgtgagcagc (SEQ ID NO.: 219) |

TABLE 10-continued

| $V_H/V_L$ SEQ ID NO. and identifier | Exemplary nucleic acid (coding) sequence |
|---|---|
| 167 A36443-VH | gaagtgcagctggtgcagagcggcgcggaagtgaaaaaaccgggcgcgaccgtgaaaatt agctgcaaagtgagcggctatacctttaccaactttttatattcattgggtgcgccaggcg cgcggccagcgcctggaatggattggcagcatttatccgaactatggcgataccgcgtat aaccagaaatttaaagatcgcgtgaccattaccgcggataaaagcaccagcaccgcgtat atggaactgagcagcctgcgcagcgaagataccgcggtgtattattgcgcgcgcggctat agctatgcgatggattattggggccagggcaccaccgtgaccgtgagcagc (SEQ ID NO.: 220) |
| 168 A35777-VH | gaagtgcagctggtgcagagcggcgcggaagtgaaaaaaccgggcgcgaccgtgaaaatt agctgcaaagtgagcggctatacctttaccaactttttatattcattgggtgcgccaggcg ccgggcaaaggcctggaatggatgggcagcatttatccgaactatggcgataccgcgtat aaccagaaatttaaagatcgcgtgaccattaccgcggataaaagcaccagcaccgcgtat atggaactgagcagcctgcgcagcgaagataccgcggtgtattattgcgcgcgcggctat agctatgcgatggattattggggccagggcaccaccgtgaccgtgagcagc (SEQ ID NO.: 221) |
| 169 A35789-VH | gaagtgcagctggtgcagagcggcgcggaagtgaaaaaaccgggcgaaagcctgaaaatt agctgcaaaggcagcggctatagctttaccaactttttatattcattgggtgcgccagatg ccgggcaaaggcctggaatggatgggcagcatttatccgaactatggcgataccgcgtat aaccagaaatttaaagatcgcgtgaccattaccgcggataaaagcaccagcaccgcgtat atggaactgagcagcctgcgcagcgaagataccgcggtgtattattgcgcgcgcggctat agctatgcgatggattattggggccagggcaccaccgtgaccgtgagcagc (SEQ ID NO.: 222) |
| 170 A36448-VH | gaagtgcagctggtgcagagcggcgcggaagtgaaaaaaccgggcgaaagcctgaaaatt agctgcaaaggcagcggctatagctttaccaactttttatattcattgggtgcgccagatg ccgggcaaaggcctggaatggatgggcagcatttatccgaactatggcgataccgcgtat aaccagaaatttaaagatcgctttgtgtttagcctggataccagcgtgagcaccgcgtat ctgcagattagcagcctgaaagcggaagataccgcggtgtattattgcgcgcgcggctat agctatgcgatggattattggggccagggcaccaccgtgaccgtgagcagc (SEQ ID NO.: 223) |
| 171 A36437-VH | gaagtgcagctggtgcagagcggcgcgcggaagtgaaaaaaccgggcgaaagcctgaaaatt agctgcaaaggcagcggctatagctttaccaactttttatattcattgggtgcgccagatg ccgggcaaaggcctggaatggatgggcagcatttatccgaactatggcgataccgcgtat aaccagaaatttaaagatcgctttgtgtttagcctggataccagcgtgagcaccgcgtat ctgcagattagcagcctgaaagcggaagataccgcggtgtattattgcgcgcgcggctat agctatgcgatggattattggggccagggcaccaccgtgaccgtgagcagc (SEQ ID NO.: 224) |
| 172 135C VH1 | caggtgcagctggtgcagagcggcgcggaagtgaaaaaaccgggcgcgagcgtgaaagtg agctgcaaagcgagcggctatacctttaccaactttttatattcattgggtgcgccaggcg ccgggccagggcctggaatggatgggcagcatttatccgaactatggcgataccgcgtat aaccagaaatttaaagatcgcgtgaccatgacccgcgataccagcaccagcaccgtgtat atggaactgagcagcctgcgcagcgaagataccgcggtgtattattgcgcgcgcggctat agctatgcgatggattattggggccagggcaccctggtgaccgtgagcagc (SEQ ID NO.: 225) |
| 173 135C VH2 | caggtgcagctggtgcagagcggcgcggaagtgaaaaaaccgggcgcgagcgtgaaagtg agctgcaaagcgagcggctatacctttaccaactttttatattcattgggtgcgccaggcg ccgggccagggcctggaatggatgggcagcatttatccgaactatggcgataccgcgtat aaccagaaatttaaagatcgcgtgaccatgaccgtggataaaagcaccagcaccgtgtat atggaactgcgcagcctgcgcagcgaagataccgcggtgtattattgcgcgcgcggctat agctatgcgatggattattggggccagggcaccctggtgaccgtgagcagc (SEQ ID NO.: 226) |
| 174 135C VH3 | caggtgcagctggtgcagagcggcgcggaagtgaaaaaaccgggcgcgagcgtgaaagtg agctgcaaagcgagcggctatacctttaccaactttttatattcattgggtgaaacaggcg catggccagggcctggaatggatgggcagcatttatccgaactatggcgataccgcgtat aaccagaaatttaaagatcgcgtgaccatgaccgtggataaaagcaccagcaccgtgtat atggaactgcgcagcctgcgcagcgaagataccgcggtgtattattgcgcgcgcggctat agctatgcgatggattattggggccagggcaccctggtgaccgtgagcagc (SEQ ID NO.: 227) |
| 175 135C VH1b | caggtgcagctggtgcagagcggcgcggaagtgaaaaaaccgggcgcgagcgtgaaagtg agctgcaaagcgagcggctatacctttaccaactttttatattcattgggtgcgccaggcg ccgggccagggcctggaatggattggcagcatttatccgaactatggcgataccgcgtat aaccagaaatttaaagatcgcgtgaccatgaccgtggataccagcaccagcaccgtgtat atggaactgagcagcctgcgcagcgaagataccgcggtgtattattgcgcgcgcggctat agctatgcgatggattattggggccagggcaccctggtgaccgtgagcagc (SEQ ID NO.: 228) |
| 176 135C VH1c | caggtgcagctggtgcagagcggcgcggaagtgaaaaaaccgggcgcgagcgtgaaaatg agctgcaaagcgagcggctatacctttaccaactttttatattcattgggtgcgccaggcg ccgggccagggcctggaatggattggcagcatttatccgaactatggcgataccgcgtat aaccagaaatttaaagatcgcgcgaccctgaccgtggataccagcaccagcaccgcgtat |

TABLE 10-continued

| V$_H$/V$_L$ SEQ ID NO. and identifier | Exemplary nucleic acid (coding) sequence |
|---|---|
| | atggaactgagcagcctgcgcagcgaagataccgcggtgtattattgcgcgcgcggctat agctatgcgatggattattggggccagggcaccctggtgaccgtgagcagc (SEQ ID NO.: 229) |
| 177<br>135C VH1d | caggtgcagctggtgcagagcggcgcggaagtgaaaaaaccgggcgcgagcgtgaaaatg agctgcaaagcgagcggctataccctttaccaactttatattcattgggtgcgccaggcg ccgggccagggcctggaatggattggcagcatttatccgaactatggcgataccgcgtat aaccagaaatttaaagatcgcgcgaccctgaccgtggataaaagcaccagcaccgcgtat atggaactgagcagcctgcgcagcgaagataccgcggtgtattattgcgcgcgcggctat agctatgcgatggattattggggccagggcaccctggtgaccgtgagcagc (SEQ ID NO.: 230) |
| 178<br>A35775-VL | gatattcagatgacccagagcccgagcagcgtgagcgcgagcgtgggcgatcgcgtgacc attacctgcagcgcgagccagggcattagcggcgatctgaactggtatcagcagaaaccg ggccaggcgccgcgcctgctgatttatcataccagcagcctgcatagcggcgtgccgagc cgctttagcggcagcggcagcggcaccgattttaccctgaccattagcagcctgcagccg gaagattttgcgacctattattgccagtattatagcaaagatctgctgacctttggcggc ggcaccaaactggaaattaaa (SEQ ID NO.: 231) |
| 179<br>A35783-VL | gatattcagatgacccagagcccgagcagcctgagcgcgagcgtgggcgatcgcgtgacc attacctgcagcgcgagccagggcattagcggcgatctgaactggtatcagcagaaaccg ggcaaaaccccgaaactgctgatttatcataccagcagcctgcatagcggcgtgccgagc cgctttagcggcagcggcagcggcaccgattttaccctgaccattagcagcctgcagccg gaagattttgcgacctattattgccagtattatagcaaagatctgctgacctttggcggc ggcaccaaactggaaattaaa (SEQ ID NO.: 232) |
| 180<br>A35774-VL | gatattcagatgacccagagcccgagcagcgtgagcgcgagcgtgggcgatcgcgtgacc attacctgcagcgcgagccagggcattagcggcgatctgaactggtatcagcagaaaccg ggcaaagcgccgaaactgctgatttatcataccagcagcctgcatagcggcgtgccgagc cgctttagcggcagcggcagcggcaccgattttaccctgaccattagcagcctgcagccg gaagattttgcgacctattattgccagtattatagcaaagatctgctgacctttggcggc ggcaccaaactggaaattaaa (SEQ ID NO.: 233) |
| 181<br>A36443-VL | gatattcagatgacccagagcccgagcagcgtgagcgcgagcgtgggcgatcgcgtgacc attacctgcagcgcgagccagggcattagcggcgatctgaactggtatcagcagaaaccg ggccaggcgccgcgcctgctgatttatcataccagcagcctgcatagcggcgtgccgagc cgctttagcggcagcggcagcggcaccgaatttaccctgaccattagccgcctggaaccg gaagattttgcggtgtattattgccagtattatagcaaagatctgctgacctttggcggc ggcaccaaactggaaattaaa (SEQ ID NO.: 234) |
| 182<br>A35777-VL | gatattcagatgacccagagcccgagcaccctgagcgcgagcgtgggcgatcgcgtgacc attacctgcagcgcgagccagggcattagcggcgatctgaactggtatcagcagaaaccg ggccaggcgccgcgcctgctgatttatcataccagcagcctgcatagcggcgtgccgagc cgctttagcggcagcggcagcggcaccgattttaccctgaccattagcagcctgcagccg gaagattttgcgacctattattgccagtattatagcaaagatctgctgacctttggcggc ggcaccaaactggaaattaaa (SEQ ID NO.: 235) |
| 183<br>A35789-VL | gatattcagatgacccagagcccgagcagcgtgagcgcgagcgtgggcgatcgcgtgacc attacctgcagcgcgagccagggcattagcggcgatctgaactggtatcagcagaaaccg ggccaggcgccgcgcctgctgatttatcataccagcagcctgcatagcggcattccggcg cgctttagcggcagcggcagcggcaccgattttaccctgaccattagccgcctggaaccg gaagattttgcggtgtattattgccagtattatagcaaagatctgctgacctttggcggc ggcaccaaactggaaattaaa (SEQ ID NO.: 236) |
| 184<br>A36448-VL | gatattcagatgacccagagcccgagcaccctgagcgcgagcgtgggcgatcgcgtgacc attacctgcagcgcgagccagggcattagcggcgatctgaactggtatcagcagaaaccg ggcaaaaccccgaaactgctgatttatcataccagcagcctgcatagcggcgtgccgagc cgctttagcggcagcggcagcggcaccgattttaccctgaccattagcagcctgcagccg gaagattttgcgacctattattgccagtattatagcaaagatctgctgacctttggcggc ggcaccaaactggaaattaaa (SEQ ID NO.: 237) |
| 185<br>A36437-VL | gatattcagatgacccagagcccgagcaccctgagcgcgagcgtgggcgatcgcgtgacc attacctgcagcgcgagccagggcattagcggcgatctgaactggtatcagcagaaaccg ggccaggcgccgcgcctgctgatttatcataccagcagcctgcatagcggcattccggcg cgctttagcggcagcggcagcggcaccgattttaccctgaccattagcagcctgcagccg gaagattttgcggtgtattattgccagtattatagcaaagatctgctgacctttggcggc ggcaccaaactggaaattaaa (SEQ ID NO.: 238) |
| 186<br>135C VL1 | gatattcagatgacccagagcccgagcagcctgagcgcgagcgtgggcgatcgcgtgacc attacctgcagcgcgagccagggcattagcggcgatctgaactggtatcagcagaaaccg ggcaaagcgccgaaactgctgatttatcataccagcagcctgcatagcggcgtgccgagc cgctttagcggcagcggcagcggcaccgattttaccctgaccattagcagcctgcagccg gaagattttgcgacctattattgccagtattatagcaaagatctgctgacctttggcggc ggcaccaaactggaaattaaa (SEQ ID NO.: 239) |

TABLE 10-continued

| $V_H/V_L$ SEQ ID NO. and identifier | Exemplary nucleic acid (coding) sequence |
|---|---|
| 187<br>135C VL2 | gatattcagatgacccagagcccgagcagcctgagcgcgagcgtgggcgatcgcgtgacc<br>attacctgcagcgcgagccagggcattagcggcgatctgaactggtatcagcagaaaccg<br>ggcaaagcggtgaaactgctgatttatcataccagcagcctgcatagcggcgtgccgctg<br>cgctttagcggcagcggcagcggcaccgattatacccctgaccattagcagcctgcagccg<br>gaagattttgcgacctattattgccagtattatagcaaagatctgctgacctttggcggc<br>ggcaccaaactggaaattaaa (SEQ ID NO.: 240) |
| 188<br>135C VL3 | gatattcagatgacccagagcccgagcagcctgagcgcgagcgtgggcgatcgcgtgacc<br>attacctgcagcgcgagccagggcattagcggcgatctgaactggtatcagcagaaaagc<br>gatggcgcggtgaaactgctgatttatcataccagcagcctgcatagcggcgtgccgctg<br>cgctttagcggcagcggcagcggcaccgattatacccctgaccattagcagcctgcagccg<br>gaagattttgcgacctattattgccagtattatagcaaagatctgctgacctttggcggc<br>ggcaccaaactggaaattaaa (SEQ ID NO.: 241) |
| 189<br>135C VL1b | gatattcagatgacccagagcccgagcagcctgagcgcgagcgtgggcgatcgcgtgacc<br>attacctgcagcgcgagccagggcattagcggcgatctgaactggtatcagcagaaaccg<br>ggcaaagcgccgaaactgctgatttatcataccagcagcctgcatagcggcgtgccgagc<br>cgctttagcggcagcggcagcggcaccgattatacccctgaccattagcagcctgcagccg<br>gaagattttgcgacctattattgccagtattatagcaaagatctgctgacctttggcggc<br>ggcaccaaactggaaattaaa (SEQ ID NO.: 242) |
| 190<br>135C VL1c | gatattcagatgacccagagcccgagcagcctgagcgcgagcgtgggcgatcgcgtgacc<br>attacctgcagcgcgagccagggcattagcggcgatctgaactggtatcagcagaaaccg<br>ggcaaagcggtgaaactgctgatttatcataccagcagcctgcatagcggcgtgccgagc<br>cgctttagcggcagcggcagcggcaccgattatacccctgaccattagcagcctgcagccg<br>gaagattttgcgacctattattgccagtattatagcaaagatctgctgacctttggcggc<br>ggcaccaaactggaactgaaaaaactgatgaacccgcagcgcagcaccgtgtggtattaa<br>(SEQ ID NO.: 243) |

As is understood by those of ordinary skill in the art, the sequences used above may be modified for use by, for instance, codon optimization or other technique(s) available in the art. Methods for producing such preparations are described herein and/or otherwise well-known and available by and those of ordinary skill in the art.

To determine the amino acid sequences of the variable regions (e.g., CDRs) of interest, hybridoma cells from mice immunized with a PD-1 antigen/immunogen may be selected using the functional assays described herein and cloning techniques that are readily available to those of ordinary skill in the art. For instance, to isolate and sequence nucleic acids encoding the heavy and light chain variable regions of the selected hybridomas, total RNA may be extracted from fresh hybridoma cells using TRIzol reagent according to the manufacturer's protocol. cDNA may be synthesized from the RNA using isotype-specific anti-sense primers or universal primers using standard techniques (e.g., following the technical manual of PrimeScript™ 1st Strand cDNA Synthesis Kit). Polymerase chain reaction (PCR) may then be performed to amplify the nucleic acids encoding the variable regions (heavy and light chains) of the antibody produced by the selected hybridoma, which may then be cloned into a standard cloning vector separately and sequenced. Colony PCR screening may then be performed to identify clones with inserts of correct sizes. Preferably, no less than five single colonies with inserts of correct sizes are sequenced for each antibody variable region. Standard protocols may then be used for the expression and purification of the anti-PD-1 antibodies. For instance, hybridoma clones may be grown in serum-free medium and the cell culture broth centrifuged and then filtered. The filtered supernatant containing the antibody may then be loaded onto an affinity column (e.g., Protein A) column, washed and eluted with an appropriate buffer (e.g., Pierce IgG elute buffer). The eluted fractions may then be pooled and buffer-exchanged into PBS, pH 7.2. The purified antibody may then be analyzed by SDS-PAGE and Western blot by using standard protocols for molecular weight, yield and purity. Size exclusion chromatography HPLC may then be performed on an appropriate column (e.g., TSK GEL-G3000 SWXL column (Tosoh)) for biophysical characterization in order to ensure high antibody purity (generally >90%) with low presence of protein aggregates. These procedures were used in isolating and sequencing nucleic acids encoding SEQ ID NOS. 1-190 from selected cells and other sources. These techniques, variations thereof, and/or other may also be of use for these purposes as would be understood by those of ordinary skill in the art.

Nucleic acid molecules encoding one or more PD-1 binding agents may be contained within a viral and/or a non-viral vector. In one embodiment, a DNA vector is utilized to deliver nucleic acids encoding one or more PD-1 binding agents to the patient. In doing so, various strategies may be utilized to improve the efficiency of such mechanisms including, for example, the use of self-replicating viral replicons (Caley, et al. 1999. *Vaccine*, 17: 3124-2135; Dubensky, et al. 2000. *Mol. Med.* 6: 723-732; Leitner, et al. 2000. *Cancer Res.* 60: 51-55), codon optimization (Liu, et al. 2000. *Mol. Ther.*, 1: 497-500; Dubensky, supra; Huang, et al. 2001. *J. Virol.* 75: 4947-4951), in vivo electroporation (Widera, et al. 2000. *J. Immunol.* 164: 4635-3640), incorporation of nucleic acids encoding co-stimulatory molecules, cytokines and/or chemokines (Xiang, et al. 1995. *Immunity*, 2: 129-135; Kim, et al. 1998. *Eur. J. Immunol.*, 28: 1089-1103; Iwasaki, et al. 1997. *J. Immunol.* 158: 4591-3601; Sheerlinck, et al. 2001. *Vaccine*, 19: 2647-2656), incorporation of stimulatory motifs such as CpG (Gurunathan, supra; Leitner, supra), sequences for targeting of the endocytic or ubiquitin-processing pathways (Thomson, et al. 1998. *J. Virol.* 72: 2246-2252; Velders, et al. 2001. *J. Immunol.* 166: 5366-5373), prime-boost regimens (Gurunathan, supra; Sullivan, et al. 2000. *Nature*, 408: 605-609; Hanke, et al. 1998. *Vaccine*, 16: 439-445; Amara, et al. 2001.

Science, 292: 69-74), proteasome-sensitive cleavage sites, and the use of mucosal delivery vectors such as *Salmonella* (Darji, et al. 1997. *Cell*, 91: 765-775; Woo, et al. 2001. *Vaccine*, 19: 2945-2954). Other methods are known in the art, some of which are described below. Various viral vectors that have been successfully utilized for introducing a nucleic acid to a host include retrovirus, adenovirus, adeno-associated virus (AAV), herpes virus, and poxvirus, among others. The vectors may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, ca). "Non-viral" plasmid vectors may also be suitable in certain embodiments. Preferred plasmid vectors are compatible with bacterial, insect, and/or mammalian host cells. Such vectors include, for example, PCR-ii, PCR3, and pcDNA3.1 (Invitrogen, San Diego, Calif.), pBSii (Stratagene, La Jolla, Calif.), pet15 (Novagen, Madison, Wis.), pGEX (Pharmacia Biotech, Piscataway, N.J.), pEGFp-n2 (Clontech, Palo Alto, Calif.), pETI (Bluebacii, Invitrogen), pDSR-alpha (PCT pub. No. WO 90/14363) and pFASTBACdual (Gibco-BRL, Grand island, NY) as well as Bluescript® plasmid derivatives (a high copy number COLe1-based phagemid, Stratagene Cloning Systems, La Jolla, Calif.), PCR cloning plasmids designed for cloning TAQ-amplified PCR products (e.g., TOPO™ TA Cloning® kit, PCR2.1® plasmid derivatives, Invitrogen, Carlsbad, Calif.). Bacterial vectors may also be used. These vectors include, for example, *Shigella, Salmonella, Vibrio cholerae, Lactobacillus, Bacille Calmette Guérin* (BCG), and *Streptococcus* (see for example, WO 88/6626; WO 90/0594; WO 91/13157; WO 92/1796; and WO 92/21376). Many other non-viral plasmid expression vectors and systems are known in the art and may be use. Other delivery techniques may also suffice including, for example, DNA-ligand complexes, adenovirus-ligand-DNA complexes, direct injection of DNA, $CaPO_4$ precipitation, gene gun techniques, electroporation, and colloidal dispersion systems. Colloidal dispersion systems include macromolecule complexes, nanocapsules, microspheres, beads, and lipid-based systems including oil-in-water emulsions, micelles, mixed micelles, and liposomes. The preferred colloidal system is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, *Trends Biochem. Sci.*, 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

A cultured cell comprising the vector is also provided. The cultured cell may be a cultured cell transfected with the vector or a progeny of the cell, wherein the cell expresses the immunogenic polypeptide. Suitable cell lines are known to those of skill in the art and are commercially available, for example, through the American Type Culture Collection (ATCC). The transfected cells can be used in a method of producing an immunogenic polypeptide. The method comprises culturing a cell comprising the vector under conditions that allow expression of the immunogenic polypeptide, optionally under the control of an expression sequence. The immunogenic polypeptide can be isolated from the cell or the culture medium using standard protein purification methods.

The skilled artisan has many suitable techniques for using the binding agents (e.g., antibodies) described herein to identify biological samples containing proteins that bind thereto. For instance, antibodies may be utilized to isolate PD-1 using, for example, immunoprecipitation or other capture-type assay. This well-known technique is performed by attaching the antibody to a solid support or chromatographic material (e.g., a bead coated with Protein A, Protein G and/or Protein L). The bound antibody is then introduced into a solution either containing or believed to contain the PD-1 (e.g., an HIV-infected T cell lysate). PD-1 may then bind to the antibody and non-binding materials are washed away under conditions in which the PD-1 remains bound to the antibody. The bound protein may then be separated from the antibody and analyzed as desired. Similar methods for isolating a protein using an antibody are well-known in the art. The binding agents (e.g., antibodies) may also be utilized to detect PD-1 within a biological sample. For instance, the antibodies may be used in assays such as, for example, flow cytometric analysis, ELISA, immunoblotting (e.g., western blot), in situ detection, immunocytochemistry, and/or immunhistochemistry. Methods of carrying out such assays are well-known in the art.

The binding agents described herein may be also be used to determine the presence of a disease state in a patient, to predict prognosis, or to determine the effectiveness of a chemotherapeutic or other treatment regimen. Expression profile assays, performed as described herein or as is otherwise known in the art, may be used to determine the relative level of expression of PD-1. The level of expression may then be correlated with base (e.g., control) levels to determine whether a particular disease is present within the patient, the patient's prognosis, or whether a particular treatment regimen is effective. For example, if the patient is being treated with a particular anti-infective regimen, an increased or decreased level of expression of PD-1 in the patient's tissues (e.g., in peripheral blood, breast tissue biopsy) may indicate the regimen is worsening or improving the load of the infectious agent in that host. The increase or decrease in expression may indicate the regimen is having or not having the desired effect and another therapeutic modality may therefore be selected.

It is also possible to use the binding agents described herein as reagents in drug screening assays to test, for example, new drug candidates. The reagents may be used to ascertain the effect of a drug candidate on the expression of the immunogenic target in a cell line, or a cell or tissue of a patient. The expression profiling technique may be combined with high throughput screening techniques to allow rapid identification of useful compounds and monitor the effectiveness of treatment with a drug candidate (see, for example, Zlokarnik, et al., Science 279, 84-8 (1998)). Drug candidates may be chemical compounds, nucleic acids, proteins, antibodies, or derivatives therefrom, whether naturally occurring or synthetically derived. Drug candidates thus identified may be utilized, among other uses, as pharmaceutical compositions for administration to patients or for use in further screening assays.

In some embodiments, the binding agents are in purified form. A "purified" binding agent (e.g., antibody) may be one that is separated from at least about 50% of the proteins and/or other components with which it is initially found (e.g., as part of a hybridoma supernatant or ascites preparation in the case of a monoclonal antibody). A purified binding agent (e.g., antibody) may be one that is separated from at least about 50%, 60%, 75%, 90%, or 95% of the proteins and/or other components with which it is initially found.

The polypeptides and nucleic acids described herein may be combined with one or more pharmaceutically acceptable carriers prior to administration to a host. A pharmaceutically acceptable carrier is a material that is not biologically or otherwise undesirable, e.g., the material may be administered to a subject, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. Suitable pharmaceutical carriers and their formulations are described in, for example, *Remington's: The Science and Practice of Pharmacy, 21$^{st}$ Edition*, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained-release preparations such as semipermeable matrices of solid hydrophobic polymers containing polypeptides or fragments thereof. Matrices may be in the form of shaped articles, e.g., films, liposomes or microparticles. It will be apparent to those persons skilled in the art that certain carriers may be more preferable depending upon, for instance, the route of administration and concentration of composition being administered. Carriers are those suitable for administration of polypeptides and/or fragments thereof to humans or other subjects. Pharmaceutical compositions may also include carriers, thickeners, diluents, buffers, preservatives, surface active agents, adjuvants, immunostimulants, in addition to the immunogenic polypeptide. Pharmaceutical compositions may also include one or more active ingredients such as antimicrobial agents, antiinflammatory agents and anesthetics. The pharmaceutical composition may be administered orally, parentally, by inhalation spray, rectally, intranodally, or topically in dosage unit formulations containing conventional pharmaceutically acceptable carriers, adjuvants, and vehicles. The term "pharmaceutically acceptable carrier" or "physiologically acceptable carrier" as used herein refers to one or more formulation materials suitable for accomplishing or enhancing the delivery of a nucleic acid, polypeptide, or peptide as a pharmaceutical composition. A "pharmaceutical composition" is a composition comprising a therapeutically effective amount of a nucleic acid or polypeptide. The terms "effective amount" and "therapeutically effective amount" each refer to the amount of a binding agent, nucleic acid or the like used to observe the desired therapeutic effect (e.g., restore T cell function).

Methods for treating one or more disease conditions (e.g., HIV or cancer) in a mammalian host comprising administering to the mammal at least one or more effective doses of one or more binding agents (and/or derivative(s) thereof) described herein are also provided. In some embodiments, the binding agent is a monoclonal antibody or fragment or derivative thereof comprising one or more of SEQ ID NOS. 1-190, and/or shown in Tables 1A and 1B. For example, in some preferred embodiments, the binding agent or at least one of the binding agents in a combination may include SEQ ID NOS. 143 and 155 (e.g., as in antibody A35795), SEQ ID NOS. 166 and 180 (e.g., as in antibody A35774), SEQ ID NOS. 176 and 189 (e.g., as in antibody 135CH1cL1b), and/or SEQ ID NOS. 176 and 190 (e.g., as in antibody 135CH1cL1c), and/or a conservatively or non-conservatively substituted variant thereof. Preferably, the CDR regions (i.e., SEQ ID NOS. 1-138) of such binding agents are not substituted. The one or more binding agents may be administered in a dosage amount of about 0.1 to about 50 mg/kg, about 1 to about 30 mg/kg, or about 5 to about 30 mg/kg (e.g., about any of 0.1, 0.2, 0.25, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, or 40 mg/kg). The amounts of each individual binding agent may be the same or different. In certain embodiments, the one or more binding agents may be administered to the mammal (e.g., intradermally, intravenously, orally, rectally) at about 10 mg/kg one or more times. When multiple doses are administered, the doses may comprise about the same or different amount of binding agent in each dose. The doses may also be separated in time from one another by the same or different intervals. For instance, the doses may be separated by about any of 6, 12, 24, 36, 48, 60, 72, 84, or 96 hours, one week, two weeks, three weeks, one month, two months, three months, four months, five months, six months, seven months, eight months, nine months, 10 months, 11 months, 12 months, 1.5 years, 2 years, 3 years, 4 years, 5 years, or any time period before, after, and/or between any of these time periods. In some embodiments, the binding agents may be administered in conjunction with other agents (e.g., anti-infective agents and/or chemotherapeutic agent). Such other agents may be administered about simultaneously with the binding agents, or at a different time and/or frequency. Other embodiments of such methods may also be appropriate as could be readily determined by one of ordinary skill in the art.

To assist the skilled artisan in using the binding agent(s) such as antibodies described herein, the same may be provided in kit format. A kit including such binding agent such as antibodies and optionally other components necessary for using the antibodies to detect cells expressing PD-1 is provided. The binding agent(s) such as antibodies of the kit may be provided in any suitable form, including frozen, lyophilized, or in a pharmaceutically acceptable buffer such as TBS or PBS. The kit may also include other reagents required for utilization of the antibodies in vitro or in vivo such as buffers (e.g., TBS, PBS), blocking agents (solutions including nonfat dry milk, normal sera, Tween-20 Detergent, BSA, or casein), and/or detection reagents (e.g., goat anti-mouse IgG biotin, streptavidin-HRP conjugates, allophycocyanin, B-phycoerythrin, R-phycoerythrin, peroxidase, detectable labels, and other labels and/or staining kits (e.g., ABC Staining Kit, Pierce)). The kits may also include other reagents and/or instructions for using the antibodies in commonly utilized assays described above such as, for example, flow cytometric analysis, ELISA, immunoblotting (e.g., western blot), in situ detection, immunocytochemistry, immunhistochemistry. In one embodiment, the kit provides a binding agent in purified form. In another embodiment, the binding agent may be provided in biotinylated form either alone or along with an avidin-conjugated detection reagent (e.g., antibody). In another embodiment, the kit includes a binding agents comprising one or more detectable labels that may be used to directly detect PD-1. Buffers and the like required for using any of these systems are well-known in the art and/or may be prepared by the end-user or provided as a component of the kit. The kit may also include a solid support containing positive- and negative-control protein and/or tissue samples. For example, kits for performing spotting or western blot-type assays may include control cell or tissue lysates for use in SDS-PAGE or nylon or other membranes containing pre-fixed control samples with additional space for experimental samples. Kits for visualization of PD-1 in cells on slides may include pre-formatted slides containing control cell or tissue samples with additional space for experimental samples. Other embodiments of kits are also contemplated herein as would be understood by those of ordinary skill in the art.

Thus, this disclosure provides a binding agent that binds PD-1 agonistically or antagonistically. In some embodiments, the binding agent is a polypeptide comprising at least one amino acid sequence selected from the group consisting of SEQ ID NOS. 1-190 and/or shown in Tables 1A and 1B. In some embodiments, the binding agent is a polypeptide comprising one or more combinations of SEQ ID NOS. 1-138 (e.g., as shown in Tables 1A and/or 1B), and/or any of SEQ ID NOS. 139-190. In some embodiments, the binding agent is an antibody. In some embodiments, the binding agent is a polypeptide such as an antibody comprising a heavy chain CDR1 amino acid sequence selected from the group consisting of SEQ ID NOS. 1-23. In some embodiments, the binding agent is a polypeptide such as an antibody comprising a heavy chain CDR2 amino acid sequence selected from the group consisting of SEQ ID NOS. 24-46. In some embodiments, the binding agent is a polypeptide such as an antibody comprising a heavy chain CDR3 amino acid sequence selected from the group consisting of SEQ ID NOS. 47-69. In some embodiments, the binding agent is a polypeptide such as an antibody comprising a light chain CDR1 amino acid sequence selected from the group consisting of SEQ ID NOS. 70-92. In some embodiments, the binding agent is a polypeptide such as an antibody comprising a heavy chain CDR2 amino acid sequence selected from the group consisting of SEQ ID NOS. 93-115. In some embodiments, the binding agent is a polypeptide such as an antibody comprising a heavy chain CDR3 amino acid sequence selected from the group consisting of SEQ ID NOS. 116-138. In some embodiments, the binding agent is a polypeptide such as an antibody comprising one or more of SEQ ID NOS. 164-190, and/or a conservatively or non-conservatively substituted derivative thereof. In some embodiments, the binding agent is a polypeptide such as an antibody comprising one or more of SEQ ID NOS. 139-150 and one or more of SEQ ID NOS. 151-163. In some embodiments, the binding agent is a polypeptide such as an antibody comprising one or more of SEQ ID NOS. 164-177 and one or more of SEQ ID NOS. 178-190. For example, in some preferred embodiments, the binding agent or at least one of the binding agents in a combination may include SEQ ID NOS. 143 and 155 (e.g., as in antibody A35795), SEQ ID NOS. 166 and 180 (e.g., as in antibody A35774), SEQ ID NOS. 176 and 189 (e.g., as in antibody 135C H1cL1b), and/or SEQ ID NOS. 176 and 190 (e.g., as in antibody 135C H1cL1c), and/or a conservatively or non-conservatively substituted variant thereof (as shown in, e.g., Tables 5-8). In some embodiments, the binding agent comprises the combinations of CDRs shown in Tables 1A and/or 1B and/or has the properties described in any one or more of Tables 3 and/or Tables 11-13.

In some embodiments, the binding agent is derived from or related to (e.g., by sequence or derivation) a human antibody, human IgG, human IgG1, human IgG2, human IgG2a, human IgG2b, human IgG3, human IgG4, human IgM, human IgA, human IgA1, human IgA2, human IgD, human IgE, canine antibody, canine IgGA, canine IgGB, canine IgGC, canine IgGD, chicken antibody, chicken IgA, chicken IgD, chicken IgE, chicken IgG, chicken IgM, chicken IgY, goat antibody, goat IgG, mouse antibody, mouse IgG, pig antibody, and/or rat antibody, and/or a derivative thereof. In some embodiments, the derivative may be selected from the group consisting of an $F_{ab}$, $F_{ab2}$, Fab' single chain antibody, $F_v$, single chain (e.g., scF$_v$), $V_{HH}/V_H$, mono-specific antibody, bispecific antibody, trimeric antibody, multi-specific antibody, multivalent antibody, chimeric antibody, canine-human chimeric antibody, canine-mouse chimeric antibody, antibody comprising a canine Fc, humanized antibody, human antibody, caninized antibody, CDR-grafted antibody, shark antibody, nanobody, and/or canelid antibody, among others. Such antibodies, fragments and the like may be produced using any of the widely available techniques for doing so. For instance, humanized antibodies may be produced using the procedures described in U.S. Pat. No. 9,090,994 B2 (Zhang et al.) and/or using one of the widely available kits and/or systems (e.g., as may be available from commercial entities such as GenScript® (e.g., the FASEBA system)). In some embodiments, the binding agent may be a humanized antibody comprising one or more of the amino acid sequence(s) (or be encoded by a nucleic acid sequence encoding such amino acid sequence(s)) of SEQ ID NOS. 139-190, and/or derivatives or variants thereof (e.g., conservatively substituted derivatives or variants thereof). Other embodiments are also contemplated as would be understood by those of ordinary skill in the art.

In some embodiments, the binding agent may be a humanized antibody comprising at least one of SEQ ID NOS. 139-150 and at least one of SEQ ID NOS. 151-163, and/or derivatives or variants thereof (e.g., conservatively substituted derivatives or variants thereof). In some embodiments, the binding agent exhibits approximately (i.e., within about any of 250%, 200%, 150%, 100%, 75%, 50%, 25%, 20%, 15%, or 10% of; and/or a minimum 10 nM affinity (KD $10^{-8}$ M)) the binding affinities (ka ($M^{-1}/s^{-1}$), kd ($s^{-1}$), and KD (M)) for human and monkey PD-1 demonstrated by humanized antibody A35796 (comprising SEQ ID NOS. 140 and 152), humanized antibody A35793 (comprising SEQ ID NOS. 141 and 153), humanized antibody A35818 (comprising SEQ ID NOS. 142 and 154), humanized antibody A35795 (comprising SEQ ID NOS. 143 and 155), humanized antibody A35797 (comprising SEQ ID NOS. 144 and 156), humanized antibody A35799 (comprising SEQ ID NOS. 145 and 157), humanized antibody A35805 (comprising SEQ ID NOS. 146 and 158) as shown in Table 12; humanized antibody 137F VH1/VL1 (comprising SEQ ID NOS. 147 and 159), humanized antibody 137F VH2/VL2 (comprising SEQ ID NOS. 148 and 160), humanized antibody 137F VH1b/VL1b (comprising SEQ ID NOS. 149 and 161), humanized antibody 137F VH1c/VL1c (comprising SEQ ID NOS. 150 and 162), or a humanized antibody comprising 137F VH1b/VL1d (comprising SEQ ID NO. 149 and 163). In some embodiments, 137F VL1d may be combined (or paired) with any other 137F variable heavy chain.

In other embodiments, the binding agent may be a humanized antibody comprising at least one of SEQ ID NOS. 164-177 and at least one of SEQ ID NOS. 178-190, and/or derivatives or variants thereof (e.g., conservatively substituted derivatives or variants thereof). In some embodiments, the binding agent exhibits approximately (i.e., within about 25%, about 20%, about 15%, or about 10% of; and/or a minimum 10 nM affinity ($K_D$ $10^{-8}$ M)) the binding affinities (ka ($M^{-1}/s^{-1}$), kd ($s^{-1}$), and $K_D$ (M)) for human and monkey PD-1 as humanized antibody A35775 (comprising SEQ ID NOS. 164 and 178), humanized antibody A35783 (comprising SEQ ID NOS. 165 and 179), humanized antibody A35774 (comprising SEQ ID NOS. 166 and 180), humanized antibody A36443 (comprising SEQ ID NOS. 167 and 181), humanized antibody A35777 (comprising SEQ ID NOS. 168 and 182), humanized antibody A35789 (comprising SEQ ID NOS. 169 and 183), humanized antibody A36448 (comprising SEQ ID NOS. 170 and 184), or humanized antibody A36437 (comprising SEQ ID NOS. 171 and 185), as shown in Table 13; humanized antibody 135C VH1/VL1 (comprising SEQ ID NOS. 172 and 186), humanized antibody 135C VH2/VL2 (comprising SEQ ID NOS. 173 and 187), humanized antibody 135C VH3/VL3 (comprising SEQ ID NOS. 174 and 188), humanized antibody 135C VH1b/VL1b (comprising SEQ ID NOS. 175 and 189), humanized antibody 135C VH1c/VL1b (comprising SEQ ID NOS. 176 and 189), humanized antibody 135C VH1c/VL1c (comprising SEQ ID NOS. 176 and 190), or a humanized antibody comprising 135C VH1d/VL1c (comprising SEQ ID NO. 177 and 190).

In some embodiments, the binding agent comprises at least a least a first and second specificity, the first being against PD-1 and the second being against a different antigen (e.g., an antigen of an infectious agent such as HIV (e.g., Env) and/or a tumor antigen). In some embodiments, the binding agent and/or derivative thereof may comprise a detectable label fixably attached thereto. In some embodiments, the binding agent of any one and/or derivative thereof comprises an effector moiety (e.g., a cytotoxic drug, toxin, diphtheria A chain, exotoxin A chain, ricin A chain, abrin A chain, curcin, crotin, phenomycin, enomycin, and radiochemical) fixably attached thereto. In some embodiments, polynucleotides encoding one or more binding agents are also provided (e.g., as an expression vector). Host cells comprising and/or expressing the polypeptide products of such polynucleotides are also provided. In some embodiments, compositions comprising at least one binding agent or derivative; at least one isolated polynucleotide; at least one expression vector; and/or, at least one host cell; or a combination thereof; and, a pharmaceutically acceptable carrier are also provided.

This disclosure also provides methods for detecting PD-1 on a cell, the method comprising contacting a test biological sample with a binding agent or derivative described herein and detecting the binding agent bound to the biological sample or components thereof. Such methods may be an in vivo method or an in vitro method. In some embodiments, the method may comprise comparing the amount of binding to the test biological sample or components thereof to the amount of binding to a control biological sample or components thereof, wherein increased binding to the test biological sample or components thereof relative to the control biological sample or components thereof indicates the presence of a cell expressing PD-1 in the test biological sample (e.g., mammalian blood). In some embodiments, a system for identifying a PD-1 antibody binding agent by assaying the candidate binding agent by the exhaustion functional recovery assay (EFRA); determining the affinity of the candidate binding agent for PD-1; and, determining the nucleotide sequence of the CDR of the candidate binding agent is provided.

In some embodiments, a kit for detecting the expression of PD-1 in or on a cell, the kit comprising a binding agent or derivative thereof and instructions for use. In some embodiments, the binding agent and/or derivative thereof is in lyophilized form.

In some embodiments, this disclosure provides methods for treating, preventing and/or ameliorating an infectious disease, cancer and/or autoimmunity in a mammal comprising administering to the mammal at least one effective dose of a pharmaceutical composition comprising a binding agent or derivative thereof. In some embodiments, the infectious disease is human immunodeficiency virus (HIV). In some embodiments, the binding agent and/or derivative thereof used to treat infectious disease and/or cancer is a PD-1 antagonist. In some embodiments, the binding agent and/or derivative thereof used to treat an autoimmune condition is a PD-1 agonist. In some embodiments, multiple doses are administered to the animal. In some embodiments, the binding agent and/or derivative thereof may be administered in a dosage amount of about 0.1 to about 50 mg/kg, about 1 to about 30 mg/kg, or about 5 to about 30 mg/kg (e.g., about any of 0.1, 0.2, 0.25, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, or 40 mg/kg).

This disclosure also provides combinations of PD-1 binding agents. In some embodiments, the combination comprises a first binding agent that blocks the interaction of PD-1 and PD-L1 and a second binding agent that does not block the interaction of PD-1 and PD-L1. Exemplary combinations may include, for instance, one or more of the blocking anti-PD-1 antibodies and one or more of the non-blocking binding agents described herein, such as any one or more of those comprising the amino acid sequences of 135C12 (SEQ ID NOS. 17, 40, 63, 86, 109, and 132), 139D6 (SEQ ID NOS. 2, 25, 48, 71, 94, and 117), 135D1 (SEQ ID NOS. 3, 26, 49, 72, 95, and 118), and/or 136B4 (SEQ ID NOS. 19, 42, 65, 88, 111, and 134). Exemplary embodiments include the combination of blocking antibody MK3475 (Pembrolizumab) or a blocking binding agent comprising the amino acid sequences SEQ ID NOS. 8, 31, 54, 77, 100, and 123 (137F2) with a non-blocking PD-1 binding agent comprising the amino acid sequences SEQ ID NOS. 17, 40, 63, 86, 109, and 132 (135C12). As illustrated in FIG. 9A, B, both of these exemplary combinations results in an enhanced relief of functional exhaustion and increased proliferation of HIV-specific CD8⁺ T cells beyond what either antibody alone can achieve. Other exemplary non-blocking antibodies that may be useful in combination with the blocking antibodies MK3475 or 137F2 and the non-blocking P2 patch-specific (M4 (FIG. 3A, B)) binding agent 135D1 (comprising SEQ ID NOS. 3, 26, 49, 72, 95, and 118), and/or binding agent 139D6 (SEQ ID NOS. 2, 25, 48, 71, 94, and 117), and/or the non-blocking P2 patch-specific (M17 (FIG. 3A, E)) binding agent 136B4 (comprising SEQ ID NOS. 19, 42, 65, 88, 111, and 134). Other combinations may also be suitable as may be determined by those of ordinary skill in the art.

Such combinations may be used for any use described herein or as may be otherwise ascertained by those of ordinary skill in the art. For instance, such combinations may be used in the methods for treating, preventing and/or ameliorating an infectious disease, cancer and/or autoimmunity in a mammal described herein. In some embodiments, methods for treating inflammation in a subject comprising administering a combination of at least two antagonistic PD-1 binding agents, wherein each of said binding agents having specificity for different epitopes on PD-1, at least one of said binding agents being blocking of the interaction of PD-1 and PD-L1, and at least one of said binding agents is non-blocking of the interaction of PD-1 and PD-L1 are also provided. This disclosure also provides methods for treating a chronic neurodegenerative condition in a subject by administering a combination of at least two antagonistic PD-1 binding agents, wherein each of said binding agents having specificity for different epitopes on PD-1, at least one of said binding agents being blocking of the interaction of PD-1 and PD-L1, and at least one of said binding agents is non-blocking of the interaction of PD-1 and PD-L1. In some embodiments, the chronic neurodegenerative condition is Alzheimer's disease. This disclosure also provides methods for inhibiting the growth of a tumor cell such as a human tumor cell in vivo, such as in the treatment of cancer, the method comprising administering a combination of at least two antagonistic PD-1 binding agents, wherein each of said binding agents having specificity for different epitopes on PD-1, at least the first of said binding agents being blocking of the interaction of PD-1 and PD-L1, and at least the second of said binding agents is non-blocking of the interaction of PD-1 and PD-L1. In some embodiments, the combination may comprise a blocking binding agent, such as an antibody, comprises at least one of RASKGVSTSGYSYLH (SEQ ID NO. 287), LASYLES (SEQ ID NO. 288), QHSRDLPLT (SEQ ID NO. 289), NYYMY (SEQ ID NO. 290), GINPSNGGTNFNEKFKN (SEQ ID NO. 291), and/or RDYRFDMGFDY (SEQ ID NO. 292); MK3475; and/or Keytruda® (also referred to as pembrolizumab). In some embodiments, the non-blocking binding agent, such as an antibody, may comprise at least one of SEQ ID NOS. 17, 40, 63, 86, 109 and 132 or any one or more of SEQ ID NOS. 164-190 (such as SEQ ID NOS. 176 and 190), and/or a derivative comprising at least one amino acid substitution thereof. In some embodiments, multiple doses are administered to the mammal which may be separated by about a week, about two weeks, about three weeks, or preferably about a month, or longer.

This disclosure also provides methods for producing the binding agents described herein by expressing the binding agent in a cell and isolating the binding agent from the cell or a culture supernatant of the cell. In some embodiments, such methods may further comprise expressing a nucleic acid encoding such binding agent(s). In some embodiments, such methods may also include combining the binding agent(s) following isolation with one or more pharmaceutically acceptable excipients.

Methods for producing a combination(s) of binding agents, such as a first binding agent that blocks the interaction of PD-1 and PD-L1 and a second binding agent that does not block the interaction of PD-1 and PD-L1, are also provided by this disclosure. In some embodiments, the second binding agent binds PD-1. In some embodiments, the first and/or second binding agents are antibodies such monoclonal antibodies or fragments or derivatives thereof. In some embodiments, the second binding agent comprises the amino acid sequences SEQ ID NOS. 17, 40, 63, 86, 109, and 132 (e.g., 135C12); SEQ ID NOS. 2, 25, 48, 71, 94 and 117 (e.g., 139D6); SEQ ID NOS. 3, 26, 49, 72, 95, and 118 (e.g., 135D1); and/or SEQ ID NOS. 19, 42, 65, 88, 111, and 134 (e.g., 136B4). In some embodiments, these methods may further include the addition of a pharmaceutically acceptable excipient.

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto.

As used herein, a subject or a host is meant to be an individual. The subject can include domesticated animals, such as cats and dogs, livestock (e.g., cattle, horses, pigs, sheep, and goats), laboratory animals (e.g., mice, rabbits, rats, guinea pigs) and birds. In one aspect, the subject is a mammal such as a primate or a human.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

The term "combined" or "in combination" or "in conjunction" may refer to a physical combination of agents that are administered together or the use of two or more agents in a regimen (e.g., administered separately, physically and/or in time) for treating, preventing and/or ameliorating a particular disease.

When the terms treat, prevent, and/or ameliorate or derivatives thereof are used herein in connection with a given treatment for a given condition (e.g., preventing cancer or infection by HIV), it is meant to convey that the treated patient either does not develop a clinically observable level of the condition at all, or develops it more slowly and/or to a lesser degree than he/she would have absent the treatment. These terms are not limited solely to a situation in which the patient experiences no aspect of the condition whatsoever. For example, a treatment will be said to have prevented the condition if it is given during exposure of a patient to a stimulus that would have been expected to produce a given manifestation of the condition, and results in the patient's experiencing fewer and/or milder symptoms of the condition than otherwise expected. For instance, a treatment can "prevent" infection by resulting in the patient's displaying only mild overt symptoms of the infection; it does not imply that there must have been no penetration of any cell by the infecting microorganism.

Similarly, reduce, reducing, and reduction as used herein in connection with prevention, treatment and/or amelioration of a given condition by a particular treatment typically refers to a subject developing an infection more slowly or to a lesser degree as compared to a control or basal level of developing an infection in the absence of a treatment (e.g., administration of one or more PD-1 binding agents). A reduction in the risk of infection may result in the patient's displaying only mild overt symptoms of the infection or delayed symptoms of infection; it does not imply that there must have been no penetration of any cell by the infecting microorganism.

All references cited within this disclosure are hereby incorporated by reference in their entirety. Certain embodiments are further described in the following examples. These embodiments are provided as examples only and are not intended to limit the scope of the claims in any way.

EXAMPLES

Example 1

Generation and Characterization of PD-1 Binding Agents

Four mice strains (total of 16 mice) have been immunized with two PD-1 proteins, i.e. human PD-1 Fc fusion protein and a human PD-1 monomeric protein. Mice showing serum reactivity to PD-1 expressed on activated human T lymphocytes have been selected for generation of anti-PD-1 hybridoma cell lines. A total of 240 PD-1 hybridoma cell lines were selected for producing antibodies that bind to recombinant PD-1 protein. The primary criteria for the first round of antibodies selection were: i) staining of PD-1 on activated human T lymphocytes by flow cytometry; ii) diversity of CDR VH and VL sequences as compared to those of the existing anti-PD-1 antibodies; and, iii) epitope mapping performed by competitive binding studies with PD-1 conjugated Luminex beads with two commercially available anti-PD-1 antibodies binding to different epitopes on PD-1. A second round of selection was then carried out by: iv) affinity binding assays (not a primary criteria as it does not correlate with the stimulatory potential of anti-PD-1 antibodies); v) evaluation of anti-PD-1 antibodies that bind PD-1 and are either blocking or non-blocking with the binding of PD-L1 in a Luminex biochemical assay; and, vi) functional characterization of antibodies as agonist (not able to restore T-cells from functional exhaustion) or antagonist (able to restore T-cells from functional exhaustion). In these studies, the antibodies were tested and differentiated based on their ability to rescue proliferation in HIV-specific exhausted CD8 T-cells.

In a primary screen of antibody supernatants from individual cell cultured hybridoma cell clones, the EFRA assay was carried out to evaluate the functional effect of anti-PD1 antibodies on the proliferation of HIV-specific CD8 T cells. Antibody clones E8-3, C2-3, E1-3, F3-3, H8-3, C10-2, G2-1, G3-2, H2-1, and H4-2 were found to act as PD-1 antagonists and stimulate proliferation while antibody clones C8-1 and G10-2 are agonistic and promote the PD-1 negative regulatory effect. The level of proliferation induced by the peptide control (Pep 8) is just below 1% and the induced proliferation by the Merck MK-3475 anti-PD1 antibody is just above 2%. Antibodies of interest identified by these processes underwent a second round of subcloning and the resulting hybridoma clones were used for the production and purification of the antibodies in Table 3. Binding assays were carried out with the purified anti-PD-1 antibodies to ensure that the subclones retained their affinity for PD-1. The concentration response binding of anti-PD-1 antibodies to cell surface PD-1 was evaluated on activated CD4 T-cells.

The EFRA provides for the selection of binding agents that restore T-cells from functional exhaustion but are not necessarily limited to binding agents that do not interfere with the interaction between PD-1 and its biological ligand(s) (e.g., PD-L1 or PD-L2). An embodiment of the EFRA was to identify such binding agents (antibodies) that bind PD-1. Epitope mapping of antibody binding to PD-1 was performed with two separate biochemical assays. In one assay, competitive binding to PD-1 Fc fusion protein labeled beads was evaluated between one of two commercial anti-PD-1 antibodies (clones EH12.2H7 and J116) and the anti-PD-1 antibodies listed (also described in Table 3). Four classes of monoclonal antibodies binding to distinct epitopes were identified based on this assay. These are: class 1 (competitive with the EH12.2H7 commercial monoclonal antibody clone that blocks the interaction of PD-1 with PD-L1), class 2 (competitive with the J116 commercial monoclonal antibody clone that binds PD-1 but does not effectively block the interaction of PD-1 with PD-L1), class 3 (competitive with both the EH12.2H7 and J116 commercial monoclonal antibodies), and class 4 (non-competitive with either the EH12.2H7 or J116 commercial antibodies). Antibodies were binned into one of the four binding classes and the relative binding of these antibodies for cell surface PD-1 is represented by the mean fluorescence intensity (MFI) relative to a control anti-PD-1 antibody. These results showed that tight binding antibodies were identified from all four binding classes. A second Luminex binding assay was used to directly evaluate if an anti-PD-1 antibody blocks the interaction between PD-1 and PD-L1. This assay was carried out using PD-1 Fc fusion protein coated beads that were incubated with 20 nM of an anti-PD-1 antibody from Table 3 followed by an incubation of the PD-1/antibody complex with different concentrations of biotinylated PD-L1. Binding curves were compared with the binding of PD-L1 in the absence of an anti-PD-1 antibody competitor. It was found that a some anti-PD-1 antibody from Table 3 can completely block the interaction between PD-1 and PD-L1 (antibody 137F2 shown in FIG. 1 A). Antibodies listed in Table 3 as non-blocking of the PD-1/PD-L1 interaction results in a shift in the binding affinity of PD-L1 for PD-1, but do not block the interaction when concentration of PD-L1 are increased (antibodies 135C12 and 136B4 shown in FIGS. 1B and C, respectively). In one interpretations, these antibodies are either non-competitive or partially competitive with the PD-1/PD-L1 interaction. Some of these antibodies were also shown to exhibit statistically significant increases in proliferation relative to controls. Class 1 antibodies (competitive with the EH12.2H7 commercial monoclonal antibody that blocks the interaction of PD-1 with PD-L1) or blocking in the PD-1/PD-L1 intereaction assay were generally determined to provide improved proliferative restoration. In combining the data from multiple EFRA experiments and using MK-3475 as the common comparator, select antibodies described in Table 2 exhibited equivalent or statistically improved activity (p<0.007) compared to the benchmark MK-3475 antibody.

Example 2

Antibody Combinations

Combinations of antibodies binding to different PD-1 epitopes were found to enhance restoration of HIV peptide specific CD8+ T-cell proliferation in a functional exhaustion recovery assay. Synergy between antibody types was also observed. For instance, it was determined that class 1 (MK-3475) and class 2 (139D6) antibodies are able to simultaneously bind PD-1. While the maximum stimulation observed for MK-3475 is consistently about 200% relative to the HIV peptide, combinations of MK-3475 and 139D6 monoclonal antibodies at 5 µg/ml each exhibited synergy with a 288% increase in HIV-specific CD8 T cell proliferation relative to the HIV peptide control alone or a 144% increased proliferation relative to MK-3475 or 139D6 added alone. This synergistic increase in proliferation was observed in several experimental tests with a statistically significant p value of 0.007. As a comparison, addition of 10 µg/ml of either MK-3475 or 139D6 alone did not result in an increased proliferation in the EFRA. Thus, the combination of a first binding agent that blocks the interaction of PD-1 and PD-L1 with a second binding agent that does not block the interaction of PD-1 and PD-L1 has been determined to act synergistically to rescue T cells from exhaustion.

Example 3

Epitope Mapping of Anti-PD-1 Antibodies

Figure 8:
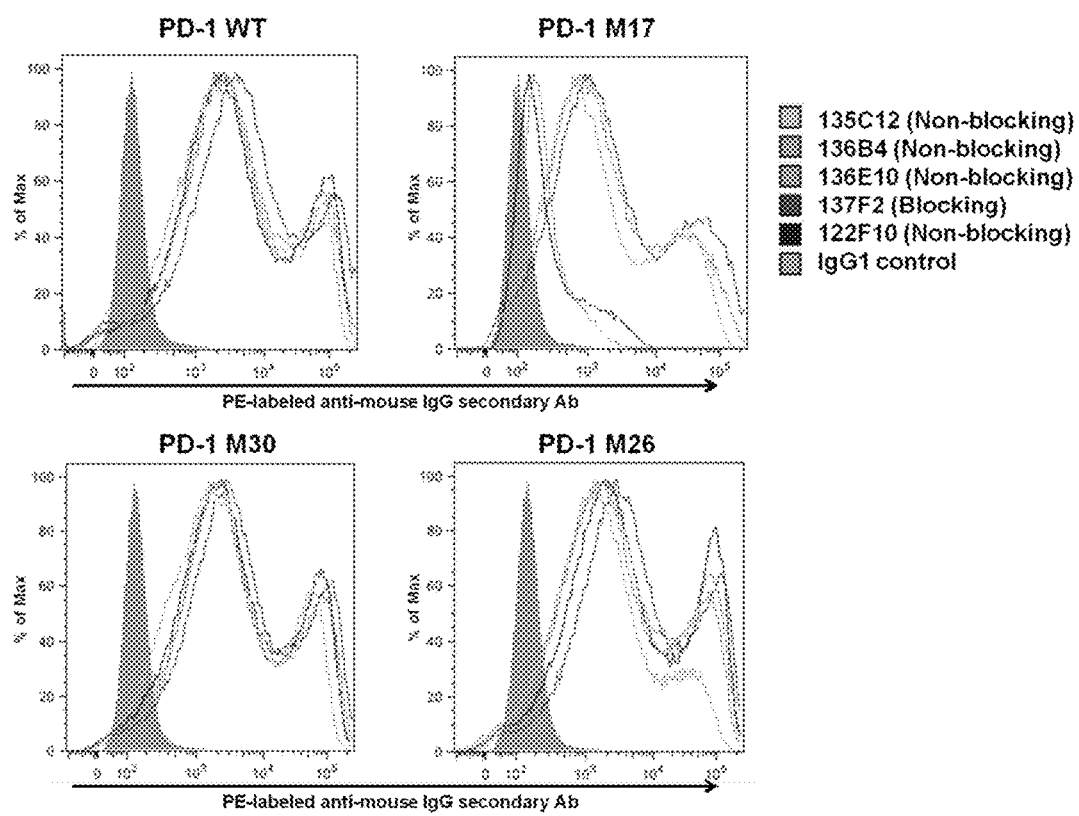
FIG. 8. Binding of blocking and non-blocking anti-PD-1 antibodies to modified PD-1 proteins M17, M30 and M26 (wild-type (WT) control (SEQ ID NO. 275)) expressed at the surface of transiently transfected HeLa cells.
Figure 13:
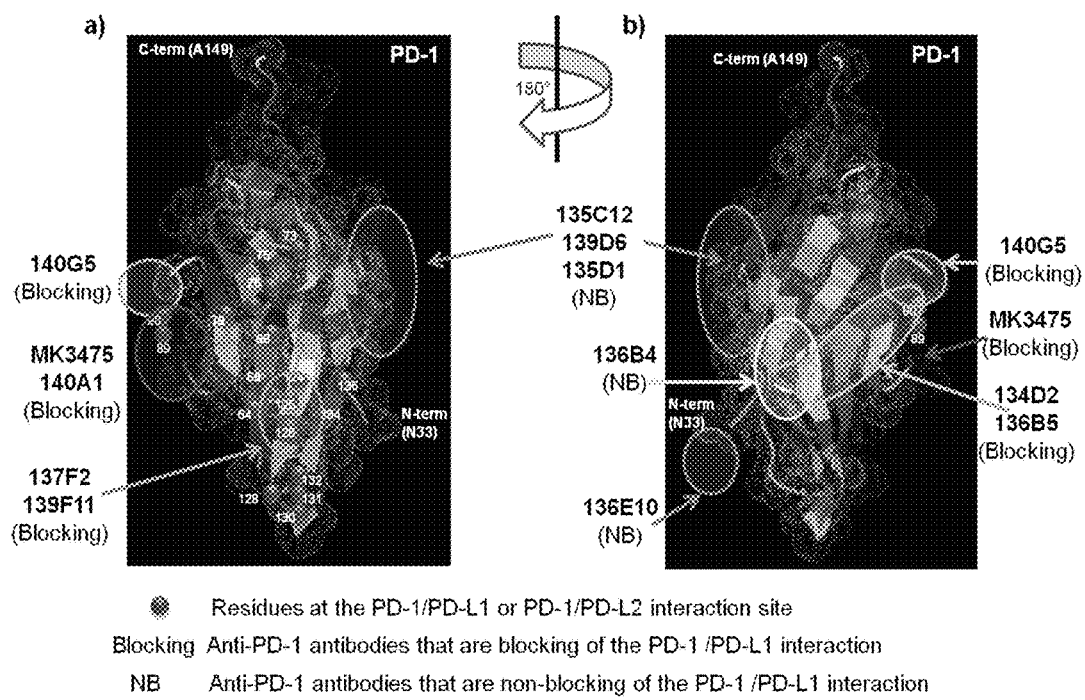
FIG. 13a-b. Epitope mapping of antibody binding sites to the structure of PD-1 using a combination of both site directed mutagenesis and antibody competition binding results.

Preliminary epitope mapping evaluations relied on biochemical competitive binding assay studies between commercially available anti-PD-1 antibodies (EH12.2H3 and J116) and the newly identified anti-PD-1 antibodies defined in this patent. This procedure allowed us to categorize the antibodies into one of four binding classes based on binding competitively or non-competitively with either of the two commercial antibodies. A more precise method of defining the antibody binding epitopes on PD-1 is to monitor the interaction of the antibody with different PD-1 proteins that have discreet amino acid substitutions at solvent accessible residues. If these residues are important for tight binding of the anti-PD-1 antibodies, the substitution can result in a reduced binding for the PD-1 protein. These studies were performed by site directed mutagenesis of the PD-1 gene encoded within the pReceiver-M67 mammalian expression vector under the control of CMV promoter. Using the 3RRQ PDB published structural data for the PD-1 protein, 31 different PD-1 clones were designed with single, double or triple amino acid substitutions at solvent accessible residues. The residues implicated in the interaction between PD-1 and PD-L1/L2 were determined based on the published crystal structure of the complex between human PD-1 and PD-L2 (Lazar-Molnar, PNAS, 2008, p10483-10488) and mapped to the PD-1 structure in FIG. 2 as numbered spheres (the numbering corresponding to amino acid residues of human PD-1 (FIG. 2H, SEQ ID NO. 275)). Substitutions were selected at residues that are implicated in the PD-1/PD-L1 interaction (represented by M10, M11, M12, M14, M23, M24, M25), or on opposite or adjacent surfaces of the PD-1 protein not directly implicated in the PD-L1 interaction (represented by M1, M2, M3, M4, M5, M6, M7, M8, M9, M13, M15, M16, M17, M18, M19, M20, M21, M22, M26, M27, M28, M29, M30, M31) and are defined in FIG. 3. The PD-1 encoding DNA vectors were then used to transiently transfect HeLa cells using the Lipofectamine 2000 transfection reagent. Cells were incubated in a cell culture incubator at 37° C. for 36-48 hours to allow for cell surface expression of the PD-1 protein, and then cells were re-suspended and incubated for 30 minutes with between 0.3 to 2 µg/ml of a given anti-PD-1 antibody selected from Table 3. Following a wash step, cells were stained with a PE labeled anti-mouse IgG secondary antibody then analyzed by flow cytometry. In each experiment, the wild type PD-1 protein was used as a positive control for antibody binding and several antibodies binding different epitopes on PD-1 (as determine by being blocking or non-blocking of the PD-1/PD-L1 interaction or from competitive binding studies with commercially available PD-1 clones) were evaluated in parallel to monitor the relative expression level of the PD-1 protein with the different amino acid substitutions. All anti-PD-1 antibodies tested from Table 3 bound specifically to HeLa cells transfected with wild type PD-1 but not to cells that were transfected with an empty vector control. All mutant PD-1 proteins expressed at near wild type levels or gave a significant shift in mean fluorescence intensity relative to an untransfected control when stained with anti-PD-1 antibodies that were either blocking or non-blocking of the PD-1/PD-L1 interaction. A select set of antibodies from Table 3 were then systematically tested for their ability to bind either wild type or mutant PD-1 protein expressed at the cell surface of the transfected HeLa cells. These results are summarized in Table 11 with the mutations indicated that abrogate or reduce binding for each of the different anti-PD-1 antibody clones. Flow cytometry histograms depicted in FIGS. 4-8 provide examples of different antibodies that either bind effectively or with reduced affinity to HeLa cells transfected with the indicated mutant PD-1 constructs. As predicted, antibodies that were shown to be blocking of the PD-1/PD-L1 interaction in a biochemical assay (MK-3475, 137F2, 140G5, and 139F11) also bound to epitopes on PD-1 that are overlapping with this interaction site. Consistent with the biochemical PD-1/PD-L1 interaction studies, antibodies that were non-blocking of the PD-1/PD-L1 interaction (136B4, 135C12, 136E10) bound to distinct epitopes that were distal to amino acid residues implicated in the PD-1/PD-L1 interaction. In FIG. 8, a significant shift in binding to the M17 PD-1 protein was observed for 136B4 and 122F10 antibodies, whereas a small shift in binding for the 135C12 antibody was observed for the M26 PD-1 protein. These differences highlight the fact that 136B4 and 135C12 have CDR loops that belong to distinct families and bind to different epitopes on PD-1 that both overlap with the P2 patch as depicted in FIG. 13.

TABLE 11

Epitope mapping of the different anti-PD-1 antibody clones that are either blocking or non-blocking of the PD-1/PD-L1 interaction.

| Clone | Affinity* (nM) | Antibody competition with Binding Class** | the PD-1/PD-L1 interaction*** | EFRA % relative to peptide alone‡ | PD-1 mutation that induces a reduced affinity |
|---|---|---|---|---|---|
| 137F2 | 1.5 | 1 | Blocking | 250% | M23 |
| 139F11 | 3.1 | 1 | Blocking | 250% | M23 |

TABLE 11-continued

Epitope mapping of the different anti-PD-1 antibody clones that are either blocking or non-blocking of the PD-1/PD-L1 interaction.

| Clone | Affinity* (nM) | Binding Class** | Antibody competition with the PD-1/PD-L1 interaction*** | EFRA % relative to peptide alone‡ | PD-1 mutation that induces a reduced affinity |
|---|---|---|---|---|---|
| 140G5 | 1.6 | 1 | Blocking | 205% | M15 |
| 135C12 | 1.7 | 2 | Non-blocking | 195% | M4, M17§, M18§, M26§, M28§, M31§ |
| 139D6 | 2.4 | 2 | Non-blocking | 195% | M4 |
| 135D1 | 6.5 | 2 | Non-blocking | 187% | M4 |
| 136B4 | 1.4 | 2 | Non-blocking | 185% | M17, M18 |
| 140A1 | 1.4 | 3 | Blocking | 160% | M13 |
| 122F10 | 2.2 | 4 | Non-blocking | 146% | M17 |
| 134D2 | 4.8 | 4 | Blocking | 205% | M13, M15, M17§ |
| 136E10 | 7.1 | 4 | Non-blocking | 148% | M1 |
| MK3575 | 0.6 | 1 | Blocking | 198% | M13, M14 |

*Binding affinity for the antibodies listed in Table 1 was evaluated by FACS staining of endogenous cell surface PD-1 on activated CD4 T cells.
**Binding class was determined by Luminex assay competitive binding studies. Binding class 1 mAb clones are competitive with the EH12.2H7 clone commercial antibody, class 2 mAb clones are competitive with the J116 clone commercial antibody, class 3 mAb clones are competitive with both EH12.2H7 and J116 antibodies and class 4 mAb clones bind in the presence of both EH12.2H7 and J116 antibodies.
***Antibody competition with the PD-1/PD-L1 interaction was determined in a second Luminex binding assay. In this assays, PD-1 Fc fusion protein coated beads were incubated in the absence or presence of an anti-PD-1 antibody from Table 3 at a concentration of 20 nM. A fixed concentration of 1.25 nM biotinylated PD-L1, approximately equivalent to the $IC_{50}$ of the PD-1/PD-L1 interaction, was then incubated with the PD-1/antibody complex and PD-L1 binding was detected by fluorescence with phycoerythrin labeled streptavidin. Based on PD-L1 binding to the PD-1/antibody complex, antibodies were defined as being blocking or non-blocking of the PD-1/PD-L1 interaction.
‡Proliferative effect is evaluated using a CFSE assay (an embodiment of the Exhaustion Functional Recovery Assay, "EFRA"). PBMCs isolated from a chronically infected HIV subject were stimulated with an HIV specific peptide in the presence and absence of an anti-PD-1 antibody. Following a 6 day incubation, proliferation of HIV specific CD8 T cells was evaluated in the anti-PD-1 treated samples relative to the peptide alone control.
§Small shift in antibody binding to mutant PD-1 encoding amino acid substitutions.
NA = not available Example 4

Non-blocking Antibody Epitope Connected with a Novel Antagonistic Action of PD-1

Figure 10:
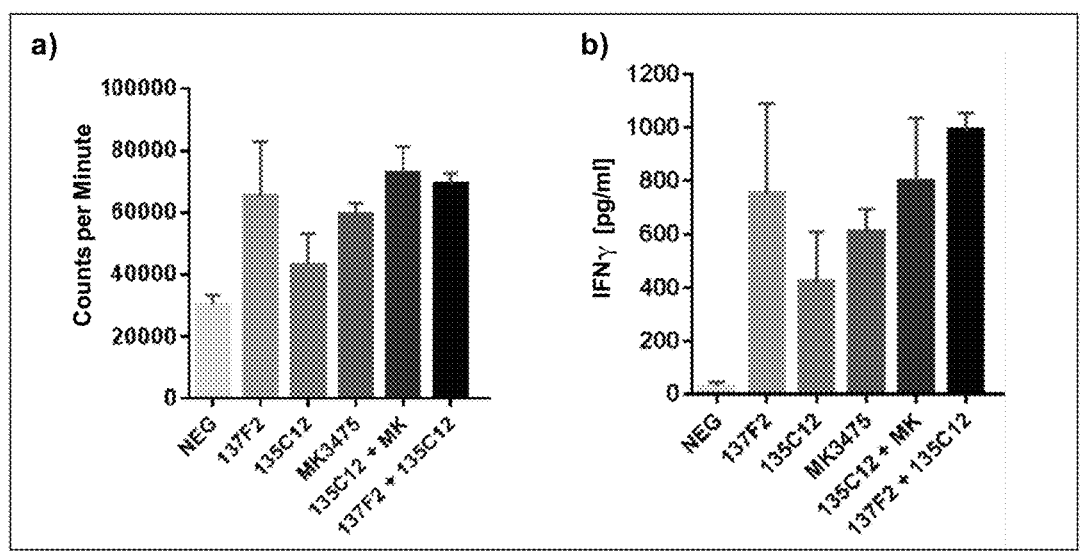
FIG. 10. Individual antagonistic anti-PD-1 antibodies and combinations of two antagonistic anti-PD-1 antibodies binding to different epitopes on PD-1 result in enhanced proliferation (a) and IFNγ production (b) from PD-1+ memory CD4 T cells in a mixed lymphocyte reaction assay.

Antibodies binding to diverse epitopes on PD-1 were evaluated for their antagonistic activity in a functional exhaustion recovery assay. These studies revealed antagonistic antibodies could be either blocking or non-blocking of the PD-1/PD-L1 interaction. Considering that the mode of action attributed to functional activity of anti-PD-1 antibodies is through PD-1 blockade, these results point to a novel function of PD-1 that is being inhibited by the non-blocking antagonistic antibodies. This assertion is supported by the fact that the combination of blocking and non-blocking anti-PD-1 antibodies leads to an enhanced antagonistic activity in the in vitro exhaustion functional recovery assay. This enhanced functional activity is beyond the level of induction that can be reached with either antibody when administered alone and was demonstrated with different combination of blocking (i.e., competitive) anti-PD-1 antibodies (MK3475 or 137F2) with the non-blocking (i.e., non-competitive or partially competitive in the biochemical PD-1/PD-L1 interaction assay) anti-PD-1 antibodies 135C12 (FIG. 9A) or 139D6 (FIG. 9B). As a further proof of their functional activity, anti-PD-1 antibodies were tested either alone or in combinations between PD-1/PD-L1 blocking and non-blocking antagonistic antibodies in a mixed lymphocyte reaction assay (MLR). The MLR assay involved the mixing of monocytes from one healthy donor with the PD-1+ memory CD4 T cells from a second healthy donor. Monocytes were isolated from peripheral blood mononuclear cells (PBMCs) by CD14 positive selection with magnetic beads. PBMCs from a second donor were first depleted of CD45RA expressing cells with magnetic beads then a different set of magnetic beads were used for positive selection for CD4 positive T cells. These memory CD4 T cells (CD4+ CD45RA−) were then stained with an Aqua Live/Dead staining kit and the 127C2 anti-PD-1 antibody clone (shown to have no antagonistic activity and to not compete with MK3475, 137F2 or 135C12 for binding to PD-1) and a secondary anti-Mouse PE antibody in order to sort on the viable PD-1+cell population. After mixing monocytes and CD4+ T cells from the two different donors at 1:2 or 1:5 ratios, cells were either left untreated or treated with 1 µg/ml of the anti-PD-1 antibodies indicated in FIG. 10. Following five days in a cell culture incubator, aliquots of cell culture supernatants were collected and analyzed for secreted IFNγ by ELISA. Tritiated thymidine ($^3$H-TdR) was added to the cell culture medium and the cells were incubated for a further 18 hours. $^3$H-TdR incorporation was used as a measure of cellular proliferation. This second independent in vitro assay confirmed the functional activity of our anti-PD-1 antibodies. In FIG. 10a, increased proliferation of up to 2-fold for CD4+ T cells induced by individual and combinations of anti-PD-1 antibodies. In FIG. 10b, a strong increase in IFNγ production for all anti-PD-1 antibodies when tested individually with 137F2 giving the highest levels of induction was observed. In combinations of blocking and non-blocking anti-PD-1 antibodies (either MK3475 and 135C12 or 137F2 and 135C12), a trend towards an increased proliferation and increased production of IFNγ from PD-1+ memory CD4 T cells was observed. Given that increased IFNγ production from CD4+ T cells is associated with reduced pathology and improved memory in a mouse model for Alzheimer's disease when treated with a PD-1 immune checkpoint blockade therapy (Baruch K, Nature Med, 2015), treatment with anti-PD-1 antibodies or combinations of anti-PD-1 antibodies as outlined within, would be expected to have an equivalent or improved therapeutic benefit. As described below, epitope mapping revealed that the non-blocking antibodies with the greatest potency all bind to a similar patch of PD-1, referred to herein as the "P2 patch", that overlaps with the region of the M4 amino acid substitutions (serine 38 to alanine, proline 39 to alanine and leucine41 to alanine (FIG. 3; SEQ ID NO. 142)), and/or the region of the M17 amino acid substitutions (asparagine 102 to alanine and arginine 104 to leucine (FIG. 3; SEQ ID NO. 155)), and/or the region of the M18 amino acid substitutions (aspartate 105 to alanine (FIG. 3; SEQ ID NO. 156), and/or the region of the M31 amino acid substitutions (leucine 41 to alanine and valine 43 to leucine (FIG. 3; SEQ ID NO. 206).

To further investigate the regions of PD-1 that are implicated in the antagonistic activity of the anti-PD-1 antibodies, solvent accessible variant amino acid residue from different species were mapped to the human PD-1 structure. This structural representation based on the 3RRQ PDB shows the face of PD-1 that interacts with PD-L1/L2 in FIG. 11*a* and the opposite side of PD-1 in FIG. 11*b*. The residues that are dissimilar between monkey and human PD-1 are indicated by red circles, other variant residues found in rodent PD-1 (mouse and rat) are displayed as green circles and additional variant residues from dog PD-1 are shown in orange. Residues 46, 58, 74 and 116 have been implicated as sites from N-linked glycosylation and are marked by cyan circles. Alignments of human, monkey, horse, dog, mouse and rat PD-1 ectodomain amino acid sequences are shown in FIG. 11*c* and the corresponding homologies with human PD-1 are 96.6%, 79.9%, 73.2%, 62.4% and 66.4%, respectively. With these cross-species variant residues of PD-1 displayed on the structure, it becomes evident that there are two conserved patches on PD-1 that are designated P1 and P2 in FIGS. 11*a* and 11*b*. The P1 patch corresponds to the central region involved in the interaction between PD-1 and the PD-L1/PD-L2 ligands (compare the residues marked with spheres in FIG. 2 with those of FIG. 11*a*). Cross-species conservation of this P1 patch is anticipated since variant residues that accumulate in PD-1 during evolution would still need to maintain the interaction with the PD-L1/L2 ligands. Select substitutions of residues implicated in the PD-1/PD-L1 interaction are observed with mouse variants (e.g. residues 64 and 68) and could be attributed to co-evolution of PD-1 with its PD-L1/L2 ligands however; the core interaction region within P1 remains conserved. The evolutionarily conserved P2 patch occupies a similar surface area to the P1 patch and yet, this region has no previously identified role for PD-1, either structurally or functionally. The fact that the P2 patch is evolutionarily conserved in the species investigated indicates that PD-1 was under functional pressure to preserve the P2 site. This conservation is all the more significant given that the PD-1 ectodomain is only 62.4% to 79.9% conserved in four of the species investigated. Taking into account all the variant residues across these four species compared to human PD-1 give an even lower 52.3% sequence conservation (FIG. 11*c*, blue arrows represent the structural region depicted in FIG. 11*a* and 11*b*). Whether this functional pressure is attributed to the P2 patch serving as an interaction site for an as yet unidentified ligand, site for higher order complex formation or linked with PD-1 related signaling events remains to be determines. However, anti-PD-1 antibodies described herein including 135C12, 139D6, 135D1 and 136B4 with overlapping binding epitopes with P2 patch provide direct evidence for the functional importance of this region.

Given that this region has no previous implication in the functional activity of PD-1, it is proposed herein that antibodies exemplified by 135C12 with binding that overlaps with Patch 2 on PD-1 shown in FIG. 11*b* represent a novel mechanism and site to exert an antagonistic activity on PD-1. It is further proposed herein that other antibodies, antibody fragments, or other protein binding agents that can interact with this Patch 2 region of PD-1 would also act as an antagonist of PD-1 in a manner that is distinct from and complementary to anti-PD-1 antibodies that act through blockade of the PD-1/PD-L1 interaction as demonstrated in FIGS. 9, 10 and 17-20. As a further example of the importance of the Patch 2 region on PD-1, the 136B4 antibody binds to a distinct epitope on PD-1 compared to antibodies 135C12, 139D6 and 135D1 that also overlaps with the Patch 2. 136B4 shows a strongly reduced affinity in binding with the M17 and M18 PD-1 mutations which are situate on the edge of the P2 patch (M17: asparagine 102 to alanine and arginine 104 to alanine, M18: aspartic acid 105 to alanine). Along with 135C12, 139D6 and 135D1 antibodies, 136B4 demonstrated the highest functional activity of all the non-blocking antibodies tested.

Example 5

Antibody Competitive Binding Studies

To further characterize the binding epitopes of select antibodies listed in Table 3, a series of antibody competition studies were performed for binding to cell surface PD-1. Antibodies binding to distinct epitopes on PD-1 (MK3475, 137F2, 135C12 and 134D2) were chemically conjugated using a Maxpar antibody labeling kit (Fluidigm). In this procedure, the antibody disulfide bonds are partially reduced in order to conjugate cysteine residues with a metal chelating polymer. These metal isotope modified antibodies were then be used to stain cell for the expression levels of surface PD-1 with the analysis performed by mass cytometry. In order to generate CD4 T-cells with high expression levels of PD-1, peripheral blood mononuclear cells from a health donor were stimulated with PHA and IL-2 and incubated for 5 days. Following cell staining, gating was performed to select viable, CD3+/CD4+ cells and cell surface levels of PD-1 were evaluated for each sample by mass cytometry. In the antibody competition assay, samples of $2\times10^6$ cells were incubated for 30 minutes at 4° C. with 15 μg/ml of one of the indicated competitor antibodies indicated in FIG. 12. One of the staining anti-PD-1 antibodies labeled with a metal isotope (MK3475, 137F2, 135C12, or 134D2) was then added to the cells at <1 μg/ml, incubated for a further 20 minutes then washed to remove unbound antibody and analyzed for the levels of cell surface PD-1. A mouse IgG1 isotype control antibody was used as a negative control and as a reference to calculate the percent PD-1 positive cells relative to samples incubated with the anti-PD-1 competitor antibody clones.

The Class 1 anti-PD-1 antibodies that are blocking of the PD-1/PD-L1 interaction are all competitive (as shown in FIG. 12 with ≤29% staining of PD-1 positive cells relative to the IgG1 control) in experiments were PD-1 high cells were stained with either MK3475 or 137F2. These results are expected given that epitope mapping for several of these antibodies have binding sites that are either identical or overlapping. Class 1 antibodies were also competitive or partially competitive (as shown in FIG. 12 with 30-59% staining relative to the IgG1 control) with the 134D2 antibody. Although blocking of the PD-1/PD-L1 interaction, 134D2 binds to an epitope that is overlaps primarily with the M15 mutant but also to a lesser extent with the 17 mutation.

Class 1 antibodies were found to be non-competitive (≥60% binding of labeled antibody staining of PD-1 positive cells relative to the IgG1 control as shown in FIG. 12) with the 135C12 antibody confirming the epitope binding studies that show that these antibodies bind distinct sites on PD-1.

Using Class 2 antibodies as the competitors, both MK3475 and 137F2 labeled antibodies bind with little to no reduction in binding relative to the IgG1 control. The one exception is the 135D1 antibody that blocked the PD-1 binding of labeled 137F2. Given that the 135D1 epitope is near the M4 mutation, it seems likely that there is some stearic hingerance in the 137F2 antibody binding in the region of the M23 mutation region. The 135C12 and 139D6 clones also have a shift in binding to PD-1 encoding the M4 mutation, however given that they do not compete with the binding of 137F2, binding of these class 2 antibodies is centered more on the P2 patch region. The 135C12 antibody also had small shifts in binding to M17, M18, M26, M28, and M31 mutations which are all found at the edge of the P2 patch. All Class 2 antibodies used as competitors block the binding of labeled 135C12 which confirms that they are binding to overlapping epitopes on PD-1. Most Class 2 competitor antibodies do not compete with labeled 134D2 for binding to PD-1. The 136B4 antibody is an exception for the Class 2 antibodies that blocks the binding of 134D2. These results are consistent with the epitope binding studies in Example 3 where 134D2 binding to PD-1 is partially disrupted by the M17 mutation but primarily by the M13 and M15 mutations. Binding of the 136B4 antibody is only disrupted by the M17 and M18 mutations that are on the edge or within the P2 patch.

The Class 3 antibodies are competitive to partially competitive (defined as 30-59% staining relative to the IgG1 control as shown in FIG. 12) with MK3475 and 137F2 and bind PD-1 non-competitively with 135C12. The 135E10 Class 3 antibody is competitive with labeled 134D2 while the 140A1 class 3 antibody is non-competitive with labeled 134D2. Epitope mapping shows that 140A1 binds in the region of the M13 mutation which is distinct from the binding epitope for 134D2 (M15 major and M17 minor).

In evaluating the functional data for the Class 4 antibodies, only 134D2 and 136B5 have significant antagonistic activity that leads to an increased proliferation of HIV specific CD8 T cells in the exhaustion functional recovery assay (>150% increased proliferation as indicated in FIG. 12). These antibodies also block the interaction of PD-1 with PD-L1 in a biochemical assay and hence most likely function as antagonists through PD-1/PD-L1 blockade. Since excess 136B5 blocks the staining of PD-1+ cells with labeled 134D2, these antibodies bind PD-1 at similar or overlapping epitopes (FIG. 12). The competitive binding data with the remaining class 4 antibodies show that they bind to diverse sites on PD-1 and that this binding is generally non-overlapping with the 135C12 antibody. The 122F10 antibody is an exception which binds an analogous or overlapping epitope to 136B4 since these two antibodies have a similar binding profile in the antibody competition studies (FIG. 12) and both have reduced binding to the M17 mutant PD-1 construct (Table 11).

In combining the information from the epitope mapping studies performed by amino acid substitutions at solvent accessible residues of PD-1 (Example 3) and the antibody competition studies (FIG. 12), a consistent structural map of the regions on PD-1 that are bound by the different anti-PD-1 antibody clones is shown in FIGS. 13*a* and 13*b*). These binding epitopes are indicated with different colored circular patches for most of the clones in Table 11. FIG. 13*a* shows the face of PD-1 that has the majority of the residues involved in the PD-1/PD-L1 or PD-1/PD-L2 interactions. The exceptions are residues 89 and 90 that are found on the left side of FIG. 13*a* on a flexible loop region. The primary set of antibodies that are competitive with the PD-1/PD-L1 interaction all bind to this face of PD-1 including clones 137F2, 139F11, 140A1, 140G5 and MK3475. It should be noted that the two antibodies that we identified with the highest antagonistic activity in the functional assay (Table 11) both bind to the center of the P1 patch that is shown in FIGS. 11*a* and 13*a* and centered on residues 124-126 of PD-1. This finding is confirmed by the fact that 137F2 and 139F11 have significantly different heavy and light chain CDR sequences and belong to distinct families based on sequence alignments of all the antibody clones discussed in this application. Antibody clones 134D2 and 136B5 were shown to be competitive with the PD-1/PD-L1 interaction in a biochemical assay although they bind to a region of PD-1 in FIG. 13*b* that is overlapping with the M13, M15 and M17 mutations. Based on this mapped epitope, these antibodies bind near residues 85 and 86 of PD-1 that are part of a loop region on PD-1 containing residues 89 and 90. Since residues 89 and 90 are involved in the interaction with PD-L1 (FIG. 2*a*) binding to this loop region may induce a conformational change in PD-1 that inhibits binding to PD-L1. Consistent with these observations, antibody competition studies show that addition of a competitor Class 1 antibodies results in a significantly reduced binding of the labeled 134D2 antibody (FIG. 12).

Antibodies that are non-blocking of the PD-1/PD-L1 interaction listed in Table 3 all bind to epitopes that are distant from residues involved in the PD-1/PD-L1 interaction. Antibodies that have strong functional activity (>150% enhanced CD8 T cell proliferation in the functional recovery assay, FIG. 12), all bind in epitopes that are overlapping with the P2 patch illustrated in FIG. 13*b*. The 135C12 (all mutants tested), 139D6 (selected mutants tested) and 135D1 (selected mutants tested) antibody clones have related heavy and light chain CDR sequences and bind to a site that overlaps with the M4, M18 and M31 mutations. The 136B4 antibody clone has distinct CDR sequences and large shifts in binding affinity were observed with M17 and M18 mutant PD-1 indicates that it binds a distinct epitope on the edge of the P2 patch. The 135C12 antibody binds competitively with the 136B4 clone but not with either the 134D2 or 136E10 clone. These antibody competitive binding studies further supports the binding of 135C12, 139D6 135C1, and 136B4 to an epitope that overlaps with the P2 patch. The binding epitope for the 136E10 antibody is localized by the M1 mutations which completely abrogates binding of this antibody to PD-1.

Example 6

Figure 14:
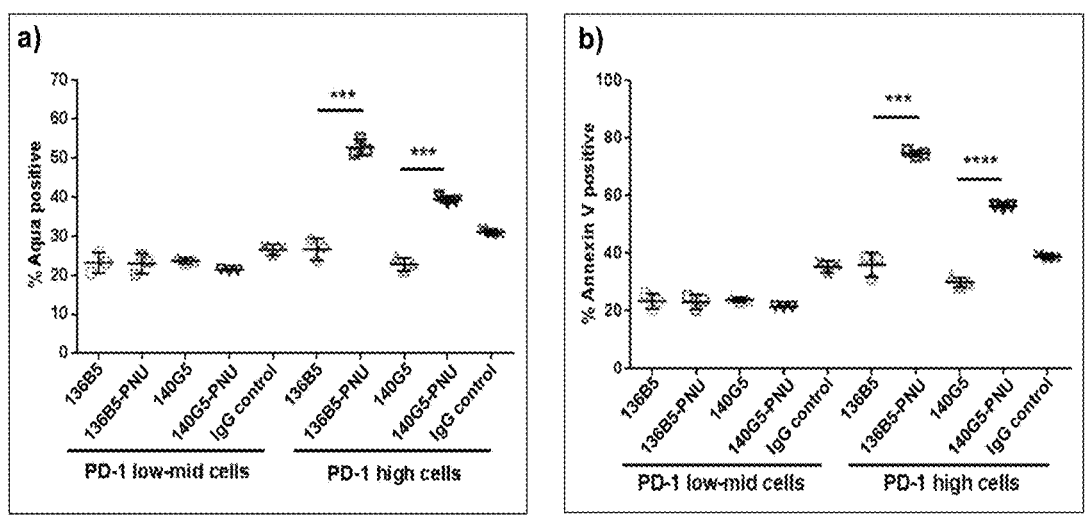
FIG. 14a-b. Selective increase in cell death (Aqua staining (panel a)) or apoptosis (Annexing V staining (panel b)) in PD-1 high CD4 T cells from a viremic HIV infected donor upon treatment with an anti-PD-1 ADC as opposed to either anti-PD-1 antibodies alone or an IgG control antibody.

Targeted Cell Killing Through Antibody Drug Conjugates

As discussed herein, the binding agents such as antibodies (e.g., Table 3) may be conjugated with a toxin in order to perform a targeted killing of PD-1 expressing cells. An example of the therapeutic benefits of this strategy would include the targeted elimination of HIV-infected $CD4^+$ T-cells that are predominantly PD-1 positive. To perform these studies, two different anti-PD-1 antibodies (140G5 and 136B5) were chemically conjugated with PEG4-vc-PAB-PNU-159682 (referred to as PNU from this point forward) through accessible cysteine groups following partial reduction of the antibody disulfide bonds. The antibody drug conjugates (ADC) were profiled by hydrophobic interaction chromatography and size exclusion chromatography, and both samples found to contain >95% PNU conjugated antibody. In the ADC killing assay, CD4+ T cells were isolated from the PBMCs of a patient that was chronically infected with the HIV-1 virus. These CD4+ T cells were incubated with an isotype control antibody, 140G5 mAb, 140G5-PNU mAb conjugate, 136B5 mAb, or 136B5-PNU mAb conjugate. Antibody concentrations were all at 10 µg/ml and cells were incubated at 37° C. in a cell culture incubator with 5% $CO_2$ for 5 days. On the fifth day, cells were stained for flow cytometry analysis with antibodies for monitoring cell surface levels of CD4 and PD-1 along with Aqua staining for cell viability and Annexin V staining to identify cells undergoing apoptosis. As shown in FIG. 14, all samples treated with the different antibodies or ADCs have equivalent levels of Aqua positive (FIG. 14a) or Annexin V positive (FIG. 14b) or CD4+ T-cells that possess low- to mid-level expression of PD-1. However, in cell populations with high levels of PD-1, there is a significant increase in the amount of Annexin V and Aqua positive cells in samples treated with the anti-PD-1 ADCs (140G5-PNU and 136B5-PNU in FIGS. 14a and 14b).

Figure 15:
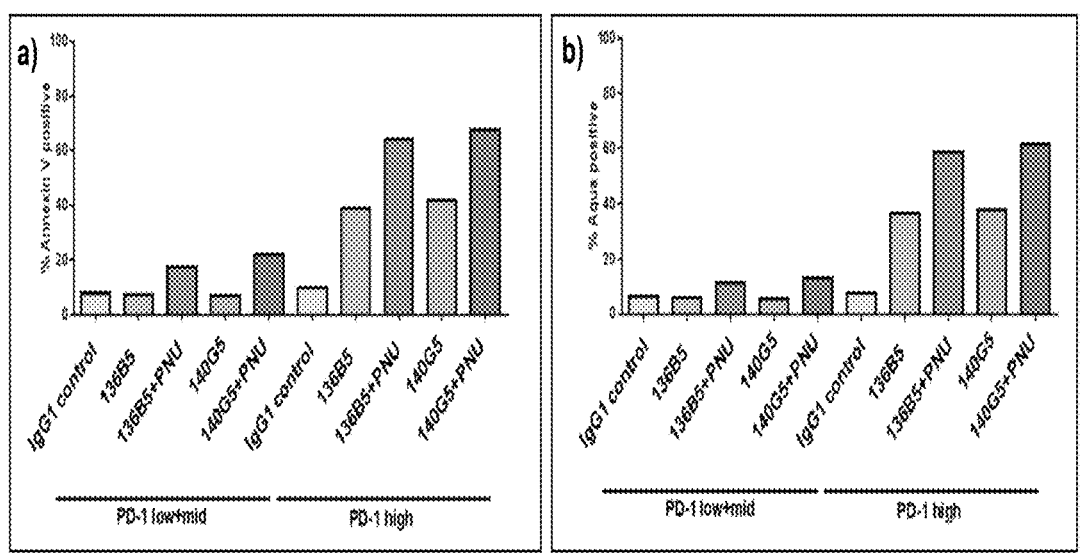
FIG. 15. Anti-PD-1 antibody drug conjugate (ADC) treatment results in an increased apoptosis (Annexin V staining (A)) and/or cell death (Aqua staining (B)) in PD-1 high CD4$^+$ T cells from multiple different viremic HIV infected donors. Low cell death/apoptosis is observed in control samples treated with either anti-PD-1 antibodies alone or an IgG1 control antibody.
Figure 16:
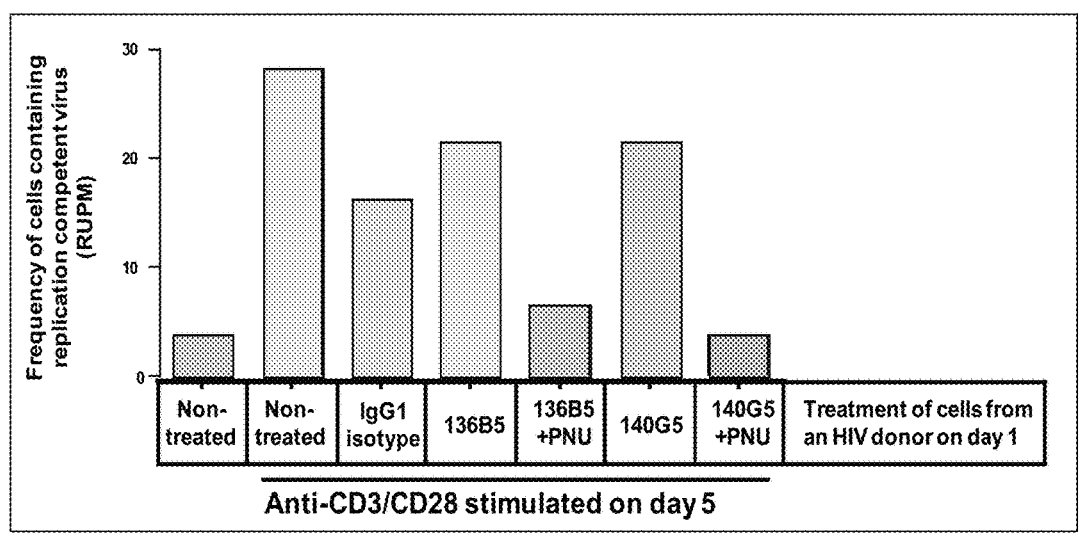
FIG. 16. Evaluation of the anti-PD-1 antibody drug conjugate (ADC) mediated killing of PD-1 positive infected CD4$^+$ T cells from a chronically infected HIV donor. Following five days of antibody treatment, cells were used in a quantitative viral outgrown assay to monitor the number of infectious cells in the different treated samples.

To provide further evidence for the potential therapeutic benefit of an anti-PD-1 ADC, the CD4+ T cells treated for five days with the different antibodies or ADCs (isotype control antibody, 140G5 mAb, 140G5-PNU mAb conjugate, 136B5 mAb, or 136B5-PNU mAb conjugate) were evaluated for the frequency of HIV infected cells using a quantitative viral outgrowth assay. In this assay, the antibody or ADC treated cells from an HIV infected patients are either left unstimulated or stimulated with anti-CD3/anti-CD28 antibodies then incubated at different dilutions in the presence of allogenic CD8-depleted PBMCs. Performing the tests with different dilutions of CD4+ T cells from each sample allows for an estimate of the frequency of cells containing replication competent virus after the five-day treatment with antibodies or ADCs. Following a 14-day incubation of CD4+ T cells and allogenic CD8-depleted PBMCs, samples are tested in both a p24 ELISA and for the presence of HIV RNA in order to establish the frequency of cells containing replication competent virus. In accordance with the specific depletion of PD-1 high cells shown in FIG. 14, an increased percentage of PD-1 high cells that are Annexin V or Aqua positive was observed indicating increased levels of cell undergoing apoptosis and cell death, respectively (FIGS. 15a and 15b). In the viral outgrown assay shown in FIG. 16, samples of CD4+ T cells from an HIV infected donor that were treated with IgG1 isotype control antibody, anti-PD-1 antibodies (136B5 or 140G5) or left without treatment for five days all have a similar frequency of cells containing replication competent virus (16 to 28 HIV-1 RNA positive cells per million (RUPM)). However, in samples treated with anti-PD-1 ADCs (140G5-PNU mAb conjugate, 136B5 mAb, or 136B5-PNU mAb conjugate) there is a significant decrease in the frequency of infected cells that corresponds with a 4- to 5-fold reduction in cells that can produce infectious virus. These results have been reproduced in several separate experiments with up to a 10-fold reduction in RUPM associated with a five day anti-PD-1 ADC treatment. As such, these studies provide an in vitro proof of principle for the concept that an anti-PD-1 ADC could be an effective therapy for the depletion of infected cells from HIV-1 positive patients.

Example 7

Humanization of Mouse Anti-PD-1 Antibodies

The mouse IgG1 antibody sequences for select anti-PD-1 clones were compared against a human immunoglobulin germ line V gene database to find heavy and light chain frameworks most similar to those of mouse antibodies. Using these framework sequences, a combinatorial library was designed and used to construct a phage display library that incorporated the heavy and light chain CDR loops of the antibodies to be humanized. The phage library was then used in panning experiments against recombinant human PD-1 in an $F_c$ fusion construct. A phage ELISA was used to evaluate the humanized anti-PD-1 output phage that bound recombinant PD-1. $F_{ab}$-fragment DNA from positive clones were introduced into a FASEBA (fast screening for expression, biophysical-properties and affinity) library and used for the production of $F_{ab}$ protein fragments. These $F_{ab}$ fragments were evaluated for expression level, protein stability/biophysical properties and for affinity to recombinant human $F_c$-PD-1 proteins as determined by Biacore studies. The 137F2 and 135C12 mouse antibody clones of Table 3 were humanized in this manner and the resulting VH and VL sequences for clones with the desired expression, stability and affinity properties are shown below. Biacore affinity measurements of the 137F2 and 135C12 humanized $F_{ab}$ clones for human and monkey $F_c$-PD-1 proteins are shown in Tables 12 and 13, respectively. The variable region amino acid sequences (heavy and light chains, as indicated) of these exemplary humanized antibodies are shown below.

A. Humanized 137F2 heavy chain sequences
1. Mouse VH reference sequence
(SEQ ID NO. 277)
QVQLQQPGAELVRPGTSVKMSCKAAGYTFTNYWIGWIKQRPGHGLEWIGD

IYPGGGYTNYNEKFKGKATLTADTSSSTAYMQVSSLTSEDTGIYYCARGY

DFVLDRWGQGTSVTVSS

2. A35790-VH
(SEQ ID NO. 139)
QMQLVQSGPEVKKPGTSVKVSCKASGFTFTNYWIGWVRQAPGQALEWMGD

IYPGGGYTNYNEKFKGRVTITADKSTSTAYMELSSLRSEDTAVYYCARGY

DFVLDRWGQGTTVTVSS

3. A35796-VH
(SEQ ID NO. 140)
QMQLVQSGPEVKKPGTSVKVSCKASGFTFTNYWIGWVRQAPGQALEWMGD

IYPGGGYTNYNEKFKGRVTITADKSTSTAYMELSSLRSEDTAVYYCARGY

DFVLDRWGQGTTVTVSS

4. A35793-VH
(SEQ ID NO. 141)
QMQLVQSGPEVKKPGTSVKVSCKASGFTFTNYWIGWVRQAPGQALEWMGD

IYPGGGYTNYNEKFKGRVTITADKSTSTAYMELSSLRSEDTAVYYCARGY

DFVLDRWGQGTTVTVSS

5. A35818-VH
(SEQ ID NO. 142)
QMQLVQSGPEVKKPGTSVKVSCKASGFTFTNYWIGWVRQAPGQALEWMGD

IYPGGGYTNYNEKFKGRVTITADKSTSTAYMELSSLRSEDTAVYYCARGY

DFVLDRWGQGTTVTVSS

6. A35795-VH
(SEQ ID NO. 143)
QVQLVQSGAEVKKPGASVKVSCKASGYTFTNYWIGWVRQAPGQGLEWMGD
IYPGGGYTNYNEKFKGRVTITADKSTSTAYMELSSLRSEDTAVYYCARGY
DFVLDRWGQGTTVTVSS

7. A35797-VH
(SEQ ID NO. 144)
EVQLVQSGAEVKKHGESLKISCKGSGYSFTNYWIGWVRQATGQGLEWMGD
IYPGGGYTNYNEKFKGRVTITADKSTSTAYMELSSLRSEDTAVYYCARGY
DFVLDRWGQGTTVTVSS

8. A35799-VH
(SEQ ID NO. 145)
QMQLVQSGAEVKKTGSSVKVSCKASGYTFTNYWIGWVRQMPGKGLEWMGD
IYPGGGYTNYNEKFKGRVTITADKSTSTAYMELSSLRSEDTAVYYCARGY
DFVLDRWGQGTTVTVSS

9. A35805-VH
(SEQ ID NO. 146)
QVQLVQSGSELKKPGASVKVSCKASGYTFTNYWIGWVRQAPGKGLEWMGD
IYPGGGYTNYNEKFKGRVTITADKSTSTAYMELSSLRSEDTAVYYCARGY
DFVLDRWGQGTTVTVSS 10. 137F VH1
(SEQ ID NO. 147)
QVQLVQSGAEVKKPGASVKVSCKASGYTFTNYWIGWVRQAPGQGLEWMGD
IYPGGGYTNYNEKFKGRVTMTRDTSTSTVYMELSSLRSEDTAVYYCARGY
DFVLDRWGQGTLVTVSS 11. 137F VH2
(SEQ ID NO. 148)
QVQLVQSGAEVKKPGASVKVSCKAAGYTFTNYWIGWVRQAPGQGLEWMGD
IYPGGGYTNYNEKFKGRVTMTADTSTSTVYMELSSLRSEDTAVYYCARGY
DFVLDRWGQGTLVTVSS 12. 137F VH1b
(SEQ ID NO. 149)
QVQLVQSGAEVKKPGASVKVSCKASGYTFTNYWIGWVRQAPGQGLEWIGD
IYPGGGYTNYNEKFKGRVTMTADTSTSTVYMELSSLRSEDTAVYYCARGY
DFVLDRWGQGTLVTVSS 13. 137F VH1c
(SEQ ID NO. 150)
QVQLVQSGAEVKKPGASVKVSCKASGYTFTNYWIGWIRQAPGQGLEWIGD
IYPGGGYTNYNEKFKGRATLTADTSTSTVYMEVSSLRSEDTAVYYCARGY
DFVLDRWGQGTLVTVSS

B. Humanized 137F2 light chain sequences
1. Mouse VL reference sequence
(SEQ ID NO. 278)
DIVMSQSPSSLAVSTGEKVTMTCKSSQSLFNSETQKNYLAWYQQKPGQPP
KLLIFWASTRESGVPDRFLGSGSGTDFTLTISSVQAEDLAVYYCKQSYTL
RTFGGGTKLEIK 2. A35790-VL
(SEQ ID NO. 151)
DVVMTQSPAFLSVTPGEKVTITCKSSQSLFNSETQKNYLAWYQQKPGQPP
KLLIYWASTRESGVPSRFSGSGSGTDFTLTISSLQPEDFATYYCKQSYTL
RTFGGGTKLEIK 3. A35796-VL
(SEQ ID NO. 152)
DVVMTQSPAFLSVTPGEKVTITCKSSQSLFNSETQKNYLAWYQQKPGQPP
KLLIYWASTRESGVPSRFSGSGSGTDFTLTISSLQPEDFATYYCKQSYTL
RTFGGGTKLEIK 4. A35793-VL
(SEQ ID NO. 153)
DVVMTQSPAFLSVTPGEKVTITCKSSQSLFNSETQKNYLAWYQQKPGQPP
KLLIYWASTRESGVPSRFSGSGSGTDFTFTISSLEAEDAATYYCKQSYTL
RTFGGGTKLEIK 5. A35818-VL
(SEQ ID NO. 154)
DVVMTQSPAFLSVTPGEKVTITCKSSQSLFNSETQKNYLAWYQQKPGQAP
RLLIYWASTRESGVPSRFSGSGSGTDFTFTISSLEAEDAATYYCKQSYTL
RTFGGGTKLEIK 6. A35795-VL
(SEQ ID NO. 155)
DVVMTQSPAFLSVTPGEKVTITCKSSQSLFNSETQKNYLAWYQQKPGQAP
RLLIYWASTRESGVPSRFSGSGSGTDFTLTISSLQPEDFATYYCKQSYTL
RTFGGGTKLEIK 7. A35797-VL
(SEQ ID NO. 156)
DIQMTQSPSSLSASVGDRVTITCKSSQSLFNSETQKNYLAWYQQKPGQPP
KLLIYWASTRESGVPSRFSGSGSGTDFTLTISSLQPEDFATYYCKQSYTL
RTFGGGTKLEIK 8. A35799-VL
(SEQ ID NO. 157)
DVVMTQSPAFLSVTPGEKVTITCKSSQSLFNSETQKNYLAWYQQKPGQPP
KLLIYWASTRESGVPSRFSGSGSGTDFTLTISSLQPEDFATYYCKQSYTL
RTFGGGTKLEIK 9. A35805-VL
(SEQ ID NO. 158)
DVVMTQSPAFLSVTPGEKVTITCKSSQSLFNSETQKNYLAWYQQKPGQPP
KLLIYWASTRESGVPSRFSGSGSGTDFTFTISSLEAEDAATYYCKQSYTL
RTFGGGTKLEIK 10. 137F VL1
(SEQ ID NO. 159)
DIVMTQSPDSLAVSLGERATINCKSSQSLFNSETQKNYLAWYQQKPGQPP
KLLIYWASTRESGVPDRFSGSGSGTDFTLTISSLQAEDVAVYYCKQSYTL
RTFGQGTKLEIK 11. 137F VL2
(SEQ ID NO. 160)
DIVMTQSPDSLAVSLGERATINCKSSQSLFNSETQKNYLAWYQQKPGQPP
KLLIFWASTRESGVPDRFLGSGSGTDFTLTISSLQAEDVAVYYCKQSYTL
RTFGQGTKLEIK 12. 137F VL1b
(SEQ ID NO. 161)
DIVMTQSPDSLAVSLGERATINCKSSQSLFNSETQKNYLAWYQQKPGQPP
KLLIYWASTRESGVPDRFSGSGSGTDFTLTISSLQAEDVAVYYCKQSYTL
RTFGQGTKLEIK 13. 137F VL1c (SEQ ID NO. 162)
DIVMTQSPDSLAVSLGERATITCKSSQSLFNSETQKNYLAWYQQKPGQPP
KLLIFWASTRESGVPDRFSGSGSGTDFTLTISSLQAEDVAVYYCKQSYTL
RTFGQGTKLEIK 14. 137F VL1d (SEQ ID NO. 163)
DIVMTQSPDSLAVSLGERATMTCKSSQSLFNSETQKNYLAWYQQKPGQPP
KLLIFWASTRESGVPDRFSGSGSGTDFTLTISSVQAEDVAVYYCKQSYTL
RTFGQGTKLEIK C. Humanized 135C12 heavy chain sequences
1. Mouse VH reference sequence (SEQ ID NO. 279)
EVQLHQSGPELLKPGASVRMSCKASGYTFTNFYIHWVKQSHGKSIEWIGS
IYPNYGDTAYNQKFKDKATLTVDKSSSTAYMALRSLTSEDSAVYYCARGY
SYAMDYWGQGTSVTVSS

2. A35775-VH (SEQ ID NO. 164)
EVQLVQSGAEVKKPGESLKISCKGSGYSFTNFYIHWVRQAPGQRLEWMGS
IYPNYGDTAYNQKFKDRFVFSLDTSVSTAYLQISSLKAEDTAVYYCARGY
SYAMDYWGQGTTVTVSS

3. A35783-VH (SEQ ID NO. 165)
EVQLVQSGAEVKKPGESLKISCKGSGYSFTNFYIHWVRQARGQRLEWIGS
IYPNYGDTAYNQKFKDRFVFSLDTSVSTAYLQISSLKAEDTAVYYCARGY
SYAMDYWGQGTTVTVSS

4. A35774-VH (SEQ ID NO. 166)
EVQLVQSGAEVKKPGESLKISCKGSGYSFTNFYIHWVRQAPGQRLEWMGS
IYPNYGDTAYNQKFKDRFVFSLDTSVSTAYLQISSLKAEDTAVYYCARGY
SYAMDYWGQGTTVTVSS

5. A36443-VH (SEQ ID NO. 167)
EVQLVQSGAEVKKPGATVKISCKVSGYTFTNFYIHWVRQARGQRLEWIGS
IYPNYGDTAYNQKFKDRVTITADKSTSTAYMELSSLRSEDTAVYYCARGY
SYAMDYWGQGTTVTVSS

6. A35777-VH (SEQ ID NO. 168)
EVQLVQSGAEVKKPGATVKISCKVSGYTFTNFYIHWVRQAPGKGLEWMGS
IYPNYGDTAYNQKFKDRVTITADKSTSTAYMELSSLRSEDTAVYYCARGY
SYAMDYWGQGTTVTVSS

7. A35789-VH (SEQ ID NO. 169)
EVQLVQSGAEVKKPGESLKISCKGSGYSFTNFYIHWVRQMPGKGLEWMGS
IYPNYGDTAYNQKFKDRVTITADKSTSTAYMELSSLRSEDTAVYYCARGY
SYAMDYWGQGTTVTVSS

8. A36448-VH (SEQ ID NO. 170)
EVQLVQSGAEVKKPGESLKISCKGSGYSFTNFYIHWVRQMPGKGLEWMGS
IYPNYGDTAYNQKFKDRFVFSLDTSVSTAYLQISSLKAEDTAVYYCARGY
SYAMDYWGQGTTVTVSS

9. A36437-VH (SEQ ID NO. 171)
EVQLVQSGAEVKKPGESLKISCKGSGYSFTNFYIHWVRQMPGKGLEWMGS
IYPNYGDTAYNQKFKDRFVFSLDTSVSTAYLQISSLKAEDTAVYYCARGY
SYAMDYWGQGTTVTVSS 10. 135C VH1

(SEQ ID NO. 172)
QVQLVQSGAEVKKPGASVKVSCKASGYTFTNFYIHWVRQAPGQGLEWMGS
IYPNYGDTAYNQKFKDRVTMTRDTSTSTVYMELSSLRSEDTAVYYCARGY
SYAMDYWGQGTLVTVSS 11. 135C VH2

(SEQ ID NO. 173)
QVQLVQSGAEVKKPGASVKVSCKASGYTFTNFYIHWVRQAPGQGLEWMGS
IYPNYGDTAYNQKFKDRVTMTVDKSTSTVYMELRSLRSEDTAVYYCARGY
SYAMDYWGQGTLVTVSS 12. 135C VH3

(SEQ ID NO. 174)
QVQLVQSGAEVKKPGASVKVSCKASGYTFTNFYIHWVKQAHGQGLEWMGS
IYPNYGDTAYNQKFKDRVTMTVDKSTSTVYMELRSLRSEDTAVYYCARGY
SYAMDYWGQGTLVTVSS 13. 135C VH1b (SEQ ID NO. 175)
QVQLVQSGAEVKKPGASVKVSCKASGYTFTNFYIHWVRQAPGQGLEWIGS
IYPNYGDTAYNQKFKDRVTMTVDTSTSTVYMELSSLRSEDTAVYYCARGY
SYAMDYWGQGTLVTVSS 14. 135C VH1c (SEQ ID NO. 176)
QVQLVQSGAEVKKPGASVKMSCKASGYTFTNFYIHWVRQAPGQGLEWIGS
IYPNYGDTAYNQKFKDRATLTVDTSTSTAYMELSSLRSEDTAVYYCARGY
SYAMDYWGQGTLVTVSS 15. 135C VH1d (SEQ ID NO. 177)
QVQLVQSGAEVKKPGASVKMSCKASGYTFTNFYIHWVRQAPGQGLEWIGS
IYPNYGDTAYNQKFKDRATLTVDKSTSTAYMELSSLRSEDTAVYYCARGY
SYAMDYWGQGTLVTVSS

D. Humanized 135C12 Light chain sequences
1. Mouse VL reference sequence (SEQ ID NO. 280)
NIVMTQSPKSMSMSVGERVTLTCKASENVVTYVSWYQQKPEQSPKLLIYG
ASNRYTGVPDRFTGSGSATDFTLTISSVQAEDLADYHCGQGYSYPYTFGG
GTKLEIK

2. A35775-VL (SEQ ID NO. 178)
DIQMTQSPSSVSASVGDRVTITCSASQGISGDLNWYQQKPGQAPRLLIYH
TSSLHSGVPSRFSGSGSGTDFTLTISSLQPEDFATYYCQYYSKDLLTFGG
GTKLEIK

3. A35783-VL (SEQ ID NO. 179)
DIQMTQSPSSLSASVGDRVTITCSASQGISGDLNWYQQKPGKTPKLLIYH
TSSLHSGVPSRFSGSGSGTDFTLTISSLQPEDFATYYCQYYSKDLLTFGG
GTKLEIK 4. 35774-VL
(SEQ ID NO. 180)
DIQMTQSPSSVSASVGDRVTITCSASQGISGDLNWYQQKPGKAPKLLIYH

TSSLHSGVPSRFSGSGSGTDFTLTISSLQPEDFATYYCQYYSKDLLTFGG

GTKLEIK

5. A36443-VL
(SEQ ID NO. 181)
DIQMTQSPSSVSASVGDRVTITCSASQGISGDLNWYQQKPGQAPRLLIYH

TSSLHSGVPSRFSGSGSGTEFTLTISRLEPEDFAVYYCQYYSKDLLTFGG

GTKLEIK

6. A35777-VL
(SEQ ID NO. 182)
DIQMTQSPSTLSASVGDRVTITCSASQGISGDLNWYQQKPGQAPRLLIYH

TSSLHSGVPSRFSGSGSGTDFTLTISSLQPEDFATYYCQYYSKDLLTFGG

GTKLEIK

7. A35789-VL
(SEQ ID NO. 183)
DIQMTQSPSSVSASVGDRVTITCSASQGISGDLNWYQQKPGQAPRLLIYH

TSSLHSGIPARFSGSGSGTDFTLTISRLEPEDFAVYYCQYYSKDLLTFGG

GTKLEIK

8. A36448-VL
(SEQ ID NO. 184)
DIQMTQSPSTLSASVGDRVTITCSASQGISGDLNWYQQKPGKTPKLLIYH

TSSLHSGVPSRFSGSGSGTDFTLTISSLQPEDFATYYCQYYSKDLLTFGG

GTKLEIK

9. A36437-VL
(SEQ ID NO. 185)
DIQMTQSPSTLSASVGDRVTITCSASQGISGDLNWYQQKPGQAPRLLIYH

TSSLHSGIPARFSGSGSGTDFTLTISSLQPEDFAVYYCQYYSKDLLTFGG

GTKLEIK 10. 135C VL1
(SEQ ID NO. 186)
DIQMTQSPSSLSASVGDRVTITCSASQGISGDLNWYQQKPGKAPKLLIYH

TSSLHSGVPSRFSGSGSGTDFTLTISSLQPEDFATYYCQYYSKDLLTFGG

GTKLEIK 11. 135C VL2
(SEQ ID NO. 187)
DIQMTQSPSSLSASVGDRVTITCSASQGISGDLNWYQQKPGKAVKLLIYH

TSSLHSGVPLRFSGSGSGTDYTLTISSLQPEDFATYYCQYYSKDLLTFGG

GTKLEIK 12. 135C VL3
(SEQ ID NO. 188)
DIQMTQSPSSLSASVGDRVTITCSASQGISGDLNWYQQKSDGAVKLLIYH

TSSLHSGVPLRFSGSGSGTDYTLTISSLQPEDFATYYCQYYSKDLLTFGG

GTKLEIK 13. 135C VL1b
(SEQ ID NO. 189)
DIQMTQSPSSLSASVGDRVTITCSASQGISGDLNWYQQKPGKAPKLLIYH

TSSLHSGVPSRFSGSGSGTDYTLTISSLQPEDFATYYCQYYSKDLLTFGG

GTKLEIK 14. 135C VL1c
(SEQ ID NO. 190)
DIQMTQSPSSLSASVGDRVTITCSASQGISGDLNWYQQKPGKAVKLLIYH

TSSLHSGVPSRFSGSGSGTDYTLTISSLQPEDFATYYCQYYSKDLLTFGG

GTKLELK

Biacore binding affinity measurements for the indicated humanized antibodies are presented in Tables 12 and 13 below.

TABLE 12

Biacore binding affinity measurements of humanized anti-PD-1 Fab clones relating to 137F2 for human and monkey PD-1

| | Human PD-1 | | | Monkey PD-1 | | |
|---|---|---|---|---|---|---|
| Ligand | ka ($M^{-1}/s^{-1}$) | kd ($s^{-1}$) | KD (M) | ka ($M^{-1}/s^{-1}$) | kd ($s^{-1}$) | KD (M) |
| mouse 137F2A11 | 1.37E+05 | 2.10E−04 | 1.54E−09 | 1.38E+05 | 3.05E−04 | 2.22E−09 |
| A35796 | 1.04E+05 | 1.23E−04 | 1.18E−09 | 9.53E+04 | 9.81E−05 | 1.03E−09 |
| A35793 | 1.04E+05 | 9.49E−05 | 9.12E−10 | 9.32E+04 | 1.05E−04 | 1.13E−09 |
| A35818 | 9.88E+04 | 1.04E−04 | 1.06E−09 | 9.14E+04 | 1.16E−04 | 1.27E−09 |
| A35795 | 1.03E+05 | 8.24E−05 | 7.97E−10 | 9.25E+04 | 1.52E−04 | 1.64E−09 |
| A35797 | 1.00E+05 | 8.02E−05 | 8.02E−10 | 9.37E+04 | 1.06E−04 | 1.13E−09 |
| A35799 | 1.01E+05 | 7.43E−05 | 7.34E−10 | 8.97E+04 | 1.69E−04 | 1.88E−09 |
| A35805 | 9.37E+04 | 8.78E−05 | 9.37E−10 | 8.82E+04 | 9.49E−05 | 1.08E−09 |

TABLE 13

Biacore binding affinity measurements of humanized anti-PD-1 Fab clones relating to 135C12 for human and monkey PD-1

| | Human PD-1 | | | Monkey PD-1 | | |
|---|---|---|---|---|---|---|
| Ligand | ka ($M^{-1}/s^{-1}$) | kd ($s^{-1}$) | KD (M) | ka ($M^{-1}/s^{-1}$) | kd ($s^{-1}$) | KD (M) |
| mouse 135C12 | 9.52E+04 | 1.52E−04 | 1.60E−09 | 8.40E+04 | 2.38E−04 | 2.83E−09 |
| A35775 | 8.02E+04 | 2.03E−04 | 2.54E−09 | 6.05E+04 | 3.47E−04 | 5.73E−09 |

TABLE 13-continued

Biacore binding affinity measurements of humanized anti-PD-1 Fab clones relating to 135C12 for human and monkey PD-1

| | Human PD-1 | | | Monkey PD-1 | | |
|---|---|---|---|---|---|---|
| Ligand | ka $(M^{-1}/s^{-1})$ | kd $(s^{-1})$ | KD (M) | ka $(M^{-1}/s^{-1})$ | kd $(s^{-1})$ | KD (M) |
| A35783 | 7.68E+04 | 1.96E−04 | 2.55E−09 | 4.21E+05 | 8.00E−04 | 1.90E−09 |
| A35774 | 8.09E+04 | 2.11E−04 | 2.61E−09 | 6.93E+04 | 1.94E−04 | 2.79E−09 |
| A36443 | 7.12E+04 | 2.15E−04 | 3.02E−09 | 9.49E+04 | 5.85E−04 | 6.16E−09 |
| A35777 | 6.86E+04 | 3.52E−04 | 5.13E−09 | 1.15E+05 | 5.75E−04 | 5.00E−09 |
| A35789 | 7.01E+04 | 2.93E−04 | 4.17E−09 | 6.67E+04 | 4.13E−04 | 6.19E−09 |
| A36448 | 8.96E+04 | 3.86E−04 | 4.31E−09 | NA | NA | NA |
| A36437 | 7.10E+04 | 3.17E−04 | 4.46E−09 | 6.07E+04 | 3.68E−04 | 6.07E−09 |

Example 8

Stimulation of T Cells Using Anti-PD1 Antibodies and Combinations Thereof

Figure 17:
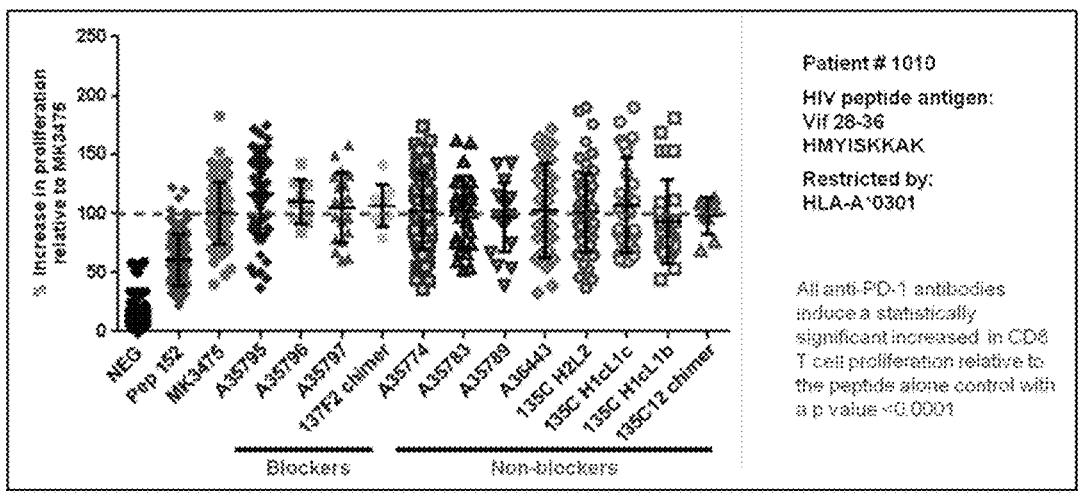
FIG. 17. Functional activity of a panel of humanized antibodies containing the heavy and light chain variable CDR loops from the 137F2 blocking (of PD-1/PD-L1 interaction (A35795, A35796, A35797, 137F2 chimera)) and the 135C12 non-blocking of the PD-1/PD-L1 interaction (A35774, A35783, A35789, A346443, 135C H2L2, 135C H1cL1c, 135C H1cL1b, 135C12 chimera) anti-PD-1 antibodies show antagonistic activity equivalent to MK3475 in the restoration of HIV peptide specific CD8 T-cell proliferation in a functional exhaustion recovery assay.
Figure 18:
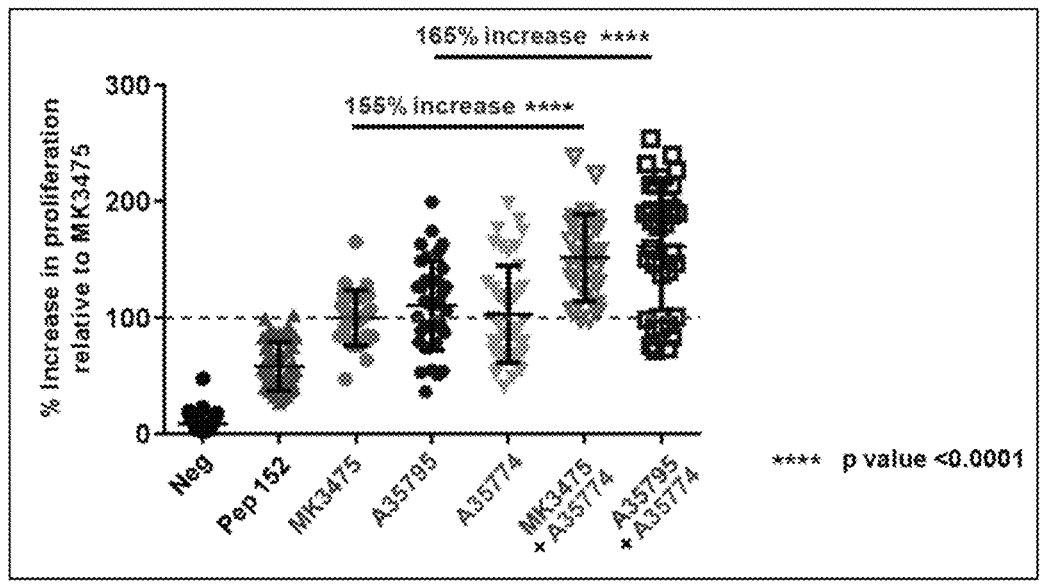
FIG. 18. Combination of two antagonistic anti-PD-1 antibodies binding to different epitopes on PD-1, one blocking (MK3475 or A35795) and one non-blocking (A35774) of the PD-1/PD-L1 interaction, results in an enhanced relief of functional exhaustion and increased proliferation of HIV specific CD8 T cells beyond what either antibody alone can achieve.
Figure 19:
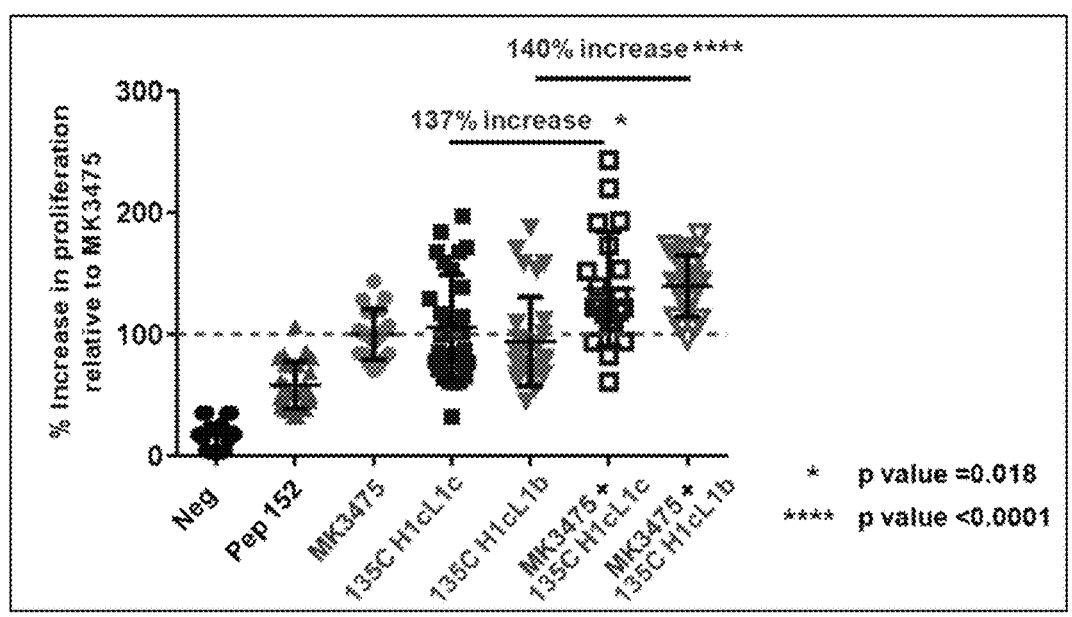
FIG. 19. Combination of two antagonistic anti-PD-1 antibodies binding to different epitopes on PD-1, one blocking (MK3475) and one non-blocking (135C H1cL1b or 135C H1cL1c) of the PD-1/PD-L1 interaction, results in an enhanced relief of functional exhaustion and increased proliferation of HIV specific CD8 T cells beyond what either antibody alone can achieve alone.

The results of antigen-specific stimulation of PBMCs from a chronically infected HIV donor results in the proliferation of HIV specific CD8$^+$ T cells are illustrated in FIGS. 17-19. Due to the exhausted state of the CD8$^+$ T cells in the viremic donor, the addition of anti-PD-1 antibodies enhances antigen specific proliferation by up to approximately 200% (p value<0.0001).

Humanized anti-PD-1 antibodies encoding CDRs derived from the mouse blocking anti-PD-1 antibody 137F2 and the mouse non-blocking anti-PD-1 antibody 135C12 were evaluated for their ability to relieve functional exhaustion in antigen specific CD8 T cells in the CFSE functional exhaustion assay. Several humanized antibodies for 137F2 and 135C12 clones with variations in the human antibody framework region were tested in multiple assays and all demonstrated similar activity in promoting CD8$^+$ T cell proliferation compared to MK3475 and the mouse/human chimeric antibodies ($V_L$ and $V_H$ portions from mouse and human constant regions of IgG4) of 137F2 and 135C12. Due to the exhausted state of the CD8 T cells in the viremic donor, the addition of the anti-PD-1 antibodies enhances antigen specific proliferation by up to approximately 200% (p value<0.0001) (FIG. 17). Humanized anti-PD-1 antibodies encoding CDRs derived from the mouse blocking anti-PD-1 antibody (i.e., blocking the PD-1/PD-L1 interaction) 137F2 (i.e., humanized antibodies A35795 (comprising SEQ ID NOS. 143 and 155), A35796 (comprising SEQ ID NOS. 140 and 152) and A35797 (comprising SEQ ID NOS. 144 and 156), and the mouse-human chimera 137F2 (comprising SEQ ID NOS. 8, 31, 54, 77, 100, and 123)) and the mouse non-blocking anti-PD-1 antibody 135C12 (i.e., humanized antibodies A35774 (comprising SEQ ID NOS. 166 and 180), A35783 (comprising SEQ ID NOS. 165 and 179), A35789 (comprising SEQ ID NOS. 169 and 183), A36443 (comprising SEQ ID NOS. 167 and 181), 135C H2L2 (comprising SEQ ID NOS. 173 and 187), 135C H1cL1c (comprising SEQ ID NOS. 176 and 190), 135C H1cL1b (comprising SEQ ID NOS. 176 and 189), and the mouse-human chimera 135C12 (comprising SEQ ID NOS. 17, 40, 63, 86, 109 and 132)) were evaluated for their ability to relieve functional exhaustion in antigen specific CD8$^+$ T cells in the CFSE functional exhaustion assay. Several humanized antibodies for 137F2 (blocking) and 135C12 (non-blocking) clones with variations in the human antibody framework region were tested in multiple assays. All demonstrated similar activity in promoting CD8$^+$ T cell proliferation compared to MK3475 and the mouse/human chimeric antibodies of 137F2 and 135C12.

FIG. 18 illustrates the results of the combination of an antibody that blocks the PD-1/PD-L1 interaction (MK3475 or A35795) with a non-blocking anti-PD-1 antibody (A35774) resulted in a statistically significant increase in proliferation relative to either antibody alone (p value<0.0001). The data shown in FIG. 18 is the average of three experiments for MK3475 combinations and four experiments for A35795 combinations with A35774.

FIG. 19 shows the effect of other combinations of an antibody blocking the PD-1/PD-L1 interaction (MK3475) and a non-blocking anti-PD-1 antibody (135C H1cL1c (comprising SEQ ID NOS. 176 and 190) or 135C H1cL1b (comprising SEQ ID NOS. 176 and 189). As shown therein, the combination of the blocking antibody MK3475 and a non-blocking anti-PD-1 antibody (135C H1cL1c or 135C H1cL1b) results in a statistically significant increase in proliferation relative to either antibody alone (p values of 0.018 or <0.0001 as indicated). The data shown in FIG. 19 is the average of two experiments for each combination.

Example 9

Activation of Jurkat PD-1 Reporter Cells with Combined Treatment of Blocking and Non-blocking Anti-PD-1 Antibodies In these experiments, a Jurkat PD-1 NFAT reporter cell line was stimulated with a transiently transfected 293T cell line that co-expresses a TCR activator and the PD-L1 protein. In the absence of an anti-PD-1 antibody, the PD-L1/PD-1 interaction suppressed Jurkat cell stimulation leading to a reduced NFAT activation and lower levels of luciferase production. Addition of a blocking anti-PD-1 antibody (e.g., MK3475) resulted in an enhanced NFAT activation, greater production of luciferase and an increased amount of chemoluminescent light produced upon addition of luciferase substrate. Under these extreme assay conditions with a large excess of PD-1 and PD-L1, non-blocking anti-PD-1 antibodies (exemplified by A35774 in FIG. 20A and 135C H1cL1c in FIG. 20B have reduced activity relative to the blocking anti-PD-1 antibodies. However, combination of blocking and non-blocking anti-PD-1 antibodies leads to a further increase in T cell activation to levels beyond those that can be achieved with MK3475 alone. This enhanced NFAT activation with blocking and non-blocking anti-PD-1 antibodies is observed at both low and high concentrations of each antibody tested. The data shown is the average of three replicates with statistically significant increases in NFAT activation shown for the combinations of either blocking antibody MK3475+non-blocking A35774 (FIG. 20A) or blocking antibody MK3475+non-blocking antibody 135 H1cL1c (FIG. 20B).

Example 10

Internalization of Cell Surface PD-1 with Anti-PD-1 Antibody Treatment

Figure 21:
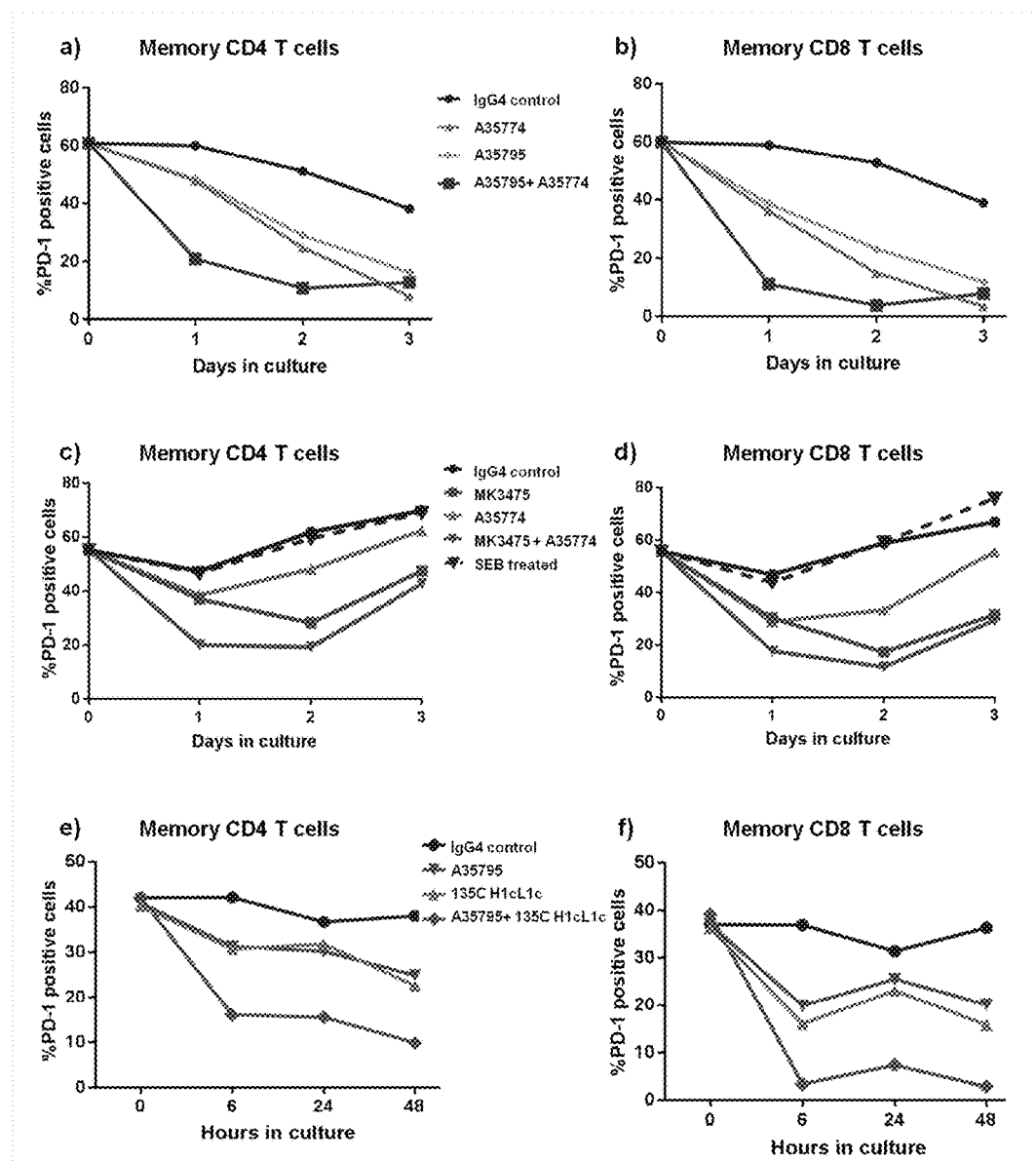
FIG. 21. Internalization of cell surface PD-1 upon incubation of either blocking, non-blocking or combinations of blocking and non-blocking anti-PD-1 antibodies with memory T-cells from a chronically infected HIV donor. Cell surface levels of PD-1 on memory CD4+T cells (FIG. 21, panels a, c, and e) and CD8+T cells (FIG. 21, panels b, d, and f) was measured at different time points following antibody treatment.

PBMCs from a chronically infected HIV donor with memory T cells having high basal levels of PD-1 were incubated with either blocking, non-blocking or combinations of blocking and non-blocking anti-PD-1 antibodies to determine the effect on PD-1 internalization (FIG. 21). Cell surface levels of PD-1 were monitored on memory CD4$^+$ T cells (FIG. 21, panels a, c, and e) and CD8$^+$ T cells (FIG. 21, panels b, d, and f) by flow cytometry to determine whether anti-PD-1 antibodies induced cell surface PD-1 internalization over 48 to 72 hours. Three separate experiments are shown using the antibody combinations A35795 (comprising SEQ ID NOS. 143 and 155) and A35774 (comprising SEQ ID NOS. 166 and 180) (FIG. 21, panels a,b); MK3475 and A35774 (comprising SEQ ID NOS. 166 and 180) (FIG. 21, panels c,d); as well as A35795 (comprising SEQ ID NOS. 143 and 155) and 135C H1cL1c (comprising SEQ ID NOS. 176 and 190) (FIG. 21, panels e, f). In all cases, the combination of blocking (exemplified by A35795 or MK3475) and non-blocking (exemplified by A35774 (comprising SEQ ID NOS. 166 and 180) or 135C H1cL1c (comprising SEQ ID NOS. 176 and 190)) anti-PD-1 antibodies was observed to induce a more rapid and/or more pronounced internalization of the PD-1 receptor. In each experiment, PBMCs were incubated with a human IgG4 isotype control antibody which acted as a reference for the untreated T cells that maintained elevated levels of PD-1 throughout the cell culture incubations. Mechanistically, internalization of PD-1 may contribute to the antagonistic functional activity of anti-PD-1 antibodies (either alone or in combinations of blocking and non-blocking antibodies) since a reduced cell surface expression of PD-1 could limit the negative regulation of the T cells through the PD-1/PD-L1 interaction.

Example 11

IFN-γ Production Following Anti-PD-1 Antibody Treatment

PBMCs from a chronically infected HIV donor possessing memory T cells with high basal levels of PD-1 were incubated with either blocking, non-blocking or combinations of blocking and non-blocking anti-PD-1 antibodies. The PBMC/antibody mixtures were then layered over 293T cells that were transiently transfected to express either an anti-CD3 TCR activator or to co-express the anti-CD3 TCR activator and PD-L1. Following a 24 hr stimulation of the PBMCs with the TCR activator cells in the presence or absence of PD-L1, supernatants were collected and analyzed for IFN-γ production by ELISA. Similar levels of IFN-γ were detected in all antibody treated samples when stimulated with the anti-CD3 TCR activator cells (FIG. 22A). In contrast, lower levels of IFN-γ were detected in the IgG4 isotype control treated sample and there was an enhanced production IFN-γ in sample treated with anti-PD-1 antibodies. The highest levels of cytokine production were observed in samples treated with both blocking (MK3475) and non-blocking (A35774) anti-PD-1 antibodies (* p<0.05).

In another experiment, PBMCs from a chronically infected HIV donor possessing memory T cells with high basal levels of PD-1 were incubated with either blocking, non-blocking (A35774), blocking (MK3475), or a combination of blocking and non-blocking anti-PD-1 antibodies (A35774 and MK3475 (FIG. 22B)). The PBMC/antibody mixtures were then layered over 293T cells that were transiently transfected to co-express the anti-CD3 TCR activator and the PD-L1 protein. The GolgiPlug™ protein transport inhibitor was added and the cells were incubated for approximately 18 hours to allow for cytokine accumulation within the cells. The percentages of IFN-γ producing cells were evaluated for each of the antibody treatment conditions by flow cytometry (FIG. 22B). Production of IFN-γ was increased in PD-1 positive cells with anti-PD-1 therapy and combination of a blocking (MK3475) and non-blocking (A35774) antibody lead to a further increase in cytokine production (data shown for PD-1+CD8 T cells).

Example 12

Crystallography

Figure 23:
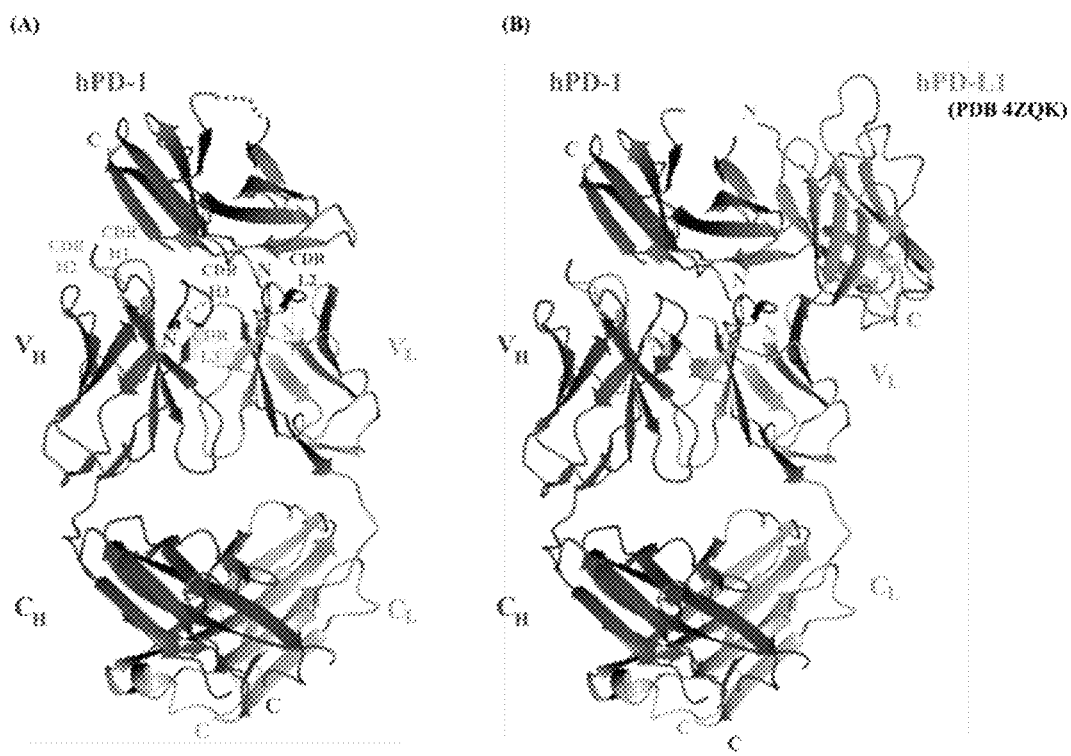
FIG. 23. hPD-1/Fab A35774 complex protein crystals. A. Heavy and light chain CDR loops of A35774 that interact with the human PD-1 protein. B Modeling of the hPD-1/Fab A35774 structure with human PD-L1 (PDB 4ZQK) confirms that the non-blocking anti-PD-1 antibodies bind a distinct, non-overlapping epitope on PD-1 compared to PD-L1.

Recombinant expressed purified human PD-1 protein (residues 33 to 150 of the receptor ectodomain ("hPD1")) was incubated with the Fab fragment of the humanized A35774 antibody, and the complex purified by size-exclusion chromatography. Protein crystals were generated for the hPD-1/Fab A35774 (comprising SEQ ID NOS. 166 and 180) complex and the structure solved by X-ray crystallography. The co-crystal structure in FIG. 23A shows the heavy and light chain CDR loops of A35774 (comprising SEQ ID NOS. 166 and 180, the CDRs being represented by SEQ ID NOS. 17, 40, 63, 86, 109, and 132) that interact with hPD-1. The data indicates the primary residues that serve as binding epitope on PD-1 for A35774 include F37, P39, A40, L41, V43, L138, R139 and R143 for the $V_H$ CDR loops and P34, E136, S137 and R139 for the $V_L$ CDR loops. These structural studies are consistent with the epitope mapping performed with the mouse 135C12 antibody which possesses the same heavy and light chain CDRs as A35774 as described in Examples 3 and 5. In those antibody binding experiments with PD-1 encoding amino acid substitutions, a shift in binding was observed between the 135C12 antibody and PD-1 mutant M4 including substitutions S36A/P37A/L41A, M26 with substitutions R139A/E141A; and PD-1 mutant M31 with substitutions L141A/V143L. Other PD-1 mutations that resulted in a small shift in the binding affinity of 135C12 (those present in M17, M18 and M28) are within close proximity to the binding site of the A35774 $F_{ab}$ on PD-1 and these amino acid substitutions could introduce local conformational changes in PD-1 that reduced antibody binding affinity in these tests. Together, the co-crystallography, epitope mapping and competitive antibody binding studies provide conclusive evidence that antibody binding that overlaps with the P2 patch region can possess an antagonistic functional activity that is distinct from antibodies that act though PD-1/PD-L1 blockade. Additional proof that antibodies exemplified by A35774 do not block the interaction between PD-1 and PD-L1 is provided in FIG. 23B where a model was generated between our hPD-1/$F_{ab}$ A35774 co-crystal structure and the 4ZQK co-crystal structure of PD-1 with PD-L1. This model shows a non-overlapping binding of the A35774 $F_{ab}$ and the PD-L1 protein to human PD-1 (FIG. 23B).

Example 13

In Vivo Efficacy Studies

Figure 24:
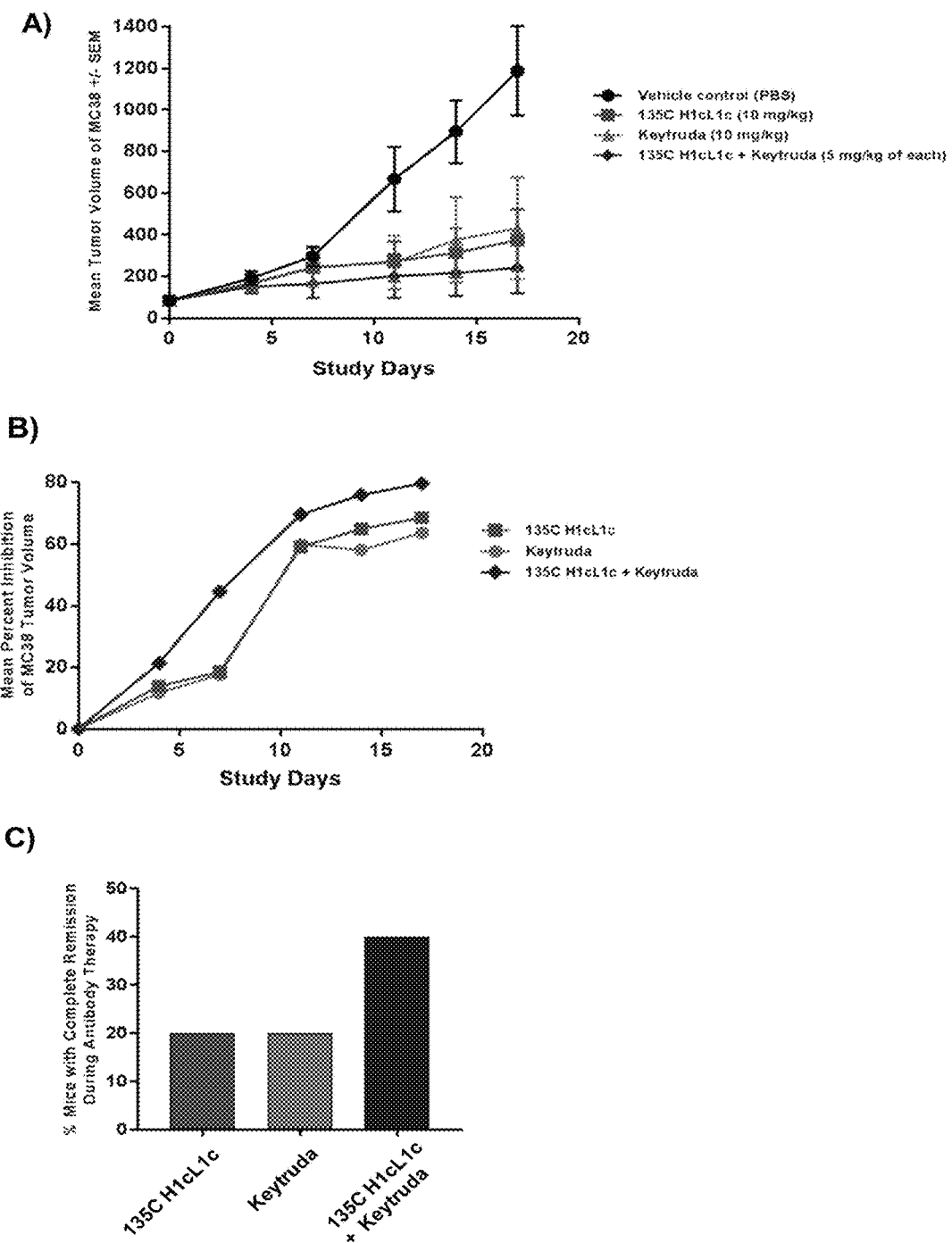
FIG. 24. In vivo efficacy study was performed in PD-1 HuGEMM mice to evaluate the therapeutic potential of either a humanized IgG4 non-blocking anti-PD-1 antibodies (135C H1cL1c) the blocking anti-PD-1 antibody Keytruda (MK3475) or a combination of 135C H1cL1c+Keytruda. (A) Mean tumor volume of the MC38 cells are given for the vehicle control mice relative to the different antibody treatments. (B) Mean percent inhibition of tumor growth for antibody treatments compared to the vehicle alone control. (C) Percentage of mice in each anti-PD-1 treatment group that exhibited a complete remission of the implanted MC38 tumor.

An in vivo efficacy study was performed in PD-1 HuGEMM mice to evaluate the therapeutic potential of a non-blocking anti-PD-1 antibody 135C H1cL1c (comprising SEQ ID NOS. 176 and 190)) in comparison to Keytruda® (MK3475), each administered individually at 10 mg/kg bi-weekly (FIG. 24). An additional therapeutic treatment included the co-administration of 135C H1cL1c and Keytruda® at 5 mg/kg each bi-weekly. The HuGEMM mice were genetically engineered to express a chimeric human/mouse PD-1 protein where the majority of the receptor ectodomain encodes the human PD-1 protein (human PD-1 sequence from residues 26 to 146). Prior to the in vivo study, flow cytometry tests confirmed that 135C H1cL1c and Keytruda® anti-PD-1 antibodies bound specifically to the HuGEMM human/mouse chimeric PD-1 at the surface of stimulated T cells. In preparation for the study, MC38 cells derived from a colon adenocarcinoma were subcutaneously inoculated into a number of PD-1 HuGEMM mice for tumor development. When the tumors reached a volume of about 95 $mm^3 \pm 50$, a total of 40 mice were randomized into four groups with an average tumor size of 84 $mm^3$ and dosing (vehicle, 135C H1cL1c, Keytruda® and 135C H1cL1c+ Keytruda®) initiated on study day 0. Therapeutic anti-PD-1 antibodies were administered bi-weekly with the tumor size and mouse body weight measured twice a week. Tumor growth inhibition was monitored relative to the untreated PBS buffer vehicle control mice and efficacy was compared to that of Keytruda®. The non-blocking anti-PD-1 antibody 135C H1cL1c induced a reduction in tumor growth at levels comparable to Keytruda®. The co-administration of 135C H1cL1c and Keytruda® also induced a reduction of tumor grown that was at least as effective as Keytruda® administered alone at 10 mg/kg. However, at all post-treatment timepoints during the study, mice treated with the combination of 135C H1cL1c and Keytruda® exhibited a trend towards an improved response and lower mean tumor volume relative to the Keytruda® positive control. Importantly, the combination of 135C H1cL1c and Keytruda® showed a statistically significant reduction in tumor volume relative to the vehicle control on Day 4 (p-value of 0.0676, close to statistical limit), Day 7 (p-value of 0.0266), Day 11 (p-value of 0.0067), Day 14 (p-value of 0.0037), and Day 17 (p-value of 0.0021) of the study (using pairwise Wilcox test for statistical analysis). In contrast, Keytruda® administered alone only showed a statistically significant reduction in tumor volume relative to the vehicle control on Day 11 (p-value of 0.0205), Day 14 (p-value of 0.0145), Day 17 (p-value of 0.0145). Administration of 135C H1cL1c alone showed a statistically significant reduction in tumor volume relative to the vehicle control on Day 11 (p-value of 0.0266), Day 14 (p-value of 0.0062), and Day 17 (p-value of 0.0044) of the study (FIG. 24A). Interpretation of the data in terms of the mean percentage inhibition of the MC38 tumor volume relative to the vehicle control also shows a strong trend towards and improved anti-tumor activity of the 135C H1cL1c and Keytruda® combination relative to either Keytruda® or 135C H1cL1c administered alone (FIG. 24B). This profile supports in vitro evidence that the combination of a blocking Keytruda® or MK3475) and a non-blocking (135C H1cL1c) anti-PD-1 leads to an enhanced T cell functional activities (e.g., proliferation (Examples 2 and 8) and cytokine production (Example 11)). An additional observation is that the 135C H1cL1c and Keytruda® combination begins exerting an anti-tumor effect at much earlier timepoints (e.g. Day 4 or 7 of the study) relative to Keytruda® alone despite the fact that equivalent total amounts of antibody were dosed for each arm of the study (Keytruda®: 10 mg/kg and 135C H1cL1c and Keytruda®: 5 mg/kg of each). Finally, the in vivo tumor model data was interpreted in terms of the percentage of mice that experienced a complete remission of the M38 tumor during the antibody therapy (FIG. 24C). Consistent with the improved percent tumor inhibition observed with the 135C H1cL1c and Keytruda® combination, this arm of the study (the combination of 135C H1cL1c and Keytruda®) exhibited a 2-fold increase in mice that had a complete remission of the implanted tumor (four mice for the 135C H1cL1c and Keytruda® combination versus two mice for either Keytruda® or 135C H1cL1c administered individually/alone). Together, this in vivo data confirms that binding to an epitope of PD-1 that overlaps with the P2 patch and non-blocking of the PD-1/PD-L1 interaction, activates a tumor-specific immune response that is distinct from and cooperative with anti-PD-1 antibodies that act through PD-1/PD-L1 blockade.

While certain embodiments have been described in terms of the preferred embodiments, it is understood that variations and modifications will occur to those skilled in the art. Therefore, it is intended that the appended claims cover all such equivalent variations that come within the scope of the following claims.

REFERENCES

1. Chun T W et al. *Nature* 387: 183-188, 1997
2. Chun T W et al. *Proc Natl Acad Sci USA* 94: 13193-13197, 1997
3. Finzi D et al. *Science* 278: 1295-1300, 1997
4. Chomont N et al. *Nat Med* 15:893-900, 2009
5. Siliciano J D et al. *Nat Med* 9:727-728, 203
6. Perreau M et al. *J Exp Med* 210: 143-156, 2013
7. Rong L and Perelson A J *Theoret Biol* 260:308-331, 2009
8. Sigal A et al. *Nature* 477:95-98, 2011
9. Katlama C et al. *Lancet* 381:2109-2117, 2013
10. Hansen S G et al. *Nature* 503:100-106, 2013
11. Klein F et al. *Nature* 492: 518.522, 2012
12. Barouch D H et al. *Nature* 503:224-228, 2013
13. Trautmann L et al. *Nat Med* 12:1198-1202, 2006
14. Day C L et al. *Nature* 443:350-354, 2006
15. Archin N M et al. *Nature* 487:482-485, 2012
16. Sievers E L and Senter P D *Annu Rev Med.* 64:15-29, 2013
17. Zolot R S et al. *Nat Rev Drug Discov* 4:259-260, 2013

What is claimed is:

1. A humanized antibody or fragment thereof that binds human PD-1 and comprises a heavy chain variable region (VH) comprising the amino acid sequence set forth in SEQ ID NO: 176 and a light chain variable region (VL) comprising the amino acid sequence set forth in SEQ ID NO: 190.

2. A composition comprising the humanized antibody or fragment thereof of claim 1 and at least one pharmaceutically acceptable carrier.

3. A method of inducing internalization of PD-1 from the surface of a T cell by contacting the T cell with the composition of claim 2.

4. The method of claim 3, wherein the T cell is a human T cell infected with human immunodeficiency virus (HIV).

5. A method of relieving functional exhaustion and increasing proliferation of antigen-specific CD8 T cells by contacting the CD8 T cells with the composition of claim 2.

6. The method of claim 5, wherein the T cells are specific for human immunodeficiency virus (HIV).

7. The method of claim 3 or 5, wherein the method further comprises contacting the T cells with the anti-PD-1 antibody pembrolizumab.

8. A method of treating cancer in a human patient, the method comprising administering to the patient with the cancer an effective amount of the composition of claim 2.

9. The method of claim 8, wherein the method further comprises administering pembrolizumab to the patient.

10. The fragment of claim 1, wherein the fragment is an $F_{ab}$, $F_{ab2}$, Fab', single chain antibody, or $F_v$ fragment.

11. A composition comprising the fragment of claim 10 and at least one pharmaceutically acceptable carrier.

12. A composition comprising the humanized antibody or fragment thereof of claim 1 and the anti-PD-1 antibody pembrolizumab.

13. A binding agent that comprises the humanized antibody or fragment thereof of claim 1 and a second binding specificity against a different antigen.

14. A composition comprising the binding agent of claim 13 and a pharmaceutically acceptable carrier.

15. A derivative of the humanized antibody or fragment thereof of claim 1, wherein the derivative comprises the humanized antibody or fragment thereof of claim 1 and a detectable label or an effector moiety fixably attached thereto.

16. A composition comprising the derivative of claim 15 and a pharmaceutically acceptable carrier.

17. An isolated polynucleotide encoding a humanized antibody or fragment thereof that binds human PD-1 and comprises a heavy chain variable region (VH) comprising the amino acid sequence set forth in SEQ ID NO: 176 and a light chain variable region (VL) comprising the amino acid sequence set forth in SEQ ID NO: 190.

18. An isolated polynucleotide comprising the nucleic acid sequence set forth in SEQ ID NO: 229 or SEQ ID NO: 243.

19. An expression vector comprising one or more polynucleotide of claim 17 or 18.

20. A host cell comprising the expression vector of claim 19.

21. A host cell comprising one or more polynucleotide of claim 17 or 18.

22. A humanized antibody or fragment thereof that binds human PD-1 and comprises a combination of a heavy chain variable region (VH) and a light chain variable region (VL), wherein the humanized antibody comprises:
   (a) a VH comprising an amino acid sequence as set forth in one of SEQ ID NOS: 147-150 and a VL comprising an amino acid sequence set forth in one of SEQ ID NOS: 159-163; or
   (b) a VH comprising an amino acid sequence as set forth in one of SEQ ID NOS: 172-177 and a VL comprising an amino acid sequence as set forth in one of SEQ ID NOS: 186-190.

23. A composition comprising the humanized antibody or fragment thereof of claim 22 and a pharmaceutically acceptable carrier.

24. A composition comprising the humanized antibody or fragment thereof of claim 22 and the anti-PD-1 antibody pembrolizumab.

25. A method of treating cancer in a human patient, the method comprising administering to the patient with the cancer an effective amount of the composition of claim 22.

26. The method of claim 25, wherein the method further comprises administering pembrolizumab to the patient.

27. An isolated polynucleotide encoding a humanized antibody or fragment that binds human PD-1 and comprises a combination of a heavy chain variable region (VH) and a light chain variable region (VL), wherein the humanized antibody comprises:
   (a) a VH encoded by a nucleic acid sequence as set forth in one of SEQ ID NOS: 200-203 and a VL encoded by a nucleic acid sequence as set forth in one of SEQ ID NOS: 212-216;
   or
   (b) a VH encoded by a nucleic acid sequence as set forth in one of SEQ ID NOS: 225-230 and a VL encoded by a nucleic acid sequence as set forth in one of SEQ ID NOS: 239-243.

28. A vector comprising the polynucleotide of claim 27.

29. A host cell comprising the vector of claim 28.

* * * * *

SEQUENCE LISTING

<160> NUMBER OF SEQ ID NOS: 292

<210> SEQ ID NO 1

```
<211> LENGTH: 5
<212> TYPE: PRT
<213> ORGANISM: Artificial Sequence
<220> FEATURE:
<223> OTHER INFORMATION: Synthetic

<400> SEQUENCE: 1

Asp Asp Phe Leu His
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Asn Tyr Tyr Ile His
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Asn Tyr Tyr Ile His
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Ser Asn Trp Met His
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

Arg Tyr Trp Met His
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Ser Asn Trp Met His
1               5

<210> SEQ ID NO 7
<211> LENGTH: 5
```

```
<212> TYPE: PRT
<213> ORGANISM: Artificial Sequence
<220> FEATURE:
<223> OTHER INFORMATION: Synthetic

<400> SEQUENCE: 7

Asn Ser Tyr Ile His
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Asn Tyr Trp Ile Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Ser Tyr Ala Met Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Ser Asp Tyr Ala Trp Asn
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Ser Tyr Trp Ile Asn
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Ser Ser Tyr Ile His
1               5

<210> SEQ ID NO 13
<211> LENGTH: 5
<212> TYPE: PRT
```

-continued

```
<213> ORGANISM: Artificial Sequence
<220> FEATURE:
<223> OTHER INFORMATION: Synthetic

<400> SEQUENCE: 13

Asn His Gly Met Ser
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

Asn Tyr Trp Ile Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Asp Ser Tyr Ile His
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic

<400> SEQUENCE: 16

Asp Thr Tyr Ile His
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic

<400> SEQUENCE: 17

Asn Phe Tyr Ile His
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic

<400> SEQUENCE: 18

Asp Ser Tyr Ile His
1               5

<210> SEQ ID NO 19
<211> LENGTH: 5
<212> TYPE: PRT
<213> ORGANISM: Artificial Sequence
```

```
<220> FEATURE:
<223> OTHER INFORMATION: Synthetic

<400> SEQUENCE: 19

Asp Asp Phe Leu His
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic

<400> SEQUENCE: 20

Ser Tyr Phe Met Ser
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic

<400> SEQUENCE: 21

Asn His Gly Met Ser
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic

<400> SEQUENCE: 22

Asn Tyr Trp Ile Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic

<400> SEQUENCE: 23

Ser Phe Ala Met Ser
1               5

<210> SEQ ID NO 24
<211> LENGTH: 17
<212> TYPE: PRT
<213> ORGANISM: Artificial Sequence
<220> FEATURE:
<223> OTHER INFORMATION: Synthetic

<400> SEQUENCE: 24

Arg Ile Asp Pro Ala Asn Gly Glu Ser Arg Tyr Ala Pro Lys Phe Gln
1               5                   10                  15

Asp

<210> SEQ ID NO 25
<211> LENGTH: 17
<212> TYPE: PRT
```

<213> ORGANISM: Artificial Sequence
<220> FEATURE:
<223> OTHER INFORMATION: Synthetic

<400> SEQUENCE: 25

Ser Ile Tyr Pro Asn Tyr Gly Asp Thr Asn Tyr Asn Gln Lys Val Lys
1               5                   10                  15

Asp

<210> SEQ ID NO 26
<211> LENGTH: 17
<212> TYPE: PRT
<213> ORGANISM: Artificial Sequence
<220> FEATURE:
<223> OTHER INFORMATION: Synthetic

<400> SEQUENCE: 26

Ser Ile Tyr Pro Asn Tyr Gly Glu Thr Asn Tyr Asn Gln Glu Phe Lys
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Synthetic

<400> SEQUENCE: 27

Ala Val Asn Pro Gly Asn Ser Asp Thr Thr Tyr Asn Gln Lys Phe Lys
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: Synthetic

<400> SEQUENCE: 28

Asn Ile Asp Pro Ser Asp Ser Thr Thr His Tyr Asn Pro Lys Phe Arg
1               5                   10                  15

Asp

<210> SEQ ID NO 29
<211> LENGTH: 17
<212> TYPE: PRT
<213> ORGANISM: Artificial Sequence
<220> FEATURE:
<223> OTHER INFORMATION: Synthetic

<400> SEQUENCE: 29

Ala Val Tyr Pro Gly Asn Ser Asp Thr Thr Tyr Asn Gln Asn Phe Lys
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic

<400> SEQUENCE: 30

Trp Ile Ser Pro Gly Asp Gly Ser Thr Asn Tyr Asn Glu Lys Phe Lys
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Synthetic

<400> SEQUENCE: 31

Asp Ile Tyr Pro Gly Gly Gly Tyr Thr Asn Tyr Asn Glu Lys Phe Lys
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Synthetic

<400> SEQUENCE: 32

Thr Ile Ser Gly Gly Gly Ala Asp Thr Tyr Tyr Leu Asp Asn Val Lys
1               5                   10                  15

Gly

<210> SEQ ID NO 33
<211> LENGTH: 16
<212> TYPE: PRT
<213> ORGANISM: Artificial Sequence
<220> FEATURE:
<223> OTHER INFORMATION: Synthetic

<400> SEQUENCE: 33

Tyr Ile Asn Tyr Ser Gly Tyr Thr Asn Tyr Asn Pro Phe Leu Lys Ser
1               5                   10                  15

<210> SEQ ID NO 34
<211> LENGTH: 17
<212> TYPE: PRT
<213> ORGANISM: Artificial Sequence
<220> FEATURE:
<223> OTHER INFORMATION: Synthetic

<400> SEQUENCE: 34

Asn Ile Tyr Pro Gly Ser Ser Ser Thr Asp Tyr Asn Glu Lys Phe Lys
1               5                   10                  15

Ser

<210> SEQ ID NO 35
<211> LENGTH: 17
<212> TYPE: PRT
<213> ORGANISM: Artificial Sequence
<220> FEATURE:
<223> OTHER INFORMATION: Synthetic

<400> SEQUENCE: 35

Trp Ile Phe Pro Gly Asp Gly Lys Thr Asn Tyr Asn Glu Lys Phe Arg
1               5                   10                  15

Asp

<210> SEQ ID NO 36
<211> LENGTH: 17
<212> TYPE: PRT
<213> ORGANISM: Artificial Sequence
<220> FEATURE:
<223> OTHER INFORMATION: Synthetic

<400> SEQUENCE: 36

Ser Ile Asn Thr Gly Gly Tyr Ser Thr Tyr Tyr Pro Asp Asn Val Lys
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

Asp Ile Tyr Pro Gly Ser Glu Tyr Glu Asn Tyr Asn Glu Lys Phe Lys
1               5                   10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: Synthetic

<400> SEQUENCE: 38

Arg Ile Asp Pro Ala His Gly Asn Val Ile Tyr Ala Ser Lys Phe Arg
1               5                   10                  15

Asp

<210> SEQ ID NO 39
<211> LENGTH: 17
<212> TYPE: PRT
<213> ORGANISM: Artificial Sequence
<220> FEATURE:
<223> OTHER INFORMATION: Synthetic

<400> SEQUENCE: 39

Arg Ile Asp Leu Ala Asn Asp Ile Leu Tyr Ala Ser Lys Phe Gln
1               5                   10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Ser Ile Tyr Pro Asn Tyr Gly Asp Thr Ala Tyr Asn Gln Lys Phe Lys
1               5                   10                  15

Asp

<210> SEQ ID NO 41
<211> LENGTH: 17

```
<212> TYPE: PRT
<213> ORGANISM: Artificial Sequence
<220> FEATURE:
<223> OTHER INFORMATION: Synthetic

<400> SEQUENCE: 41

Arg Ile Asp Pro Ala Arg Asp Asn Ile Ile Tyr Ala Ser Lys Phe Arg
1               5                   10                  15
Asp

<210> SEQ ID NO 42
<211> LENGTH: 17
<212> TYPE: PRT
<213> ORGANISM: Artificial Sequence
<220> FEATURE:
<223> OTHER INFORMATION: Synthetic

<400> SEQUENCE: 42

Arg Ile Asp Pro Ala Asn Gly Glu Ser Arg Tyr Ala Pro Gln Phe Gln
1               5                   10                  15
Asp

<210> SEQ ID NO 43
<211> LENGTH: 17
<212> TYPE: PRT
<213> ORGANISM: Artificial Sequence
<220> FEATURE:
<223> OTHER INFORMATION: Synthetic

<400> SEQUENCE: 43

Gly Ile Ser Thr Gly Gly Ala Asp Thr Tyr Tyr Ala Asp Ser Met Lys
1               5                   10                  15
Gly

<210> SEQ ID NO 44
<211> LENGTH: 17
<212> TYPE: PRT
<213> ORGANISM: Artificial Sequence
<220> FEATURE:
<223> OTHER INFORMATION: Synthetic

<400> SEQUENCE: 44

Ser Ile Ser Gly Gly Gly Asp Asn Thr Tyr Tyr Pro Asp Asn Leu Lys
1               5                   10                  15
Gly

<210> SEQ ID NO 45
<211> LENGTH: 17
<212> TYPE: PRT
<213> ORGANISM: Artificial Sequence
<220> FEATURE:
<223> OTHER INFORMATION: Synthetic

<400> SEQUENCE: 45

Asp Ile Tyr Pro Gly Gly Asp His Lys Asn Tyr Asn Glu Lys Phe Lys
1               5                   10                  15
Asp

<210> SEQ ID NO 46
<211> LENGTH: 17
<212> TYPE: PRT
<213> ORGANISM: Artificial Sequence
<220> FEATURE:
<223> OTHER INFORMATION: Synthetic
```

```
<400> SEQUENCE: 46

Thr Ile Thr Gly Gly Val Asn Thr Tyr Tyr Pro Asp Thr Val Lys
1               5                   10                  15

Gly

<210> SEQ ID NO 47
<211> LENGTH: 12
<212> TYPE: PRT
<213> ORGANISM: Artificial Sequence
<220> FEATURE:
<223> OTHER INFORMATION: Synthetic

<400> SEQUENCE: 47

Thr Asp Tyr Arg Gly Tyr Tyr Tyr Ala Met Asp Tyr
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Synthetic

<400> SEQUENCE: 48

Gly Tyr Ser Tyr Ala Met Asp Tyr
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic

<400> SEQUENCE: 49

Gly Tyr Ser Tyr Ala Met Asp Tyr
1               5

<210> SEQ ID NO 50
<211> LENGTH: 10
<212> TYPE: PRT
<213> ORGANISM: Artificial Sequence
<220> FEATURE:
<223> OTHER INFORMATION: Synthetic

<400> SEQUENCE: 50

Gly Arg Ser Tyr Asp Gly Ser Phe Asp Tyr
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Synthetic

<400> SEQUENCE: 51

Asp Leu Asp Asp Phe Tyr Val Gly Ser His Glu Asp Phe Asp Tyr
1               5                   10                  15

<210> SEQ ID NO 52
<211> LENGTH: 10
<212> TYPE: PRT
<213> ORGANISM: Artificial Sequence
<220> FEATURE:
```

```
<223> OTHER INFORMATION: Synthetic

<400> SEQUENCE: 52

Gly Arg Ser Tyr Asp Gly Ser Phe Asp Tyr
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Synthetic

<400> SEQUENCE: 53

Glu Glu Tyr Asp Tyr Asp Asn Tyr
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Gly Tyr Asp Phe Val Leu Asp Arg
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Gln Arg Gly Glu Asn Leu Phe Ala His
1               5

<210> SEQ ID NO 56
<211> LENGTH: 11
<212> TYPE: PRT
<213> ORGANISM: Artificial Sequence
<220> FEATURE:
<223> OTHER INFORMATION: Synthetic

<400> SEQUENCE: 56

Tyr Gly Gly Ser Tyr Pro Trp Asn Phe Asp Val
1               5                   10

<210> SEQ ID NO 57
<211> LENGTH: 8
<212> TYPE: PRT
<213> ORGANISM: Artificial Sequence
<220> FEATURE:
<223> OTHER INFORMATION: Synthetic

<400> SEQUENCE: 57

Gly Leu Tyr Trp Tyr Phe Asp Val
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic
```

<400> SEQUENCE: 58

Asn Asp Phe Asp Arg Gly Val Tyr
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic

<400> SEQUENCE: 59

Asp Asp Tyr Asn Trp Phe Ala Tyr
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic

<400> SEQUENCE: 60

Gly Tyr Asp Phe Val Leu Asp His
1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic

<400> SEQUENCE: 61

Ile Tyr Tyr Asp Tyr Gly Glu Gly Asp Phe
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic

<400> SEQUENCE: 62

Ile Tyr Tyr Asp Tyr Gly Glu Gly Asp Tyr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Synthetic

<400> SEQUENCE: 63

Gly Tyr Ser Tyr Ala Met Asp Tyr
1               5

<210> SEQ ID NO 64
<211> LENGTH: 10
<212> TYPE: PRT
<213> ORGANISM: Artificial Sequence
<220> FEATURE:
<223> OTHER INFORMATION: Synthetic

```
<400> SEQUENCE: 64

Ile Tyr Tyr Asp Tyr Gly Glu Gly Asp Tyr
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic

<400> SEQUENCE: 65

Thr Asp Tyr Arg Gly Tyr Tyr Tyr Ala Met Asp Tyr
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic

<400> SEQUENCE: 66

Leu Ser His Tyr Tyr Asp Gly Ile Pro Leu Asp Cys
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic

<400> SEQUENCE: 67

Val Arg Gln Leu Gly Leu His Arg Ala Ala Met Asp Tyr
1               5                   10

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Asp Phe Val Leu Asp Tyr
1               5

<210> SEQ ID NO 69
<211> LENGTH: 12
<212> TYPE: PRT
<213> ORGANISM: Artificial Sequence
<220> FEATURE:
<223> OTHER INFORMATION: Synthetic

<400> SEQUENCE: 69

Gln Ala Ile Tyr Asp Gly His Tyr Val Leu Asp Tyr
1               5                   10

<210> SEQ ID NO 70
<211> LENGTH: 17
<212> TYPE: PRT
<213> ORGANISM: Artificial Sequence
<220> FEATURE:
<223> OTHER INFORMATION: Synthetic

<400> SEQUENCE: 70
```

```
Lys Ser Ser Gln Ser Val Leu Tyr Ser Asn Gln Lys Asn Tyr Leu
1               5                   10                  15

Ala

<210> SEQ ID NO 71
<211> LENGTH: 11
<212> TYPE: PRT
<213> ORGANISM: Artificial Sequence
<220> FEATURE:
<223> OTHER INFORMATION: Synthetic

<400> SEQUENCE: 71

Ser Ala Ser Gln Gly Ile Ser Asp Gly Leu Asn
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic

<400> SEQUENCE: 72

Ser Ala Ser Gln Gly Ile Ser Asn Gly Leu Asn
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic

<400> SEQUENCE: 73

Lys Ala Ser Gln Asp Ile Asn Lys Tyr Ile Ala
1               5                   10

<210> SEQ ID NO 74
<211> LENGTH: 16
<212> TYPE: PRT
<213> ORGANISM: Artificial Sequence
<220> FEATURE:
<223> OTHER INFORMATION: Synthetic

<400> SEQUENCE: 74

Arg Ser Ser Gln Ser Ile Val Tyr Ser Asn Gly Asn Thr Tyr Leu Glu
1               5                   10                  15

<210> SEQ ID NO 75
<211> LENGTH: 11
<212> TYPE: PRT
<213> ORGANISM: Artificial Sequence
<220> FEATURE:
<223> OTHER INFORMATION: Synthetic

<400> SEQUENCE: 75

Lys Ala Ser Gln Asp Ile Asn Lys Tyr Met Ala
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic
```

```
<400> SEQUENCE: 76

Lys Ala Ser Gln Asn Val Gly Thr Asn Val Gly
1               5                   10

<210> SEQ ID NO 77
<211> LENGTH: 17
<212> TYPE: PRT
<213> ORGANISM: Artificial Sequence
<220> FEATURE:
<223> OTHER INFORMATION: Synthetic

<400> SEQUENCE: 77

Lys Ser Ser Gln Ser Leu Phe Asn Ser Glu Thr Gln Lys Asn Tyr Leu
1               5                   10                  15

Ala

<210> SEQ ID NO 78
<211> LENGTH: 11
<212> TYPE: PRT
<213> ORGANISM: Artificial Sequence
<220> FEATURE:
<223> OTHER INFORMATION: Synthetic

<400> SEQUENCE: 78

Leu Ala Ser Gln Thr Ile Gly Thr Trp Leu Ala
1               5                   10

<210> SEQ ID NO 79
<211> LENGTH: 16
<212> TYPE: PRT
<213> ORGANISM: Artificial Sequence
<220> FEATURE:
<223> OTHER INFORMATION: Synthetic

<400> SEQUENCE: 79

Arg Ser Ser Gln Thr Ile Val His Asn Gly Asp Thr Tyr Leu Glu
1               5                   10                  15

<210> SEQ ID NO 80
<211> LENGTH: 17
<212> TYPE: PRT
<213> ORGANISM: Artificial Sequence
<220> FEATURE:
<223> OTHER INFORMATION: Synthetic

<400> SEQUENCE: 80

Lys Ser Ser Gln Ser Leu Phe Asn Ser Gly Thr Arg Lys Asn Tyr Leu
1               5                   10                  15

Ala

<210> SEQ ID NO 81
<211> LENGTH: 11
<212> TYPE: PRT
<213> ORGANISM: Artificial Sequence
<220> FEATURE:
<223> OTHER INFORMATION: Synthetic

<400> SEQUENCE: 81

Lys Ala Ser Gln Asn Val Asp Thr Asn Val Ala
1               5                   10

<210> SEQ ID NO 82
<211> LENGTH: 17
<212> TYPE: PRT
<213> ORGANISM: Artificial Sequence
```

<220> FEATURE:
<223> OTHER INFORMATION: Synthetic

<400> SEQUENCE: 82

Lys Ser Ser Gln Ser Leu Leu Asn Ser Gly Asn Gln Lys Asn Tyr Leu
1               5                   10                  15
Thr

<210> SEQ ID NO 83
<211> LENGTH: 17
<212> TYPE: PRT
<213> ORGANISM: Artificial Sequence
<220> FEATURE:
<223> OTHER INFORMATION: Synthetic

<400> SEQUENCE: 83

Lys Ser Ser Gln Ser Leu Phe Asn Ser Gly Thr Arg Lys Ser Tyr Leu
1               5                   10                  15
Ala

<210> SEQ ID NO 84
<211> LENGTH: 11
<212> TYPE: PRT
<213> ORGANISM: Artificial Sequence
<220> FEATURE:
<223> OTHER INFORMATION: Synthetic

<400> SEQUENCE: 84

His Ala Ser Gln Asn Ile Asn Val Trp Leu Ser
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic

<400> SEQUENCE: 85

His Ala Ser Gln Asn Ile Asn Val Trp Leu Ser
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic

<400> SEQUENCE: 86

Ser Ala Ser Gln Gly Ile Ser Gly Asp Leu Asn
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic

<400> SEQUENCE: 87

His Ala Ser Gln Asn Ile Asn Val Trp Leu Ser
1               5                   10

<210> SEQ ID NO 88

```
<211> LENGTH: 17
<212> TYPE: PRT
<213> ORGANISM: Artificial Sequence
<220> FEATURE:
<223> OTHER INFORMATION: Synthetic

<400> SEQUENCE: 88

Lys Ser Ser Gln Ser Val Leu Tyr Ser Ser Asn Gln Lys Asn Tyr Leu
1               5                   10                  15
Ala

<210> SEQ ID NO 89
<211> LENGTH: 15
<212> TYPE: PRT
<213> ORGANISM: Artificial Sequence
<220> FEATURE:
<223> OTHER INFORMATION: Synthetic

<400> SEQUENCE: 89

Arg Ala Ser Glu Ser Val Asp Asn Ser Gly Val Ser Phe Leu Thr
1               5                   10                  15

<210> SEQ ID NO 90
<211> LENGTH: 11
<212> TYPE: PRT
<213> ORGANISM: Artificial Sequence
<220> FEATURE:
<223> OTHER INFORMATION: Synthetic

<400> SEQUENCE: 90

Lys Ala Ser Gln Ser Val Ser Asp Asp Val Ser
1               5                   10

<210> SEQ ID NO 91
<211> LENGTH: 17
<212> TYPE: PRT
<213> ORGANISM: Artificial Sequence
<220> FEATURE:
<223> OTHER INFORMATION: Synthetic

<400> SEQUENCE: 91

Lys Ser Ser Gln Ser Leu Phe Asn Ser Gly Thr Arg Lys Asn Tyr Leu
1               5                   10                  15
Ala

<210> SEQ ID NO 92
<211> LENGTH: 11
<212> TYPE: PRT
<213> ORGANISM: Artificial Sequence
<220> FEATURE:
<223> OTHER INFORMATION: Synthetic

<400> SEQUENCE: 92

Arg Thr Ser Gly Asn Ile His Asn Tyr Leu Ala
1               5                   10

<210> SEQ ID NO 93
<211> LENGTH: 7
<212> TYPE: PRT
<213> ORGANISM: Artificial Sequence
<220> FEATURE:
<223> OTHER INFORMATION: Synthetic

<400> SEQUENCE: 93

Trp Ala Ser Thr Arg Glu Ser
1               5
```

<210> SEQ ID NO 94
<211> LENGTH: 7
<212> TYPE: PRT
<213> ORGANISM: Artificial Sequence
<220> FEATURE:
<223> OTHER INFORMATION: Synthetic

<400> SEQUENCE: 94

His Thr Ser Thr Leu His Ser
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic

<400> SEQUENCE: 95

His Thr Ser Thr Leu His Ser
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic

<400> SEQUENCE: 96

Tyr Thr Ser Thr Leu Arg Pro
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic

<400> SEQUENCE: 97

Lys Val Ser His Arg Phe Ser
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic

<400> SEQUENCE: 98

Tyr Thr Ser Thr Leu Arg Pro
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic

<400> SEQUENCE: 99

Ser Ala Ser Tyr Arg Tyr Asn
1               5

```
<210> SEQ ID NO 100
<211> LENGTH: 7
<212> TYPE: PRT
<213> ORGANISM: Artificial Sequence
<220> FEATURE:
<223> OTHER INFORMATION: Synthetic

<400> SEQUENCE: 100

Trp Ala Ser Thr Arg Glu Ser
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic

<400> SEQUENCE: 101

Ala Ala Thr Ser Leu Ala Asp
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Lys Ile Ser Asn Arg Phe Phe
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic

<400> SEQUENCE: 103

Trp Ala Ser Thr Arg Asp Ser
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic

<400> SEQUENCE: 104

Ser Ala Ser Tyr Arg Tyr Asn
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic

<400> SEQUENCE: 105

Trp Ala Ser Thr Arg Glu Ser
1               5
```

```
<210> SEQ ID NO 106
<211> LENGTH: 7
<212> TYPE: PRT
<213> ORGANISM: Artificial Sequence
<220> FEATURE:
<223> OTHER INFORMATION: Synthetic

<400> SEQUENCE: 106

Trp Ala Ser Thr Arg Glu Thr
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic

<400> SEQUENCE: 107

Lys Ala Ser Asn Leu His Thr
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic

<400> SEQUENCE: 108

Lys Ala Ser Asn Leu His Thr
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic

<400> SEQUENCE: 109

His Thr Ser Ser Leu His Ser
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic

<400> SEQUENCE: 110

Lys Ala Ser Asn Leu His Thr
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic

<400> SEQUENCE: 111

Trp Ala Ser Thr Arg Glu Ser
1               5

<210> SEQ ID NO 112
```

<211> LENGTH: 7
<212> TYPE: PRT
<213> ORGANISM: Artificial Sequence
<220> FEATURE:
<223> OTHER INFORMATION: Synthetic

<400> SEQUENCE: 112

Ala Ala Ser Asn Gln Gly Ser
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic

<400> SEQUENCE: 113

Ser Ala Phe Phe Arg Tyr Pro
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic

<400> SEQUENCE: 114

Trp Ala Ser Thr Arg Glu Ser
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic

<400> SEQUENCE: 115

Asn Val Lys Thr Leu Thr Asp
1               5

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

His Gln Tyr Leu Ser Ser Tyr Thr
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic

<400> SEQUENCE: 117

Gln Gln Tyr Ser Lys Phe Pro Leu Thr
1               5

<210> SEQ ID NO 118
<211> LENGTH: 9

```
<212> TYPE: PRT
<213> ORGANISM: Artificial Sequence
<220> FEATURE:
<223> OTHER INFORMATION: Synthetic

<400> SEQUENCE: 118

Gln Gln Tyr Ser Lys Phe Pro Leu Thr
1               5

<210> SEQ ID NO 119
<211> LENGTH: 8
<212> TYPE: PRT
<213> ORGANISM: Artificial Sequence
<220> FEATURE:
<223> OTHER INFORMATION: Synthetic

<400> SEQUENCE: 119

Leu Gln Tyr Asp Asn Leu Trp Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic

<400> SEQUENCE: 120

Phe Gln Gly Ser His Val Pro Tyr Thr
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic

<400> SEQUENCE: 121

Leu Gln Tyr Asp Asn Leu Trp Thr
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic

<400> SEQUENCE: 122

Gln Gln Tyr Asn Thr Tyr Pro Trp Thr
1               5

<210> SEQ ID NO 123
<211> LENGTH: 8
<212> TYPE: PRT
<213> ORGANISM: Artificial Sequence
<220> FEATURE:
<223> OTHER INFORMATION: Synthetic

<400> SEQUENCE: 123

Lys Gln Ser Tyr Thr Leu Arg Thr
1               5

<210> SEQ ID NO 124
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 124

Gln Gln Leu Tyr Ser Thr Pro Trp Thr
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic

<400> SEQUENCE: 125

Phe Gln Gly Ser His Val Pro Tyr Thr
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic

<400> SEQUENCE: 126

Lys Gln Ser Tyr Asn Leu Tyr Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic

<400> SEQUENCE: 127

Gln Gln Tyr Asn Asn Tyr Pro Tyr Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Ser Asp Tyr Ser Tyr Pro Leu Thr
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic

<400> SEQUENCE: 129

Met Gln Ser Tyr Asn Leu Arg Thr
1               5

<210> SEQ ID NO 130
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 130

Gln Gln Gly Gln Ser Trp Pro Leu Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic

<400> SEQUENCE: 131

Gln Gln Gly Gln Ser Tyr Pro Leu Thr
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic

<400> SEQUENCE: 132

Gln Tyr Tyr Ser Lys Asp Leu Leu Thr
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic

<400> SEQUENCE: 133

Gln Gln Gly Gln Ser Trp Pro Leu Thr
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

His Gln Tyr Leu Ser Ser Tyr Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic

<400> SEQUENCE: 135

Gln Gln Thr Lys Glu Val Pro Trp Thr
1               5

<210> SEQ ID NO 136
<211> LENGTH: 9
<212> TYPE: PRT
<213> ORGANISM: Artificial Sequence
<220> FEATURE:
```

<223> OTHER INFORMATION: Synthetic

<400> SEQUENCE: 136

Gln Gln Asp Tyr Ser Ser Pro Leu Thr
1               5

<210> SEQ ID NO 137
<211> LENGTH: 8
<212> TYPE: PRT
<213> ORGANISM: Artificial Sequence
<220> FEATURE:
<223> OTHER INFORMATION: Synthetic

<400> SEQUENCE: 137

Met Gln Ser Phe Asn Leu Arg Thr
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic

<400> SEQUENCE: 138

Gln Gln Phe Trp Ser Ile Pro Trp Thr
1               5

<210> SEQ ID NO 139
<211> LENGTH: 117
<212> TYPE: PRT
<213> ORGANISM: Artificial Sequence
<220> FEATURE:
<223> OTHER INFORMATION: Synthetic

<400> SEQUENCE: 139

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Asn Tyr
                20                  25                  30

Trp Ile Gly Trp Val Arg Gln Ala Pro Gly Gln Ala Leu Glu Trp Met
            35                  40                  45

Gly Asp Ile Tyr Pro Gly Gly Gly Tyr Thr Asn Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Phe Val Leu Asp Arg Trp Gly Gln Gly Thr Thr
                100                 105                 110

Val Thr Val Ser Ser
        115

<210> SEQ ID NO 140
<211> LENGTH: 117
<212> TYPE: PRT
<213> ORGANISM: Artificial Sequence
<220> FEATURE:
<223> OTHER INFORMATION: Synthetic

<400> SEQUENCE: 140

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Asn Tyr
            20                  25                  30

Trp Ile Gly Trp Val Arg Gln Ala Pro Gly Gln Ala Leu Glu Trp Met
        35                  40                  45

Gly Asp Ile Tyr Pro Gly Gly Gly Tyr Thr Asn Tyr Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Phe Val Leu Asp Arg Trp Gly Gln Gly Thr Thr
            100                 105                 110

Val Thr Val Ser Ser
        115

<210> SEQ ID NO 141
<211> LENGTH: 117
<212> TYPE: PRT
<213> ORGANISM: Artificial Sequence
<220> FEATURE:
<223> OTHER INFORMATION: Synthetic

<400> SEQUENCE: 141

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Asn Tyr
            20                  25                  30

Trp Ile Gly Trp Val Arg Gln Ala Pro Gly Gln Ala Leu Glu Trp Met
        35                  40                  45

Gly Asp Ile Tyr Pro Gly Gly Gly Tyr Thr Asn Tyr Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Phe Val Leu Asp Arg Trp Gly Gln Gly Thr Thr
            100                 105                 110

Val Thr Val Ser Ser
        115

<210> SEQ ID NO 142
<211> LENGTH: 117
<212> TYPE: PRT
<213> ORGANISM: Artificial Sequence
<220> FEATURE:
<223> OTHER INFORMATION: Synthetic

<400> SEQUENCE: 142

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Asn Tyr
            20                  25                  30

Trp Ile Gly Trp Val Arg Gln Ala Pro Gly Gln Ala Leu Glu Trp Met
        35                  40                  45

Gly Asp Ile Tyr Pro Gly Gly Gly Tyr Thr Asn Tyr Asn Glu Lys Phe
50                  55                  60

Lys Gly Arg Val Thr Ile Thr Ala Asp Lys Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Gly Tyr Asp Phe Val Leu Asp Arg Trp Gly Gln Gly Thr Thr
                100                 105                 110

Val Thr Val Ser Ser
        115

<210> SEQ ID NO 143
<211> LENGTH: 117
<212> TYPE: PRT
<213> ORGANISM: Artificial Sequence
<220> FEATURE:
<223> OTHER INFORMATION: Synthetic

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Ile Gly Trp Val Arg Gln Ala Pro Gly Gln Gly Leu Glu Trp Met
            35                  40                  45

Gly Asp Ile Tyr Pro Gly Gly Gly Tyr Thr Asn Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Gly Tyr Asp Phe Val Leu Asp Arg Trp Gly Gln Gly Thr Thr
                100                 105                 110

Val Thr Val Ser Ser
        115

<210> SEQ ID NO 144
<211> LENGTH: 117
<212> TYPE: PRT
<213> ORGANISM: Artificial Sequence
<220> FEATURE:
<223> OTHER INFORMATION: Synthetic

<400> SEQUENCE: 144

Glu Val Gln Leu Val Gln Ser Gly Ala Glu Val Lys Lys His Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Ala Thr Gly Gln Gly Leu Glu Trp Met
            35                  40                  45

Gly Asp Ile Tyr Pro Gly Gly Gly Tyr Thr Asn Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Gly Tyr Asp Phe Val Leu Asp Arg Trp Gly Gln Gly Thr Thr
                100                 105                 110

Val Thr Val Ser Ser
        115
```

<210> SEQ ID NO 145
<211> LENGTH: 117
<212> TYPE: PRT
<213> ORGANISM: Artificial Sequence
<220> FEATURE:
<223> OTHER INFORMATION: Synthetic

<400> SEQUENCE: 145

```
Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asn Tyr
            20                  25                  30

Trp Ile Gly Trp Val Arg Gln Met Pro Gly Lys Gly Leu Glu Trp Met
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Phe Val Leu Asp Arg Trp Gly Gln Gly Thr Thr
            100                 105                 110

Val Thr Val Ser Ser
        115
```

<210> SEQ ID NO 146
<211> LENGTH: 117
<212> TYPE: PRT
<213> ORGANISM: Artificial Sequence
<220> FEATURE:
<223> OTHER INFORMATION: Synthetic

<400> SEQUENCE: 146

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Gly Trp Val Arg Gln Ala Pro Gly Lys Gly Leu Glu Trp Met
        35                  40                  45

Gly Asp Ile Tyr Pro Gly Gly Tyr Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Phe Val Leu Asp Arg Trp Gly Gln Gly Thr Thr
            100                 105                 110

Val Thr Val Ser Ser
        115
```

<210> SEQ ID NO 147
<211> LENGTH: 117
<212> TYPE: PRT
<213> ORGANISM: Artificial Sequence
<220> FEATURE:
<223> OTHER INFORMATION: Synthetic

<400> SEQUENCE: 147

```
Gln Val Gln Leu Val Gln Ser Gly Ala Glu Val Lys Lys Pro Gly Ala
```

```
            1               5                  10                 15
Ser Val Lys Val Ser Cys Lys Ala Ser Gly Tyr Thr Phe Thr Asn Tyr
            20                 25                 30

Trp Ile Gly Trp Val Arg Gln Ala Pro Gly Gln Gly Leu Glu Trp Met
            35                 40                 45

Gly Asp Ile Tyr Pro Gly Gly Gly Tyr Thr Asn Tyr Asn Glu Lys Phe
            50                 55                 60

Lys Gly Arg Val Thr Met Thr Arg Asp Thr Ser Thr Ser Thr Val Tyr
65                  70                 75                    80

Met Glu Leu Ser Ser Leu Arg Ser Glu Asp Thr Ala Val Tyr Tyr Cys
                85                 90                 95

Ala Arg Gly Tyr Asp Phe Val Leu Asp Arg Trp Gly Gln Gly Thr Leu
                100                105                110

Val Thr Val Ser Ser
            115

<210> SEQ ID NO 148
<211> LENGTH: 117
<212> TYPE: PRT
<213> ORGANISM: Artificial Sequence
<220> FEATURE:
<223> OTHER INFORMATION: Synthetic

<400> SEQUENCE: 148

Gln Val Gln Leu Val Gln Ser Gly Ala Glu Val Lys Lys Pro Gly Ala
1               5                  10                 15

Ser Val Lys Val Ser Cys Lys Ala Ala Gly Tyr Thr Phe Thr Asn Tyr
            20                 25                 30

Trp Ile Gly Trp Val Arg Gln Ala Pro Gly Gln Gly Leu Glu Trp Met
            35                 40                 45

Gly Asp Ile Tyr Pro Gly Gly Gly Tyr Thr Asn Tyr Asn Glu Lys Phe
            50                 55                 60

Lys Gly Arg Val Thr Met Thr Ala Asp Thr Ser Thr Ser Thr Val Tyr
65                  70                 75                    80

Met Glu Leu Ser Ser Leu Arg Ser Glu Asp Thr Ala Val Tyr Tyr Cys
                85                 90                 95

Ala Arg Gly Tyr Asp Phe Val Leu Asp Arg Trp Gly Gln Gly Thr Leu
                100                105                110

Val Thr Val Ser Ser
            115

<210> SEQ ID NO 149
<211> LENGTH: 117
<212> TYPE: PRT
<213> ORGANISM: Artificial Sequence
<220> FEATURE:
<223> OTHER INFORMATION: Synthetic

<400> SEQUENCE: 149

Gln Val Gln Leu Val Gln Ser Gly Ala Glu Val Lys Lys Pro Gly Ala
1               5                  10                 15

Ser Val Lys Val Ser Cys Lys Ala Ser Gly Tyr Thr Phe Thr Asn Tyr
            20                 25                 30

Trp Ile Gly Trp Val Arg Gln Ala Pro Gly Gln Gly Leu Glu Trp Ile
            35                 40                 45

Gly Asp Ile Tyr Pro Gly Gly Gly Tyr Thr Asn Tyr Asn Glu Lys Phe
            50                 55                 60
```

-continued

```
Lys Gly Arg Val Thr Met Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Tyr Asp Phe Val Leu Asp Arg Trp Gly Gln Gly Thr Leu
            100                 105                 110

Val Thr Val Ser Ser
            115
```

<210> SEQ ID NO 150
<211> LENGTH: 117
<212> TYPE: PRT
<213> ORGANISM: Artificial Sequence
<220> FEATURE:
<223> OTHER INFORMATION: Synthetic

<400> SEQUENCE: 150

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asn Tyr
                 20                  25                  30

Trp Ile Gly Trp Ile Arg Gln Ala Pro Gly Gln Gly Leu Glu Trp Ile
             35                  40                  45

Gly Asp Ile Tyr Pro Gly Gly Gly Tyr Thr Asn Tyr Asn Glu Lys Phe
         50                  55                  60

Lys Gly Arg Ala Thr Leu Thr Ala Asp Thr Ser Thr Ser Thr Val Tyr
 65                  70                  75                  80

Met Glu Val Ser Ser Leu Arg Ser Glu Asp Thr Ala Val Tyr Tyr Cys
                 85                  90                  95

Ala Arg Gly Tyr Asp Phe Val Leu Asp Arg Trp Gly Gln Gly Thr Leu
            100                 105                 110

Val Thr Val Ser Ser
            115
```

<210> SEQ ID NO 151
<211> LENGTH: 112
<212> TYPE: PRT
<213> ORGANISM: Artificial Sequence
<220> FEATURE:
<223> OTHER INFORMATION: Synthetic

<400> SEQUENCE: 151

```
Asp Val Val Met Thr Gln Ser Pro Ala Phe Leu Ser Val Thr Pro Gly
  1               5                  10                  15

Glu Lys Val Thr Ile Thr Cys Lys Ser Ser Gln Ser Leu Phe Asn Ser
                 20                  25                  30

Glu Thr Gln Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Lys Gln
                 85                  90                  95

Ser Tyr Thr Leu Arg Thr Phe Gly Gly Gly Thr Lys Leu Glu Ile Lys
            100                 105                 110
```

<210> SEQ ID NO 152

<211> LENGTH: 112
<212> TYPE: PRT
<213> ORGANISM: Artificial Sequence
<220> FEATURE:
<223> OTHER INFORMATION: Synthetic

<400> SEQUENCE: 152

Asp Val Val Met Thr Gln Ser Pro Ala Phe Leu Ser Val Thr Pro Gly
1               5                   10                  15

Glu Lys Val Thr Ile Thr Cys Lys Ser Ser Gln Ser Leu Phe Asn Ser
            20                  25                  30

Glu Thr Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Thr Leu Arg Thr Phe Gly Gly Gly Thr Lys Leu Glu Ile Lys
            100                 105                 110

<210> SEQ ID NO 153
<211> LENGTH: 112
<212> TYPE: PRT
<213> ORGANISM: Artificial Sequence
<220> FEATURE:
<223> OTHER INFORMATION: Synthetic

<400> SEQUENCE: 153

Asp Val Val Met Thr Gln Ser Pro Ala Phe Leu Ser Val Thr Pro Gly
1               5                   10                  15

Glu Lys Val Thr Ile Thr Cys Lys Ser Ser Gln Ser Leu Phe Asn Ser
            20                  25                  30

Glu Thr Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Lys Gln
                85                  90                  95

Ser Tyr Thr Leu Arg Thr Phe Gly Gly Gly Thr Lys Leu Glu Ile Lys
            100                 105                 110

<210> SEQ ID NO 154
<211> LENGTH: 112
<212> TYPE: PRT
<213> ORGANISM: Artificial Sequence
<220> FEATURE:
<223> OTHER INFORMATION: Synthetic

<400> SEQUENCE: 154

Asp Val Val Met Thr Gln Ser Pro Ala Phe Leu Ser Val Thr Pro Gly
1               5                   10                  15

Glu Lys Val Thr Ile Thr Cys Lys Ser Ser Gln Ser Leu Phe Asn Ser
            20                  25                  30

Glu Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Lys Gln
                85                  90                  95

Ser Tyr Thr Leu Arg Thr Phe Gly Gly Gly Thr Lys Leu Glu Ile Lys
                100                 105                 110

<210> SEQ ID NO 155
<211> LENGTH: 112
<212> TYPE: PRT
<213> ORGANISM: Artificial Sequence
<220> FEATURE:
<223> OTHER INFORMATION: Synthetic

<400> SEQUENCE: 155

Asp Val Val Met Thr Gln Ser Pro Ala Phe Leu Ser Val Thr Pro Gly
1               5                   10                  15

Glu Lys Val Thr Ile Thr Cys Lys Ser Ser Gln Ser Leu Phe Asn Ser
                20                  25                  30

Glu Thr Gln Lys Asn Tyr Leu Ala Trp Tyr Gln Gln Lys Pro Gly Gln
            35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Thr Leu Arg Thr Phe Gly Gly Gly Thr Lys Leu Glu Ile Lys
                100                 105                 110

<210> SEQ ID NO 156
<211> LENGTH: 112
<212> TYPE: PRT
<213> ORGANISM: Artificial Sequence
<220> FEATURE:
<223> OTHER INFORMATION: Synthetic

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
                20                  25                  30

Glu Thr Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Thr Leu Arg Thr Phe Gly Gly Gly Thr Lys Leu Glu Ile Lys
                100                 105                 110

<210> SEQ ID NO 157
<211> LENGTH: 112
<212> TYPE: PRT
<213> ORGANISM: Artificial Sequence
<220> FEATURE:
<223> OTHER INFORMATION: Synthetic

<400> SEQUENCE: 157

```
Asp Val Val Met Thr Gln Ser Pro Ala Phe Leu Ser Val Thr Pro Gly
1               5                   10                  15

Glu Lys Val Thr Ile Thr Cys Lys Ser Ser Gln Ser Leu Phe Asn Ser
            20                  25                  30

Glu Thr Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Thr Leu Arg Thr Phe Gly Gly Gly Thr Lys Leu Glu Ile Lys
            100                 105                 110
```

<210> SEQ ID NO 158
<211> LENGTH: 112
<212> TYPE: PRT
<213> ORGANISM: Artificial Sequence
<220> FEATURE:
<223> OTHER INFORMATION: Synthetic

<400> SEQUENCE: 158

```
Asp Val Val Met Thr Gln Ser Pro Ala Phe Leu Ser Val Thr Pro Gly
1               5                   10                  15

Glu Lys Val Thr Ile Thr Cys Lys Ser Ser Gln Ser Leu Phe Asn Ser
            20                  25                  30

Glu Thr Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Lys Gln
                85                  90                  95

Ser Tyr Thr Leu Arg Thr Phe Gly Gly Gly Thr Lys Leu Glu Ile Lys
            100                 105                 110
```

<210> SEQ ID NO 159
<211> LENGTH: 112
<212> TYPE: PRT
<213> ORGANISM: Artificial Sequence
<220> FEATURE:
<223> OTHER INFORMATION: Synthetic

<400> SEQUENCE: 159

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Glu Thr Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60
```

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Thr Leu Arg Thr Phe Gly Gln Gly Thr Lys Leu Glu Ile Lys
            100                 105                 110

<210> SEQ ID NO 160
<211> LENGTH: 112
<212> TYPE: PRT
<213> ORGANISM: Artificial Sequence
<220> FEATURE:
<223> OTHER INFORMATION: Synthetic

<400> SEQUENCE: 160

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Leu Phe Asn Ser
                20                  25                  30

Glu Thr Gln Lys Asn Tyr Leu Ala Trp Tyr Gln Gln Lys Pro Gly Gln
            35                  40                  45

Pro Pro Lys Leu Leu Ile Phe Trp Ala Ser Thr Arg Glu Ser Gly Val
    50                  55                  60

Pro Asp Arg Phe Leu Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Thr Leu Arg Thr Phe Gly Gln Gly Thr Lys Leu Glu Ile Lys
            100                 105                 110

<210> SEQ ID NO 161
<211> LENGTH: 112
<212> TYPE: PRT
<213> ORGANISM: Artificial Sequence
<220> FEATURE:
<223> OTHER INFORMATION: Synthetic

<400> SEQUENCE: 161

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
                20                  25                  30

Glu Thr Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Thr Leu Arg Thr Phe Gly Gln Gly Thr Lys Leu Glu Ile Lys
            100                 105                 110

<210> SEQ ID NO 162
<211> LENGTH: 112
<212> TYPE: PRT
<213> ORGANISM: Artificial Sequence
<220> FEATURE:
<223> OTHER INFORMATION: Synthetic
```

<400> SEQUENCE: 162

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Leu Phe Asn Ser
            20                  25                  30

Glu Thr Gln Lys Asn Tyr Leu Ala Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Thr Leu Arg Thr Phe Gly Gln Gly Thr Lys Leu Glu Ile Lys
            100                 105                 110

<210> SEQ ID NO 163
<211> LENGTH: 112
<212> TYPE: PRT
<213> ORGANISM: Artificial Sequence
<220> FEATURE:
<223> OTHER INFORMATION: Synthetic

<400> SEQUENCE: 163

Asp Ile Val Met Thr Gln Ser Pro Asp Ser Leu Ala Val Ser Leu Gly
1               5                   10                  15

Glu Arg Ala Thr Met Thr Cys Lys Ser Ser Gln Ser Leu Phe Asn Ser
            20                  25                  30

Glu Thr Gln Lys Asn Tyr Leu Ala Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Lys Gln
                85                  90                  95

Ser Tyr Thr Leu Arg Thr Phe Gly Gln Gly Thr Lys Leu Glu Ile Lys
            100                 105                 110

<210> SEQ ID NO 164
<211> LENGTH: 117
<212> TYPE: PRT
<213> ORGANISM: Artificial Sequence
<220> FEATURE:
<223> OTHER INFORMATION: Synthetic

<400> SEQUENCE: 164

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Phe
            20                  25                  30

Tyr Ile His Trp Val Arg Gln Ala Pro Gly Gln Arg Leu Glu Trp Met
        35                  40                  45

Gly Ser Ile Tyr Pro Asn Tyr Gly Asp Thr Ala Tyr Asn Gln Lys Phe
    50                  55                  60

Lys Asp Arg Phe Val Phe Ser Leu Asp Thr Ser Val Ser Thr Ala Tyr
65                  70                  75                  80

```
Leu Gln Ile Ser Ser Leu Lys Ala Glu Asp Thr Ala Val Tyr Tyr Cys
                85                  90                  95

Ala Arg Gly Tyr Ser Tyr Ala Met Asp Tyr Trp Gly Gln Gly Thr Thr
            100                 105                 110

Val Thr Val Ser Ser
        115

<210> SEQ ID NO 165
<211> LENGTH: 117
<212> TYPE: PRT
<213> ORGANISM: Artificial Sequence
<220> FEATURE:
<223> OTHER INFORMATION: Synthetic

<400> SEQUENCE: 165

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Phe
            20                  25                  30

Tyr Ile His Trp Val Arg Gln Ala Arg Gly Gln Arg Leu Glu Trp Ile
        35                  40                  45

Gly Ser Ile Tyr Pro Asn Tyr Gly Asp Thr Ala Tyr Asn Gln Lys Phe
    50                  55                  60

Lys Asp Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Tyr Ser Tyr Ala Met Asp Tyr Trp Gly Gln Gly Thr Thr
            100                 105                 110

Val Thr Val Ser Ser
        115

<210> SEQ ID NO 166
<211> LENGTH: 117
<212> TYPE: PRT
<213> ORGANISM: Artificial Sequence
<220> FEATURE:
<223> OTHER INFORMATION: Synthetic

<400> SEQUENCE: 166

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Phe
            20                  25                  30

Tyr Ile His Trp Val Arg Gln Ala Pro Gly Gln Arg Leu Glu Trp Met
        35                  40                  45

Gly Ser Ile Tyr Pro Asn Tyr Gly Asp Thr Ala Tyr Asn Gln Lys Phe
    50                  55                  60

Lys Asp Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Tyr Ser Tyr Ala Met Asp Tyr Trp Gly Gln Gly Thr Thr
            100                 105                 110

Val Thr Val Ser Ser
        115

<210> SEQ ID NO 167
```

```
<211> LENGTH: 117
<212> TYPE: PRT
<213> ORGANISM: Artificial Sequence
<220> FEATURE:
<223> OTHER INFORMATION: Synthetic

<400> SEQUENCE: 167

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asn Phe
            20                  25                  30

Tyr Ile His Trp Val Arg Gln Ala Arg Gly Gln Arg Leu Glu Trp Ile
        35                  40                  45

Gly Ser Ile Tyr Pro Asn Tyr Gly Asp Thr Ala Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Tyr Ala Met Asp Tyr Trp Gly Gln Gly Thr Thr
            100                 105                 110

Val Thr Val Ser Ser
        115

<210> SEQ ID NO 168
<211> LENGTH: 117
<212> TYPE: PRT
<213> ORGANISM: Artificial Sequence
<220> FEATURE:
<223> OTHER INFORMATION: Synthetic

<400> SEQUENCE: 168

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asn Phe
            20                  25                  30

Tyr Ile His Trp Val Arg Gln Ala Pro Gly Lys Gly Leu Glu Trp Met
        35                  40                  45

Gly Ser Ile Tyr Pro Asn Tyr Gly Asp Thr Ala Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Tyr Ala Met Asp Tyr Trp Gly Gln Gly Thr Thr
            100                 105                 110

Val Thr Val Ser Ser
        115

<210> SEQ ID NO 169
<211> LENGTH: 117
<212> TYPE: PRT
<213> ORGANISM: Artificial Sequence
<220> FEATURE:
<223> OTHER INFORMATION: Synthetic

<400> SEQUENCE: 169

Glu Val Gln Leu Val Gln Ser Gly Ala Glu Val Lys Lys Pro Gly Glu
1               5                   10                  15
```

Ser Leu Lys Ile Ser Cys Lys Gly Ser Gly Tyr Ser Phe Thr Asn Phe
            20                  25                  30

Tyr Ile His Trp Val Arg Gln Met Pro Gly Lys Gly Leu Glu Trp Met
        35                  40                  45

Gly Ser Ile Tyr Pro Asn Tyr Gly Asp Thr Ala Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Tyr Ala Met Asp Tyr Trp Gly Gln Gly Thr Thr
                100                 105                 110

Val Thr Val Ser Ser
        115

<210> SEQ ID NO 170
<211> LENGTH: 117
<212> TYPE: PRT
<213> ORGANISM: Artificial Sequence
<220> FEATURE:
<223> OTHER INFORMATION: Synthetic

<400> SEQUENCE: 170

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Phe
            20                  25                  30

Tyr Ile His Trp Val Arg Gln Met Pro Gly Lys Gly Leu Glu Trp Met
        35                  40                  45

Gly Ser Ile Tyr Pro Asn Tyr Gly Asp Thr Ala Tyr Asn Gln Lys Phe
    50                  55                  60

Lys Asp Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Tyr Ser Tyr Ala Met Asp Tyr Trp Gly Gln Gly Thr Thr
                100                 105                 110

Val Thr Val Ser Ser
        115

<210> SEQ ID NO 171
<211> LENGTH: 117
<212> TYPE: PRT
<213> ORGANISM: Artificial Sequence
<220> FEATURE:
<223> OTHER INFORMATION: Synthetic

<400> SEQUENCE: 171

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Phe
            20                  25                  30

Tyr Ile His Trp Val Arg Gln Met Pro Gly Lys Gly Leu Glu Trp Met
        35                  40                  45

Gly Ser Ile Tyr Pro Asn Tyr Gly Asp Thr Ala Tyr Asn Gln Lys Phe
    50                  55                  60

Lys Asp Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Tyr Ser Tyr Ala Met Asp Tyr Trp Gly Gln Gly Thr Thr
            100                 105                 110

Val Thr Val Ser Ser
        115

<210> SEQ ID NO 172
<211> LENGTH: 117
<212> TYPE: PRT
<213> ORGANISM: Artificial Sequence
<220> FEATURE:
<223> OTHER INFORMATION: Synthetic

<400> SEQUENCE: 172

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Tyr Ile His Trp Val Arg Gln Ala Pro Gly Gln Gly Leu Glu Trp Met
        35                  40                  45

Gly Ser Ile Tyr Pro Asn Tyr Gly Asp Thr Ala Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Tyr Ala Met Asp Tyr Trp Gly Gln Gly Thr Leu
            100                 105                 110

Val Thr Val Ser Ser
        115

<210> SEQ ID NO 173
<211> LENGTH: 117
<212> TYPE: PRT
<213> ORGANISM: Artificial Sequence
<220> FEATURE:
<223> OTHER INFORMATION: Synthetic

<400> SEQUENCE: 173

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Tyr Ile His Trp Val Arg Gln Ala Pro Gly Gln Gly Leu Glu Trp Met
        35                  40                  45

Gly Ser Ile Tyr Pro Asn Tyr Gly Asp Thr Ala Tyr Asn Gln Lys Phe
    50                  55                  60

Lys Asp Arg Val Thr Met Thr Val Asp Lys Ser Thr Ser Thr Val Tyr
65                  70                  75                  80

Met Glu Leu Arg Ser Leu Arg Ser Glu Asp Thr Ala Val Tyr Tyr Cys
                85                  90                  95

Ala Arg Gly Tyr Ser Tyr Ala Met Asp Tyr Trp Gly Gln Gly Thr Leu
            100                 105                 110

Val Thr Val Ser Ser
        115

```
<210> SEQ ID NO 174
<211> LENGTH: 117
<212> TYPE: PRT
<213> ORGANISM: Artificial Sequence
<220> FEATURE:
<223> OTHER INFORMATION: Synthetic

<400> SEQUENCE: 174

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Tyr Ile His Trp Val Lys Gln Ala His Gly Gln Gly Leu Glu Trp Met
        35                  40                  45

Gly Ser Ile Tyr Pro Asn Tyr Gly Asp Thr Ala Tyr Asn Gln Lys Phe
    50                  55                  60

Lys Asp Arg Val Thr Met Thr Val Asp Lys Ser Thr Ser Thr Val Tyr
65                  70                  75                  80

Met Glu Leu Arg Ser Leu Arg Ser Glu Asp Thr Ala Val Tyr Tyr Cys
                85                  90                  95

Ala Arg Gly Tyr Ser Tyr Ala Met Asp Tyr Trp Gly Gln Gly Thr Leu
            100                 105                 110

Val Thr Val Ser Ser
        115

<210> SEQ ID NO 175
<211> LENGTH: 117
<212> TYPE: PRT
<213> ORGANISM: Artificial Sequence
<220> FEATURE:
<223> OTHER INFORMATION: Synthetic

<400> SEQUENCE: 175

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Tyr Ile His Trp Val Arg Gln Ala Pro Gly Gln Gly Leu Glu Trp Ile
        35                  40                  45

Gly Ser Ile Tyr Pro Asn Tyr Gly Asp Thr Ala Tyr Asn Gln Lys Phe
    50                  55                  60

Lys Asp Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Tyr Ala Met Asp Tyr Trp Gly Gln Gly Thr Leu
            100                 105                 110

Val Thr Val Ser Ser
        115

<210> SEQ ID NO 176
<211> LENGTH: 117
<212> TYPE: PRT
<213> ORGANISM: Artificial Sequence
<220> FEATURE:
<223> OTHER INFORMATION: Synthetic

<400> SEQUENCE: 176

Gln Val Gln Leu Val Gln Ser Gly Ala Glu Val Lys Lys Pro Gly Ala
1               5                   10                  15
```

Ser Val Lys Met Ser Cys Lys Ala Ser Gly Tyr Thr Phe Thr Asn Phe
            20                  25                  30

Tyr Ile His Trp Val Arg Gln Ala Pro Gly Gln Gly Leu Glu Trp Ile
        35                  40                  45

Gly Ser Ile Tyr Pro Asn Tyr Gly Asp Thr Ala Tyr Asn Gln Lys Phe
    50                  55                  60

Lys Asp Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Tyr Ala Met Asp Tyr Trp Gly Gln Gly Thr Leu
            100                 105                 110

Val Thr Val Ser Ser
        115

<210> SEQ ID NO 177
<211> LENGTH: 117
<212> TYPE: PRT
<213> ORGANISM: Artificial Sequence
<220> FEATURE:
<223> OTHER INFORMATION: Synthetic

<400> SEQUENCE: 177

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asn Phe
            20                  25                  30

Tyr Ile His Trp Val Arg Gln Ala Pro Gly Gln Gly Leu Glu Trp Ile
        35                  40                  45

Gly Ser Ile Tyr Pro Asn Tyr Gly Asp Thr Ala Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Tyr Ala Met Asp Tyr Trp Gly Gln Gly Thr Leu
            100                 105                 110

Val Thr Val Ser Ser
        115

<210> SEQ ID NO 178
<211> LENGTH: 107
<212> TYPE: PRT
<213> ORGANISM: Artificial Sequence
<220> FEATURE:
<223> OTHER INFORMATION: Synthetic

<400> SEQUENCE: 178

Asp Ile Gln Met Thr Gln Ser Pro Ser Ser Val Ser Ala Ser Val Gly
1               5                   10                  15

Asp Arg Val Thr Ile Thr Cys Ser Ala Ser Gln Gly Ile Ser Gly Asp
            20                  25                  30

Leu Asn Trp Tyr Gln Gln Lys Pro Gly Gln Ala Pro Arg Leu Leu Ile
        35                  40                  45

Tyr His Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Tyr Tyr Ser Lys Asp Leu Leu
                    85                  90                  95

Thr Phe Gly Gly Gly Thr Lys Leu Glu Ile Lys
            100                 105

<210> SEQ ID NO 179
<211> LENGTH: 107
<212> TYPE: PRT
<213> ORGANISM: Artificial Sequence
<220> FEATURE:
<223> OTHER INFORMATION: Synthetic

<400> SEQUENCE: 179

Asp Ile Gln Met Thr Gln Ser Pro Ser Leu Ser Ala Ser Val Gly
1               5                   10                  15

Asp Arg Val Thr Ile Thr Cys Ser Ala Ser Gln Gly Ile Ser Gly Asp
                20                  25                  30

Leu Asn Trp Tyr Gln Gln Lys Pro Gly Lys Thr Pro Lys Leu Leu Ile
            35                  40                  45

Tyr His Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Tyr Tyr Ser Lys Asp Leu Leu
                    85                  90                  95

Thr Phe Gly Gly Gly Thr Lys Leu Glu Ile Lys
            100                 105

<210> SEQ ID NO 180
<211> LENGTH: 107
<212> TYPE: PRT
<213> ORGANISM: Artificial Sequence
<220> FEATURE:
<223> OTHER INFORMATION: Synthetic

<400> SEQUENCE: 180

Asp Ile Gln Met Thr Gln Ser Pro Ser Val Ser Ala Ser Val Gly
1               5                   10                  15

Asp Arg Val Thr Ile Thr Cys Ser Ala Ser Gln Gly Ile Ser Gly Asp
                20                  25                  30

Leu Asn Trp Tyr Gln Gln Lys Pro Gly Lys Ala Pro Lys Leu Leu Ile
            35                  40                  45

Tyr His Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Tyr Tyr Ser Lys Asp Leu Leu
                    85                  90                  95

Thr Phe Gly Gly Gly Thr Lys Leu Glu Ile Lys
            100                 105

<210> SEQ ID NO 181
<211> LENGTH: 107
<212> TYPE: PRT
<213> ORGANISM: Artificial Sequence
<220> FEATURE:
<223> OTHER INFORMATION: Synthetic

<400> SEQUENCE: 181
```

```
Asp Ile Gln Met Thr Gln Ser Pro Ser Ser Val Ser Ala Ser Val Gly
1               5                   10                  15

Asp Arg Val Thr Ile Thr Cys Ser Ala Ser Gln Gly Ile Ser Gly Asp
            20                  25                  30

Leu Asn Trp Tyr Gln Gln Lys Pro Gly Gln Ala Pro Arg Leu Leu Ile
        35                  40                  45

Tyr His Thr Ser Ser Leu His Ser Gly Val Pro Ser Arg Phe Ser Gly
    50                  55                  60

Ser Gly Ser Gly Thr Glu Phe Thr Leu Thr Ile Ser Arg Leu Glu Pro
65                  70                  75                  80

Glu Asp Phe Ala Val Tyr Tyr Cys Gln Tyr Tyr Ser Lys Asp Leu Leu
                85                  90                  95

Thr Phe Gly Gly Gly Thr Lys Leu Glu Ile Lys
            100                 105

<210> SEQ ID NO 182
<211> LENGTH: 107
<212> TYPE: PRT
<213> ORGANISM: Artificial Sequence
<220> FEATURE:
<223> OTHER INFORMATION: Synthetic

<400> SEQUENCE: 182

Asp Ile Gln Met Thr Gln Ser Pro Ser Thr Leu Ser Ala Ser Val Gly
1               5                   10                  15

Asp Arg Val Thr Ile Thr Cys Ser Ala Ser Gln Gly Ile Ser Gly Asp
            20                  25                  30

Leu Asn Trp Tyr Gln Gln Lys Pro Gly Gln Ala Pro Arg Leu Leu Ile
        35                  40                  45

Tyr His Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Tyr Tyr Ser Lys Asp Leu Leu
                85                  90                  95

Thr Phe Gly Gly Gly Thr Lys Leu Glu Ile Lys
            100                 105

<210> SEQ ID NO 183
<211> LENGTH: 107
<212> TYPE: PRT
<213> ORGANISM: Artificial Sequence
<220> FEATURE:
<223> OTHER INFORMATION: Synthetic

<400> SEQUENCE: 183

Asp Ile Gln Met Thr Gln Ser Pro Ser Val Ser Ala Ser Val Gly
1               5                   10                  15

Asp Arg Val Thr Ile Thr Cys Ser Ala Ser Gln Gly Ile Ser Gly Asp
            20                  25                  30

Leu Asn Trp Tyr Gln Gln Lys Pro Gly Gln Ala Pro Arg Leu Leu Ile
        35                  40                  45

Tyr His Thr Ser Ser Leu His Ser Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Tyr Tyr Ser Lys Asp Leu Leu
```

```
                    85                  90                  95

Thr Phe Gly Gly Gly Thr Lys Leu Glu Ile Lys
                100                 105

<210> SEQ ID NO 184
<211> LENGTH: 107
<212> TYPE: PRT
<213> ORGANISM: Artificial Sequence
<220> FEATURE:
<223> OTHER INFORMATION: Synthetic

<400> SEQUENCE: 184

Asp Ile Gln Met Thr Gln Ser Pro Ser Thr Leu Ser Ala Ser Val Gly
1               5                   10                  15

Asp Arg Val Thr Ile Thr Cys Ser Ala Ser Gln Gly Ile Ser Gly Asp
            20                  25                  30

Leu Asn Trp Tyr Gln Gln Lys Pro Gly Lys Thr Pro Lys Leu Leu Ile
        35                  40                  45

Tyr His Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Tyr Tyr Ser Lys Asp Leu Leu
                85                  90                  95

Thr Phe Gly Gly Gly Thr Lys Leu Glu Ile Lys
                100                 105

<210> SEQ ID NO 185
<211> LENGTH: 107
<212> TYPE: PRT
<213> ORGANISM: Artificial Sequence
<220> FEATURE:
<223> OTHER INFORMATION: Synthetic

<400> SEQUENCE: 185

Asp Ile Gln Met Thr Gln Ser Pro Ser Thr Leu Ser Ala Ser Val Gly
1               5                   10                  15

Asp Arg Val Thr Ile Thr Cys Ser Ala Ser Gln Gly Ile Ser Gly Asp
            20                  25                  30

Leu Asn Trp Tyr Gln Gln Lys Pro Gly Gln Ala Pro Arg Leu Leu Ile
        35                  40                  45

Tyr His Thr Ser Ser Leu His Ser Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Tyr Tyr Ser Lys Asp Leu Leu
                85                  90                  95

Thr Phe Gly Gly Gly Thr Lys Leu Glu Ile Lys
                100                 105

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Ser Leu Ser Ala Ser Val Gly
1               5                   10                  15
```

Asp Arg Val Thr Ile Thr Cys Ser Ala Ser Gln Gly Ile Ser Gly Asp
            20                  25                  30

Leu Asn Trp Tyr Gln Gln Lys Pro Gly Lys Ala Pro Lys Leu Leu Ile
        35                  40                  45

Tyr His Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Tyr Tyr Ser Lys Asp Leu Leu
                85                  90                  95

Thr Phe Gly Gly Gly Thr Lys Leu Glu Ile Lys
            100                 105

<210> SEQ ID NO 187
<211> LENGTH: 107
<212> TYPE: PRT
<213> ORGANISM: Artificial Sequence
<220> FEATURE:
<223> OTHER INFORMATION: Synthetic

<400> SEQUENCE: 187

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Gly Asp
            20                  25                  30

Leu Asn Trp Tyr Gln Gln Lys Pro Gly Lys Ala Val Lys Leu Leu Ile
        35                  40                  45

Tyr His Thr Ser Ser Leu His Ser Gly Val Pro Leu Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Tyr Tyr Ser Lys Asp Leu Leu
                85                  90                  95

Thr Phe Gly Gly Gly Thr Lys Leu Glu Ile Lys
            100                 105

<210> SEQ ID NO 188
<211> LENGTH: 107
<212> TYPE: PRT
<213> ORGANISM: Artificial Sequence
<220> FEATURE:
<223> OTHER INFORMATION: Synthetic

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Gly Asp
            20                  25                  30

Leu Asn Trp Tyr Gln Gln Lys Ser Asp Gly Ala Val Lys Leu Leu Ile
        35                  40                  45

Tyr His Thr Ser Ser Leu His Ser Gly Val Pro Leu Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Tyr Tyr Ser Lys Asp Leu Leu
                85                  90                  95

Thr Phe Gly Gly Gly Thr Lys Leu Glu Ile Lys

<210> SEQ ID NO 189
<211> LENGTH: 107
<212> TYPE: PRT
<213> ORGANISM: Artificial Sequence
<220> FEATURE:
<223> OTHER INFORMATION: Synthetic

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Gly Asp
            20                  25                  30

Leu Asn Trp Tyr Gln Gln Lys Pro Gly Lys Ala Pro Lys Leu Leu Ile
        35                  40                  45

Tyr His Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Tyr Tyr Ser Lys Asp Leu Leu
                85                  90                  95

Thr Phe Gly Gly Gly Thr Lys Leu Glu Ile Lys
            100                 105

<210> SEQ ID NO 190
<211> LENGTH: 107
<212> TYPE: PRT
<213> ORGANISM: Artificial Sequence
<220> FEATURE:
<223> OTHER INFORMATION: Synthetic

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Gly Asp
            20                  25                  30

Leu Asn Trp Tyr Gln Gln Lys Pro Gly Lys Ala Val Lys Leu Leu Ile
        35                  40                  45

Tyr His Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Tyr Tyr Ser Lys Asp Leu Leu
                85                  90                  95

Thr Phe Gly Gly Gly Thr Lys Leu Glu Leu Lys
            100                 105

<210> SEQ ID NO 191
<211> LENGTH: 15
<212> TYPE: DNA
<213> ORGANISM: Artificial Sequence
<220> FEATURE:
<223> OTHER INFORMATION: Synthetic

<400> SEQUENCE: 191
gatgattttt tacat                                                   15

<210> SEQ ID NO 192
<211> LENGTH: 351

```
<212> TYPE: DNA
<213> ORGANISM: Artificial Sequence
<220> FEATURE:
<223> OTHER INFORMATION: Synthetic

<400> SEQUENCE: 192
cagatgcagc tggtgcagag cggcccggaa gtgaaaaaac cgggcaccag cgtgaaagtg      60
agctgcaaag cgagcggctt tacctttacc aactattgga ttggctgggt gcgccaggcg     120
ccgggccagg cgctggaatg gatgggcgat atttatccgg gcggcggcta taccaactat     180
aacgaaaaat ttaaaggccg cgtgaccatt accgcggata aaagcaccag caccgcgtat     240
atggaactga gcagcctgcg cagcgaagat accgcggtgt attattgcgc gcgcggctat     300
gattttgtgc tggatcgctg gggccagggc accaccgtga ccgtgagcag c              351

<210> SEQ ID NO 193
<211> LENGTH: 351
<212> TYPE: DNA
<213> ORGANISM: Artificial Sequence
<220> FEATURE:
<223> OTHER INFORMATION: Synthetic

<400> SEQUENCE: 193
cagatgcagc tggtgcagag cggcccggaa gtgaaaaaac cgggcaccag cgtgaaagtg      60
agctgcaaag cgagcggctt tacctttacc aactattgga ttggctgggt gcgccaggcg     120
ccgggccagg cgctggaatg gatgggcgat atttatccgg gcggcggcta taccaactat     180
aacgaaaaat ttaaaggccg cgtgaccatt accgcggata aaagcaccag caccgcgtat     240
atggaactga gcagcctgcg cagcgaagat accgcggtgt attattgcgc gcgcggctat     300
gattttgtgc tggatcgctg gggccagggc accaccgtga ccgtgagcag c              351

<210> SEQ ID NO 194
<211> LENGTH: 351
<212> TYPE: DNA
<213> ORGANISM: Artificial Sequence
<220> FEATURE:
<223> OTHER INFORMATION: Synthetic

<400> SEQUENCE: 194
cagatgcagc tggtgcagag cggcccggaa gtgaaaaaac cgggcaccag cgtgaaagtg      60
agctgcaaag cgagcggctt tacctttacc aactattgga ttggctgggt gcgccaggcg     120
ccgggccagg cgctggaatg gatgggcgat atttatccgg gcggcggcta taccaactat     180
aacgaaaaat ttaaaggccg cgtgaccatt accgcggata aaagcaccag caccgcgtat     240
atggaactga gcagcctgcg cagcgaagat accgcggtgt attattgcgc gcgcggctat     300
gattttgtgc tggatcgctg gggccagggc accaccgtga ccgtgagcag c              351

<210> SEQ ID NO 195
<211> LENGTH: 351
<212> TYPE: DNA
<213> ORGANISM: Artificial Sequence
<220> FEATURE:
<223> OTHER INFORMATION: Synthetic

<400> SEQUENCE: 195
cagatgcagc tggtgcagag cggcccggaa gtgaaaaaac cgggcaccag cgtgaaagtg      60
agctgcaaag cgagcggctt tacctttacc aactattgga ttggctgggt gcgccaggcg     120
ccgggccagg cgctggaatg gatgggcgat atttatccgg gcggcggcta taccaactat     180
```

```
aacgaaaaat ttaaaggccg cgtgaccatt accgcggata aaagcaccag caccgcgtat    240
atggaactga gcagcctgcg cagcgaagat accgcggtgt attattgcgc gcgcggctat    300
gattttgtgc tggatcgctg gggccagggc accaccgtga ccgtgagcag c             351
```

<210> SEQ ID NO 196
<211> LENGTH: 351
<212> TYPE: DNA
<213> ORGANISM: Artificial Sequence
<220> FEATURE:
<223> OTHER INFORMATION: Synthetic

<400> SEQUENCE: 196

```
caggtgcagc tggtgcagag cggcgcggaa gtgaaaaaac cgggcgcgag cgtgaaagtg    60
agctgcaaag cgagcggcta tacctttacc aactattgga ttggctgggt gcgccaggcg   120
ccgggccagg gcctggaatg gatgggcgat atttatccgg gcggcggcta taccaactat   180
aacgaaaaat ttaaaggccg cgtgaccatt accgcggata aaagcaccag caccgcgtat   240
atggaactga gcagcctgcg cagcgaagat accgcggtgt attattgcgc gcgcggctat   300
gattttgtgc tggatcgctg gggccagggc accaccgtga ccgtgagcag c            351
```

<210> SEQ ID NO 197
<211> LENGTH: 351
<212> TYPE: DNA
<213> ORGANISM: Artificial Sequence
<220> FEATURE:
<223> OTHER INFORMATION: Synthetic

<400> SEQUENCE: 197

```
gaagtgcagc tggtgcagag cggcgcggaa gtgaaaaaac atggcgaaag cctgaaaatt    60
agctgcaaag cgagcggcta tagctttacc aactattgga ttggctgggt gcgccaggcg   120
accggccagg gcctggaatg gatgggcgat atttatccgg gcggcggcta taccaactat   180
aacgaaaaat ttaaaggccg cgtgaccatt accgcggata aaagcaccag caccgcgtat   240
atggaactga gcagcctgcg cagcgaagat accgcggtgt attattgcgc gcgcggctat   300
gattttgtgc tggatcgctg gggccagggc accaccgtga ccgtgagcag c            351
```

<210> SEQ ID NO 198
<211> LENGTH: 351
<212> TYPE: DNA
<213> ORGANISM: Artificial Sequence
<220> FEATURE:
<223> OTHER INFORMATION: Synthetic

<400> SEQUENCE: 198

```
cagatgcagc tggtgcagag cggcgcggaa gtgaaaaaaa ccggcagcag cgtgaaagtg    60
agctgcaaag cgagcggcta tacctttacc aactattgga ttggctgggt gcgccagatg   120
ccgggcaaag gcctggaatg gatgggcgat atttatccgg gcggcggcta taccaactat   180
aacgaaaaat ttaaaggccg cgtgaccatt accgcggata aaagcaccag caccgcgtat   240
atggaactga gcagcctgcg cagcgaagat accgcggtgt attattgcgc gcgcggctat   300
gattttgtgc tggatcgctg gggccagggc accaccgtga ccgtgagcag c            351
```

<210> SEQ ID NO 199
<211> LENGTH: 351
<212> TYPE: DNA
<213> ORGANISM: Artificial Sequence
<220> FEATURE:
<223> OTHER INFORMATION: Synthetic

<400> SEQUENCE: 199

```
caggtgcagc tggtgcagag cggcagcgaa ctgaaaaaac cgggcgcgag cgtgaaagtg      60
agctgcaaag cgagcggcta tacctttacc aactattgga ttggctgggt gcgccaggcg     120
ccgggcaaag gcctggaatg gatgggcgat atttatccgg gcggcggcta taccaactat     180
aacgaaaaat ttaaaggccg cgtgaccatt accgcggata aagcaccag caccgcgtat      240
atggaactga gcagcctgcg cagcgaagat accgcggtgt attattgcgc gcgcggctat     300
gattttgtgc tggatcgctg gggccagggc accaccgtga ccgtgagcag c              351
```

<210> SEQ ID NO 200
<211> LENGTH: 351
<212> TYPE: DNA
<213> ORGANISM: Artificial Sequence
<220> FEATURE:
<223> OTHER INFORMATION: Synthetic

<400> SEQUENCE: 200

```
caggtgcagc tggtgcagag cggcgcggaa gtgaaaaaac cgggcgcgag cgtgaaagtg      60
agctgcaaag cgagcggcta tacctttacc aactattgga ttggctgggt gcgccaggcg     120
ccgggccagg gcctggaatg gatgggcgat atttatccgg gcggcggcta taccaactat     180
aacgaaaaat ttaaaggccg cgtgaccatg accgcgata ccagcaccag caccgtgtat      240
atggaactga gcagcctgcg cagcgaagat accgcggtgt attattgcgc gcgcggctat     300
gattttgtgc tggatcgctg gggccagggc accctggtga ccgtgagcag c              351
```

<210> SEQ ID NO 201
<211> LENGTH: 351
<212> TYPE: DNA
<213> ORGANISM: Artificial Sequence
<220> FEATURE:
<223> OTHER INFORMATION: Synthetic

<400> SEQUENCE: 201

```
caggtgcagc tggtgcagag cggcgcggaa gtgaaaaaac cgggcgcgag cgtgaaagtg      60
agctgcaaag cggcgggcta tacctttacc aactattgga ttggctgggt gcgccaggcg     120
ccgggccagg gcctggaatg gatgggcgat atttatccgg gcggcggcta taccaactat     180
aacgaaaaat ttaaaggccg cgtgaccatg accgcgata ccagcaccag caccgtgtat      240
atggaactga gcagcctgcg cagcgaagat accgcggtgt attattgcgc gcgcggctat     300
gattttgtgc tggatcgctg gggccagggc accctggtga ccgtgagcag c              351
```

<210> SEQ ID NO 202
<211> LENGTH: 351
<212> TYPE: DNA
<213> ORGANISM: Artificial Sequence
<220> FEATURE:
<223> OTHER INFORMATION: Synthetic

<400> SEQUENCE: 202

```
caggtgcagc tggtgcagag cggcgcggaa gtgaaaaaac cgggcgcgag cgtgaaagtg      60
agctgcaaag cgagcggcta tacctttacc aactattgga ttggctgggt gcgccaggcg     120
ccgggccagg gcctggaatg gattggcgat atttatccgg gcggcggcta taccaactat     180
aacgaaaaat ttaaaggccg cgtgaccatg accgcggata ccagcaccag caccgtgtat     240
atggaactga gcagcctgcg cagcgaagat accgcggtgt attattgcgc gcgcggctat     300
```

```
gattttgtgc tggatcgctg gggccagggc accctggtga ccgtgagcag c          351
```

<210> SEQ ID NO 203
<211> LENGTH: 351
<212> TYPE: DNA
<213> ORGANISM: Artificial Sequence
<220> FEATURE:
<223> OTHER INFORMATION: Synthetic

<400> SEQUENCE: 203

```
caggtgcagc tggtgcagag cggcgcggaa gtgaaaaaac cgggcgcgag cgtgaaagtg    60
agctgcaaag cgagcggcta cctttacc aactattgga ttggctggat tcgccaggcg    120
ccgggccagg gcctggaatg gattggcgat atttatccgg gcggcggcta taccaactat    180
aacgaaaaat ttaaaggccg cgcgaccctg accgcggata ccagcaccag caccgtgtat    240
atggaagtga gcagcctgcg cagcgaagat accgcggtgt attattgcgc gcgcggctat    300
gattttgtgc tggatcgctg gggccagggc accctggtga ccgtgagcag c           351
```

<210> SEQ ID NO 204
<211> LENGTH: 336
<212> TYPE: DNA
<213> ORGANISM: Artificial Sequence
<220> FEATURE:
<223> OTHER INFORMATION: Synthetic

<400> SEQUENCE: 204

```
gatgtggtga tgacccagag cccggcgttt ctgagcgtga ccccgggcga aaaagtgacc    60
attacctgca aaagcagcca gagcctgttt aacagcgaaa cccagaaaaa ctatctggcg    120
tggtatcagc agaaaccggg ccagccgccg aaactgctga tttattgggc gagcacccgc    180
gaaagcggcg tgccgagccg ctttagcggc agcggcagcg gcaccgattt taccctgacc    240
attagcagcc tgcagccgga agattttgcg acctattatt gcaaacagag ctataccctg    300
cgcacctttg gcggcggcac caaactggaa attaaa                              336
```

<210> SEQ ID NO 205
<211> LENGTH: 336
<212> TYPE: DNA
<213> ORGANISM: Artificial Sequence
<220> FEATURE:
<223> OTHER INFORMATION: Synthetic

<400> SEQUENCE: 205

```
gatgtggtga tgacccagag cccggcgttt ctgagcgtga ccccgggcga aaaagtgacc    60
attacctgca aaagcagcca gagcctgttt aacagcgaaa cccagaaaaa ctatctggcg    120
tggtatcagc agaaaccggg ccagccgccg aaactgctga tttattgggc gagcacccgc    180
gaaagcggcg tgccgagccg ctttagcggc agcggcagcg gcaccgattt taccctgacc    240
attagcagcc tgcagccgga agattttgcg acctattatt gcaaacagag ctataccctg    300
cgcacctttg gcggcggcac caaactggaa attaaa                              336
```

<210> SEQ ID NO 206
<211> LENGTH: 336
<212> TYPE: DNA
<213> ORGANISM: Artificial Sequence
<220> FEATURE:
<223> OTHER INFORMATION: Synthetic

<400> SEQUENCE: 206

```
gatgtggtga tgacccagag cccggcgttt ctgagcgtga ccccgggcga aaaagtgacc    60
```

```
attacctgca aaagcagcca gagcctgttt aacagcgaaa cccagaaaaa ctatctggcg    120
tggtatcagc agaaaccggg ccagccgccg aaactgctga tttattgggc gagcacccgc    180
gaaagcggcg tgccgagccg ctttagcggc agcggcagcg gcaccgattt tacctttacc    240
attagcagcc tggaagcgga agatgcggcg acctattatt gcaaacagag ctatacccctg    300 cgcacctttg gcggcggcac caaactggaa attaaa                              336
```

```
<210> SEQ ID NO 207
<211> LENGTH: 336
<212> TYPE: DNA
<213> ORGANISM: Artificial Sequence
<220> FEATURE:
<223> OTHER INFORMATION: Synthetic

<400> SEQUENCE: 207
gatgtggtga tgacccagag cccggcgttt ctgagcgtga ccccgggcga aaaagtgacc     60
attacctgca aaagcagcca gagcctgttt aacagcgaaa cccagaaaaa ctatctggcg    120
tggtatcagc agaaaccggg ccaggcgccg cgcctgctga tttattgggc gagcacccgc    180
gaaagcggcg tgccgagccg ctttagcggc agcggcagcg gcaccgattt tacctttacc    240
attagcagcc tggaagcgga agatgcggcg acctattatt gcaaacagag ctatacccctg    300 cgcacctttg gcggcggcac caaactggaa attaaa                              336
```

```
<210> SEQ ID NO 208
<211> LENGTH: 336
<212> TYPE: DNA
<213> ORGANISM: Artificial Sequence
<220> FEATURE:
<223> OTHER INFORMATION: Synthetic

<400> SEQUENCE: 208
gatgtggtga tgacccagag cccggcgttt ctgagcgtga ccccgggcga aaaagtgacc     60
attacctgca aaagcagcca gagcctgttt aacagcgaaa cccagaaaaa ctatctggcg    120
tggtatcagc agaaaccggg ccaggcgccg cgcctgctga tttattgggc gagcacccgc    180
gaaagcggcg tgccgagccg ctttagcggc agcggcagcg gcaccgattt taccctgacc    240
attagcagcc tgcagccgga agattttgcg acctattatt gcaaacagag ctatacccctg    300 cgcacctttg gcggcggcac caaactggaa attaaa                              336
```

```
<210> SEQ ID NO 209
<211> LENGTH: 336
<212> TYPE: DNA
<213> ORGANISM: Artificial Sequence
<220> FEATURE:
<223> OTHER INFORMATION: Synthetic

<400> SEQUENCE: 209
gatattcaga tgacccagag cccgagcagc ctgagcgcga gcgtgggcga tcgcgtgacc     60
attacctgca aaagcagcca gagcctgttt aacagcgaaa cccagaaaaa ctatctggcg    120
tggtatcagc agaaaccggg ccagccgccg aaactgctga tttattgggc gagcacccgc    180
gaaagcggcg tgccgagccg ctttagcggc agcggcagcg gcaccgattt taccctgacc    240
attagcagcc tgcagccgga agattttgcg acctattatt gcaaacagag ctatacccctg    300 cgcacctttg gcggcggcac caaactggaa attaaa                              336
```

```
<210> SEQ ID NO 210
```

```
<211> LENGTH: 336
<212> TYPE: DNA
<213> ORGANISM: Artificial Sequence
<220> FEATURE:
<223> OTHER INFORMATION: Synthetic

<400> SEQUENCE: 210
gatgtggtga tgacccagag cccggcgttt ctgagcgtga ccccgggcga aaaagtgacc      60
attacctgca aaagcagcca gagcctgttt aacagcgaaa cccagaaaaa ctatctggcg     120
tggtatcagc agaaaccggg ccagccgccg aaactgctga tttattgggc gagcacccgc     180
gaaagcggcg tgccgagccg ctttagcggc agcggcagcg gcaccgattt taccctgacc     240
attagcagcc tgcagccgga agattttgcg acctattatt gcaaacagag ctataccctg     300
cgcacctttg gcggcggcac caaactggaa attaaa                              336

<210> SEQ ID NO 211
<211> LENGTH: 336
<212> TYPE: DNA
<213> ORGANISM: Artificial Sequence
<220> FEATURE:
<223> OTHER INFORMATION: Synthetic

<400> SEQUENCE: 211
gatgtggtga tgacccagag cccggcgttt ctgagcgtga ccccgggcga aaaagtgacc      60
attacctgca aaagcagcca gagcctgttt aacagcgaaa cccagaaaaa ctatctggcg     120
tggtatcagc agaaaccggg ccagccgccg aaactgctga tttattgggc gagcacccgc     180
gaaagcggcg tgccgagccg ctttagcggc agcggcagcg gcaccgattt tacctttacc     240
attagcagcc tggaagcgga agatgcggcg acctattatt gcaaacagag ctataccctg     300
cgcacctttg gcggcggcac caaactggaa attaaa                              336

<210> SEQ ID NO 212
<211> LENGTH: 336
<212> TYPE: DNA
<213> ORGANISM: Artificial Sequence
<220> FEATURE:
<223> OTHER INFORMATION: Synthetic

<400> SEQUENCE: 212
gatattgtga tgacccagag cccggatagc ctggcggtga gcctgggcga acgcgcgacc      60
attaactgca aaagcagcca gagcctgttt aacagcgaaa cccagaaaaa ctatctggcg     120
tggtatcagc agaaaccggg ccagccgccg aaactgctga tttattgggc gagcacccgc     180
gaaagcggcg tgccggatcg ctttagcggc agcggcagcg gcaccgattt taccctgacc     240
attagcagcc tgcaggcgga agatgtggcg gtgtattatt gcaaacagag ctataccctg     300
cgcacctttg gccagggcac caaactggaa attaaa                              336

<210> SEQ ID NO 213
<211> LENGTH: 336
<212> TYPE: DNA
<213> ORGANISM: Artificial Sequence
<220> FEATURE:
<223> OTHER INFORMATION: Synthetic

<400> SEQUENCE: 213
gatattgtga tgacccagag cccggatagc ctggcggtga gcctgggcga acgcgcgacc      60
attacctgca aaagcagcca gagcctgttt aacagcgaaa cccagaaaaa ctatctggcg     120
tggtatcagc agaaaccggg ccagccgccg aaactgctga tttttgggc gagcacccgc      180
```

```
gaaagcggcg tgccggatcg ctttctgggc agcggcagcg gcaccgattt taccctgacc    240
attagcagcc tgcaggcgga agatgtggcg gtgtattatt gcaaacagag ctataccctg    300
cgcacctttg gccagggcac caaactggaa attaaa                              336
```

<210> SEQ ID NO 214
<211> LENGTH: 336
<212> TYPE: DNA
<213> ORGANISM: Artificial Sequence
<220> FEATURE:
<223> OTHER INFORMATION: Synthetic

<400> SEQUENCE: 214

```
gatattgtga tgacccagag cccggatagc ctggcggtga gcctgggcga acgcgcgacc    60
attaactgca aaagcagcca gagcctgttt aacagcgaaa cccagaaaaa ctatctggcg    120
tggtatcagc agaaaccggg ccagccgccg aaactgctga tttattgggc gagcacccgc    180
gaaagcggcg tgccggatcg ctttagcggc agcggcagcg gcaccgattt taccctgacc    240
attagcagcc tgcaggcgga agatgtggcg gtgtattatt gcaaacagag ctataccctg    300
cgcacctttg gccagggcac caaactggaa attaaa                              336
```

<210> SEQ ID NO 215
<211> LENGTH: 336
<212> TYPE: DNA
<213> ORGANISM: Artificial Sequence
<220> FEATURE:
<223> OTHER INFORMATION: Synthetic

<400> SEQUENCE: 215

```
gatattgtga tgacccagag cccggatagc ctggcggtga gcctgggcga acgcgcgacc    60
attacctgca aaagcagcca gagcctgttt aacagcgaaa cccagaaaaa ctatctggcg    120
tggtatcagc agaaaccggg ccagccgccg aaactgctga ttttttgggc gagcacccgc    180
gaaagcggcg tgccggatcg ctttagcggc agcggcagcg gcaccgattt taccctgacc    240
attagcagcc tgcaggcgga agatgtggcg gtgtattatt gcaaacagag ctataccctg    300
cgcacctttg gccagggcac caaactggaa attaaa                              336
```

<210> SEQ ID NO 216
<211> LENGTH: 336
<212> TYPE: DNA
<213> ORGANISM: Artificial Sequence
<220> FEATURE:
<223> OTHER INFORMATION: Synthetic

<400> SEQUENCE: 216

```
gatattgtga tgacccagag cccggatagc ctggcggtga gcctgggcga acgcgcgacc    60
atgacctgca aaagcagcca gagcctgttt aacagcgaaa cccagaaaaa ctatctggcg    120
tggtatcagc agaaaccggg ccagccgccg aaactgctga ttttttgggc gagcacccgc    180
gaaagcggcg tgccggatcg ctttagcggc agcggcagcg gcaccgattt taccctgacc    240
attagcagcg tgcaggcgga agatgtggcg gtgtattatt gcaaacagag ctataccctg    300
cgcacctttg gccagggcac caaactggaa attaaa                              336
```

<210> SEQ ID NO 217
<211> LENGTH: 357
<212> TYPE: DNA
<213> ORGANISM: Artificial Sequence
<220> FEATURE:

<223> OTHER INFORMATION: Synthetic

<400> SEQUENCE: 217

| gtgcatgaag tgcagctggt gcagagcggc gcggaagtga aaaaaccggg cgaaagcctg | 60 |
| aaaattagct gcaaaggcag cggctatagc tttaccaact tttatattca ttgggtgcgc | 120 |
| caggcgccgg ccagcgcct ggaatggatg gcagcattt atccgaacta tggcgatacc | 180 |
| gcgtataacc agaaatttaa agatcgcttt gtgtttagcc tggataccag cgtgagcacc | 240 |
| gcgtatctgc agattagcag cctgaaagcg aagataccg cggtgtatta ttgcgcgcgc | 300 |
| ggctatagct atgcgatgga ttattggggc cagggcacca ccgtgaccgt gagcagc | 357 |

<210> SEQ ID NO 218
<211> LENGTH: 351
<212> TYPE: DNA
<213> ORGANISM: Artificial Sequence
<220> FEATURE:
<223> OTHER INFORMATION: Synthetic

<400> SEQUENCE: 218

| gaagtgcagc tggtgcagag cggcgcggaa gtgaaaaaac cgggcgaaag cctgaaaatt | 60 |
| agctgcaaag gcagcggcta tagctttacc aactttata ttcattgggt gcgccaggcg | 120 |
| cgcggccagc gcctggaatg gattggcagc atttatccga actatggcga taccgcgtat | 180 |
| aaccagaaat ttaaagatcg cttgtgttt agcctggata ccagcgtgag caccgcgtat | 240 |
| ctgcagatta gcagcctgaa agcggaagat accgcggtgt attattgcgc gcgcggctat | 300 |
| agctatgcga tggattattg gggccagggc accaccgtga ccgtgagcag c | 351 |

<210> SEQ ID NO 219
<211> LENGTH: 351
<212> TYPE: DNA
<213> ORGANISM: Artificial Sequence
<220> FEATURE:
<223> OTHER INFORMATION: Synthetic

<400> SEQUENCE: 219

| gaagtgcagc tggtgcagag cggcgcggaa gtgaaaaaac cgggcgaaag cctgaaaatt | 60 |
| agctgcaaag gcagcggcta tagctttacc aactttata ttcattgggt gcgccaggcg | 120 |
| ccgggccagc gcctggaatg gattggcagc atttatccga actatggcga taccgcgtat | 180 |
| aaccagaaat ttaaagatcg cttgtgttt agcctggata ccagcgtgag caccgcgtat | 240 |
| ctgcagatta gcagcctgaa agcggaagat accgcggtgt attattgcgc gcgcggctat | 300 |
| agctatgcga tggattattg gggccagggc accaccgtga ccgtgagcag c | 351 |

<210> SEQ ID NO 220
<211> LENGTH: 351
<212> TYPE: DNA
<213> ORGANISM: Artificial Sequence
<220> FEATURE:
<223> OTHER INFORMATION: Synthetic

<400> SEQUENCE: 220

| gaagtgcagc tggtgcagag cggcgcggaa gtgaaaaaac cgggcgcgac cgtgaaaatt | 60 |
| agctgcaaag tgagcggcta tacctttacc aactttata ttcattgggt gcgccaggcg | 120 |
| cgcggccagc gcctggaatg gattggcagc atttatccga actatggcga taccgcgtat | 180 |
| aaccagaaat ttaaagatcg cgtgaccatt accgcggata aaagcaccag caccgcgtat | 240 |
| atggaactga gcagcctgcg cagcgaagat accgcggtgt attattgcgc gcgcggctat | 300 |

```
agctatgcga tggattattg gggccagggc accaccgtga ccgtgagcag c          351
```

<210> SEQ ID NO 221
<211> LENGTH: 351
<212> TYPE: DNA
<213> ORGANISM: Artificial Sequence
<220> FEATURE:
<223> OTHER INFORMATION: Synthetic

<400> SEQUENCE: 221

```
gaagtgcagc tggtgcagag cggcgcggaa gtgaaaaaac cgggcgcgac cgtgaaaatt  60
agctgcaaag tgagcggcta cctttacc aacttttata ttcattgggt gcgccaggcg  120
ccgggcaaag gcctggaatg gatgggcagc atttatccga actatggcga taccgcgtat  180
aaccagaaat ttaaagatcg cgtgaccatt accgcgata aaagcaccag caccgcgtat  240
atggaactga gcagcctgcg cagcgaagat accgcggtgt attattgcgc gcgcggctat  300
agctatgcga tggattattg gggccagggc accaccgtga ccgtgagcag c           351
```

<210> SEQ ID NO 222
<211> LENGTH: 351
<212> TYPE: DNA
<213> ORGANISM: Artificial Sequence
<220> FEATURE:
<223> OTHER INFORMATION: Synthetic

<400> SEQUENCE: 222

```
gaagtgcagc tggtgcagag cggcgcggaa gtgaaaaaac cgggcgaaag cctgaaaatt  60
agctgcaaag gcagcggcta tagctttacc aacttttata ttcattgggt gcgccagatg  120
ccgggcaaag gcctggaatg gatgggcagc atttatccga actatggcga taccgcgtat  180
aaccagaaat ttaaagatcg cgtgaccatt accgcgata aaagcaccag caccgcgtat  240
atggaactga gcagcctgcg cagcgaagat accgcggtgt attattgcgc gcgcggctat  300
agctatgcga tggattattg gggccagggc accaccgtga ccgtgagcag c           351
```

<210> SEQ ID NO 223
<211> LENGTH: 351
<212> TYPE: DNA
<213> ORGANISM: Artificial Sequence
<220> FEATURE:
<223> OTHER INFORMATION: Synthetic

<400> SEQUENCE: 223

```
gaagtgcagc tggtgcagag cggcgcggaa gtgaaaaaac cgggcgaaag cctgaaaatt  60
agctgcaaag gcagcggcta tagctttacc aacttttata ttcattgggt gcgccagatg  120
ccgggcaaag gcctggaatg gatgggcagc atttatccga actatggcga taccgcgtat  180
aaccagaaat ttaaagatcg ctttgtgttt agcctggata ccagcgtgag caccgcgtat  240
ctgcagatta gcagcctgaa agcggaagat accgcggtgt attattgcgc gcgcggctat  300
agctatgcga tggattattg gggccagggc accaccgtga ccgtgagcag c           351
```

<210> SEQ ID NO 224
<211> LENGTH: 351
<212> TYPE: DNA
<213> ORGANISM: Artificial Sequence
<220> FEATURE:
<223> OTHER INFORMATION: Synthetic

<400> SEQUENCE: 224

```
gaagtgcagc tggtgcagag cggcgcggaa gtgaaaaaac cgggcgaaag cctgaaaatt    60
agctgcaaag gcagcggcta tagctttacc aactttttata ttcattgggt gcgccagatg   120
ccgggcaaag gcctggaatg gatgggcagc atttatccga actatggcga taccgcgtat   180
aaccagaaat ttaaagatcg ctttgtgttt agcctggata ccagcgtgag caccgcgtat   240
ctgcagatta gcagcctgaa agcggaagat accgcggtgt attattgcgc gcgcggctat   300
agctatgcga tggattattg gggccagggc accaccgtga ccgtgagcag c            351
```

<210> SEQ ID NO 225
<211> LENGTH: 351
<212> TYPE: DNA
<213> ORGANISM: Artificial Sequence
<220> FEATURE:
<223> OTHER INFORMATION: Synthetic

<400> SEQUENCE: 225

```
caggtgcagc tggtgcagag cggcgcggaa gtgaaaaaac cgggcgcgag cgtgaaagtg    60
agctgcaaag cgagcggcta tacctttacc aactttttata ttcattgggt gcgccaggcg   120
ccgggccagg gcctggaatg gatgggcagc atttatccga actatggcga taccgcgtat   180
aaccagaaat ttaaagatcg cgtgaccatg acccgcgata ccagcaccag caccgtgtat   240
atggaactga gcagcctgcg cagcgaagat accgcggtgt attattgcgc gcgcggctat   300
agctatgcga tggattattg gggccagggc accctggtga ccgtgagcag c            351
```

<210> SEQ ID NO 226
<211> LENGTH: 351
<212> TYPE: DNA
<213> ORGANISM: Artificial Sequence
<220> FEATURE:
<223> OTHER INFORMATION: Synthetic

<400> SEQUENCE: 226

```
caggtgcagc tggtgcagag cggcgcggaa gtgaaaaaac cgggcgcgag cgtgaaagtg    60
agctgcaaag cgagcggcta tacctttacc aactttttata ttcattgggt gcgccaggcg   120
ccgggccagg gcctggaatg gatgggcagc atttatccga actatggcga taccgcgtat   180
aaccagaaat ttaaagatcg cgtgaccatg accgtggata aaagcaccag caccgtgtat   240
atggaactgc gcagcctgcg cagcgaagat accgcggtgt attattgcgc gcgcggctat   300
agctatgcga tggattattg gggccagggc accctggtga ccgtgagcag c            351
```

<210> SEQ ID NO 227
<211> LENGTH: 351
<212> TYPE: DNA
<213> ORGANISM: Artificial Sequence
<220> FEATURE:
<223> OTHER INFORMATION: Synthetic

<400> SEQUENCE: 227

```
caggtgcagc tggtgcagag cggcgcggaa gtgaaaaaac cgggcgcgag cgtgaaagtg    60
agctgcaaag cgagcggcta tacctttacc aactttttata ttcattgggt gaaacaggcg   120
catggccagg gcctggaatg gatgggcagc atttatccga actatggcga taccgcgtat   180
aaccagaaat ttaaagatcg cgtgaccatg accgtggata aaagcaccag caccgtgtat   240
atggaactgc gcagcctgcg cagcgaagat accgcggtgt attattgcgc gcgcggctat   300
agctatgcga tggattattg gggccagggc accctggtga ccgtgagcag c            351
```

<210> SEQ ID NO 228
<211> LENGTH: 351
<212> TYPE: DNA
<213> ORGANISM: Artificial Sequence
<220> FEATURE:
<223> OTHER INFORMATION: Synthetic

<400> SEQUENCE: 228

```
caggtgcagc tggtgcagag cggcgcggaa gtgaaaaaac cgggcgcgag cgtgaaagtg      60
agctgcaaag cgagcggcta ccctttacc aactttttata ttcattgggt gcgccaggcg     120
ccgggccagg gcctggaatg gattggcagc atttatccga actatggcga taccgcgtat     180
aaccagaaat ttaaagatcg cgtgaccatg accgtgata ccagcaccag caccgtgtat      240
atggaactga gcagcctgcg cagcgaagat accgcggtgt attattgcgc gcgcggctat     300
agctatgcga tggattattg gggccagggc accctggtga ccgtgagcag c              351
```

<210> SEQ ID NO 229
<211> LENGTH: 351
<212> TYPE: DNA
<213> ORGANISM: Artificial Sequence
<220> FEATURE:
<223> OTHER INFORMATION: Synthetic

<400> SEQUENCE: 229

```
caggtgcagc tggtgcagag cggcgcggaa gtgaaaaaac cgggcgcgag cgtgaaaatg      60
agctgcaaag cgagcggcta ccctttacc aactttttata ttcattgggt gcgccaggcg     120
ccgggccagg gcctggaatg gattggcagc atttatccga actatggcga taccgcgtat     180
aaccagaaat ttaaagatcg cgcgaccctg accgtggata ccagcaccag caccgcgtat    240
atggaactga gcagcctgcg cagcgaagat accgcggtgt attattgcgc gcgcggctat     300
agctatgcga tggattattg gggccagggc accctggtga ccgtgagcag c              351
```

<210> SEQ ID NO 230
<211> LENGTH: 351
<212> TYPE: DNA
<213> ORGANISM: Artificial Sequence
<220> FEATURE:
<223> OTHER INFORMATION: Synthetic

<400> SEQUENCE: 230

```
caggtgcagc tggtgcagag cggcgcggaa gtgaaaaaac cgggcgcgag cgtgaaaatg      60
agctgcaaag cgagcggcta ccctttacc aactttttata ttcattgggt gcgccaggcg     120
ccgggccagg gcctggaatg gattggcagc atttatccga actatggcga taccgcgtat     180
aaccagaaat ttaaagatcg cgcgaccctg accgtggata aaagcaccag caccgcgtat    240
atggaactga gcagcctgcg cagcgaagat accgcggtgt attattgcgc gcgcggctat     300
agctatgcga tggattattg gggccagggc accctggtga ccgtgagcag c              351
```

<210> SEQ ID NO 231
<211> LENGTH: 321
<212> TYPE: DNA
<213> ORGANISM: Artificial Sequence
<220> FEATURE:
<223> OTHER INFORMATION: Synthetic

<400> SEQUENCE: 231

```
gatattcaga tgacccagag cccgagcagc gtgagcgcga gcgtgggcga tcgcgtgacc      60
attacctgca gcgcgagcca gggcattagc ggcgatctga ctggtatca gcagaaaccg     120
```

```
ggccaggcgc cgcgcctgct gatttatcat accagcagcc tgcatagcgg cgtgccgagc    180
cgctttagcg gcagcggcag cggcaccgat tttaccctga ccattagcag cctgcagccg    240
gaagattttg cgacctatta ttgccagtat tatagcaaag atctgctgac ctttggcggc    300
ggcaccaaac tggaaattaa a                                              321
```

<210> SEQ ID NO 232
<211> LENGTH: 321
<212> TYPE: DNA
<213> ORGANISM: Artificial Sequence
<220> FEATURE:
<223> OTHER INFORMATION: Synthetic

<400> SEQUENCE: 232

```
gatattcaga tgacccagag cccgagcagc ctgagcgcga gcgtgggcga tcgcgtgacc    60
attacctgca gcgcgagcca gggcattagc ggcgatctga actggtatca gcagaaaccg    120
ggcaaaaccc cgaaactgct gatttatcat accagcagcc tgcatagcgg cgtgccgagc    180
cgctttagcg gcagcggcag cggcaccgat tttaccctga ccattagcag cctgcagccg    240
gaagattttg cgacctatta ttgccagtat tatagcaaag atctgctgac ctttggcggc    300
ggcaccaaac tggaaattaa a                                              321
```

<210> SEQ ID NO 233
<211> LENGTH: 321
<212> TYPE: DNA
<213> ORGANISM: Artificial Sequence
<220> FEATURE:
<223> OTHER INFORMATION: Synthetic

<400> SEQUENCE: 233

```
gatattcaga tgacccagag cccgagcagc gtgagcgcga gcgtgggcga tcgcgtgacc    60
attacctgca gcgcgagcca gggcattagc ggcgatctga actggtatca gcagaaaccg    120
ggcaaagcgc cgaaactgct gatttatcat accagcagcc tgcatagcgg cgtgccgagc    180
cgctttagcg gcagcggcag cggcaccgat tttaccctga ccattagcag cctgcagccg    240
gaagattttg cgacctatta ttgccagtat tatagcaaag atctgctgac ctttggcggc    300
ggcaccaaac tggaaattaa a                                              321
```

<210> SEQ ID NO 234
<211> LENGTH: 321
<212> TYPE: DNA
<213> ORGANISM: Artificial Sequence
<220> FEATURE:
<223> OTHER INFORMATION: Synthetic

<400> SEQUENCE: 234

```
gatattcaga tgacccagag cccgagcagc gtgagcgcga gcgtgggcga tcgcgtgacc    60
attacctgca gcgcgagcca gggcattagc ggcgatctga actggtatca gcagaaaccg    120
ggccaggcgc cgcgcctgct gatttatcat accagcagcc tgcatagcgg cgtgccgagc    180
cgctttagcg gcagcggcag cggcaccgaa tttaccctga ccattagccg cctggaaccg    240
gaagattttg cggtgtatta ttgccagtat tatagcaaag atctgctgac ctttggcggc    300
ggcaccaaac tggaaattaa a                                              321
```

<210> SEQ ID NO 235
<211> LENGTH: 321
<212> TYPE: DNA
<213> ORGANISM: Artificial Sequence -continued
<220> FEATURE:
<223> OTHER INFORMATION: Synthetic

<400> SEQUENCE: 235
gatattcaga tgacccagag cccgagcacc ctgagcgcga gcgtgggcga tcgcgtgacc   60
attacctgca gcgcgagcca gggcattagc ggcgatctga actggtatca gcagaaaccg  120
ggccaggcgc cgcgcctgct gatttatcat accagcagcc tgcatagcgg cgtgccgagc  180
cgctttagcg gcagcggcag cggcaccgat tttaccctga ccattagcag cctgcagccg  240
gaagattttg cgacctatta ttgccagtat tatagcaaag atctgctgac ctttggcggc  300
ggcaccaaac tggaaattaa a                                            321

<210> SEQ ID NO 236
<211> LENGTH: 321
<212> TYPE: DNA
<213> ORGANISM: Artificial Sequence
<220> FEATURE:
<223> OTHER INFORMATION: Synthetic

<400> SEQUENCE: 236
gatattcaga tgacccagag cccgagcagc gtgagcgcga gcgtgggcga tcgcgtgacc   60
attacctgca gcgcgagcca gggcattagc ggcgatctga actggtatca gcagaaaccg  120
ggccaggcgc cgcgcctgct gatttatcat accagcagcc tgcatagcgg cattccggcg  180
cgctttagcg gcagcggcag cggcaccgat tttaccctga ccattagccg cctggaaccg  240
gaagattttg cggtgtatta ttgccagtat tatagcaaag atctgctgac ctttggcggc  300
ggcaccaaac tggaaattaa a                                            321

<210> SEQ ID NO 237
<211> LENGTH: 321
<212> TYPE: DNA
<213> ORGANISM: Artificial Sequence
<220> FEATURE:
<223> OTHER INFORMATION: Synthetic

<400> SEQUENCE: 237
gatattcaga tgacccagag cccgagcacc ctgagcgcga gcgtgggcga tcgcgtgacc   60
attacctgca gcgcgagcca gggcattagc ggcgatctga actggtatca gcagaaaccg  120
ggcaaaaccc cgaaactgct gatttatcat accagcagcc tgcatagcgg cgtgccgagc  180
cgctttagcg gcagcggcag cggcaccgat tttaccctga ccattagcag cctgcagccg  240
gaagattttg cgacctatta ttgccagtat tatagcaaag atctgctgac ctttggcggc  300
ggcaccaaac tggaaattaa a                                            321

<210> SEQ ID NO 238
<211> LENGTH: 321
<212> TYPE: DNA
<213> ORGANISM: Artificial Sequence
<220> FEATURE:
<223> OTHER INFORMATION: Synthetic

<400> SEQUENCE: 238
gatattcaga tgacccagag cccgagcacc ctgagcgcga gcgtgggcga tcgcgtgacc   60
attacctgca gcgcgagcca gggcattagc ggcgatctga actggtatca gcagaaaccg  120
ggccaggcgc cgcgcctgct gatttatcat accagcagcc tgcatagcgg cattccggcg  180
cgctttagcg gcagcggcag cggcaccgat tttaccctga ccattagcag cctgcagccg  240

| gaagattttg cggtgtatta ttgccagtat tatagcaaag atctgctgac ctttggcggc | 300 |
| ggcaccaaac tggaaattaa a | 321 |

<210> SEQ ID NO 239
<211> LENGTH: 321
<212> TYPE: DNA
<213> ORGANISM: Artificial Sequence
<220> FEATURE:
<223> OTHER INFORMATION: Synthetic

<400> SEQUENCE: 239

| gatattcaga tgacccagag cccgagcagc ctgagcgcga gcgtgggcga tcgcgtgacc | 60 |
| attacctgca gcgcgagcca gggcattagc ggcgatctga actggtatca gcagaaaccg | 120 |
| ggcaaagcgc cgaaactgct gatttatcat accagcagcc tgcatagcgg cgtgccgagc | 180 |
| cgctttagcg gcagcggcag cggcaccgat tttaccctga ccattagcag cctgcagccg | 240 |
| gaagattttg cgacctatta ttgccagtat tatagcaaag atctgctgac ctttggcggc | 300 |
| ggcaccaaac tggaaattaa a | 321 |

<210> SEQ ID NO 240
<211> LENGTH: 321
<212> TYPE: DNA
<213> ORGANISM: Artificial Sequence
<220> FEATURE:
<223> OTHER INFORMATION: Synthetic

<400> SEQUENCE: 240

| gatattcaga tgacccagag cccgagcagc ctgagcgcga gcgtgggcga tcgcgtgacc | 60 |
| attacctgca gcgcgagcca gggcattagc ggcgatctga actggtatca gcagaaaccg | 120 |
| ggcaaagcgg tgaaactgct gatttatcat accagcagcc tgcatagcgg cgtgccgctg | 180 |
| cgctttagcg gcagcggcag cggcaccgat tataccctga ccattagcag cctgcagccg | 240 |
| gaagattttg cgacctatta ttgccagtat tatagcaaag atctgctgac ctttggcggc | 300 |
| ggcaccaaac tggaaattaa a | 321 |

<210> SEQ ID NO 241
<211> LENGTH: 321
<212> TYPE: DNA
<213> ORGANISM: Artificial Sequence
<220> FEATURE:
<223> OTHER INFORMATION: Synthetic

<400> SEQUENCE: 241

| gatattcaga tgacccagag cccgagcagc ctgagcgcga gcgtgggcga tcgcgtgacc | 60 |
| attacctgca gcgcgagcca gggcattagc ggcgatctga actggtatca gcagaaaagc | 120 |
| gatggcgcgg tgaaactgct gatttatcat accagcagcc tgcatagcgg cgtgccgctg | 180 |
| cgctttagcg gcagcggcag cggcaccgat tataccctga ccattagcag cctgcagccg | 240 |
| gaagattttg cgacctatta ttgccagtat tatagcaaag atctgctgac ctttggcggc | 300 |
| ggcaccaaac tggaaattaa a | 321 |

<210> SEQ ID NO 242
<211> LENGTH: 321
<212> TYPE: DNA
<213> ORGANISM: Artificial Sequence
<220> FEATURE:
<223> OTHER INFORMATION: Synthetic

<400> SEQUENCE: 242

```
gatattcaga tgacccagag cccgagcagc ctgagcgcga gcgtgggcga tcgcgtgacc    60
attacctgca gcgcgagcca gggcattagc ggcgatctga actggtatca gcagaaaccg   120
ggcaaagcgc cgaaactgct gatttatcat accagcagcc tgcatagcgg cgtgccgagc   180
cgctttagcg gcagcggcag cggcaccgat tatacctga ccattagcag cctgcagccg    240
gaagattttg cgacctatta ttgccagtat tatagcaaag atctgctgac ctttggcggc   300
ggcaccaaac tggaaattaa a                                            321

<210> SEQ ID NO 243
<211> LENGTH: 360
<212> TYPE: DNA
<213> ORGANISM: Artificial Sequence
<220> FEATURE:
<223> OTHER INFORMATION: Synthetic

<400> SEQUENCE: 243
gatattcaga tgacccagag cccgagcagc ctgagcgcga gcgtgggcga tcgcgtgacc    60
attacctgca gcgcgagcca gggcattagc ggcgatctga actggtatca gcagaaaccg   120
ggcaaagcgg tgaaactgct gatttatcat accagcagcc tgcatagcgg cgtgccgagc   180
cgctttagcg gcagcggcag cggcaccgat tatacctga ccattagcag cctgcagccg    240
gaagattttg cgacctatta ttgccagtat tatagcaaag atctgctgac ctttggcggc   300
ggcaccaaac tggaactgaa aaaactgatg aacccgcagc gcagcaccgt gtggtattaa   360

<210> SEQ ID NO 244
<211> LENGTH: 288
<212> TYPE: PRT
<213> ORGANISM: Homo sapiens

<400> SEQUENCE: 244

Met Gln Ile Pro Gln Ala Pro Trp Pro Val Val Trp Ala Val Leu Gln
1               5                   10                  15

Leu Gly Trp Arg Pro Gly Trp Phe Leu Ala Ser Pro Ala Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190
```

```
Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285

<210> SEQ ID NO 245
<211> LENGTH: 288
<212> TYPE: PRT
<213> ORGANISM: Homo sapiens

<400> SEQUENCE: 245

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Ala Pro Ala
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285
```

<210> SEQ ID NO 246
<211> LENGTH: 288
<212> TYPE: PRT
<213> ORGANISM: Homo sapiens

<400> SEQUENCE: 246

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Lys Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 247
<211> LENGTH: 288
<212> TYPE: PRT
<213> ORGANISM: Homo sapiens

<400> SEQUENCE: 247

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ala Ala Ala Leu Val Val Thr Glu Gly Asp
        35                  40                  45

Asn Ala Thr Phe Thr Cys Ser Phe Ser Asn Thr Ser Glu Ser Phe Val
            50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 248
<211> LENGTH: 288
<212> TYPE: PRT
<213> ORGANISM: Homo sapiens

<400> SEQUENCE: 248

Met Gln Ile Pro Gln Ala Pro Trp Pro Val Val Trp Ala Val Leu Gln
 1                   5                  10                  15

Leu Gly Trp Arg Pro Gly Trp Phe Leu Asp Ser Pro Asp Arg Pro Trp
                 20                  25                  30

Asn Pro Pro Thr Phe Ser Pro Ala Leu Leu Val Val Thr Glu Gly Ala
             35                  40                  45

Asn Ala Thr Phe Thr Cys Ser Phe Ser Asn Thr Ser Glu Ser Phe Val
            50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val

```
                130             135             140
Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
                210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 249
<211> LENGTH: 288
<212> TYPE: PRT
<213> ORGANISM: Homo sapiens

<400> SEQUENCE: 249

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Ala Ala Ala Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
                130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
                210                 215                 220
```

-continued

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 250
<211> LENGTH: 288
<212> TYPE: PRT
<213> ORGANISM: Homo sapiens

<400> SEQUENCE: 250

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Ala Ala Cys Ala Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 251
<211> LENGTH: 288
<212> TYPE: PRT
<213> ORGANISM: Homo sapiens

<400> SEQUENCE: 251

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ala Ala Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 252
<211> LENGTH: 288
<212> TYPE: PRT
<213> ORGANISM: Homo sapiens

<400> SEQUENCE: 252

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Ser Ala Ala Phe Val
    50                  55                  60

Leu Asn Trp Tyr Arg Met Ser Pro Ser Asn Gln Thr Asp Lys Leu Ala
65                  70                  75                  80
```

```
Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
               100                 105                 110

Ala Arg Arg Asn Asp Ser Gly Thr Tyr Leu Cys Gly Ala Ile Ser Leu
               115                 120                 125

Ala Pro Lys Ala Gln Ile Lys Glu Ser Leu Arg Ala Glu Leu Arg Val
           130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
               165                 170                 175

Leu Leu Gly Ser Leu Val Leu Leu Val Trp Val Leu Ala Val Ile Cys
               180                 185                 190

Ser Arg Ala Ala Arg Gly Thr Ile Gly Ala Arg Arg Thr Gly Gln Pro
           195                 200                 205

Leu Lys Glu Asp Pro Ser Ala Val Pro Val Phe Ser Val Asp Tyr Gly
           210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
               245                 250                 255

Met Gly Thr Ser Ser Pro Ala Arg Arg Gly Ser Ala Asp Gly Pro Arg
               260                 265                 270

Ser Ala Gln Pro Leu Arg Pro Glu Asp Gly His Cys Ser Trp Pro Leu
           275                 280                 285

<210> SEQ ID NO 253
<211> LENGTH: 288
<212> TYPE: PRT
<213> ORGANISM: Homo sapiens

<400> SEQUENCE: 253

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Ala
            50                  55                  60

Leu Ala Trp Ala Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
               100                 105                 110

Ala Arg Arg Asn Asp Ser Gly Thr Tyr Leu Cys Gly Ala Ile Ser Leu
               115                 120                 125

Ala Pro Lys Ala Gln Ile Lys Glu Ser Leu Arg Ala Glu Leu Arg Val
           130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
```

```
                    165                 170                 175
Leu Leu Gly Ser Leu Val Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 254
<211> LENGTH: 288
<212> TYPE: PRT
<213> ORGANISM: Homo sapiens

<400> SEQUENCE: 254

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ala Asn Ala Ala Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255
```

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285

<210> SEQ ID NO 255
<211> LENGTH: 288
<212> TYPE: PRT
<213> ORGANISM: Homo sapiens

<400> SEQUENCE: 255

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Ala Asp Ala Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 256
<211> LENGTH: 288
<212> TYPE: PRT
<213> ORGANISM: Homo sapiens

<400> SEQUENCE: 256

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
65                  70                  75                  80

Ala Phe Pro Glu Ala Ala Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 257
<211> LENGTH: 288
<212> TYPE: PRT
<213> ORGANISM: Homo sapiens

<400> SEQUENCE: 257

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Ala Ala Gly Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                    165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                    245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 258
<211> LENGTH: 288
<212> TYPE: PRT
<213> ORGANISM: Homo sapiens

<400> SEQUENCE: 258

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Ala Ala Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                    165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

```
                195                 200                 205
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
    275                 280                 285

<210> SEQ ID NO 259
<211> LENGTH: 288
<212> TYPE: PRT
<213> ORGANISM: Homo sapiens

<400> SEQUENCE: 259

Met Gln Ile Pro Gln Ala Pro Trp Pro Val Val Trp Ala Val Leu Gln
1               5                   10                  15
Leu Gly Trp Arg Pro Gly Trp Phe Leu Asp Ser Pro Asp Arg Pro Trp
                20                  25                  30
Asn Pro Pro Thr Phe Ser Pro Ala Leu Leu Val Val Thr Glu Gly Asp
            35                  40                  45
Asn Ala Thr Phe Thr Cys Ser Phe Ser Asn Thr Ser Glu Ser Phe Val
        50                  55                  60
Leu Asn Trp Tyr Arg Met Ser Pro Ser Asn Gln Thr Asp Lys Leu Ala
65                  70                  75                  80
Ala Phe Pro Glu Asp Arg Ser Gln Pro Gly Gln Asp Cys Arg Phe Arg
                85                  90                  95
Val Thr Gln Leu Pro Asn Gly Arg Asp Phe His Met Ser Val Val Arg
                100                 105                 110
Ala Arg Arg Asn Asp Ser Gly Thr Tyr Leu Cys Gly Ala Ile Ser Leu
            115                 120                 125
Ala Pro Lys Ala Gln Ile Lys Glu Ser Leu Arg Ala Glu Leu Arg Val
        130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
        195                 200                 205
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
    275                 280                 285
```

<210> SEQ ID NO 260
<211> LENGTH: 288
<212> TYPE: PRT
<213> ORGANISM: Homo sapiens

<400> SEQUENCE: 260

Met Gln Ile Pro Gln Ala Pro Trp Pro Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Ala Gly Ala Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 261
<211> LENGTH: 288
<212> TYPE: PRT
<213> ORGANISM: Homo sapiens

<400> SEQUENCE: 261

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

```
Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Ala Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 262
<211> LENGTH: 288
<212> TYPE: PRT
<213> ORGANISM: Homo sapiens

<400> SEQUENCE: 262

Met Gln Ile Pro Gln Ala Pro Trp Pro Val Val Trp Ala Val Leu Gln
  1               5                  10                  15

Leu Gly Trp Arg Pro Gly Trp Phe Leu Asp Ser Pro Asp Arg Pro Trp
             20                  25                  30

Asn Pro Pro Thr Phe Ser Pro Ala Leu Leu Val Val Thr Glu Gly Asp
             35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe Ala Met Ala Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140
```

```
Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
                210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285
```

<210> SEQ ID NO 263
<211> LENGTH: 288
<212> TYPE: PRT
<213> ORGANISM: Homo sapiens

<400> SEQUENCE: 263

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
                50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Ala Ala
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
                130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
                210                 215                 220

Glu Leu Asp Phe Gln Trp Arg Glu Lys Thr Pro Glu Pro Pro Val Pro
```

```
            225                 230                 235                 240
Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 264
<211> LENGTH: 288
<212> TYPE: PRT
<213> ORGANISM: Homo sapiens

<400> SEQUENCE: 264

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65              70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Ala Ala Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145             150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225             230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 265
<211> LENGTH: 288
<212> TYPE: PRT
<213> ORGANISM: Homo sapiens
```

-continued

<400> SEQUENCE: 265

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Ala Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 266
<211> LENGTH: 288
<212> TYPE: PRT
<213> ORGANISM: Homo sapiens

<400> SEQUENCE: 266

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
            85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Ala Gly Ala Ser Ala
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 267
<211> LENGTH: 288
<212> TYPE: PRT
<213> ORGANISM: Homo sapiens

<400> SEQUENCE: 267

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
            85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Thr Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

```
Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 268
<211> LENGTH: 288
<212> TYPE: PRT
<213> ORGANISM: Homo sapiens

<400> SEQUENCE: 268

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Thr Ala Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
```

```
                    260                 265                 270
Ser Ala Gln Pro Leu Arg Pro Glu Asp Gly His Cys Ser Trp Pro Leu
        275                 280                 285

<210> SEQ ID NO 269
<211> LENGTH: 288
<212> TYPE: PRT
<213> ORGANISM: Homo sapiens

<400> SEQUENCE: 269

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Ala Ala Ala Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 270
<211> LENGTH: 288
<212> TYPE: PRT
<213> ORGANISM: Homo sapiens

<400> SEQUENCE: 270

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30
```

```
            20                  25                  30
Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Ala Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 271
<211> LENGTH: 288
<212> TYPE: PRT
<213> ORGANISM: Homo sapiens

<400> SEQUENCE: 271

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110
```

```
Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Ala Ala Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 272
<211> LENGTH: 288
<212> TYPE: PRT
<213> ORGANISM: Homo sapiens

<400> SEQUENCE: 272

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala Ala Ala Pro Ser Pro Ser
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205
```

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 273
<211> LENGTH: 288
<212> TYPE: PRT
<213> ORGANISM: Homo sapiens

<400> SEQUENCE: 273

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Ala Ala Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 274
<211> LENGTH: 288
<212> TYPE: PRT
<213> ORGANISM: Homo sapiens

<400> SEQUENCE: 274

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 275
<211> LENGTH: 288
<212> TYPE: PRT
<213> ORGANISM: Homo sapiens

<400> SEQUENCE: 275

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Thr Glu Gly Asp
        35                  40                  45

Asn Ala Thr Phe Thr Cys Ser Phe Ser Asn Thr Ser Glu Ser Phe Val

```
            50                  55                  60
Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 276
<211> LENGTH: 288
<212> TYPE: PRT
<213> ORGANISM: Macaca mulatta

<400> SEQUENCE: 276

Met Gln Ile Pro Gln Ala Pro Trp Pro Val Val Trp Ala Val Leu Gln
  1               5                  10                  15

Leu Gly Trp Arg Pro Gly Trp Phe Leu Glu Ser Pro Asp Arg Pro Trp
                 20                  25                  30

Asn Pro Pro Thr Phe Ser Pro Ala Leu Leu Val Val Thr Glu Gly Asp
             35                  40                  45

Asn Ala Thr Phe Thr Cys Ser Phe Ser Asn Ala Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Arg Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140
```

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Gly Gly
            165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
            245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
            275                 280                 285

<210> SEQ ID NO 277
<211> LENGTH: 117
<212> TYPE: PRT
<213> ORGANISM: Unknown
<220> FEATURE:
<223> OTHER INFORMATION: Mouse VH reference sequence

<400> SEQUENCE: 277

Gln Val Gln Leu Gln Gln Pro Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Ile Lys Gln Arg Pro Gly His Gly Leu Glu Trp Ile
            35                  40                  45

Gly Asp Ile Tyr Pro Gly Gly Gly Tyr Thr Asn Tyr Asn Glu Lys Phe
50                  55                  60

Lys Gly Lys Ala Thr Leu Thr Ala Asp Thr Ser Ser Ser Thr Ala Tyr
65                  70                  75                  80

Met Gln Val Ser Ser Leu Thr Ser Glu Asp Thr Gly Ile Tyr Tyr Cys
            85                  90                  95

Ala Arg Gly Tyr Asp Phe Val Leu Asp Arg Trp Gly Gln Gly Thr Ser
            100                 105                 110

Val Thr Val Ser Ser
            115

<210> SEQ ID NO 278
<211> LENGTH: 112
<212> TYPE: PRT
<213> ORGANISM: Unknown
<220> FEATURE:
<223> OTHER INFORMATION: Mouse VL reference sequence

<400> SEQUENCE: 278

Asp Ile Val Met Ser Gln Ser Pro Ser Ser Leu Ala Val Ser Thr Gly
1               5                   10                  15

Glu Lys Val Thr Met Thr Cys Lys Ser Ser Gln Ser Leu Phe Asn Ser
            20                  25                  30

Glu Thr Gln Lys Asn Tyr Leu Ala Trp Tyr Gln Gln Lys Pro Gly Gln
            35                  40                  45

```
Pro Pro Lys Leu Leu Ile Phe Trp Ala Ser Thr Arg Glu Ser Gly Val
    50                  55                  60

Pro Asp Arg Phe Leu Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Thr Leu Arg Thr Phe Gly Gly Gly Thr Lys Leu Glu Ile Lys
            100                 105                 110
```

<210> SEQ ID NO 279
<211> LENGTH: 117
<212> TYPE: PRT
<213> ORGANISM: Unknown
<220> FEATURE:
<223> OTHER INFORMATION: Mouse VH reference sequence

<400> SEQUENCE: 279

```
Glu Val Gln Leu His Gln Ser Gly Pro Glu Leu Leu Lys Pro Gly Ala
1               5                   10                  15

Ser Val Arg Met Ser Cys Lys Ala Ser Gly Tyr Thr Phe Thr Asn Phe
                20                  25                  30

Tyr Ile His Trp Val Lys Gln Ser His Gly Lys Ser Ile Glu Trp Ile
            35                  40                  45

Gly Ser Ile Tyr Pro Asn Tyr Gly Asp Thr Ala Tyr Asn Gln Lys Phe
        50                  55                  60

Lys Asp Lys Ala Thr Leu Thr Val Asp Lys Ser Ser Ser Thr Ala Tyr
65                  70                  75                  80

Met Ala Leu Arg Ser Leu Thr Ser Glu Asp Ser Ala Val Tyr Tyr Cys
                85                  90                  95

Ala Arg Gly Tyr Ser Tyr Ala Met Asp Tyr Trp Gly Gln Gly Thr Ser
            100                 105                 110

Val Thr Val Ser Ser
        115
```

<210> SEQ ID NO 280
<211> LENGTH: 107
<212> TYPE: PRT
<213> ORGANISM: Unknown
<220> FEATURE:
<223> OTHER INFORMATION: Mouse VL reference sequence

<400> SEQUENCE: 280

```
Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
                20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105
```

```
<210> SEQ ID NO 281
<211> LENGTH: 149
<212> TYPE: PRT
<213> ORGANISM: Homo sapiens

<400> SEQUENCE: 281

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu
145

<210> SEQ ID NO 282
<211> LENGTH: 149
<212> TYPE: PRT
<213> ORGANISM: Unknown
<220> FEATURE:
<223> OTHER INFORMATION: Monkey

<400> SEQUENCE: 282

Pro Gly Trp Phe Leu Glu Ser Pro Asp Arg Pro Trp Asn Pro Pro Thr
1               5                   10                  15

Phe Ser Pro Ala Leu Leu Leu Val Thr Glu Gly Asp Asn Ala Thr Phe
            20                  25                  30

Thr Cys Ser Phe Ser Asn Ala Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Arg Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Ala Leu
145

<210> SEQ ID NO 283
```

```
<211> LENGTH: 149
<212> TYPE: PRT
<213> ORGANISM: Unknown
<220> FEATURE:
<223> OTHER INFORMATION: Horse

<400> SEQUENCE: 283

Ser Val His Leu Leu Asp Ser Pro Asp Arg Pro Trp Asn Arg Pro Leu
1               5                   10                  15

Phe Ser Pro Ala Arg Leu Met Val Pro Glu Gly Ala Asn Ala Thr Phe
            20                  25                  30

Thr Cys Ser Phe Ser Asn Thr Ser Glu His Phe Val Leu Asn Trp Tyr
        35                  40                  45

Arg Met Ser Pro Ser Asn Gln Thr Asp Lys Leu Ala Ala Phe Pro Glu
    50                  55                  60

Asp Ser Ser Gln Pro Gly Arg Ser Gly Arg Phe Arg Val Thr Arg Leu
65                  70                  75                  80

Pro Asn Gly Arg Asp Phe His Met Ser Val Leu Ala Ala Arg Arg Asn
                85                  90                  95

Asp Ser Gly Ile Tyr Leu Cys Gly Ala Ile Ser Leu Pro Pro Lys Thr
                100                 105                 110

Gln Ile Asn Glu Ser Pro Arg Ala Glu Leu Thr Val Thr Glu Arg Ile
            115                 120                 125

Pro Glu Pro Pro Thr Glu His Pro Ser Pro Ser Pro Ala Gly
        130                 135                 140

Gln Leu Gln Gly Leu
145

<210> SEQ ID NO 284
<211> LENGTH: 149
<212> TYPE: PRT
<213> ORGANISM: Unknown
<220> FEATURE:
<223> OTHER INFORMATION: Dog

<400> SEQUENCE: 284

Pro Gly Trp Leu Leu Asp Ser Pro Asp Arg Pro Trp Ser Pro Leu Thr
1               5                   10                  15

Phe Ser Pro Ala Gln Leu Thr Val Gln Glu Gly Glu Asn Ala Thr Phe
            20                  25                  30

Thr Cys Ser Leu Ala Asp Ile Pro Asp Ser Phe Val Leu Asn Trp Tyr
        35                  40                  45

Arg Leu Ser Pro Arg Asn Gln Thr Asp Lys Leu Ala Ala Phe Gln Glu
    50                  55                  60

Asp Arg Ile Glu Pro Gly Arg Asp Arg Arg Phe Arg Val Thr Arg Leu
65                  70                  75                  80

Pro Asn Gly Arg Asp Phe His Met Ser Ile Val Ala Ala Arg Leu Asn
                85                  90                  95

Asp Ser Gly Ile Tyr Leu Cys Gly Ala Ile Tyr Leu Pro Pro Asn Thr
                100                 105                 110

Gln Ile Asn Glu Ser Pro Arg Ala Glu Leu Ser Val Thr Glu Arg Thr
            115                 120                 125

Leu Glu Pro Pro Thr Gln Ser Pro Ser Pro Arg Leu Ser Gly
        130                 135                 140

Gln Leu Gln Gly Leu
145
```

-continued

```
<210> SEQ ID NO 285
<211> LENGTH: 149
<212> TYPE: PRT
<213> ORGANISM: Unknown
<220> FEATURE:
<223> OTHER INFORMATION: Mouse

<400> SEQUENCE: 285

Ser Gly Trp Leu Leu Glu Val Pro Asn Gly Pro Trp Arg Ser Leu Thr
1               5                   10                  15

Phe Tyr Pro Ala Trp Leu Thr Val Ser Glu Gly Ala Asn Ala Thr Phe
            20                  25                  30

Thr Cys Ser Leu Ser Asn Trp Ser Glu Asp Leu Met Leu Asn Trp Asn
        35                  40                  45

Arg Leu Ser Pro Ser Asn Gln Thr Glu Lys Gln Ala Ala Phe Cys Asn
    50                  55                  60

Gly Leu Ser Gln Pro Val Gln Asp Ala Arg Phe Gln Ile Ile Gln Leu
65                  70                  75                  80

Pro Asn Arg His Asp Phe His Met Asn Ile Leu Asp Thr Arg Arg Asn
                85                  90                  95

Asp Ser Gly Ile Tyr Leu Cys Gly Ala Ile Ser Leu His Pro Lys Ala
            100                 105                 110

Lys Ile Glu Glu Ser Pro Gly Ala Glu Leu Val Val Thr Glu Arg Ile
        115                 120                 125

Leu Glu Thr Ser Thr Arg Tyr Pro Ser Pro Ser Pro Lys Pro Glu Gly
    130                 135                 140

Arg Phe Gln Gly Met
145

<210> SEQ ID NO 286
<211> LENGTH: 149
<212> TYPE: PRT
<213> ORGANISM: Unknown
<220> FEATURE:
<223> OTHER INFORMATION: Rat

<400> SEQUENCE: 286

Ser Gly Trp Leu Leu Glu Val Leu Asn Lys Pro Trp Arg Pro Leu Thr
1               5                   10                  15

Phe Ser Pro Thr Trp Leu Thr Val Ser Glu Gly Ala Asn Ala Thr Phe
            20                  25                  30

Thr Cys Ser Phe Ser Asn Trp Ser Glu Asp Leu Lys Leu Asn Trp Tyr
        35                  40                  45

Arg Leu Ser Pro Ser Asn Gln Thr Glu Lys Gln Ala Ala Phe Cys Asn
    50                  55                  60

Gly Tyr Ser Gln Pro Val Arg Asp Ala Arg Phe Gln Ile Val Gln Leu
65                  70                  75                  80

Pro Asn Gly His Asp Phe His Met Asn Ile Leu Asp Ala Arg Arg Asn
                85                  90                  95

Asp Ser Gly Ile Tyr Leu Cys Gly Ala Ile Ser Leu Pro Pro Lys Ala
            100                 105                 110

Gln Ile Lys Glu Ser Pro Gly Ala Glu Leu Val Val Thr Glu Arg Ile
        115                 120                 125

Leu Glu Thr Pro Thr Arg Tyr Pro Arg Pro Ser Pro Lys Pro Glu Gly
    130                 135                 140

Gln Phe Gln Gly Leu
145
```

<210> SEQ ID NO 287
<211> LENGTH: 15
<212> TYPE: PRT
<213> ORGANISM: Artificial Sequence
<220> FEATURE:
<223> OTHER INFORMATION: Synthetic

<400> SEQUENCE: 287

Arg Ala Ser Lys Gly Val Ser Thr Ser Gly Tyr Ser Tyr Leu His
1               5                   10                  15

<210> SEQ ID NO 288
<211> LENGTH: 7
<212> TYPE: PRT
<213> ORGANISM: Artificial Sequence
<220> FEATURE:
<223> OTHER INFORMATION: Synthetic

<400> SEQUENCE: 288

Leu Ala Ser Tyr Leu Glu Ser
1               5

<210> SEQ ID NO 289
<211> LENGTH: 9
<212> TYPE: PRT
<213> ORGANISM: Artificial Sequence
<220> FEATURE:
<223> OTHER INFORMATION: Synthetic

<400> SEQUENCE: 289

Gln His Ser Arg Asp Leu Pro Leu Thr
1               5

<210> SEQ ID NO 290
<211> LENGTH: 5
<212> TYPE: PRT
<213> ORGANISM: Artificial Sequence
<220> FEATURE:
<223> OTHER INFORMATION: Synthetic

<400> SEQUENCE: 290

Asn Tyr Tyr Met Tyr
1               5

<210> SEQ ID NO 291
<211> LENGTH: 17
<212> TYPE: PRT
<213> ORGANISM: Artificial Sequence
<220> FEATURE:
<223> OTHER INFORMATION: Synthetic

<400> SEQUENCE: 291

Gly Ile Asn Pro Ser Asn Gly Gly Thr Asn Phe Asn Glu Lys Phe Lys
1               5                   10                  15

Asn

<210> SEQ ID NO 292
<211> LENGTH: 11
<212> TYPE: PRT
<213> ORGANISM: Artificial Sequence
<220> FEATURE:

```
<223> OTHER INFORMATION: Synthetic

<400> SEQUENCE: 292

Arg Asp Tyr Arg Phe Asp Met Gly Phe Asp Tyr
1               5                   10
```